(12) United States Patent
Iyer et al.

(10) Patent No.: US 7,446,118 B2
(45) Date of Patent: Nov. 4, 2008

(54) 3-AMINO-1-ARYLPROPYL INDOLES AND AZA-SUBSTITUTED INDOLES AND USES THEREOF

(75) Inventors: Pravin Iyer, Mountain View, CA (US); Matthew C. Lucas, Sunnyvale, CA (US); Ryan Craig Schoenfeld, San Jose, CA (US); Marzia Villa, Sunnyvale, CA (US); Robert James Weikert, Boulder Creek, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 51 days.

(21) Appl. No.: 11/605,528

(22) Filed: Nov. 29, 2006

(65) Prior Publication Data

US 2007/0123527 A1    May 31, 2007

Related U.S. Application Data

(60) Provisional application No. 60/741,266, filed on Nov. 30, 2005.

(51) Int. Cl.
| | | |
|---|---|---|
| *A61K 31/427* | (2006.01) | |
| *A61K 31/404* | (2006.01) | |
| *A61K 31/416* | (2006.01) | |
| *A61K 31/42* | (2006.01) | |
| *A61K 31/4178* | (2006.01) | |
| *A61K 31/422* | (2006.01) | |
| *C07D 209/14* | (2006.01) | |
| *C07D 261/06* | (2006.01) | |
| *C07D 277/62* | (2006.01) | |
| *C07D 277/54* | (2006.01) | |
| *C07D 231/10* | (2006.01) | |
| *C07D 231/54* | (2006.01) | |

(52) U.S. Cl. ................... 514/367; 514/414; 514/425; 514/378; 514/397; 514/372; 548/469; 548/503; 548/247; 548/152; 548/159; 548/312.1; 548/335.5; 548/235; 548/361.1; 548/364.7

(58) Field of Classification Search ............... 514/414, 514/425, 378, 367, 397, 372; 548/469, 503, 548/247, 214, 152, 159, 321.1, 335.5, 235
See application file for complete search history.

(56) References Cited

U.S. PATENT DOCUMENTS

| | | | |
|---|---|---|---|
| 2,708,197 A | 5/1955 | Speeter | |
| 2,752,358 A | 6/1956 | Ehrhart et al. | |
| 2,984,670 A | 5/1961 | Szmuszkovics et al. | |
| 7,390,835 B2 * | 6/2008 | Shah et al. ................ | 514/579 |
| 2005/0222148 A1 | 10/2005 | Kim et al. | |
| 2006/0025467 A1 | 2/2006 | Greenhouse et al. | |

FOREIGN PATENT DOCUMENTS

| | | |
|---|---|---|
| DE | 849108 C1 | 7/1949 |
| EP | 0 179 546 A2 | 4/1986 |
| EP | 0 509 402 A1 | 10/1992 |
| EP | 0 534 343 A1 | 3/1993 |
| EP | 0 600 830 A1 | 6/1994 |
| EP | 0 506 532 B1 | 9/1994 |
| EP | 0 775 694 A2 | 5/1997 |
| EP | 0 780 389 A1 | 6/1997 |
| EP | 0 887 348 A1 | 12/1998 |
| FR | 2 814 073 A1 | 9/2000 |
| GB | 705652 | 9/1950 |
| GB | 992731 A | 9/1963 |
| JP | 03 14562 A | 1/1991 |
| WO | WO 94/12478 A1 | 6/1994 |
| WO | WO 97/10219 A1 | 3/1997 |
| WO | WO 97/44329 A1 | 11/1997 |
| WO | WO 97/46511 A1 | 12/1997 |
| WO | WO 98/43942 A1 | 10/1998 |
| WO | WO 99/16755 A1 | 4/1999 |
| WO | WO 99/21553 A1 | 5/1999 |
| WO | WO 99/21557 A1 | 5/1999 |
| WO | WO 00/02551 A2 | 1/2000 |
| WO | WO 00/02551 A3 | 1/2000 |
| WO | WO 00/02556 A1 | 1/2000 |
| WO | WO 01/32622 A1 | 5/2001 |
| WO | WO 02/069965 A1 | 9/2002 |
| WO | WO 03/035005 A2 | 5/2003 |
| WO | WO 03/035005 A3 | 5/2003 |
| WO | WO 03/053938 A1 | 7/2003 |
| WO | WO 03/057213 A2 | 7/2003 |
| WO | WO 03/057213 A3 | 7/2003 |
| WO | WO 03/066622 A1 | 8/2003 |
| WO | WO 2005/005439 A1 | 1/2005 |

OTHER PUBLICATIONS

Norepinephrine Transporter, Wikipedia.*
Ganellin, C.R., et. al., "Aminoalkylation of Metal Derivatives of Indole. Part III. Alkylation of Lithio-derivatives of N-Substituted Indoles with 1-Chloro-2-dimethyl-aminoethane," *J. Chem. Society* (1969) pp. 1537-1540.
Kraxner, J., et. al., "Azepino- and Diazepinoindoles: Synthesis and Dopamine Receptor Binding Profiles," *Archiv. der Pharmazie.* (2000) vol. 333 (9) pp. 287-292.

(Continued)

*Primary Examiner*—Rei-tsang Shiao
*Assistant Examiner*—Yong Chu
(74) *Attorney, Agent, or Firm*—Robert C. Hall

(57) ABSTRACT

The present invention provides compounds of the formula:

I

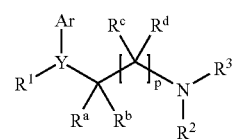

or pharmaceutically acceptable salts, solvates or prodrugs thereof, wherein p, Ar, $R^1$, $R^2$, $R^3$, $R^a$, $R^b$, $R^c$, $R^d$ and $R^e$ are defined herein. Also provided are pharmaceutical compositions, methods of using, and methods of preparing the compounds.

20 Claims, No Drawings

OTHER PUBLICATIONS

Lindner, E., "Über ein neues Antihistaminicum, das-1-Phenyl-1-Pyridyl-(2)-3-dimethylaminopropan und sein Salz mit der p-Aminosalicylsäure (A vil)", Naunyn-Schmiedbergs Archiv für Pharmakologie und Experimentelle Pathologie, (1950) vol. 211, pp. 328-344.

Schmidt, A. M. et. al., "Synthesis of Pharmacologically Relevant Indoles with Amine Side Chains via Tandem Hydroformylation/Fischer Indole Synthesis," *J. Organic Chemistry* (2005) vol. 70 (14) pp. 5528-5535.

* cited by examiner

3-AMINO-1-ARYLPROPYL INDOLES AND AZA-SUBSTITUTED INDOLES AND USES THEREOF

CROSS REFERENCE TO RELATED APPLICATIONS

This application is entitled to the benefit of provisional patent application Ser. No. 60/741,266 filed on Nov. 30, 2005, the disclosure of which is incorporated herein by reference.

FIELD OF THE INVENTION

This invention pertains to 3-amino-1-arylpropyl substituted heteroaryl compounds and methods for using the same. In particular, compounds of the present invention are useful for treatment of diseases associated with monoamine reuptake inhibitors.

BACKGROUND OF THE INVENTION

Monoamine deficiency has been long been linked to depressive, anxiolytic and other disorders (see, e.g.: Charney et al., *J. Clin. Psychiatry* (1998) 59, 1-14; Delgado et al., *J. Clin. Psychiatry* (2000) 67, 7-11; Resser et al., *Depress. Anxiety* (2000) 12 (Suppl 1) 2-19; and Hirschfeld et al., *J. Clin. Psychiatry* (2000) 61, 4-6. In particular, serotonin(5-hydroxytryptamine) and norepinephrine are recognized as key modulatory neurotransmitters that play an important role in mood regulation. Selective serotonin reuptake inhibitors (SSRIs) such as fluoxetine, sertraline, paroxetine, fluvoxamine, citalopram and escitalopram have provided treatments for depressive disorders (Masand et al., *Harv. Rev. Psychiatry* (1999) 7, 69-84). Noradrenaline or norepinephrine reuptake inhibitors such as reboxetine, atomoxetine, desipramine and nortryptyline have provided effective treatments for depressive, attention deficit and hyperactivity disorders (Scates et al., *Ann. Pharmacother.* (2000) 34, 1302-1312; Tatsumi et al., *Eur. J. Pharmacol.* (1997) 340, 249-258).

Enhancement of serotonin and norepinephrine neurotransmission is recognized to be synergistic in the pharmacotherapy of depressive and anxiolytic disorders, in comparison with enhancement of only serotonin or norepinephrine neurotransmission alone (Thase et al., *Br. J. Psychiatry* (2001) 178, 234, 241; Tran et al., *J. Clin. Psychopharmacology* (2003) 23, 78-86). Dual reuptake inhibitors of both serotonin and norepinephrine, such as duloxetine, milnacipran and venlafaxine are currently under development for treatment of depressive and anxiolytic disorders (Mallinckrodt et al., *J. Clin. Psychiatry* (2003) 5(1) 19-28; Bymaster et al., *Expert Opin. Investig. Drugs* (2003) 12(4) 531-543). Dual reuptake inhibitors of serotonin and norepinephrine also offer potential treatments for schizophrenia and other psychoses, dyskinesias, drug addition, cognitive disorders, Alzheimer's disease, obsessive-compulsive behaviour, attention deficit disorders, panic attacks, social phobias, eating disorders such as obesity, anorexia, bulimia and "binge-eating", stress, hyperglycaemia, hyperlipidemia, non-insulin-dependent diabetes, seizure disorders such as epilepsy, and treatment of conditions associated with neurological damage resulting from stroke, brain trauma, cerebral ischaemia, head injury and hemorrhage. Dual reuptake inhibitors of serotonin and norepinephrine also offer potential treatments for disorders and disease states of the urinary tract, and for pain and inflammation.

More recently, "triple reuptake" inhibitors ("broad-spectrum antidepressants" which inhibit the reuptake of norepinephrine, serotonin, and dopamine, have been recognized as useful for the treatment of depression and other CNS indications (Beer et al., *J. Clinical Pharmacology* (2004) 44:1360-1367; Skolnick et al., *Eur J Pharmacol.* (2003) February 14;461(2-3):99-104.

There is accordingly a need for compounds that are effective as serotonin reuptake inhibitors, norepinephrine reuptake inhibitors, dopamine reuptake inhibitors, and/or dual reuptake inhibitors of serotonin, norepinephrine and/or dopamine, or triple reuptake inhibitors of norepinephrine, serotonin, and dopamine, as well as methods of making and using such compounds in the treatment of depressive, anxiolytic, genitourinary, pain, and other disorders. The present invention satisfies these needs.

SUMMARY OF THE INVENTION

One aspect of the invention provides compounds of formula I:

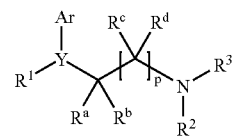

or a pharmaceutically acceptable salt thereof, wherein:

p is 1 or 2;

Y is N or $CR^e$;

Ar is:

(a) indolyl selected from indol-4-yl, indol-5-yl, indol-6-yl, and indol-7-yl, each optionally substituted;

(b) indazolyl selected from indazol-4-yl, indazol-5-yl, indazol-6-yl, and indazol-7-yl, each optionally substituted;

(c) pyrrolo[2,3-b]pyridyl selected from pyrrolo[2,3-b]pyrid-4-yl, pyrrolo[2,3-b]pyrid-5-yl, pyrrolo[2,3-b]pyrid-6-yl, and pyrrolo[2,3-b]pyrid-7-yl, each optionally substituted;

(d) benzimidazolyl selected from benzimidazol-4-yl, benzimidazol-5-yl, benzimidazol-6-yl, and benzimidazol-7-yl, each optionally substituted;

(e) benzofuranyl selected from benzofuran-4-yl, benzofuran-5-yl, benzofuran-6-yl, and benzofuran-7-yl, each optionally substituted;

(f) benzothiophenyl selected from benzothiophen-4-yl, benzothiophen-5-yl, benzothiophen-6-yl, and benzothiophen-7-yl, each optionally substituted;

(g) benzoxazolyl selected from benzoxazol-4-yl, benzoxazol-5-yl, benzoxazol-6-yl, and benzoxazol-7-yl, each optionally substituted;

(h) benzothiazolyl selected from benzothiazol-4-yl, benzothiazol-5-yl, benzothiazol-6-yl, and benzothiazol-7-yl, each optionally substituted;

(i) benzisoxazolyl selected from benzisoxazol-4-yl, benzisoxazol-5-yl, benzisoxazol-6-yl and benzisoxazol-7-yl;

(j) benzisothiazolyl selected from benzisothiazol-4-yl, benzisothiazol-5-yl, benzisothiazol-6-yl and benzisothiazol-7-yl;

(k) indolinyl selected from indolin-4-yl. indolin-5-yl, indolin-6-yl and indolin-7-yl; or (l) 1,3-dihydro-indol-2-onyl selected from 1,3-Dihydro-indol-2-on-4-yl, 1,3-Dihydro-indol-2-on-5-yl, 1,3-Dihydro-indol-2-on-6-yl and 1,3-Dihydro-indol-2-on-7-yl;

$R^1$ is:

(a) aryl selected from phenyl and naphthyl, each optionally substituted; or (b) heteroaryl selected from indolyl, indazolyl, pyridinyl, thienyl, furanyl, pyrimidinyl, pyridazinyl, pyrazinyl, oxazolyl, thiazolyl, isoxazolyl, isothiazolyl, imidazolyl, pyrazolyl, quinolinyl, isoquinolinyl, quinoxalinyl, benzothiazolyl, benzofuranyl, benzothiophenyl or benzoxazinyl, each optionally substituted;
(c) optionally substituted arylalkyl;
(d) optionally substituted heteroarylalkyl;
(e) cycloalkyl;
(f) cycloalkylmethyl; or
(g) branched alkyl;

$R^2$ and $R^3$ each independently is:
(a) hydrogen;
(b) alkyl;
(c) hydroxyalkyl;
(d) alkoxyalkyl;
(e) benzyl; or
(f) $R^2$ and $R^3$ together with the nitrogen to which they are attached may form an optionally substituted four to seven membered ring that optionally includes an additional heteroatom selected from N, O and S;

$R^a$ is:
hydrogen;
fluoro; or
alkyl;

$R^b$ is:
hydrogen;
alkyl;
hydroxy;
alkoxy;
fluoro; or
hydroxyalkyl;
or one of $R^2$ and $R^3$ together with one of $R^a$ and $R^b$ and the atoms to which are attached may form a five or six membered ring that optionally includes an additional heteroatom selected from O, N and S;

$R^c$ and $R^d$ each independently is:
hydrogen; or
alkyl;
or $R^c$ and $R^d$ together form =O, =S, or =NR$^f$, wherein $R^f$ is hydrogen, alkyl, or —OR$^g$, wherein $R^g$ is hydrogen or alkyl;
or on of $R^2$ and $R^3$ together with one of $R^c$ and $R^d$ together with the atoms to which they are attached may form a four to six membered ring that optionally includes an additional heteroatom selected from O, N and S; and $R^e$ is hydrogen or alkyl.

The invention also provides pharmaceutical compositions, methods of using, and methods of preparing the aforementioned compounds.

The methods comprise, in certain embodiments:
coupling a heteroaryl compound of the formula:

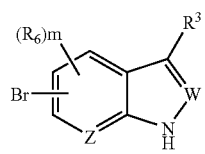

A with a vinyl compound of the formula:

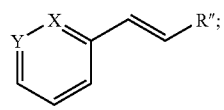

B in the presence of a coupling catalyst to provide a biaryl acrylate compound of the formula:

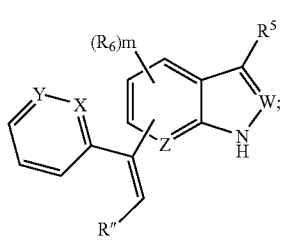

C wherein each of W, X, Y, and Z is independently CH or N, R" is —CN or —CO$_2$R$^a$ (where R$^a$ is alkyl), and m, R$^5$ and R$^6$ are as defined herein.

In certain embodiments, the biaryl acrylate compound C, where R" is CN, is then reduced to provide a compound of formula D:

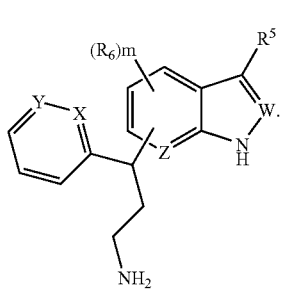

D

The compound of formula D may optionally be converted to N-alkyl or N,N-dialkyl compound of formula E:

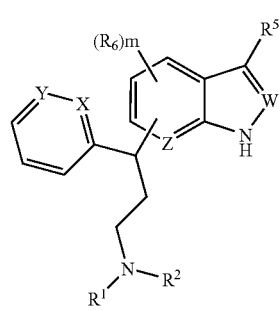

E wherein W, X, Y, Z, m, $R^1$, $R^2$, $R^5$ and $R^6$ are as defined herein.

In certain embodiments, the biaryl acrylate compound C, where R" is —CO$_2$R$^a$ (where R$^a$ is alkyl), is reacted with an amine compound of formula HNR$^1$R$^2$ to provide a compound of formula F:

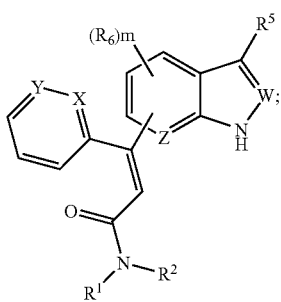

F wherein W, X, Y, Z, m, $R^1$, $R^2$ $R^5$ and $R^6$ are as defined herein.

In certain embodiments, the non-aromatic double bond of the biaryl acrylate compound C, where R'' is —$CO_2R^a$ (where $R^a$ is alkyl), is selectively reduced to provide a compound of formula G:

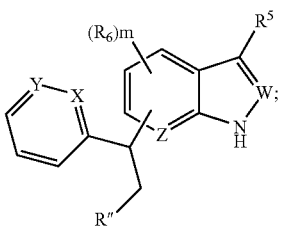

G wherein W, X, Y, Z, m, R'', $R^5$ and $R^6$ are as defined herein.

In some embodiments, the compound of formula G is then reacted with an amine compound of formula $HNR^1R^2$ to provide an amide compound of formula H:

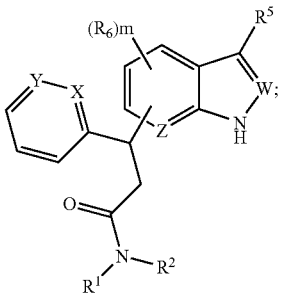

H wherein W, X, Y, Z, m, $R^1$, $R^2$, $R^5$ and $R^6$ are as defined herein.

Reduction of the carbonyl group of the amide compound of formula G then provides the compound of formula E.

In some other embodiments, the compound of formula G is reduced with a reducing agent and optionally oxidized to afford the aldehyde compound of formula I:

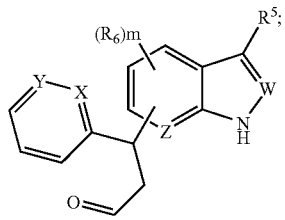

I wherein W, X, Y, Z, m, $R^5$ and $R^6$ are as defined herein;

Reductive amination of compound I with an amine compound of formula $HNR^1R^2$ in the presence of a reducing agent then affords the compound of formula E in accordance with the present invention. Suitable reducing agents useful in reductive amination reaction are well known to one skilled in the art and include, but not limited to, sodium cyanoborohydride.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" means isopropyl, isobutyl, tert-butyl, "Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, tert-butoxy and the like.

"Alkoxyalkyl" means a moiety of the formula —R'—R'', where R' is alkylene and R'' is alkoxy as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R'', where R' is oxo and R'' is alkyl as defined herein.

"Alkylsulfonyl" means a moiety of the formula —R'—R'', where R' is —$SO_2$— and R'' is alkyl as defined herein.

"Alkylsulfonylalkyl" means a moiety of the formula $R^a$—$SO_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Alkylsulfonyloxy" means a moiety of the formula $R^a$—$SO_2$—O—, where $R^a$ is alkyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Aryloxy" means a moiety of the formula —OR, wherein R is an aryl moiety as defined herein.

"Arylalkyl" and "Aralkyl", which may be used interchangeably, mean a radical—$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Aralkoxy" means a moiety of the formula —OR, wherein R is an aralkyl moiety as defined herein.

"Azaindole" means a group of the formula

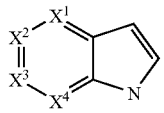

wherein one or two of any of $X^1$, $X^2$, $X^3$ and $X^4$ is N (aza), and the others are carbon. "AzaIndoles" may be optionally substituted, as defined herein for heteroaryls, at position 1, 2 and 3, and at any of positions 4- through seven that are not nitrogen. "Azaindole" thus includes: "pyrrolopyrimidines" of the above formula wherein $X^2$ and $X^4$ are N; "pyrrolopyrimidines" of the above formula wherein $X^1$ and $X^3$ are N; "pyrrolopyrazines" of the above formula wherein $X^1$ and $X^4$ are N; "pyrrolopyridines" of the above formula wherein $X^1$ is N; "pyrrolopyridines" of the above formula wherein $X^2$ is N; "pyrrolopyridines" of the above formula wherein $X^3$ is N; and "pyrrolopyridines" of the above formula wherein $X^4$ is N.

"Cyanoalkyl" means a moiety of the formula —R'—R', where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkyloxy" and "cycloalkoxy", which may be used interchangeably, mean a group of the formula —OR wherein R is cycloalkyl as defined herein. Exemplary cycloalkyloxy include cyclopropyloxy, cyclobutyloxy, cyclopentyloxy, cyclohexyloxy and the like.

"Cycloalkylalkyl" means a moiety of the formula —R'—R', where R' is alkylene and R" is cycloalkyl as defined herein.

"Cycloalkylalkyloxy" and "cycloalkylalkoxy", which may be used interchangeably, mean a group of the formula —OR wherein R is cycloalkylalkyl as defined herein. Exemplary cycloalkyloxy include cyclopropylmethoxy, cyclobutylmethoxy, cyclopentylmethoxy, cyclohexylmethoxy and the like.

"Heteroalkyl" means an alkyl radical as defined herein, including a branched $C_4$-$C_7$-alkyl, wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic, bicyclic or tricyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylalkyl" and "heteroaralkyl", which may be used interchangeably, mean a radical—$R^a R^b$ where $R^a$ is an alkylene group and $R^b$ is a heteroaryl group as defined herein The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. Examples of haloalkoxy moieties include, but are not limited to, trifluoromethoxy, difluoromethoxy, 2,2,2-trifluoroethoxy, and the like.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Optionally substituted", when used in association with "aryl", phenyl", "heteroaryl" (including indolyl such as indol-1-yl, indol-2-yl and indol-3-yl, 2,3-dihydroindolyl such as 2,3-dihydroindol-1-yl, 2,3-dihydroindol-2-yl and 2,3-dihydroindol-3-yl, indazolyl such as indazol-1-yl, indazol-2-yl and indazol-3-yl, benzimidazolyl such as benzimidazol-1-yl and benzimidazol-2-yl, benzofuranyl such as benzofuran-2-yl and benzofuran-3-yl, benzothiophenyl such as benzothiophen-2-yl and benzothiophen-3-yl, benzoxazol-2-yl, benzothiazol-2-yl, thienyl, furanyl, pyridinyl, pyrimidinyl, pyridazinyl, pyrazinyl, oxazolyl, thiazolyl, isoxazolyl, isothiazolyl, imidazolyl, pyrazolyl and quinolinyl) " or "heterocyclyl", means an aryl, phenyl, heteroaryl or heterocyclyl which is optionally substituted independently with one to four substituents, preferably one or two substituents selected from alkyl, cycloalkyl, alkoxy, halo, haloalkyl, haloalkoxy, cyano, nitro, heteroalkyl, amino, acylamino, mono-alkylamino, di-alkylamino, hydroxyalkyl, alkoxyalkyl, benzyloxy, cycloalkylalkyl, cycloalkoxy, cycloalkylalkoxy, alkylsulfonyloxy, optionally substituted thienyl, optionally substituted pyrazolyl, optionally substituted pyridinyl, morpholinocarbonyl, $-(CH_2)_q-S(O)_rR^f$; $-(CH_2)_q-NR^gR^h$; $-(CH_2)_q-C(=O)-NR^gR^h$; $-(CH_2)_q-C(=O)-C(=O)-NR^gR^h$; $-(CH_2)_q-SO_2-NR^gR^h$; $-(CH_2)_q-N(R^f)-C(=O)R^i$; $-(CH_2)_q-C(=O)$ $R^i$; or $-(CH_2)_q-N(R^f)-SO_2-R^g$; where q is 0 or 1, r is from 0 to 2, $R^f$, $R^g$, and $R^h$ each independently is hydrogen or alkyl, and each $R^i$ is independently hydrogen, alkyl, hydroxy, or alkoxy.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p1-92, Elsevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "aminoprotecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disease states" associated with serotonin and norepinephrine neurotransmission include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, haemorrhage, and disorders and disease states of the urinary tract.

"Depression" as used herein includes, but is not limited to, major depression, long-term depression, dysthymia, mental states of depressed mood characterised by feelings of sadness, despair, discouragement, "blues", melancholy, feelings of low self esteem, guilt and self reproach, withdrawal from interpersonal contact, and somatic symptoms such as eating and sleep disturbances.

"Anxiety" as used herein includes, but is not limited to, unpleasant or undesirable emotional states associated with psychophysiological responses to anticipation of unreal, imagined or exaggerated danger or harm, and physical concomitants such as increased heart rate, altered respiration rate, sweating, trembling, weakness and fatigue, feelings of impending danger, powerlessness, apprehension and tension.

"Disorders of the urinary tract" or "uropathy" used interchangeably with "symptoms of the urinary tract" means the pathologic changes in the urinary tract. Examples of urinary tract disorders include, but are not limited to, stress incontinence, urge incontence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, 28$^{th}$ Edition, W. B. Saunders Company, Philadelphia, Pa.). The goal of treatment of pain is to reduce the degree of severity of pain perceived by a treatment subject.

"Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
 (i) preventing the disease state, i.e. causing the clinical symptoms of the disease state not to develop in a subject that may be exposed to or predisposed to the disease state, but does not yet experience or display symptoms of the disease state.
 (ii) inhibiting the disease state, i.e., arresting the development of the disease state or its clinical symptoms, or
 (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. For convenience, the IUPAC numbering of the positions of representative indole and related compounds described herein is shown by the formula:

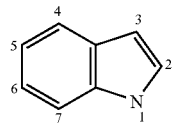

Whenever a chiral carbon is present in a chemical structure, it is intended that all stereoisomers associated with that chiral carbon are encompassed by the structure.

All patents and publications identified herein are incorporated herein by reference in their entirety.

Compounds of the Invention

The invention provides compounds of formula I:

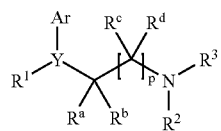

or a pharmaceutically acceptable salt thereof,
wherein:
 p is 1 or 2;
 Y is N or $CR^e$;
 Ar is:
  (a) indolyl selected from indol-4-yl, indol-5-yl, indol-6-yl, and indol-7-yl, each optionally substituted;
  (b) indazolyl selected from indazol-4-yl, indazol-5-yl, indazol-6-yl, and indazol-7-yl, each optionally substituted;
  (c) pyrrolo[2,3-b]pyridyl selected from pyrrolo[2,3-b]pyrid-4-yl, pyrrolo[2,3-b]pyrid-5-yl, pyrrolo[2,3-b]pyrid-6-yl, and pyrrolo[2,3-b]pyrid-7-yl, each optionally substituted;
  (d) benzimidazolyl selected from benzimidazol-4-yl, benzimidazol-5-yl, benzimidazol-6-yl, and benzimidazol-7-yl, each optionally substituted;
  (e) benzofuranyl selected from benzofuran-4-yl, benzofuran-5-yl, benzofuran-6-yl, and benzofuran-7-yl, each optionally substituted;
  (f) benzothiophenyl selected from benzothiophen-4-yl, benzothiophen-5-yl, benzothiophen-6-yl, and benzothiophen-7-yl, each optionally substituted;
  (g) benzoxazolyl selected from benzoxazol-4-yl, benzoxazol-5-yl, benzoxazol-6-yl, and benzoxazol-7-yl, each optionally substituted; or
  (h) benzothiazolyl selected from benzothiazol-4-yl, benzothiazol-5-yl, benzothiazol-6-yl, and benzothiazol-7-yl, each optionally substituted;
  (i) benzisoxazolyl selected from benzisoxazol-4-yl, benzisoxazol-5-yl, benzisoxazol-6-yl and benzisoxazol-7-yl;
  (j) benzisothiazolyl selected from benzisothiazol-4-yl, benzisothiazol-5-yl, benzisothiazol-6-yl and benzisothiazol-7-yl;
  (k) indolinyl selected from indolin-4-yl. indolin-5-yl, indolin-6-yl and indolin-7-yl; or
  (l) 1,3-dihydro-indol-2-onyl selected from 1,3-Dihydro-indol-2-on-4-yl, 1,3-Dihydro-indol-2-on-5-yl, 1,3-Dihydro-indol-2-on-6-yl and 1,3-Dihydro-indol-2-on-7-yl;
 $R^1$ is:
  (a) aryl selected from phenyl and naphthyl, each optionally substituted; or
  (b) heteroaryl selected from indolyl, indazolyl, pyridinyl, thienyl, furanyl, pyrimidinyl, pyridazinyl, pyrazinyl, oxazolyl, thiazolyl, isoxazolyl, isothiazolyl, imidazolyl, pyrazolyl, quinolinyl, isoquinolinyl, quinoxalinyl, benzothiazolyl, benzofuranyl, benzothiophenyl or benzoxazinyl, each optionally substituted;
  (c) optionally substituted arylalkyl;
  (d) optionally substituted heteroarylalkyl;
  (e) cycloalkyl;
  (f) cycloalkylmethyl; or
  (g) branched alkyl;
 $R^2$ and $R^3$ each independently is:
  (a) hydrogen;
  (b) alkyl;
  (c) hydroxyalkyl;
  (d) alkoxyalkyl;
  (e) benzyl; or
  (f) $R^2$ and $R^3$ together with the nitrogen to which they are attached may form an optionally substituted four to seven membered ring that optionally includes an additional heteroatom selected from N, O and S;
 $R^a$ is:
  hydrogen;
  fluoro; or
  alkyl;
 $R^b$ is:
  hydrogen;
  alkyl;
  hydroxy;
  alkoxy;
  fluoro; or
  hydroxyalkyl;
  or one of $R^2$ and $R^3$ together with one of $R^a$ and $R^b$ and the atoms to which they are attached may form a five or six membered ring that optionally includes an additional heteroatom selected from O, N and S;
 $R^c$ and $R^d$ each independently is:
  hydrogen; or
  alkyl;
  or $R^c$ and $R^d$ together form =O, =S, or =$NR^f$, wherein $R^f$ is hydrogen, alkyl, or —$OR^g$, wherein $R^g$ is hydrogen or alkyl;

or on of $R^2$ and $R^3$ together with one of $R^c$ and $R^d$ together with the atoms to which they are attached may form a four to six membered ring that optionally includes an additional heteroatom selected from O, N and S; and $R^e$ is hydrogen or alkyl.

It is to be understood that the scope of this invention encompasses not only the various isomers which may exist but also the various mixture of isomers which may be formed. Furthermore, the scope of the present invention also encompasses solvates and salts of compounds of formula I.

In certain embodiments of formula I, p is 1.

In many embodiments of formula I, $R^a$ are $R^b$ are hydrogen.

In certain embodiments of formula I, $R^c$ and $R^d$ together form =O.

In certain embodiments of formula I, $R^c$ and $R^d$ are hydrogen.

In certain embodiments of formula I, Y is $CR^e$.

In certain embodiments of formula I, Y is N.

In many embodiments of formula I, $R^e$ is hydrogen.

In certain embodiments of formula I, $R^1$ is optionally substituted aryl, preferably optionally substituted phenyl or optionally substituted naphthylenyl.

In certain embodiments of formula I, $R^1$ is optionally substituted aryl, $R^1$ is optionally substituted phenyl.

In certain embodiments of formula I, $R^1$ is optionally substituted aryl, $R^1$ is optionally substituted naphthalenyl.

In certain embodiments of formula I, $R^1$ is optionally substituted aryl, $R^1$ is optionally substituted naphthalen-1-yl.

In certain embodiments of formula I, $R^1$ s optionally substituted aryl, $R^1$ is optionally substituted naphthalen-2-yl.

In certain embodiments of formula I, $R^1$ is optionally substituted heteroaryl. Such heteroaryl may be selected from indolyl, pyridinyl, thienyl, furanyl, pyrimidinyl, pyridazinyl, pyrazinyl, oxazolyl, thiazolyl, isoxazolyl, isothiazolyl, imidazolyl, pyrazolyl, quinolinyl, isoquinolinyl, quinoxalinyl, benzothiazolyl, benzofuranyl, benzothiophenyl or benzoxazinyl, each optionally substituted.

In certain embodiments of formula I, $R^1$ is optionally substituted indolyl.

In certain embodiments of formula I, $R^1$ is indol-2-yl, indol-3-yl, indol-4-yl, indol-5-yl, indol-6-yl, or indol-7-yl, each optionally substituted.

In certain embodiments of formula I, $R^1$ is indol-5-yl or indol-6-yl, each optionally substituted.

In certain embodiments of formula I, $R^1$ optionally substituted is indol-2-yl.

In certain embodiments of formula I, $R^1$ optionally substituted is indol-3-yl.

In certain embodiments of formula I, $R^1$ optionally substituted is indol-4-yl.

In certain embodiments of formula I, $R^1$ optionally substituted is indol-5-yl.

In certain embodiments of formula I, $R^1$ optionally substituted is indol-6-yl.

In certain embodiments of formula I, $R^1$ optionally substituted is indol-7-yl.

In certain embodiments of formula I, $R^1$ is optionally substituted quinolinyl.

In certain embodiments of formula I, $R^1$ is quinolin-2-yl, quinolin-3-yl, quinolin-4-yl, quinolin-5-yl, quinolin-6-yl, quinolin-7-yl or quinolin-8-yl, each optionally substituted.

In certain embodiments of formula I, $R^1$ is optionally substituted quinolin-6-yl.

In certain embodiments of formula I, $R^1$ is optionally substituted pyridinyl.

In certain embodiments of formula I, $R^1$ is pyridin-2-yl, pyridin-3-yl or pyridin-4-yl, each optionally substituted.

In certain embodiments of formula I, $R^1$ is optionally substituted pyridin-2-yl.

In certain embodiments of formula I, $R^1$ is optionally substituted pyridin-3-yl.

In certain embodiments of formula I, $R^1$ is optionally substituted pyridin-4-yl.

In certain embodiments of formula I, $R^1$ is optionally substituted quinoxalinyl.

In certain embodiments of formula I, $R^1$ is quinoxalin-2-yl, quinoxalin-3-yl, quinoxalin-5-yl, quinoxalin-6-yl, quinoxalin-7-yl or quinoxalin-8-yl, each optionally substituted.

In certain embodiments of formula I, $R^1$ is optionally substituted quinoxalin-6-yl.

In certain embodiments of formula I, $R^1$ is optionally substituted benzothiophenyl.

In certain embodiments of formula I, $R^1$ is optionally substituted benzothiophen-5-yl.

In certain embodiments of formula I, $R^1$ is optionally substituted benzoxazinyl. In such embodiments the benzoxazinyl may be 4-methyl-3,4-dihydro-2H-benzo[1,4]oxazin-7-yl.

In certain embodiments of formula I, $R^1$ is optionally substituted benzothiazolyl.

In certain embodiments of formula I, $R^1$ is optionally substituted benzothiazol-2-yl.

In certain embodiments of formula I, $R^1$ is optionally substituted benzothiazol-5-yl.

In certain embodiments of formula I, $R^1$ is optionally substituted benzothiazol-6-yl.

In certain embodiments of formula I, $R^1$ is optionally substituted thiazolyl.

In certain embodiments of formula I, $R^1$ is optionally substituted thiazol-2-yl.

In certain embodiments of formula I, $R^1$ is optionally substituted thiazol-4-yl.

In certain embodiments of formula I, $R^1$ is optionally substituted thiazol5-yl.

In certain embodiments of formula I, $R^1$ is optionally substituted benzoxazolyl.

In certain embodiments of formula I, $R^1$ is phenyl, pyridin-3-yl, 3-methoxyphenyl, pyridin-2-yl, 2-methoxyphenyl, 4-methoxyphenyl, 3-chlorophenyl, 4-chlorophenyl, or indol-3-yl.

In certain embodiments of formula I, Ar is indol-4-yl, indol-5-yl, indol-6-yl or indol-7-yl, each optionally substituted. In such embodiments Ar is preferably indol-5-yl or indol-6-yl.

In certain embodiments of formula I, Ar is indol-5-yl.

In certain embodiments of formula I, Ar is indazol-4-yl, indazol-5-yl, indazol-6-yl or indazol-7-yl, each optionally substituted. In such embodiments Ar is preferably indazol-5-yl or indazol-6-yl.

In certain embodiments of formula I, Ar is indazol-5-yl.

In certain embodiments of formula I, Ar is benzimidazol-4-yl, benzimidazol-5-yl, benzimidazol-6-yl or benzimidazol-7-yl, each optionally substituted. In such embodiments Ar is preferably benzimidazol-5-yl or benzimidazol-6-yl.

In certain embodiments of formula I, Ar is benzoxazol-4-yl, benzoxazol-5-yl, benzoxazol-6-yl or benzoxazol-7-yl, each optionally substituted. In such embodiments Ar is preferably benzoxazol-5-yl or benzoxazol-6-yl.

In certain embodiments of formula I, Ar is benzofuran-4-yl, benzofuran-5-yl, benzofuran-6-yl or benzofuran-7-yl, each optionally substituted. In such embodiments Ar is preferably benzofuran-5-yl or benzofuran-6-yl, and more preferably benzofuran-5-yl.

In certain embodiments of formula I, Ar is benzothien-4-yl, benzothien-5-yl, benzothien-6-yl or benzothien-7-yl, each optionally substituted. In such embodiments Ar is preferably benzothien-5-yl or benzothien-6-yl, and more preferably benzothiophen-5-yl.

In certain embodiments of formula I, Ar is benzothiazol-4-yl, benzothiazol-5-yl, benzothiazol-6-yl or benzothiazol-7-yl, each optionally substituted. In such embodiments Ar is preferably benzothiazol-5-yl or benzothiazol-6-yl.

In certain embodiments of formula I, Ar is benzisoxazolyl selected from benzisoxazol-4-yl, benzisoxazol-5-yl, benzisoxazol-6-yl and benzisoxazol-7-yl. In such embodiments Ar is preferably benzisoxazol-5-yl or benzisoxazol-6-yl.

In certain embodiments of formula I, Ar is benzisothiazolyl selected from benzisothiazol-4-yl, benzisothiazol-5-yl, benzisothiazol-6-yl and benzisothiazol-7-yl. In such embodiments Ar is preferably benzisothiazol-5-yl or benzisothiazol-6-yl.

In certain embodiments of formula I, Ar is indolinyl selected from indolin-4-yl, indolin-5-yl, indolin-6-yl and indolin-7-yl. In such embodiments Ar is preferably indolin-5-yl or indolin-6-yl.

In certain embodiments of formula I, Ar is 1,3-dihydro-indol-2-onyl selected from 1,3-Dihydro-indol-2-on-4-yl, 1,3-Dihydro-indol-2-on-5-yl, 1,3-Dihydro-indol-2-on-6-yl and 1,3-Dihydro-indol-2-on-7-yl. In such embodiments Ar is preferably 1,3-Dihydro-indol-2-on-5-yl or 1,3-Dihydro-indol-2-on-6-yl.

In certain embodiments of formula I, Ar is indolyl, indazolyl or pyrrolo[2,3-b]pyridyl, each optionally substituted. In such embodiments Ar is preferably indol-4-yl, indol-5-yl, indol-6-yl, indol-7-yl, indazol-4-yl, indazol-5-yl, indazol-6-yl, indazol-7-yl, pyrrolo[2,3-b]pyrid-4-yl, pyrrolo[2,3-b]pyrid-5-yl, pyrrolo[2,3-b]pyrid-6-yl or pyrrolo[2,3-b]pyrid-7-yl each optionally substituted. Where Ar is optionally substituted indolyl, Ar is more preferably optionally substituted indol-5-yl or optionally substituted indol-6-yl. Where Ar is optionally substituted indazolyl, Ar is more preferably optionally substituted indazol-5-yl or optionally substituted indazol-6-yl. Where Ar is optionally substituted pyrrolo[2,3-b]pyridyl, Ar is more preferably optionally substituted pyrrolo[2,3-b]pyrid-5-yl or optionally substituted pyrrolo[2,3-b]pyrid-6-yl.

In certain embodiments, Ar is indol-4-yl, indoly-5-yl, indol-6-yl, indol-7-yl, 5-methoxyindol-6-yl, 3-cyano indol-6-yl, 5-methoxyindol-4-yl, 7-methoxy-indol-6-yl, 2-methylindol-5-yl, 1-methylindol-6-yl, 3-cyano indol-5-yl, 6-methoxyindol-4-yl, 4-methoxyindol-6-yl, 4-methoxyindol-7-yl, 3-cyano indol-4-yl, 7-fluoroindol-5-yl, 1H-indazol-4-yl, 1-methylsulfonylindol-5-yl, 1H-indazol-6-yl, 1H-indazol-5-yl, 3-methylindol-5-yl, 3-methylsulfonylindol-5-yl, 7-chloro-indol-5-yl, 3-carbamoylindol-6-yl, 7-methoxyindol-4-yl, 3-cyano-7-fluoroindol-5-yl, 3-methoxy-1H-indazol-5-yl, 1H-indazol-7-yl, 7-chloro-3-cyanoindol-5-yl, 3-methoxy-1H-indazol-4-yl, 1H-indazol-7-yl, 3-chloro-1H-indazol-5-yl, 3-methyl-1H-indazol-5-yl, 3-chloro-1H-indazol-5-yl, pyrrolo[2,3-b]pyrid-5-yl, 3-methoxy-1H-indazol-6-yl, 7-methoxyindoly-5-yl, 2-carbamoylindol-5-yl, 3-cyano-6-methoxyindol-4-yl, 5-methoxyindol-7-yl, 4-methoxyindol-6-yl, or 7-methoxy-1H-indazol-4-yl.

In many embodiments of formula I, one of $R^2$ and $R^3$ is hydrogen and the other is alkyl, preferably methyl.

In certain embodiments of formula I: p is 1; Y is $CR^e$; $R^a$, $R^b$, $R^c$, $R^d$ and $R^e$ are hydrogen; Ar is indolyl optionally substituted with one, two, three or four substituents each independently selected from alkyl, alkoxy, halo, haloalkyl, haloalkoxy, cyano, alkylsulfonyloxy, $-(CH_2)_q-S(O)_rR^f$; $-(CH_2)_q-NR^gR^h$; or $-(CH_2)_q-C(=O)-NR^gR^h$; where q is 0 or 1, r is from 0 to 2, and each of $R^f$, $R^g$, and $R^h$ is independently hydrogen or alkyl; $R^1$ is phenyl, pyridinyl, or indolyl each of which is optionally substituted with one, two, three or four substituents each of which is independently selected from alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be indol-4-yl, indol-5-yl, indol-6-yl or indol-7-yl. In such embodiments, Ar is preferably indol-5-yl or indol-6-yl.

In certain embodiments of formula I: p is 1; Y is $CR^e$; $R^a$, $R^b$, $R^c$, $R^d$ and $R^e$ are hydrogen; Ar is indazolyl optionally substituted with one, two, three or four substituents each independently selected from alkyl, alkoxy, halo, haloalkyl, haloalkoxy, cyano, alkylsulfonyloxy, $-(CH_2)_q-S(O)_rR^f$; $-(CH_2)_q-NR^gR^h$; or $-(CH_2)_q-C(=O)-NR^gR^h$; where q is 0 or 1, r is from 0 to 2, and each of $R^f$, $R^g$, and $R^h$ is independently hydrogen or alkyl; $R^1$ is phenyl, pyridinyl, or indolyl each of which is optionally substituted with one, two, three or four substituents each of which is independently selected from alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be indazol-4-yl, indazol-5-yl, indazol-6-yl or indazol-7-yl. In such embodiments Ar is preferably indazol-5-yl or indazol-6-yl.

In certain embodiments of formula I: p is 1; Y is $CR^e$; $R^a$, $R^b$, $R^c$, $R^d$ and $R^e$ are hydrogen; Ar is pyrrolo[2,3-b]pyridyl optionally substituted with one, two, three or four substituents each independently selected from alkyl, alkoxy, halo, haloalkyl, haloalkoxy, cyano, alkylsulfonyloxy, $-(CH_2)_q-S(O)_rR^f$; $-(CH_2)_q-NR^gR^h$; or $-(CH_2)_q-C(=O)-NR^gR^h$; where q is 0 or 1, r is from 0 to 2, and each of $R^f$, $R^g$, and $R^h$ is independently hydrogen or alkyl; $R^1$ is phenyl, pyridinyl, or indolyl each of which is optionally substituted with one, two, three or four substituents each of which is independently selected from alkyl, alkoxy, cyano, halo, haloalkyl, haloalkoxy, alkoxyalkyl or hydroxyalkyl; and one of $R^2$ and $R^3$ is hydrogen while the other is alkyl, preferably methyl. In such embodiments Ar may be pyrrolo[2,3-b]pyrid-4-yl, pyrrolo[2,3-b]pyrid-5-yl, pyrrolo[2,3-b]pyrid-6-yl or pyrrolo[2,3-b]pyrid-7-yl. In such embodiments Ar is preferably pyrrolo[2,3-b]pyrid-5-yl or pyrrolo[2,3-b]pyrid-6-yl.

In certain embodiments of formula I: p is 1; Y is $CR^e$; $R^a$, $R^b$, $R^c$, $R^d$ and $R^e$ are hydrogen; Ar is indol-5-yl or indol-6-yl optionally substituted with one or two substituents each independently selected from alkyl, alkoxy, halo, haloalkyl, haloalkoxy, cyano, alkylsulfonyloxy, $-(CH_2)_q-S(O)_rR^f$; $-(CH_2)_q-NR^gR^h$; or $-(CH_2)_q-C(=O)NR^gR^h$; where q is 0 or 1, r is from 0 to 2, and each of $R^f$, $R^g$, and $R^h$ is independently hydrogen or alkyl; $R^1$ is phenyl optionally substituted once or twice with substituents independently selected from alkyl, alkoxy, cyano, halo, haloalkyl, and haloalkoxy, alkoxyalkyl or hydroxyalkyl; and one of $R^2$ and $R^3$ is hydrogen while the other is alkyl, preferably methyl.

In certain embodiments of formula I: p is 1; Y is $CR^e$; $R^a$, $R^b$, $R^c$, $R^d$ and $R^e$ are hydrogen; Ar is indazol-5-yl or indazol-6-yl optionally substituted with one or two substituents each independently selected from alkyl, alkoxy, halo, haloalkyl, haloalkoxy, cyano, alkylsulfonyloxy, $-(CH_2)_q-S(O)_rR^f$; $-(CH_2)_q-NR^gR^h$; or $(CH_2)_q-C(=O)-NR^gR^h$; where q is 0 or 1, r is from 0 to 2, and each of $R^f$, $R^g$, and $R^h$ is independently hydrogen or alkyl; $R^1$ is phenyl optionally substituted once or twice with substituents independently selected from alkyl, alkoxy, cyano, halo, haloalkyl, and haloalkoxy, alkoxyalkyl or hydroxyalkyl; and one of $R^2$ and $R^3$ is hydrogen while the other is alkyl, preferably methyl.

In certain embodiments of formula I where p is 1 and $R^a$, $R^b$, $R^c$, $R^d$ and $R^e$ are hydrogen, the subject compounds may be represented by formula II:

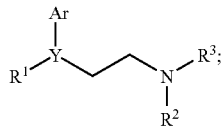

wherein:
$R^2$ and $R^3$ each independently is hydrogen or alkyl; and Y, Ar and $R^1$ are as defined herein.

In certain embodiments of formula II, Y is CH.

In certain embodiments of formula II, one of $R^2$ and $R^3$ is hydrogen and the other is alkyl, preferably methyl.

In certain embodiments of formula II, $R^1$ is optionally substituted aryl, preferably optionally substituted phenyl or optionally substituted naphthyl.

In certain embodiments of formula II, $R^1$ is optionally substituted aryl, $R^1$ is optionally substituted phenyl.

In certain embodiments of formula II, $R^1$ is optionally substituted aryl, $R^1$ is optionally substituted naphthalenyl.

In certain embodiments of formula II, $R^1$ is optionally substituted aryl, $R^1$ is optionally substituted naphthalen-1-yl.

In certain embodiments of formula II, $R^1$ is optionally substituted aryl, $R^1$ is optionally substituted naphthalen-2-yl.

In certain embodiments of formula II, $R^1$ is optionally substituted heteroaryl. Such heteroaryl may be selected from indolyl, pyridinyl, thienyl, furanyl, pyrimidinyl, pyridazinyl, pyrazinyl, oxazolyl, thiazolyl, isoxazolyl, isothiazolyl, imidazolyl, pyrazolyl, quinolinyl, isoquinolinyl, quinoxalinyl, benzothiazolyl, benzofuranyl, benzothiophenyl or benzoxazinyl, each optionally substituted.

In certain embodiments of formula II, $R^1$ is optionally substituted indolyl.

In certain embodiments of formula II, $R^1$ is indol-2-yl, indol-3-yl, indol-4-yl, indol-5-yl, indol-6-yl, or indol-7-yl, each optionally substituted.

In certain embodiments of formula II, $R^1$ is indol-5-yl or indol-6-yl, each optionally substituted.

In certain embodiments of formula II, $R^1$ optionally substituted is indol-2-yl.

In certain embodiments of formula II, $R^1$ optionally substituted is indol-3-yl.

In certain embodiments of formula II, $R^1$ optionally substituted is indol-4-yl.

In certain embodiments of formula II, $R^1$ optionally substituted is indol-5-yl.

In certain embodiments of formula II, $R^1$ optionally substituted is indol-6-yl.

In certain embodiments of formula II, $R^1$ optionally substituted is indol-7-yl.

In certain embodiments of formula II, $R^1$ is optionally substituted quinolinyl.

In certain embodiments of formula II, $R^1$ is quinolin-2-yl, quinolin-3-yl, quinolin-4-yl, quinolin-5-yl, quinolin-6-yl, quinolin-7-yl or quinolin-8-yl, each optionally substituted.

In certain embodiments of formula II, $R^1$ is optionally substituted quinolin-6-yl.

In certain embodiments of formula II, $R^1$ is optionally substituted pyridinyl.

In certain embodiments of formula II, $R^1$ is pyridin-2-yl, pyridin-3-yl or pyridin-4-yl, each optionally substituted.

In certain embodiments of formula II, $R^1$ is optionally substituted pyridin-2-yl.

In certain embodiments of formula II, $R^1$ is optionally substituted pyridin-3-yl.

In certain embodiments of formula II, $R^1$ is optionally substituted pyridin-4-yl.

In certain embodiments of formula II, $R^1$ is optionally substituted quinoxalinyl.

In certain embodiments of formula II, $R^1$ is quinoxalin-2-yl, quinoxalin-3-yl, quinoxalin-5-yl, quinoxalin-6-yl, quinoxalin-7-yl or quinoxalin-8-yl, each optionally substituted.

In certain embodiments of formula II, $R^1$ is optionally substituted quinoxalin-6-yl.

In certain embodiments of formula II, $R^1$ is optionally substituted benzothiophenyl.

In certain embodiments of formula II, $R^1$ is optionally substituted benzothiophen-5-yl.

In certain embodiments of formula II, $R^1$ is optionally substituted benzoxazinyl. In such embodiments the benzoxazinyl may be 4-methyl-3,4-dihydro-2H-benzo[1,4]oxazin-7-yl.

In certain embodiments of formula II, $R^1$ is optionally substituted benzothiazolyl.

In certain embodiments of formula II, $R^1$ is optionally substituted benzothiazol-2-yl.

In certain embodiments of formula II, $R^1$ is optionally substituted benzothiazol-5-yl.

In certain embodiments of formula II, $R^1$ is optionally substituted benzothiazol-6-yl.

In certain embodiments of formula II, $R^1$ is optionally substituted thiazolyl.

In certain embodiments of formula II, $R^1$ is optionally substituted thiazol-2-yl.

In certain embodiments of formula II, $R^1$ is optionally substituted thiazol-4-yl.

In certain embodiments of formula II, $R^1$ is optionally substituted thiazol5-yl.

In certain embodiments of formula I, $R^1$ is optionally substituted benzoxazolyl.

In certain embodiments of formula II, $R^1$ is phenyl, pyridin-3-yl, 3-methoxyphenyl, pyridin-2-yl, 2-methoxyphenyl, 4-methoxyphenyl, 3-chlorophenyl, 4-chlorophenyl, or indol-3-yl.

In certain embodiments of formula II, Ar is indol-4-yl, indol-5-yl, indol-6-yl or indol-7-yl, each optionally substituted. In such embodiments Ar is preferably indol-5-yl or indol-6-yl.

In certain embodiments of formula II, Ar is indol-5-yl.

In certain embodiments of formula II, Ar is indazol-4-yl, indazol-5-yl, indazol-6-yl or indazol-7-yl, each optionally substituted. In such embodiments Ar is preferably indazol-5-yl or indazol-6-yl.

In certain embodiments of formula II, Ar is indazol-5-yl.

In certain embodiments of formula II, Ar is benzimidazol-4-yl, benzimidazol-5-yl, benzimidazol-6-yl or benzimidazol-7-yl, each optionally substituted. In such embodiments Ar is preferably benzimidazol-5-yl or benzimidazol-6-yl.

In certain embodiments of formula II, Ar is benzoxazol-4-yl, benzoxazol-5-yl, benzoxazol-6-yl or benzoxazol-7-yl, each optionally substituted. In such embodiments Ar is preferably benzoxazol-5-yl or benzoxazol-6-yl.

In certain embodiments of formula II, Ar is benzofuran-4-yl, benzofuran-5-yl, benzofuran-6-yl or benzofuran-7-yl, each optionally substituted. In such embodiments Ar is preferably benzofuran-5-yl or benzofuran-6-yl, and more preferably benzofuran-5-yl.

In certain embodiments of formula II, Ar is benzothien-4-yl, benzothiophen-5-yl, benzothiophen-6-yl or benzothiophen-7-yl, each optionally substituted. In such embodiments Ar is preferably benzothiophen-5-yl or benzothiophen-6-yl, and more preferably benzothiophen-5-yl.

In certain embodiments of formula II, Ar is benzothiazol-4-yl, benzothiazol-5-yl, benzothiazol-6-yl or benzothiazol-7-yl, each optionally substituted. In such embodiments Ar is preferably benzothiazol-5-yl or benzothiazol-6-yl.

In certain embodiments of formula II, Ar is indolyl, indazolyl, or pyrrolo[2,3-b]pyridyl, each optionally substituted. Where Ar is optionally substituted indolyl, Ar is preferably optionally substituted indol-4-yl, optionally substituted indol-5-yl, optionally substituted indol-6-yl, or optionally substituted indol-7-yl. When Ar is optionally substituted indolyl, more preferably Ar is optionally substituted indol-5-yl or optionally substituted indol-6-yl. Where Ar is optionally substituted indazolyl, Ar is preferably optionally substituted indazol-4-yl, indazol-5-yl, indazol-6-yl, or optionally substituted indazol-7-yl. When Ar is optionally substituted indazolyl, Ar is more preferably indazol-5-yl or indazol-6-yl, each of which is optionally substituted. Where Ar is optionally substituted pyrrolo[2,3-b]pyridyl, Ar is preferably optionally substituted pyrrolo[2,3-b]pyrid-4-yl, pyrrolo[2,3-b]pyrid-5-yl, pyrrolo[2,3-b]pyrid-6-yl, or optionally substituted pyrrolo[2,3-b]pyrid-7-yl. When Ar is optionally substituted pyrrolo[2,3-b]pyridyl, Ar is more preferably pyrrolo[2,3-b]pyrid-5-yl or pyrrolo[2,3-b]pyrid-6-yl, each of which is optionally substituted.

In certain embodiments of formula II, Ar is: indolyl optionally substituted with one, two, three or four substituents each independently selected from alkyl, alkoxy, halo, haloalkyl, haloalkoxy, cyano, alkylsulfonyloxy, —$(CH_2)_q$—$S(O)_rR^f$; —$(CH_2)_q$—$NR^gR^h$; or —$(CH_2)_q$—$C(=O)$—$NR^gR^h$; where q is 0 or 1, r is from 0 to 2, and each of $R^f$, $R^g$, and $R^h$ is independently hydrogen or alkyl; $R^1$ is phenyl, pyridinyl, or indolyl each of which is optionally substituted with one, two, three or four substituents each of which is independently selected from alkyl, alkoxy, cyano, halo, haloalkyl, haloalkoxy, alkoxyalkyl or hydroxyalkyl; Y is CH; and one of $R^2$ and $R^3$ is hydrogen while the other is alkyl, preferably methyl. In such embodiments Ar may be indol-4-yl, indol-5-yl, indol-6-yl or indol-7-yl. In such embodiments, Ar is preferably indol-5-yl or indol-6-yl.

In certain embodiments of formula II, Ar is: indazolyl optionally substituted with one, two, three or four substituents each independently selected from alkyl, alkoxy, halo, haloalkyl, haloalkoxy, cyano, alkylsulfonyloxy, —$(CH_2)_q$—$S(O)_rR^f$; —$(CH_2)_q$—$NR^gR^h$; or —$(CH_2)_q$—$C(=O)$—$NR^gR^h$; where q is 0 or 1, r is from 0 to 2, and each of $R^f$, $R^g$, and $R^h$ is independently hydrogen or alkyl; $R^1$ is phenyl, pyridinyl, or indolyl each of which is optionally substituted with one, two, three or four substituents each of which is independently selected from alkyl, alkoxy, cyano, halo, haloalkyl, haloalkoxy, alkoxyalkyl or hydroxyalkyl; Y is CH; and one of $R^2$ and $R^3$ is hydrogen while the other is alkyl, preferably methyl. In such embodiments Ar may be indazol-4-yl, indazol-5-yl, indazol-6-yl or indazol-7-yl. In such embodiments Ar is preferably indazol-5-yl or indazol-6-yl.

In certain embodiments of formula II, Ar is: pyrrolo[2,3-b]pyridyl optionally substituted with one, two, three or four substituents each independently selected from alkyl, alkoxy, halo, haloalkyl, haloalkoxy, cyano, alkylsulfonyloxy, —$(CH_2)_q$—$S(O)_rR^f$; —$(CH_2)_q$—$NR^gR^h$; or —$(CH_2)_q$—$C(=O)$—$NR^gR^h$; where q is 0 or 1, r is from 0 to 2, and each of $R^f$, $R^g$, and $R^h$ is independently hydrogen or alkyl; $R^1$ is phenyl, pyridinyl, or indolyl each of which is optionally substituted with one, two, three or four substituents each of which is independently selected from alkyl, alkoxy, cyano, halo, haloalkyl, haloalkoxy, alkoxyalkyl or hydroxyalkyl; Y is CH; and one of $R^2$ and $R^3$ is hydrogen while the other is alkyl, preferably methyl. In such embodiments Ar may be pyrrolo[2,3-b]pyrid-4-yl, pyrrolo[2,3-b]pyrid-5-yl, pyrrolo[2,3-b]pyrid-6-yl or pyrrolo[2,3-b]pyrid-7-yl. In such embodiments Ar is preferably pyrrolo[2,3-b]pyrid-5-yl or pyrrolo[2,3-b]pyrid-6-yl.

In certain embodiments of formula II, Ar is: indol-5-yl or indol-6-yl optionally substituted with one or two substituents each independently selected from alkyl, alkoxy, halo, haloalkyl, haloalkoxy, cyano, alkylsulfonyloxy, —$(CH_2)_q$—$S(O)_rR^f$; —$(CH_2)_q$—$NR^gR^h$; or —$(CH_2)_q$—$C(=O)$—$NR^gR^h$; where q is 0 or 1, r is from 0 to 2, and each of $R^f$, $R^g$, and $R^h$ is independently hydrogen or alkyl; $R^1$ is phenyl optionally substituted with one or two substituents each of which is independently selected from alkyl, alkoxy, cyano, halo, haloalkyl, haloalkoxy, alkoxyalkyl or hydroxyalkyl; Y is CH; and one of $R^2$ and $R^3$ is hydrogen while the other is alkyl, preferably methyl. In such embodiments Ar is preferably indol-5-yl.

In certain embodiments of formula II, Ar is: indazol-5-yl or indazol-6-yl optionally substituted with one or two substituents each independently selected from alkyl, alkoxy, halo, haloalkyl, haloalkoxy, cyano, alkylsulfonyloxy, —$(CH_2)_q$—$S(O)_rR^f$; —$(CH_2)_q$—$NR^gR^h$; or —$(CH_2)_q$—$C(=O)$—$NR^gR^h$; where q is 0 or 1, r is from 0 to 2, and each of $R^f$, $R^g$, and $R^h$ is independently hydrogen or alkyl; $R^1$ is phenyl optionally substituted with one or two substituents each of which is independently selected from alkyl, alkoxy, cyano, halo, haloalkyl, haloalkoxy, alkoxyalkyl or hydroxyalkyl; Y is CH; and one of $R^2$ and $R^3$ is hydrogen while the other is alkyl, preferably methyl. In such embodiments Ar is preferably indazol-5-yl.

In compounds of formula II in which Y is CH and Ar is optionally substituted indolyl, the subject compounds may be represented by formula III:

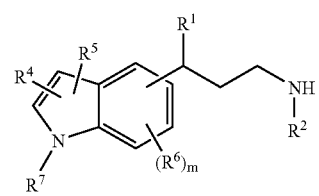

wherein
  m is an integer from 0 to 3;
  $R^4$ and $R^5$ each independently is: hydrogen; alkoxy, cycloalkylalkyoxy, cyano, alkyl, halo, —$S(O)_rR^f$; and —$C(=O)NR^gR^h$; wherein r is an integer from 0 to 2, and each of $R^f$, $R^g$, and $R^h$ is independently hydrogen or alkyl;
  each $R^6$ is independently: alkoxy, cyano, alkyl, cycloalkylalkyoxy, halo, —$S(O)_rR^f$; and —$C(=O)NR^gR^h$; wherein r is an integer from 0 to 2, and each of $R^f$, $R^g$, and $R^h$ is independently hydrogen or alkyl;
  $R^7$ is hydrogen, alkyl, or alkylsulfonyl; and
  $R^1$, $R^2$ and $R^3$ are as defined herein.

In embodiments of formula III wherein Y is CH and Ar is optionally substituted indol-4-yl, the compounds of the invention may be more specifically of formula IV:

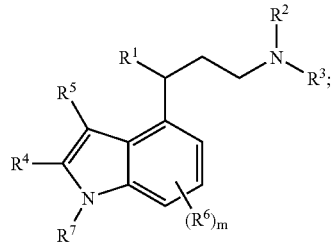

IV wherein m, $R^1$, $R^2$, $R^3$, $R^4$, $R^5$, $R^6$, and $R^7$ are as defined herein.

In certain embodiments of formula IV, the subject compounds may be more specifically of formula IVa or IVb:

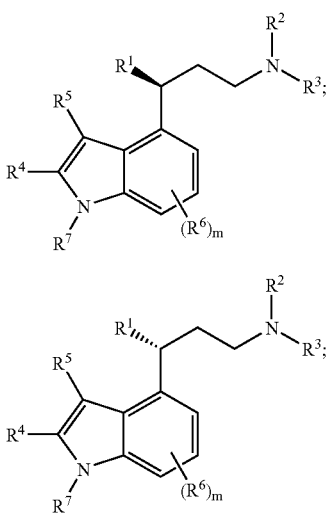

IVa

IVb wherein m, $R^1$, $R^2$, $R^3$, $R^4$, $R^5$, $R^6$, and $R^7$ are as defined herein.

In embodiments of formula II wherein Y is CH and Ar is optionally substituted indol-5-yl, the compounds of the invention may be more specifically of formula V:

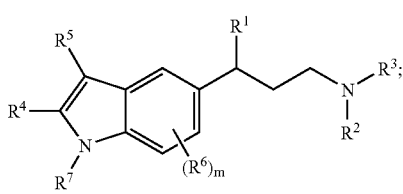

V wherein m, $R^1$, $R^2$, $R^3$, $R^4$, $R^5$, $R^6$, and $R^7$ are as defined herein.

In certain embodiments of formula V, the subject compounds may be more specifically of formula Va or Vb:

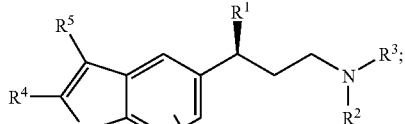

Va

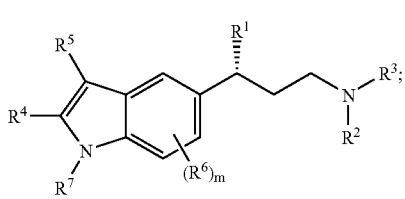

Vb wherein m, $R^1$, $R^2$, $R^3$, $R^4$, $R^5$, $R^6$, and $R^7$ are as defined herein.

In embodiments of formula II wherein Y is CH and Ar is optionally substituted indol-6-yl, the compounds of the invention may be more specifically of formula VI:

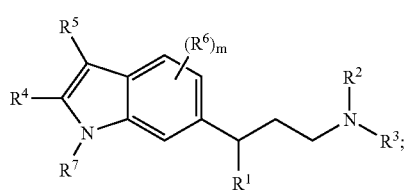

VI wherein m, $R^1$, $R^2$, $R^3$, $R^4$, $R^5$, $R^6$, and $R^7$ are as defined herein.

In certain embodiments of formula VI, the subject compounds may be more specifically of formula VIa or VIb:

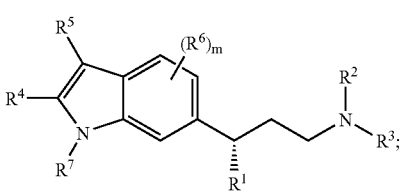

VIa

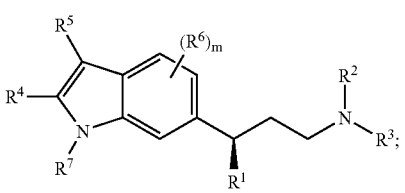

VIb wherein m, $R^1$, $R^2$, $R^3$, $R^4$, $R^5$, $R^6$, and $R^7$ are as defined herein.

In embodiments of formula II wherein Y is CH and Ar is optionally substituted indol-7-yl, the compounds of the invention may be more specifically of formula VII:

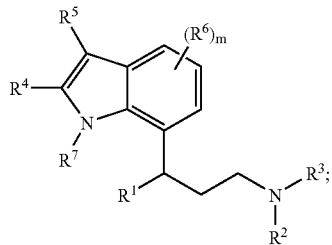

VII wherein m, $R^1$, $R^2$, $R^3$, $R^4$, $R^5$, $R^6$, and $R^7$ are as defined herein.

In certain embodiments of formula VII, the subject compounds may be more specifically of formula VIIa or VIIb:

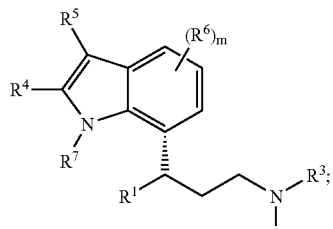

VIIa

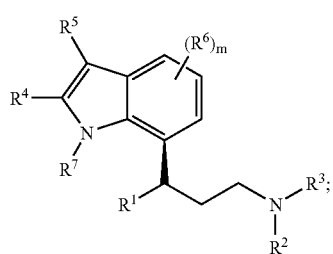

VIIb wherein m, $R^1$, $R^2$, $R^3$, $R^4$, $R^5$, $R^6$, and $R^7$ are as defined herein.

In certain embodiments of any of formulas III, IV, IVa, IVb, V, Va, Vb, VI, VIa, VIb, VII, VIIa, or VIIb, one of $R^2$ and $R^3$ is hydrogen and the other is alkyl, preferably methyl.

In certain embodiments of any of formulas III, IV, IVa, IVb, V, Va, Vb, VI, VIa, VIb, VII, VIIa, or VIIb, $R^1$ is optionally substituted aryl, $R^1$ is optionally substituted phenyl.

In certain embodiments of any of formulas III, IV, IVa, IVb, V, Va, Vb, VI, VIa, VIb, VII, VIIa, or VIIb, $R^1$ is optionally substituted aryl, $R^1$ is optionally substituted naphthalenyl.

In certain embodiments of any of formulas III, IV, IVa, IVb, V, Va, Vb, VI, VIa, VIb, VII, VIIa, or VIIb, $R^1$ is optionally substituted aryl, $R^1$ is optionally substituted naphthalen-1-yl.

In certain embodiments of any of formulas III, IV, IVa, IVb, V, Va, Vb, VI, VIa, VIb, VII, VIIa, or VIIb, $R^1$ is optionally substituted aryl, $R^1$ is optionally substituted naphthalen-2-yl.

In certain embodiments of any of formulas III, IV, IVa, IVb, V, Va, Vb, VI, VIa, VIb, VII, VIIa, or VIIb, $R^1$ is optionally substituted heteroaryl. Such heteroaryl may be selected from indolyl, pyridinyl, thienyl, furanyl, pyrimidinyl, pyridazinyl, pyrazinyl, oxazolyl, thiazolyl, isoxazolyl, isothiazolyl, imidazolyl, pyrazolyl, quinolinyl, isoquinolinyl, quinoxalinyl, benzothiazolyl, benzofuranyl, benzothiophenyl or benzoxazinyl, each optionally substituted.

In certain embodiments of any of formulas III, IV, IVa, IVb, V, Va, Vb, VI, VIa, VIb, VII, VIIa, or VIIb, $R^1$ is optionally substituted indolyl.

In certain embodiments of any of formulas III, IV, IVa, IVb, V, Va, Vb, VI, VIa, VIb, VII, VIIa, or VIIb, $R^1$ is indol-2-yl, indol-3-yl, indol-4-yl, indol-5-yl, indol-6-yl, or indol-7-yl, each optionally substituted.

In certain embodiments of any of formulas III, IV, IVa, IVb, V, Va, Vb, VI, VIa, VIb, VII, VIIa, or VIIb, $R^1$ is indol-5-yl or indol-6-yl, each optionally substituted.

In certain embodiments of any of formulas III, IV, IVa, IVb, V, Va, Vb, VI, VIa, VIb, VII, VIIa, or VIIb, $R^1$ optionally substituted is indol-2-yl.

In certain embodiments of any of formulas III, IV, IVa, IVb, V, Va, Vb, VI, VIa, VIb, VII, VIIa, or VIIb, $R^1$ optionally substituted is indol-3-yl.

In certain embodiments of any of formulas III, IV, IVa, IVb, V, Va, Vb, VI, VIa, VIb, VII, VIIa, or VIIb, $R^1$ optionally substituted is indol-4-yl.

In certain embodiments of any of formulas III, IV, IVa, IVb, V, Va, Vb, VI, VIa, VIb, VII, VIIa, or VIIb, $R^1$ optionally substituted is indol-5-yl.

In certain embodiments of any of formulas III, IV, IVa, IVb, V, Va, Vb, VI, VIa, VIb, VII, VIIa, or VIIb, $R^1$ optionally substituted is indol-6-yl.

In certain embodiments of any of formulas III, IV, IVa, IVb, V, Va, Vb, VI, VIa, VIb, VII, VIIa, or VIIb, $R^1$ optionally substituted is indol-7-yl.

In certain embodiments of any of formulas III, IV, IVa, IVb, V, Va, Vb, VI, VIa, VIb, VII, VIIa, or VIIb, $R^1$ is optionally substituted quinolinyl.

In certain embodiments of any of formulas III, IV, IVa, IVb, V, Va, Vb, VI, VIa, VIb, VII, VIIa, or VIIb, $R^1$ is quinolin-2-yl, quinolin-3-yl, quinolin-4-yl, quinolin-5-yl, quinolin-6-yl, quinolin-7-yl or quinolin-8-yl, each optionally substituted.

In certain embodiments of any of formulas III, IV, IVa, IVb, V, Va, Vb, VI, VIa, VIb, VII, VIIa, or VIIb, $R^1$ is optionally substituted quinolin-6-yl.

In certain embodiments of any of formulas III, IV, IVa, IVb, V, Va, Vb, VI, VIa, VIb, VII, VIIa, or VIIb, $R^1$ is optionally substituted pyridinyl.

In certain embodiments of any of formulas III, IV, IVa, IVb, V, Va, Vb, VI, VIa, VIb, VII, VIIa, or VIIb, $R^1$ is pyridin-2-yl, pyridin-3-yl or pyridin-4-yl, each optionally substituted.

In certain embodiments of any of formulas III, IV, IVa, IVb, V, Va, Vb, VI, VIa, VIb, VII, VIIa, or VIIb, $R^1$ is optionally substituted pyridin-2-yl.

In certain embodiments of any of formulas III, IV, IVa, IVb, V, Va, Vb, VI, VIa, VIb, VII, VIIa, or VIIb, $R^1$ is optionally substituted pyridin-3-yl.

In certain embodiments of any of formulas III, IV, IVa, IVb, V, Va, Vb, VI, VIa, VIb, VII, VIIa, or VIIb, $R^1$ is optionally substituted pyridin-4-yl.

In certain embodiments of any of formulas III, IV, IVa, IVb, V, Va, Vb, VI, VIa, VIb, VII, VIIa, or VIIb, $R^1$ is optionally substituted quinoxalinyl.

In certain embodiments of any of formulas III, IV, IVa, IVb, V, Va, Vb, VI, VIa, VIb, VII, VIIa, or VIIb, $R^1$ is quinoxalin-2-yl, quinoxalin-3-yl, quinoxalin-5-yl, quinoxalin-6-yl, quinoxalin-7-yl or quinoxalin-8-yl, each optionally substituted.

In certain embodiments of any of formulas III, IV, IVa, IVb, V, Va, Vb, VI, VIa, VIb, VII, VIIa, or VIIb,
$R^1$ is optionally substituted quinoxalin-6-yl.

In certain embodiments of any of formulas III, IV, IVa, IVb, V, Va, Vb, VI, VIa, VIb, VII, VIIa, or VIIb, $R^1$ is optionally substituted benzothiophenyl.

In certain embodiments of any of formulas III, IV, IVa, IVb, V, Va, Vb, VI, VIa, VIb, VII, VIIa, or VIIb, $R^1$ is optionally substituted benzothiophen-5-yl.

In certain embodiments of any of formulas III, IV, IVa, IVb, V, Va, Vb, VI, VIa, VIb, VII, VIIa, or VIIb, $R^1$ is optionally substituted benzoxazinyl. In such embodiments the benzoxazinyl may be 4-methyl-3,4-dihydro-2H-benzo[1,4]oxazin-7-yl.

In certain embodiments of any of formulas III, IV, IVa, IVb, V, Va, Vb, VI, VIa, VIb, VII, VIIa, or VIIb, $R^1$ is optionally substituted benzothiazolyl.

In certain embodiments of any of formulas III, IV, IVa, IVb, V, Va, Vb, VI, VIa, VIb, VII, VIIa, or VIIb, $R^1$ is optionally substituted benzothiazol-2-yl.

In certain embodiments of any of formulas III, IV, IVa, IVb, V, Va, Vb, VI, VIa, VIb, VII, VIIa, or VIIb, $R^1$ is optionally substituted benzothiazol-5-yl.

In certain embodiments of any of formulas III, IV, IVa, IVb, V, Va, Vb, VI, VIa, VIb, VII, VIIa, or VIIb, $R^1$ is optionally substituted benzothiazol-6-yl.

In certain embodiments of any of formulas III, IV, IVa, IVb, V, Va, Vb, VI, VIa, VIb, VII, VIIa, or VIIb, $R^1$ is optionally substituted thiazolyl.

In certain embodiments of any of formulas III, IV, IVa, IVb, V, Va, Vb, VI, VIa, VIb, VII, VIIa, or VIIb, $R^1$ is optionally substituted thiazol-2-yl.

In certain embodiments of any of formulas III, IV, IVa, IVb, V, Va, Vb, VI, VIa, VIb, VII, VIIa, or VIIb, $R^1$ is optionally substituted thiazol-4-yl. In certain embodiments of any of formulas III, IV, IVa, IVb, V, Va, Vb, VI, VIa, VIb, VII, VIIa, or VIIb, $R^1$ is optionally substituted thiazol-5-yl.

In certain embodiments of any of formulas III, IV, IVa, IVb, V, Va, Vb, VI, VIa, VIb, VII, VIIa, or VIIb, $R^1$ is phenyl, pyridin-3-yl, 3-methoxyphenyl, pyridin-2-yl, 2-methoxyphenyl, 4-methoxyphenyl, 3-chlorophenyl, 4-chlorophenyl, or indol-3-yl.

In certain embodiments of formula III, IV, IVa, IVb, V, Va, Vb, VI, VIa, VIb, VII, VIIa, or VIIb, $R^4$ is hydrogen, cyano, carbamoyl, or alkyl. When $R^4$ is alkyl, preferably $R^4$ is methyl.

In certain embodiments of formula III, IV, IVa, IVb, V, Va, Vb, VI, VIa, VIb, VII, VIIa, or VIIb, $R^5$ is hydrogen, cyano, carbamoyl, or alkyl. When $R^5$ is alkyl, preferably $R^4$ is methyl.

In certain embodiments of formula III, IV, IVa, IVb, V, Va, Vb, VI, VIa, VIb, VII, VIIa, or VIIb, $R^7$ is hydrogen, alkyl, or alkylsulfonyl (i.e., $-SO_2R^8$, where $R^8$ is alkyl).

In certain embodiments of any of formulas III, IV, Va, IVb, V, Va, Vb, VI, VIa, VIb, VII, VIIa, or VIIb, each $R^6$ is independently halo, alkyl, cyano, haloalkyl or alkoxy. In these cases, $R^6$ is preferably, fluoro, chloro, bromo, trifluoromethyl, cyano, or methoxy. More preferably, $R^6$ is fluoro, chloro, or methoxy.

In certain embodiments of any of formulas III, IV, IVa, IVb, V, Va, Vb, VI, VIa, VIb, VII, VIIa, or VIIb, m is 0, 1 or 2 and each $R^6$ is independently fluoro, chloro, or methoxy.

In certain embodiments of any of formulas III, IV, IVa, IVb, V, Va, Vb, VI, VIa, VIb, VII, VIIa, or VIIb, m is 0, 1 or 2 and each $R^6$ is independently halo, alkyl, alkoxy or cyano.

In certain embodiments of any of formulas III, IV, IVa, IVb, V, Va, Vb, VI, VIa, VIb, VII, VIIa, or VIIb, m is 0.

In certain embodiments of any of formulas III, IV, IVa, IVb, V, Va, Vb, VI, VIa, VIb, VII, VIIa, or VIIb, m is 1, and $R^6$ is located at the 4- or 7 position of the indole ring system.

In certain embodiments of any of formulas III, IV, IVa, IVb, V, Va, Vb, VI, VIa, VIb, VII, VIIa, or VIIb, m is 1, and $R^6$ is halo, cyano or alkoxy at the 4- or 7 position of the indole ring system.

In certain embodiments of formulas III, IV, IVa, IVb, V, Va, Vb, VI, VIa, VIb, VII, VIIa, or VIIb, $R^4$ and $R^5$ are hydrogen.

In certain embodiments of any of formulas III, IV, IVa, IVb, V, Va, Vb, VI, VIa, VIb, VII, VIIa, or VIIb, one of $R^4$ and $R^5$ is hydrogen and the other is alkyl, cyano, halo or alkoxy.

In certain embodiments of any of formulas III, IV, IVa, IVb, V, Va, Vb, VI, VIa, VIb, VII, VIIa, or VIIb, m is 0, 1 or 2, $R^1$ is optionally substituted phenyl, and one of $R^2$ and $R^3$ is hydrogen and the other is alkyl, preferably methyl.

In certain embodiments of any of formulas III, IV, IVa, IVb, V, Va, Vb, VI, VIa, VIb, VII, VIIa, or VIIb, m is 0, 1 or 2, $R^1$ is optionally substituted phenyl, one of $R^2$ and $R^3$ is hydrogen and the other is alkyl, preferably methyl, and $R^4$ and $R^5$ are hydrogen.

In certain embodiments of any of formulas III, IV, IVa, IVb, V, Va, Vb, VI, VIa, VIb, VII, VIIa, or VIIb, m is 0, 1 or 2, $R^1$ is optionally substituted phenyl, one of $R^2$ and $R^3$ is hydrogen and the other is alkyl, preferably methyl, $R^4$ and $R^5$ are hydrogen, and each $R^6$ is independently halo, cyano or alkoxy. In such embodiments optionally substituted phenyl may be phenyl optionally substituted one, two, three or four times with alkyl, alkoxy, cyano, halo, haloalkyl, haloalkoxy, alkoxyalkyl or hydroxyalkyl.

In certain embodiments of any of formulas III, IV, IVa, IVb, V, Va, Vb, VI, VIa, VIb, VII, VIIa, or VIIb, m is 0, 1 or 2, $R^1$ is optionally substituted pyridinyl, and one of $R^2$ and $R^3$ is hydrogen and the other is alkyl, preferably methyl. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In certain embodiments of formulas any of III, IV, IVa, IVb, V, Va, Vb, VI, VIa, VIb, VII, VIIa, or VIIb, m is 0, 1 or 2, $R^1$ is optionally substituted pyridinyl, one of $R^2$ and $R^3$ is hydrogen and the other is alkyl, preferably methyl, and $R^4$ and $R^5$ are hydrogen. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In certain embodiments of any of formulas III, IV, IVa, IVb, V, Va, Vb, VI, VIa, VIb, VII, VIIa, or VIIb, m is 0, 1 or 2, $R^1$ is optionally substituted pyridinyl, one of $R^2$ and $R^3$ is hydrogen and the other is alkyl, preferably methyl, $R^4$ and $R^5$ are hydrogen, and each $R^6$ is independently halo, cyano or alkoxy. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In certain embodiments of any of formulas III, IV, IVa, IVb, V, Va, Vb, VI, VIa, VIb, VII, VIIa, or VIIb, m is 0, 1 or 2, $R^1$ is optionally substituted indolyl, one of $R^2$ and $R^3$ is hydrogen and the other is alkyl, preferably methyl, $R^4$ and $R^5$ are hydrogen, and each $R^6$ is independently halo, cyano or alkoxy. In such embodiments optionally substituted indolyl may be indolyl optionally substituted one, two or three times with alkyl, alkoxy, cyano, halo, haloalkyl, haloalkoxy, alkoxyalkyl or hydroxyalkyl.

In certain embodiments of any of formulas III, IV, IVa, IVb, V, Va, Vb, VI, VIa, VIb, VII, VIIa, or VIIb, m is 0, 1 or 2, $R^1$ is optionally substituted quinolinyl, one of $R^2$ and $R^3$ is hydrogen and the other is alkyl, preferably methyl, $R^4$ and $R^5$ are hydrogen, and each $R^6$ is independently halo, cyano or alkoxy. In such embodiments optionally substituted quinolinyl may be quinolinyl optionally substituted one, two or three times with alkyl, alkoxy, cyano, halo, haloalkyl, haloalkoxy, alkoxyalkyl or hydroxyalkyl.

In compounds of formula II in which Y is CH and Ar is optionally substituted indazolyl, the subject compounds may be represented by formula VIII:

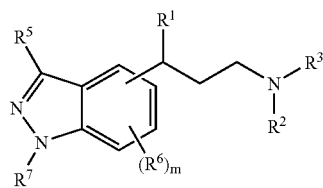

VIII wherein m, $R^1$, $R^2$, $R^3$, $R^5$, $R^6$, and $R^7$ are as defined herein.

In embodiments of formula II wherein Y is CH and Ar is optionally substituted indazol-4-yl, the compounds of the invention may be more specifically of formula IX:

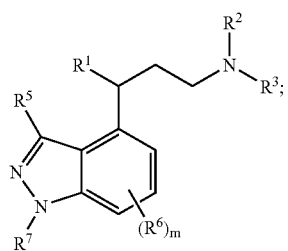

IX wherein m, $R^1$, $R^2$, $R^3$, $R^5$, $R^6$, and $R^7$ are as defined herein.

In certain embodiments of formula IX, the subject compounds may be more specifically of formula IXa or IXb:

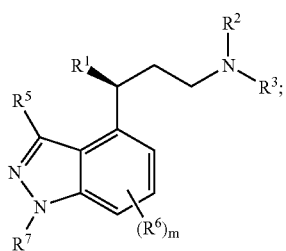

IXa

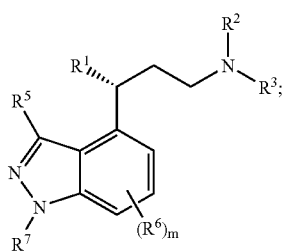

IXb wherein m, $R^1$, $R^2$, $R^3$, $R^5$, $R^6$, and $R^7$ are as defined herein.

In embodiments of formula II wherein Y is CH and Ar is optionally substituted indazol-5-yl, the compounds of the invention may be more specifically of formula X:

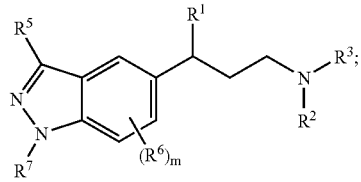

X wherein m, $R^1$, $R^2$, $R^3$, $R^5$, $R^6$, and $R^7$ are as defined herein.

In certain embodiments of formula X, the subject compounds may be more specifically of formula Xa or Xb:

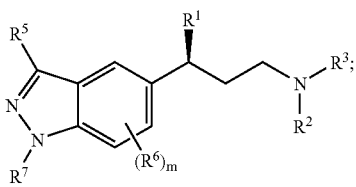

Xa

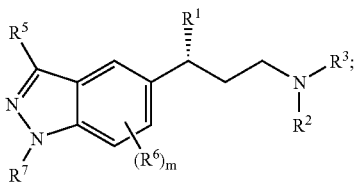

Xb wherein m, $R^1$, $R^2$, $R^3$, $R^5$, $R^6$, and $R^7$ are as defined herein.

In embodiments of formula II wherein Y is CH and Ar is optionally substituted indazol-6-yl, the compounds of the invention may be more specifically of formula XI:

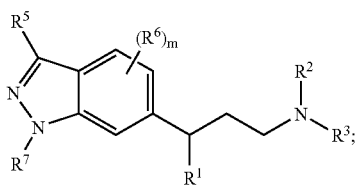

XI wherein m, $R^1$, $R^2$, $R^3$, $R^5$, $R^6$, and $R^7$ are as defined herein.

In certain embodiments of formula XI, the subject compounds may be more specifically of formula XIa or XIb:

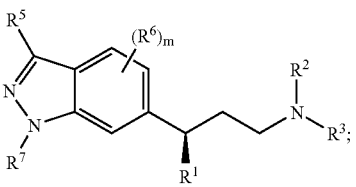

XIa

-continued

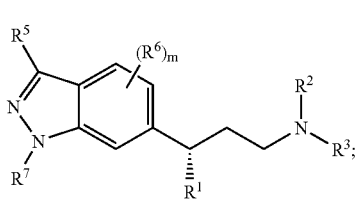
XIb wherein m, $R^1$, $R^2$, $R^3$, $R^5$, $R^6$, and $R^7$ are as defined herein.

In embodiments of formula II wherein Y is CH and Ar is optionally substituted indazol-7-yl, the compounds of the invention may be more specifically of formula XII:

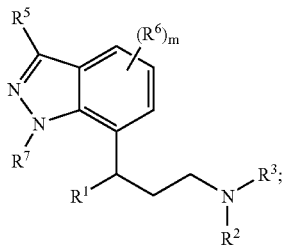
XII wherein m, $R^1$, $R^2$, $R^3$, $R^5$, $R^6$, and $R^7$ are as defined herein.

In certain embodiments of formula XII, the subject compounds may be more specifically of formula XIIa or XIIb:

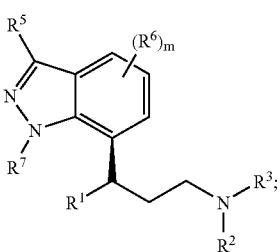
XIIa

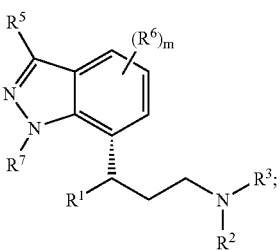
XIIb wherein m, $R^1$, $R^2$, $R^3$, $R^5$, $R^6$, and $R^7$ are as defined herein.

In certain embodiments of any of formulas VIII, IX, IXa, IXb, X, Xa, Xb, XI, XIa, XIb, XII, XIIa, or XIIb, one of $R^2$ and $R^3$ is hydrogen and the other is alkyl, preferably methyl.

In certain embodiments of any of formulas VIII, IX, IXa, IXb, X, Xa, Xb, XI, XIa, XIb, XII, XIIa, or XIIb, $R^1$ is optionally substituted aryl, $R^1$ is optionally substituted phenyl.

In certain embodiments of any of formulas VIII, IX, IXa, IXb, X, Xa, Xb, XI, XIa, XIb, XII, XIIa, or XIIb, $R^1$ is optionally substituted aryl, $R^1$ is optionally substituted naphthalenyl.

In certain embodiments of any of formulas VIII, IX, IXa, IXb, X, Xa, Xb, XI, XIa, XIb, XII, XIIa, or XIIb, $R^1$ is optionally substituted aryl, $R^1$ is optionally substituted naphthalen-1-yl.

In certain embodiments of any of formulas VIII, IX, IXa, IXb, X, Xa, Xb, XI, XIa, XIb, XII, XIIa, or XIIb, $R^1$ is optionally substituted aryl, $R^1$ is optionally substituted naphthalen-2-yl.

In certain embodiments of any of formulas VIII, IX, IXa, IXb, X, Xa, Xb, XI, XIa, XIb, XII, XIIa, or XIIb, $R^1$ is optionally substituted heteroaryl. Such heteroaryl may be selected from indolyl, pyridinyl, thienyl, furanyl, pyrimidinyl, pyridazinyl, pyrazinyl, oxazolyl, thiazolyl, isoxazolyl, isothiazolyl, imidazolyl, pyrazolyl, quinolinyl, isoquinolinyl, quinoxalinyl, benzothiazolyl, benzofuranyl, benzothiophenyl or benzoxazinyl, each optionally substituted.

In certain embodiments of any of formulas VIII, IX, IXa, IXb, X, Xa, Xb, XI, XIa, XIb, XII, XIIa, or XIIb, $R^1$ is optionally substituted indolyl.

In certain embodiments of any of formulas VIII, IX, IXa, IXb, X, Xa, Xb, XI, XIa, XIb, XII, XIIa, or XIIb, $R^1$ is indol-2-yl, indol-3-yl, indol-4-yl, indol-5-yl, indol-6-yl, or indol-7-yl, each optionally substituted.

In certain embodiments of any of formulas VIII, IX, IXa, IXb, X, Xa, Xb, XI, XIa, XIb, XII, XIIa, or XIIb, $R^1$ is indol-5-yl or indol-6-yl, each optionally substituted.

In certain embodiments of any of formulas VIII, IX, IXa, IXb, X, Xa, Xb, XI, XIa, XIb, XII, XIIa, or XIIb, $R^1$ optionally substituted is indol-2-yl.

In certain embodiments of any of formulas VIII, IX, IXa, IXb, X, Xa, Xb, XI, XIa, XIb, XII, XIIa, or XIIb, $R^1$ optionally substituted is indol-3-yl.

In certain embodiments of any of formulas VIII, IX, IXa, IXb, X, Xa, Xb, XI, XIa, XIb, XII, XIIa, or XIIb, $R^1$ optionally substituted is indol-4-yl.

In certain embodiments of any of formulas VIII, IX, IXa, IXb, X, Xa, Xb, XI, XIa, XIb, XII, XIIa, or XIIb, $R^1$ optionally substituted is indol-5-yl.

In certain embodiments of any of formulas VIII, IX, IXa, IXb, X, Xa, Xb, XI, XIa, XIb, XII, XIIa, or XIIb, $R^1$ optionally substituted is indol-6-yl.

In certain embodiments of any of formulas VIII, IX, IXa, IXb, X, Xa, Xb, XI, XIa, XIb, XII, XIIa, or XIIb, $R^1$ optionally substituted is indol-7-yl.

In certain embodiments of any of formulas VIII, IX, IXa, IXb, X, Xa, Xb, XI, XIa, XIb, XII, XIIa, or XIIb, $R^1$ is optionally substituted quinolinyl.

In certain embodiments of any of formulas VIII, IX, IXa, IXb, X, Xa, Xb, XI, XIa, XIb, XII, XIIa, or XIIb, $R^1$ is quinolin-2-yl, quinolin-3-yl, quinolin-4-yl, quinolin-5-yl, quinolin-6-yl, quinolin-7-yl or quinolin-8-yl, each optionally substituted.

In certain embodiments of any of formulas VIII, IX, IXa, IXb, X, Xa, Xb, XI, XIa, XIb, XII, XIIa, or XIIb, $R^1$ is optionally substituted quinolin-6-yl.

In certain embodiments of any of formulas VIII, IX, IXa, IXb, X, Xa, Xb, XI, XIa, XIb, XII, XIIa, or XIIb, $R^1$ is optionally substituted pyridinyl.

In certain embodiments of any of formulas VIII, IX, IXa, IXb, X, Xa, Xb, XI, XIa, XIb, XII, XIIa, or XIIb, $R^1$ is pyridin-2-yl, pyridin-3-yl or pyridin-4-yl, each optionally substituted.

In certain embodiments of any of formulas VIII, IX, IXa, IXb, X, Xa, Xb, XI, XIa, XIb, XII, XIIa, or XIIb, $R^1$ is optionally substituted pyridin-2-yl.

In certain embodiments of any of formulas VIII, IX, IXa, IXb, X, Xa, Xb, XI, XIa, XIb, XII, XIIa, or XIIb, $R^1$ is optionally substituted pyridin-3-yl.

In certain embodiments of any of formulas VIII, IX, IXa, IXb, X, Xa, Xb, XI, XIa, XIb, XII, XIIa, or XIIb, $R^1$ is optionally substituted pyridin-4-yl.

In certain embodiments of any of formulas VIII, IX, IXa, IXb, X, Xa, Xb, XI, XIa, XIb, XII, XIIa, or XIIb, $R^1$ is optionally substituted quinoxalinyl.

In certain embodiments of any of formulas VIII, IX, IXa, IXb, X, Xa, Xb, XI, XIa, XIb, XII, XIIa, or XIIb, $R^1$ is quinoxalin-2-yl, quinoxalin-3-yl, quinoxalin-5-yl, quinoxalin-6-yl, quinoxalin-7-yl or quinoxalin-8-yl, each optionally substituted.

In certain embodiments of any of formulas VIII, IX, IXa, IXb, X, Xa, Xb, XI, XIa, XIb, XII, XIIa, or XIIb, $R^1$ is optionally substituted quinoxalin-6-yl.

In certain embodiments of any of formulas VIII, IX, IXa, IXb, X, Xa, Xb, XI, XIa, XIb, XII, XIIa, or XIIb, $R^1$ is optionally substituted benzothiophenyl.

In certain embodiments of any of formulas VIII, IX, IXa, IXb, X, Xa, Xb, XI, XIa, XIb, XII, XIIa, or XIIb, $R^1$ is optionally substituted benzothiophen-5-yl.

In certain embodiments of any of formulas VIII, IX, IXa, IXb, X, Xa, Xb, XI, XIa, XIb, XII, XIIa, or XIIb, $R^1$ is optionally substituted benzoxazinyl. In such embodiments the benzoxazinyl may be 4-methyl-3,4-dihydro-2H-benzo[1,4]oxazin-7-yl.

In certain embodiments of any of formulas VIII, IX, IXa, IXb, X, Xa, Xb, XI, XIa, XIb, XII, XIIa, or XIIb, $R^1$ is optionally substituted benzothiazolyl.

In certain embodiments of any of formulas VIII, IX, IXa, IXb, X, Xa, Xb, XI, XIa, XIb, XII, XIIa, or XIIb, $R^1$ is optionally substituted benzothiazol-2-yl.

In certain embodiments of any of formulas VIII, IX, IXa, IXb, X, Xa, Xb, XI, XIa, XIb, XII, XIIa, or XIIb, $R^1$ is optionally substituted benzothiazol-5-yl.

In certain embodiments of any of formulas VIII, IX, IXa, IXb, X, Xa, Xb, XI, XIa, XIb, XII, XIIa, or XIIb, $R^1$ is optionally substituted benzothiazol-6-yl.

In certain embodiments of any of formulas VIII, IX, IXa, IXb, X, Xa, Xb, XI, XIa, XIb, XII, XIIa, or XIIb, $R^1$ is optionally substituted thiazolyl.

In certain embodiments of any of formulas VIII, IX, IXa, IXb, X, Xa, Xb, XI, XIa, XIb, XII, XIIa, or XIIb, $R^1$ is optionally substituted thiazol-2-yl.

In certain embodiments of any of formulas VIII, IX, IXa, IXb, X, Xa, Xb, XI, XIa, XIb, XII, XIIa, or XIIb, $R^1$ is optionally substituted thiazol-4-yl.

In certain embodiments of any of formulas VIII, IX, IXa, IXb, X, Xa, Xb, XI, XIa, XIb, XII, XIIa, or XIIb, $R^1$ is optionally substituted thiazol-5-yl.

In certain embodiments of any of formulas VIII, IX, IXa, IXb, X, Xa, Xb, XI, XIa, XIb, XII, XII, or XII $R^1$ is optionally substituted phenyl or optionally substituted pyridinyl.

In certain embodiments of any of formulas VIII, IX, IXa, IXb, X, Xa, Xb, XI, XIa, XIb, XII, XIIa, or XIIb, $R^1$ is phenyl, pyridin-3-yl, 3-methoxyphenyl, pyridin-2-yl, 2-methoxyphenyl, 4-methoxyphenyl, 3-chlorophenyl, 4-chlorophenyl, or indol-3-yl.

In certain embodiments of any of formulas VIII, IX, IXa, IXb, X, Xa, Xb, XI, XIa, XIb, XII, XIIa, or XIIb, $R^5$ is hydrogen, cyano, carbamoyl, or alkyl.

In certain embodiments of formula VIII, IX, IXa, IXb, X, Xa, Xb, XI, XIa, XIb, XII, XIIa, or XIIb, $R^7$ is hydrogen, alkyl, or alkylsulfonyl (i.e., —SO$_2$R$^8$, where $R^8$ is alkyl).

In certain embodiments of any of formulas VIII, IX, IXa, IXb, X, Xa, Xb, XI, XIa, XIb, XII, XIIa, or XIIb, each $R^6$ is independently halo, alkyl, cyano, haloalkyl or alkoxy. In these cases, $R^6$ is preferably, fluoro, chloro, bromo, trifluoromethyl, cyano, or methoxy. More preferably, $R^6$ is fluoro, chloro, or methoxy.

In certain embodiments of any of formulas VIII, IX, IXa, IXb, X, Xa, Xb, XI, XIa, XIb, XII, XIIa, or XIIb, m is 0, 1 or 2 and each $R^6$ is independently fluoro, chloro, or methoxy.

In certain embodiments of any of formulas VIII, IX, IXa, IXb, X, Xa, Xb, XI, XIa, XIb, XII, XIIa, or XIIb, m is 0, 1 or 2 and each $R^6$ is independently halo, alkyl, alkoxy or cyano.

In certain embodiments of any of formulas VIII, IX, IXa, IXb, X, Xa, Xb, XI, XIa, XIb, XII, XIIa, or XIIb, m is 0.

In certain embodiments of any of formulas VIII, IX, IXa, IXb, X, Xa, Xb, XI, XIa, XIb, XII, XIIa, or XIIb, m is 1, and $R^6$ is located at the 4- or 7 position of the indazole ring system.

In certain embodiments of any of formulas VIII, IX, IXa, IXb, X, Xa, Xb, XI, XIa, XIb, XII, XIIa, or XIIb, m is 1, and $R^6$ is halo, cyano or alkoxy at the 4- or 7 position of the indazole ring system.

In certain embodiments of any of formulas VIII, IX, IXa, IXb, X, Xa, Xb, XI, XIa, XIb, XII, XIIa, or XIIb, $R^5$ is hydrogen.

In certain embodiments of any of formulas VIII, IX, IXa, IXb, X, Xa, Xb, XI, XIa, XIb, XII, XIIa, or XIIb, m is 0, 1 or 2, $R^1$ is optionally substituted phenyl, and one of $R^2$ and $R^3$ is hydrogen and the other is alkyl, preferably methyl.

In certain embodiments of any of formulas VIII, IX, IXa, IXb, X, Xa, Xb, XI, XIa, XIb, XII, XIIa, or XIIb, m is 0, 1 or 2, $R^1$ is optionally substituted phenyl, one of $R^2$ and $R^3$ is hydrogen and the other is alkyl, preferably methyl, and $R^5$ is hydrogen.

In certain embodiments of any of formulas VIII, IX, IXa, IXb, X, Xa, Xb, XI, XIa, XIb, XII, XIIa, or XIIb, m is 0, 1 or 2, $R^1$ is optionally substituted phenyl, one of $R^2$ and $R^3$ is hydrogen and the other is alkyl, preferably methyl, $R^5$ is hydrogen, and each $R^6$ is independently halo, cyano or alkoxy. In such embodiments optionally substituted phenyl may be phenyl optionally substituted one, two, three or four times with alkyl, alkoxy, cyano, halo, haloalkyl, haloalkoxy, alkoxyalkyl or hydroxyalkyl.

In certain embodiments of any of formulas VIII, IX, IXa, IXb, X, Xa, Xb, XI, XIa, XIb, XII, XIIa, or XIIb, m is 0, 1 or 2, $R^1$ is optionally substituted pyridinyl, and one of $R^2$ and $R^3$ is hydrogen and the other is alkyl, preferably methyl. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In certain embodiments of any of formulas VIII, IX, IXa, IXb, X, Xa, Xb, XI, XIa, XIb, XII, XIIa, or XIIb, m is 0, 1 or 2, $R^1$ is optionally substituted pyridinyl, one of $R^2$ and $R^3$ is hydrogen and the other is alkyl, preferably methyl, and $R^5$ is hydrogen. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In certain embodiments of any of formulas VIII, IX, IXa, IXb, X, Xa, Xb, XI, XIa, XIb, XII, XIIa, or XIIb, m is 0, 1 or 2, $R^1$ is optionally substituted pyridinyl, one of $R^2$ and $R^3$ is hydrogen and the other is alkyl, preferably methyl, $R^5$ is hydrogen, and each $R^6$ is independently halo, cyano or alkoxy. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In certain embodiments of any of formulas VIII, IX, IXa, IXb, X, Xa, Xb, XI, XIa, XIb, XII, XIIa, or XIIb, m is 0, 1 or 2, $R^1$ is optionally substituted indolyl, one of $R^2$ and $R^3$ is hydrogen and the other is alkyl, preferably methyl, $R^5$ is hydrogen, and each $R^6$ is independently halo, cyano or alkoxy. In such embodiments optionally substituted indolyl may be indolyl optionally substituted one, two or three times with alkyl, alkoxy, cyano, halo, haloalkyl, haloalkoxy, alkoxyalkyl or hydroxyalkyl.

In certain embodiments of any of formulas VIII, IX, IXa, IXb, X, Xa, Xb, XI, XIa, XIb, XII, XIIa, or XIIb, m is 0, 1 or 2, $R^1$ is optionally substituted quinolinyl, one of $R^2$ and $R^3$ is hydrogen and the other is alkyl, preferably methyl, $R^5$ is hydrogen, and each $R^6$ is independently halo, cyano or alkoxy. In such embodiments optionally substituted quinolinyl may be quinolinyl optionally substituted one, two or three times with alkyl, alkoxy, cyano, halo, haloalkyl, haloalkoxy, alkoxyalkyl or hydroxyalkyl.

In compounds of formula II in which Y is CH and Ar is optionally substituted pyrrolo[2,3-b]pyridyl, the subject compounds may be represented by formula XIII:

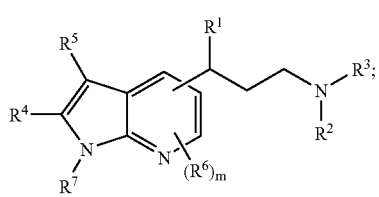

XIII wherein m, $R^1$, $R^2$, $R^3$, $R^4$, $R^5$, $R^6$, and $R^7$ are as defined herein.

In embodiments of formula II wherein Y is CH and Ar is optionally substituted pyrrolo[2,3-b]pyrid-4-yl, the compounds of the invention may be more specifically of formula XIV:

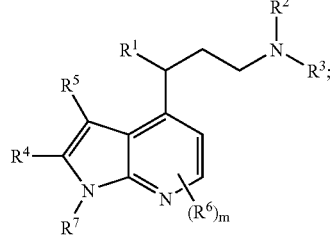

XIV wherein m, $R^1$, $R^2$, $R^3$, $R^4$, $R^5$, $R^6$, and $R^7$ are as defined herein.

In certain embodiments of formula XIV, the subject compounds may be more specifically of formula XIVa or XIVb:

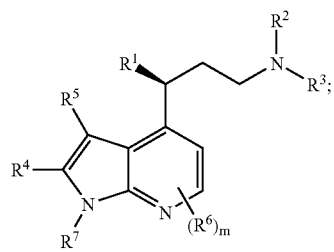

XIVa

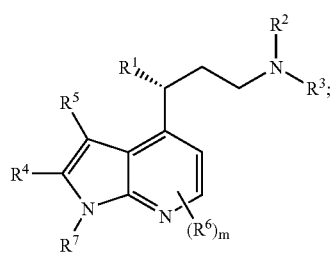

XIVb wherein m, $R^1$, $R^2$, $R^3$, $R^4$, $R^5$, $R^6$, and $R^7$ are as defined herein.

In embodiments of formula II wherein Y is CH and Ar is optionally substituted pyrrolo[2,3-b]pyrid-5-yl, the compounds of the invention may be more specifically of formula XV:

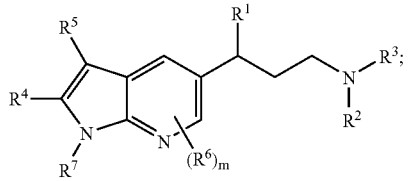

XV wherein m, $R^1$, $R^2$, $R^3$, $R^4$, $R^5$, $R^6$, and $R^7$ are as defined herein.

In certain embodiments of formula XV, the subject compounds may be more specifically of formula XVa or XVb:

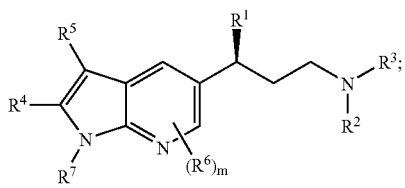

XVa

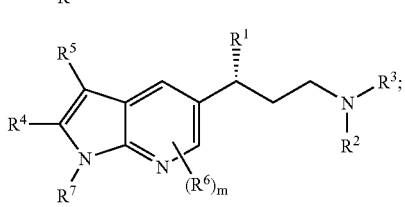

XVb wherein m, $R^1$, $R^2$, $R^3$, $R^4$, $R^5$, $R^6$, and $R^7$ are as defined herein.

In embodiments of formula II wherein Y is CH and Ar is optionally substituted pyrrolo[2,3-b]pyrid-6-yl, the compounds of the invention may be more specifically of formula XVI:

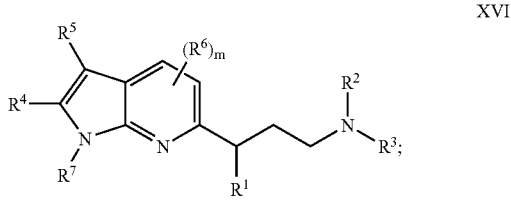

XVI wherein m, $R^1$, $R^2$, $R^3$, $R^4$, $R^5$, $R^6$, and $R^7$ are as defined herein.

In certain embodiments of formula XVI, the subject compounds may be more specifically of formula XVIa or XVIb:

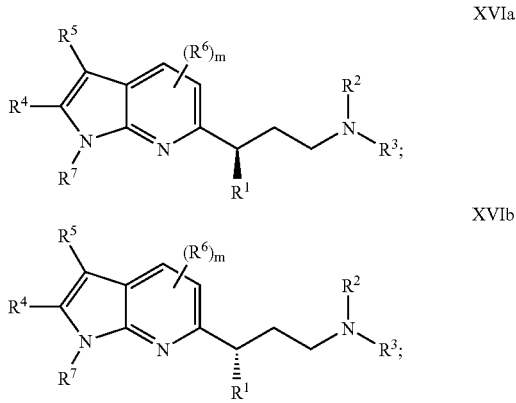

XVIa

XVIb wherein m, $R^1$, $R^2$, $R^3$, $R^4$, $R^5$, $R^6$, and $R^7$ are as defined herein.

In certain embodiments of any of formulas XIII, XIV, XIVa, XIVb, XV, XVa, XVb, XVI, XVIa or XVIb, one of $R^2$ and $R^3$ is hydrogen and the other is alkyl, preferably methyl.

In certain embodiments of any of formulas XIII, XIV, XIVa, XIVb, XV, XVa, XVb, XVI, XVIa or XVIb, $R^1$ is optionally substituted aryl, $R^1$ is optionally substituted phenyl.

In certain embodiments of any of formulas XIII, XIV, XIVa, XIVb, XV, XVa, XVb, XVI, XVIa or XVIb, $R^1$ is optionally substituted aryl, $R^1$ is optionally substituted naphthalenyl.

In certain embodiments of any of formulas XIII, XIV, XIVa, XIVb, XV, XVa, XVb, XVI, XVIa or XVIb, $R^1$ is optionally substituted aryl, $R^1$ is optionally substituted naphthalen-1-yl.

In certain embodiments of any of formulas XIII, XIV, XIVa, XIVb, XV, XVa, XVb, XVI, XVIa or XVIb, $R^1$ is optionally substituted aryl, $R^1$ is optionally substituted naphthalen-2-yl.

In certain embodiments of any of formulas XIII, XIV, XIVa, XIVb, XV, XVa, XVb, XVI, XVIa or XVIb, $R^1$ is optionally substituted heteroaryl. Such heteroaryl may be selected from indolyl, pyridinyl, thienyl, furanyl, pyrimidinyl, pyridazinyl, pyrazinyl, oxazolyl, thiazolyl, isoxazolyl, isothiazolyl, imidazolyl, pyrazolyl, quinolinyl, isoquinolinyl, quinoxalinyl, benzothiazolyl, benzofuranyl, benzothiophenyl or benzoxazinyl, each optionally substituted.

In certain embodiments of any of formulas XIII, XIV, XIVa, XIVb, XV, XVa, XVb, XVI, XVIa or XVIb, $R^1$ is optionally substituted indolyl.

In certain embodiments of any of formulas XIII, XIV, XIVa, XIVb, XV, XVa, XVb, XVI, XVIa or XVIb, $R^1$ is indol-2-yl, indol-3-yl, indol-4-yl, indol-5-yl, indol-6-yl, or indol-7-yl, each optionally substituted.

In certain embodiments of any of formulas XIII, XIV, XIVa, XIVb, XV, XVa, XVb, XVI, XVIa or XVIb, $R^1$ is indol-5-yl or indol-6-yl, each optionally substituted.

In certain embodiments of any of formulas XIII, XIV, XIVa, XIVb, XV, XVa, XVb, XVI, XVIa or XVIb, $R^1$ optionally substituted is indol-2-yl.

In certain embodiments of any of formulas XIII, XIV, XIVa, XIVb, XV, XVa, XVb, XVI, XVIa or XVIb, $R^1$ optionally substituted is indol-3-yl.

In certain embodiments of any of formulas XIII, XIV, XIVa, XIVb, XV, XVa, XVb, XVI, XVIa or XVIb, $R^1$ optionally substituted is indol-4-yl.

In certain embodiments of any of formulas XIII, XIV, XIVa, XIVb, XV, XVa, XVb, XVI, XVIa or XVIb, $R^1$ optionally substituted is indol-5-yl.

In certain embodiments of any of formulas XIII, XIV, XIVa, XIVb, XV, XVa, XVb, XVI, XVIa or XVIb, $R^1$ optionally substituted is indol-6-yl.

In certain embodiments of any of formulas XIII, XIV, XIVa, XIVb, XV, XVa, XVb, XVI, XVIa or XVIb, $R^1$ optionally substituted is indol-7-yl.

In certain embodiments of any of formulas XIII, XIV, XIVa, XIVb, XV, XVa, XVb, XVI, XVIa or XVIb, $R^1$ is optionally substituted quinolinyl.

In certain embodiments of any of formulas XIII, XIV, XIVa, XIVb, XV, XVa, XVb, XVI, XVIa or XVIb, $R^1$ is quinolin-2-yl, quinolin-3-yl, quinolin-4-yl, quinolin-5-yl, quinolin-6-yl, quinolin-7-yl or quinolin-8-yl, each optionally substituted.

In certain embodiments of any of formulas XIII, XIV, XIVa, XIVb, XV, XVa, XVb, XVI, XVIa or XVIb, $R^1$ is optionally substituted quinolin-6-yl.

In certain embodiments of any of formulas XIII, XIV, XIVa, XIVb, XV, XVa, XVb, XVI, XVIa or XVIb, $R^1$ is optionally substituted pyridinyl.

In certain embodiments of any of formulas XIII, XIV, XIVa, XIVb, XV, XVa, XVb, XVI, XVIa or XVIb, $R^1$ is pyridin-2-yl, pyridin-3-yl or pyridin-4-yl, each optionally substituted.

In certain embodiments of any of formulas XIII, XIV, XIVa, XIVb, XV, XVa, XVb, XVI, XVIa or XVIb, $R^1$ is optionally substituted pyridin-2-yl.

In certain embodiments of any of formulas XIII, XIV, XIVa, XIVb, XV, XVa, XVb, XVI, XVIa or XVIb, $R^1$ is optionally substituted pyridin-3-yl.

In certain embodiments of any of formulas XIII, XIV, XIVa, XIVb, XV, XVa, XVb, XVI, XVIa or XVIb, $R^1$ is optionally substituted pyridin-4-yl.

In certain embodiments of any of formulas XIII, XIV, XIVa, XIVb, XV, XVa, XVb, XVI, XVIa or XVIb, $R^1$ is optionally substituted quinoxalinyl.

In certain embodiments of any of formulas XIII, XIV, XIVa, XIVb, XV, XVa, XVb, XVI, XVIa or XVIb, $R^1$ is quinoxalin-2-yl, quinoxalin-3-yl, quinoxalin-5-yl, quinoxalin-6-yl, quinoxalin-7-yl or quinoxalin-8-yl, each optionally substituted.

In certain embodiments of any of formulas XIII, XIV, XIVa, XIVb, XV, XVa, XVb, XVI, XVIa or XVIb, $R^1$ is optionally substituted quinoxalin-6-yl.

In certain embodiments of any of formulas XIII, XIV, XIVa, XIVb, XV, XVa, XVb, XVI, XVIa or XVIb, $R^1$ is optionally substituted benzothiophenyl.

In certain embodiments of any of formulas XIII, XIV, XIVa, XIVb, XV, XVa, XVb, XVI, XVIa or XVIb, $R^1$ is optionally substituted benzothiophen-5-yl.

In certain embodiments of any of formulas XIII, XIV, XIVa, XIVb, XV, XVa, XVb, XVI, XVIa or XVIb, $R^1$ is optionally substituted benzoxazinyl. In such embodiments the benzoxazinyl may be 4-methyl-3,4-dihydro-2H-benzo[1,4]oxazin-7-yl.

In certain embodiments of any of formulas XIII, XIV, XIVa, XIVb, XV, XVa, XVb, XVI, XVIa or XVIb, $R^1$ is optionally substituted benzothiazolyl.

In certain embodiments of any of formulas XIII, XIV, XIVa, XIVb, XV, XVa, XVb, XVI, XVIa or XVIb, $R^1$ is optionally substituted benzothiazol-2-yl.

In certain embodiments of any of formulas XIII, XIV, XIVa, XIVb, XV, XVa, XVb, XVI, XVIa or XVIb, $R^1$ is optionally substituted benzothiazol-5-yl.

In certain embodiments of any of formulas XIII, XIV, XIVa, XIVb, XV, XVa, XVb, XVI, XVIa or XVIb, $R^1$ is optionally substituted benzothiazol-6-yl.

In certain embodiments of any of formulas XIII, XIV, XIVa, XIVb, XV, XVa, XVb, XVI, XVIa or XVIb, $R^1$ is optionally substituted thiazolyl.

In certain embodiments of any of formulas XIII, XIV, XIVa, XIVb, XV, XVa, XVb, XVI, XVIa or XVIb, $R^1$ is optionally substituted thiazol-2-yl.

In certain embodiments of any of formulas XIII, XIV, XIVa, XIVb, XV, XVa, XVb, XVI, XVIa or XVIb, $R^1$ is optionally substituted thiazol-4-yl.

In certain embodiments of any of formulas XIII, XIV, XIVa, XIVb, XV, XVa, XVb, XVI, XVIa or XVIb, $R^1$ is optionally substituted thiazol5-yl.

In certain embodiments of formula I, $R^1$ is optionally substituted benzoxazolyl.

In certain embodiments of any of formulas XIII, XIV, XIVa, XIVb, XV, XVa, XVb, XVI, XVIa or XVIb, $R^1$ is optionally substituted phenyl or optionally substituted pyridinyl.

In certain embodiments of any of formulas XIII, XIV, XIVa, XIVb, XV, XVa, XVb, XVI, XVIa or XVIb, $R^1$ is phenyl, pyridin-3-yl, 3-methoxyphenyl, pyridin-2-yl, 2-methoxyphenyl, 4-methoxyphenyl, 3-chlorophenyl, 4-chlorophenyl, or indol-3-yl.

In certain embodiments of formula XIII, XIV, XIVa, XIVb, XV, XVa, XVb, XVI, XVIa or XVIb, $R^4$ is hydrogen, cyano, carbamoyl, or alkyl. When $R^4$ is alkyl, preferably $R^4$ is methyl.

In certain embodiments of formula XIII, XIV, XIVa, XIVb, XV, XVa, XVb, XVI, XVIa or XVIb, $R^5$ is hydrogen, cyano, carbamoyl, or alkyl. When $R^5$ is alkyl, preferably $R^4$ is methyl.

In certain embodiments of formula XIII, XIV, XIVa, XIVb, XV, XVa, XVb, XVI, XVIa or XVIb, $R^7$ is hydrogen, alkyl, or alkylsulfonyl (i.e., $-SO_2R^8$, where $R^8$ is alkyl).

In certain embodiments of any of formulas XIII, XIV, XIVa, XIVb, XV, XVa, XVb, XVI, XVIa or XVIb, each $R^6$ is independently halo, alkyl, cyano, haloalkyl or alkoxy. In these cases, $R^6$ is preferably, fluoro, chloro, bromo, cyano, trifluoromethyl or methoxy. More preferably, $R^6$ is fluoro, chloro, or methoxy.

In certain embodiments of any of formulas XIII, XIV, XIVa, XIVb, XV, XVa, XVb, XVI, XVIa or XVIb, m is 0, 1 or 2 and each $R^6$ is independently fluoro, chloro, or methoxy.

In certain embodiments of any of formulas XIII, XIV, XIVa, XIVb, XV, XVa, XVb, XVI, XVIa or XVIb, m is 0, 1 or 2 and each $R^6$ is independently halo, alkoxy or cyano.

In certain embodiments of any of formulas XIII, XIV, XIVa, XIVb, XV, XVa, XVb, XVI, XVIa or XVIb, m is 0.

In certain embodiments of any of formulas XIII, XIV, XIVa, XIVb, XV, XVa, XVb, XVI, XVIa or XVIb, m is 1, and $R^6$ is located at the 4- or 7 position of the pyrrolo[2,3-b] pyridine ring system.

In certain embodiments of any of formulas XIII, XIV, XIVa, XIVb, XV, XVa, XVb, XVI, XVIa or XVIb, m is 1, and $R^6$ is halo, cyano or alkoxy at the 4- or 7 position of the pyrrolo[2,3-b]pyridine ring system.

In certain embodiments of formulas XIII, XIV, XIVa, XIVb, XV, XVa, XVb, XVI, XVIa or XVIb, $R^4$ and $R^5$ are hydrogen.

In certain embodiments of any of formulas XIII, XIV, XIVa, XIVb, XV, XVa, XVb, XVI, XVIa or XVIb, one of $R^4$ and $R^5$ is hydrogen and the other is alkyl, cyano, halo or alkoxy.

In certain embodiments of any of formulas XIII, XIV, XIVa, XIVb, XV, XVa, XVb, XVI, XVIa or XVIb, m is 0, 1 or 2, $R^1$ is optionally substituted phenyl, and one of $R^2$ and $R^3$ is hydrogen and the other is alkyl, preferably methyl.

In certain embodiments of any of formulas XIII, XIV, XIVa, XIVb, XV, XVa, XVb, XVI, XVIa or XVIb, m is 0, 1 or 2, $R^1$ is optionally substituted phenyl, one of $R^2$ and $R^3$ is hydrogen and the other is alkyl, preferably methyl, and $R^4$ and $R^5$ are hydrogen.

In certain embodiments of any of formulas XIII, XIV, XIVa, XIVb, XV, XVa, XVb, XVI, XVIa or XVIb, m is 0, 1 or 2, $R^1$ is optionally substituted phenyl, one of $R^2$ and $R^3$ is hydrogen and the other is alkyl, preferably methyl, $R^4$ and $R^5$ are hydrogen, and each $R^6$ is independently halo, cyano or alkoxy. In such embodiments optionally substituted phenyl may be phenyl optionally substituted one, two, three or four times with alkyl, alkoxy, cyano, halo, haloalkyl, haloalkoxy, alkoxyalkyl or hydroxyalkyl.

In certain embodiments of any of formulas XIII, XIV, XIVa, XIVb, XV, XVa, XVb, XVI, XVIa or XVIb, or VIIb, m is 0, 1 or 2, $R^1$ is optionally substituted pyridinyl, and one of $R^2$ and $R^3$ is hydrogen and the other is alkyl, preferably methyl. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In certain embodiments of formulas any of XIII, XIV, XIVa, XIVb, XV, XVa, XVb, XVI, XVIa or XVIb, m is 0, 1 or 2, $R^1$ is optionally substituted pyridinyl, one of $R^2$ and $R^3$ is hydrogen and the other is alkyl, preferably methyl, and $R^4$ and $R^5$ are hydrogen. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In certain embodiments of any of formulas XIII, XIV, XIVa, XIVb, XV, XVa, XVb, XVI, XVIa or XVIb, m is 0, 1 or 2, $R^1$ is optionally substituted pyridinyl, one of $R^2$ and $R^3$ is hydrogen and the other is alkyl, preferably methyl, $R^4$ and $R^5$ are hydrogen, and each $R^6$ is independently halo, cyano or alkoxy. In such embodiments optionally substituted pyridinyl may be pyridinyl optionally substituted one, two or three times with alkyl, alkoxy, cyano, halo, haloalkyl, haloalkoxy, alkoxyalkyl or hydroxyalkyl. In such embodiments $R^1$ is preferably pyridin-3-yl or pyridin-2-yl.

In embodiments of the invention wherein $R^1$ is substituted, preferred substituents are halo, alkyl, haloalkyl, alkoxy and haloalkoxy.

Where any of $R^1$, $R^2$, $R^3$, $R^4$, $R^5$, $R^6$, $R^7$, $R^a$, $R^b$, $R^c$, $R^d$, $R^e$, $R^f$, $R^g$ or $R^h$ herein are alkyl or contain an alkyl moiety, such alkyl is preferably lower alkyl, i.e. $C_1$-$C_6$alkyl, and more preferably $C_1$-$C_4$alkyl.

Representative compounds in accordance with the methods of the invention are shown in Table 1.

TABLE 1

| # | Structure | Name (Sysname) | MP (°C.) or M + H |
|---|---|---|---|
| 1 | 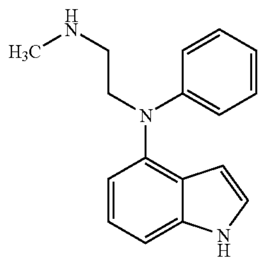 | N-(1H-Indol-4-yl)-N'-methyl-N-phenyl-ethane-1,2-diamine | 266 |
| 2 | 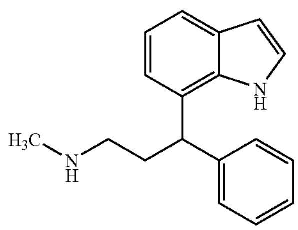 | [3-(1H-Indol-7-yl)-3-phenyl-propyl]-methyl-amine hydrochloride | 115.3-117.0 (HCl salt) |
| 3 | 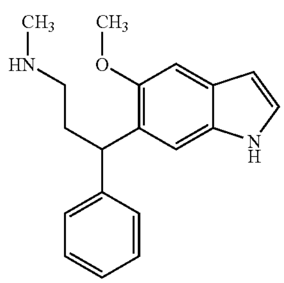 | 3-(5-Methoxy-1H-indol-6-yl)-3-phenyl-propyl]-methyl-amine | 295 |
| 4 | 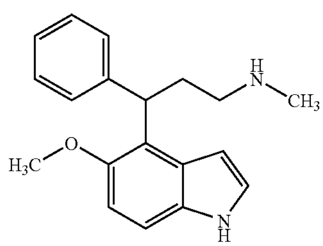 | [3-(5-Methoxy-1H-indol-4-yl)-3-phenyl-propyl]-methyl-amine | 295 |
| 5 | 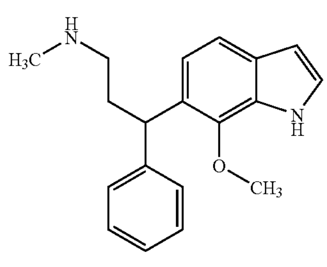 | [3-(7-Methoxy-1H-indol-6-yl)-3-phenyl-propyl]-methyl-amine | 295 |
| 6 | 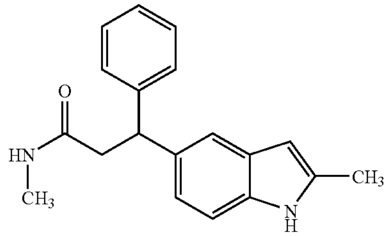 | N-Methyl-3-(2-methyl-1H-indol-5-yl)-3-phenyl-propionamide | 293 |

TABLE 1-continued

| # | Name (Sysname) | MP (°C.) or M + H |
|---|---|---|
| 7 | Methyl-[3-(2-methyl-1H-indol-5-yl)-3-phenyl-propyl]-amine | 95.7-98.6 (HCl salt) |
| 8 | N-Methyl-3-(1-methyl-1H-indol-6-yl)-3-phenyl-propionamide | 293 |
| 9 | Methyl-[3-(1-methyl-1H-indol-6-yl)-3-phenyl-propyl]-amine | 81.3-83.0 (HCl salt) |
| 10 | 5-(3-Methylamino-1H-phenyl-propyl)-1H-indole-3-carbonitrile | 170.3-171.9 |
| 11 | [3-(4-Methoxy-1H-indol-7-yl)-3-phenyl-propyl]-methyl-amine | 170.3-171.9 (HCl salt) |
| 12 | 4-(3-Methylamino-1-phenyl-propyl)-1H-indole-3-carbonitrile | 77.3-78.9 |

TABLE 1-continued

| # | Structure | Name (Sysname) | MP (°C.) or M + H |
|---|---|---|---|
| 13 | 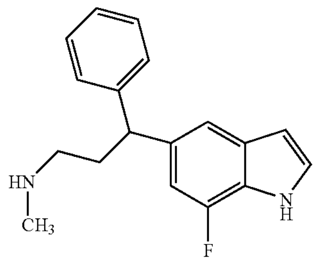 | 3-(7-Fluoro-1H-indol-5-yl)-3-phenyl-propyl]-methyl-amine | 192.3-194.3 (HCl salt) |
| 14 | 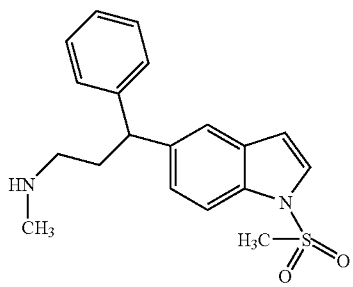 | [3-(1-Methanesulfonyl-1H-indol-5-yl)-3-phenyl-propyl]-methyl-amine hydrochloride | 192.3-194.3 (HCl salt) |
| 15 | 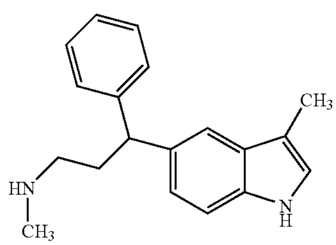 | Methyl-[3-(3-methyl-1H-indol-5-yl)-3-phenyl-propyl]-amine | 279 |
| 16 | 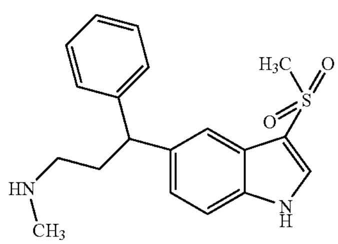 | 3-(3-Methanesulfonyl-1H-indol-5-yl)-3-phenyl-propyl]-methyl-amine | 343 |
| 17 | 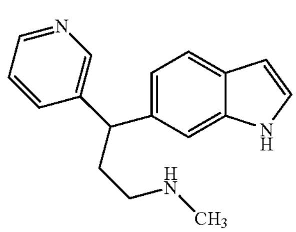 | [3-(1H-Indol-6-yl)-3-pyridin-3-yl-propyl]-methyl-amine | 266 |

TABLE 1-continued

| # | Structure | Name (Sysname) | MP (°C.) or M + H |
|---|---|---|---|
| 18 | 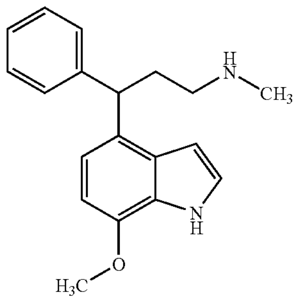 | [3-(7-Methoxy-1H-indol-4-yl)-3-phenyl-propyl]-methyl-amine | 295 |
| 19 | 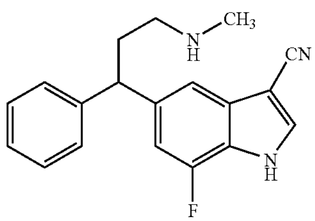 | 7-Fluoro-5-(3-methylamino-1-phenyl-propyl)-1H-indole-3-carbonitrile | 308 |
| 20 | 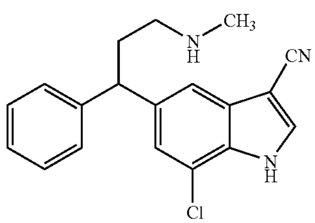 | 7-Chloro-5-(3-methylamino-1-phenyl-propyl)-1H-indole-3-carbonitrile | 206.2-207.9 |
| 21 | 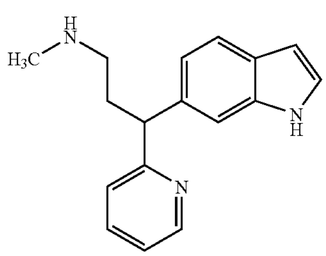 | [3-(1H-Indol-6-yl)-3-pyridin-2-yl-propyl]-methyl-amine | >300 (HCl hydrate) |
| 22 | 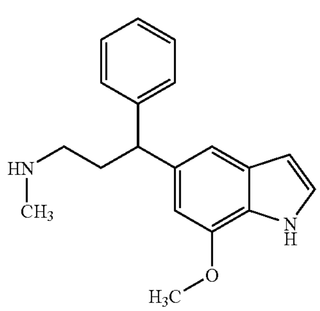 | [3-(7-Methoxy-1H-indol-5-yl)-3-phenyl-propyl]-methyl-amine | 198.1-199.9 (HCl salt) |

TABLE 1-continued

| # | Structure | Name (Sysname) | MP (°C.) or M + H |
|---|---|---|---|
| 23 | 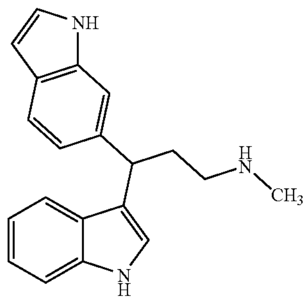 | [3-(1H-Indol-6-yl)-3-(1H-indol-3-yl)-propyl]-methyl-amine | 92.2-94.0 |
| 24 | 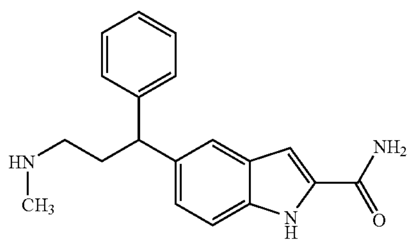 | 5-(3-Methylamino-1-phenyl-propyl)-1H-indole-2-carboxylic acid amide | 308 |
| 25 | 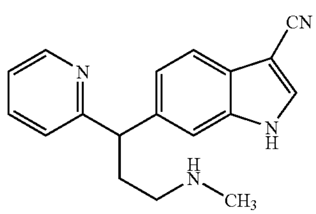 | 6-(3-Methylamino-1-pyridin-2-yl-propyl)-1H-indole-3-carbonitrile | 291 |
| 26 | 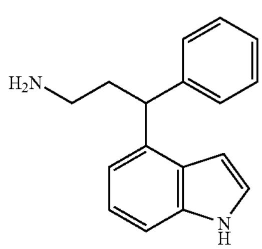 | 3-(1H-Indol-4-yl)-3-phenyl-propylamine | 79-89 (HCl salt) |
| 27 | 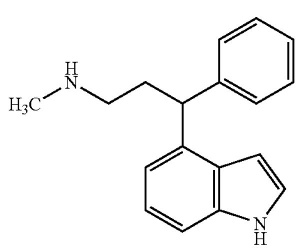 | [3-(1H-Indol-4-yl)-3-phenyl-propyl]-methyl-amine | 239-242 (HCl salt) |
| 28 | 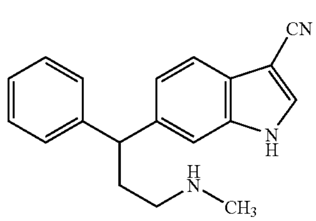 | 6-(3-Methylamino-1-phenyl-propyl)-1H-indole-3-carbonitrile | 152-154 |

TABLE 1-continued

| # | Structure | Name (Sysname) | MP (°C.) or M + H |
|---|---|---|---|
| 29 | 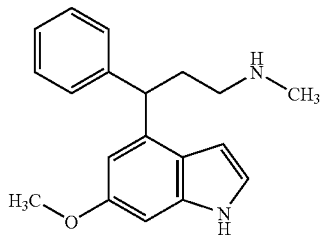 | [3-(6-Methoxy-1H-indol-4-yl)-3-phenyl-propyl]-methyl-amine | 130-134 |
| 30 | 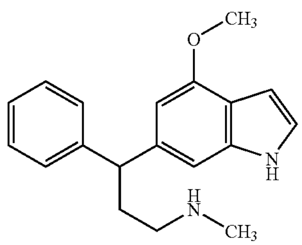 | 3-(4-Methoxy-1H-indol-6-yl)-3-phenyl-propyl]-methyl-amine | 157-158 |
| 31 | 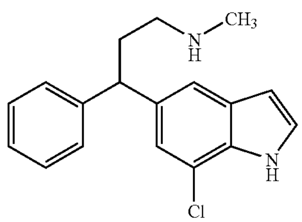 | [3-(7-Chloro-1H-indol-5-yl)-3-phenyl-propyl]-methyl-amine | 120.3-120.6 |
| 32 | 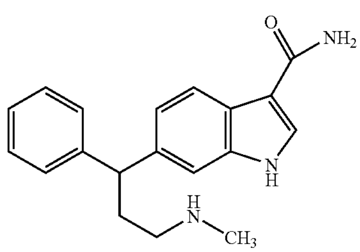 | 6-(3-Methylamino-1-phenyl-propyl)-1H-indole-3-carboxylic acid amide | 181-182 |
| 33 | 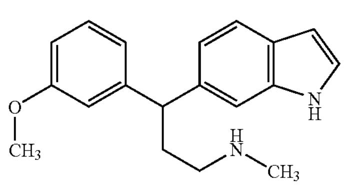 | [3-(1H-Indol-6-yl)-3-(3-methoxy-phenyl)-propyl]-methyl-amine | 124-126 (HCl salt) |
| 34 | 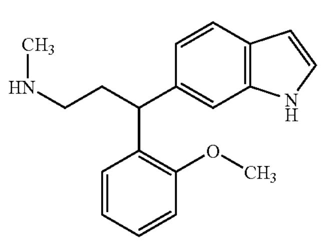 | [3-(1H-Indol-6-yl)-3-(2-methoxy-phenyl)-propyl]-methyl-amine | 157-159 |

TABLE 1-continued

| # | Structure | Name (Sysname) | MP (°C.) or M + H |
|---|---|---|---|
| 35 | 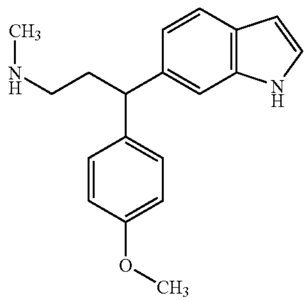 | [3-(1H-Indol-6-yl)-3-(4-methoxy-phenyl)-propyl]-methyl-amine hydrochloride | 122-124 (HCl salt) |
| 36 | 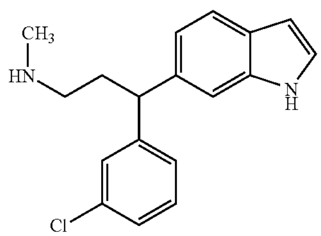 | [3-(3-Chloro-phenyl)-3-(1H-indol-6-yl)-propyl]-methyl-amine | 62-63 (HCl salt) |
| 37 | 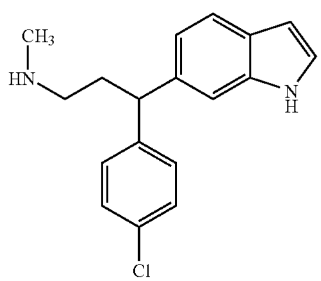 | [3-(4-Chloro-phenyl)-3-(1H-indol-6-yl)-propyl]-methyl-amine hydrochloride | 110-111 (HCl salt) |
| 38 | 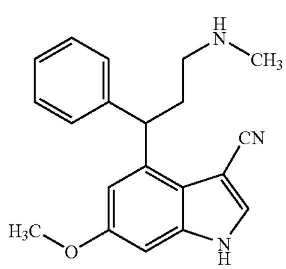 | 6-Methoxy-4-(3-methylamino-1-phenyl-propyl)-1H-indole-3-carbonitrile | 181.7-182.4 |
| 39 | 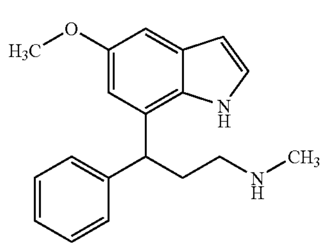 | [3-(5-Methoxy-1H-indol-7-yl)-3-phenyl-propyl]-methyl-amine | 102-104 |

TABLE 1-continued

| # | Structure | Name (Sysname) | MP (°C.) or M + H |
|---|---|---|---|
| 40 | 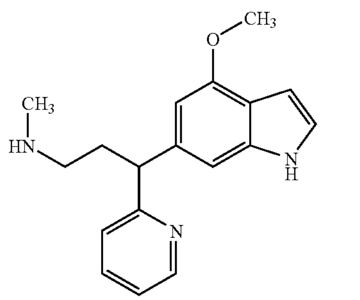 | [3-(4-Methoxy-1H-indol-6-yl)-3-pyridin-2-yl-propyl]-methyl-amine | 74-75 |
| 41 | 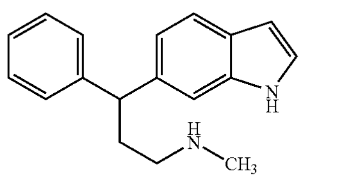 | [3-(1H-Indol-6-yl)-3-phenyl-propyl]-methyl-amine | 218-221 (HCl salt) |
| 42 | 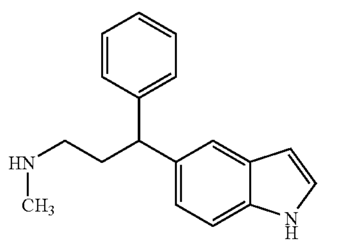 | [3-(1H-Indol-5-yl)-3-phenyl-propyl]-methyl-amine | 76-85 (HCl salt) |
| 43 | 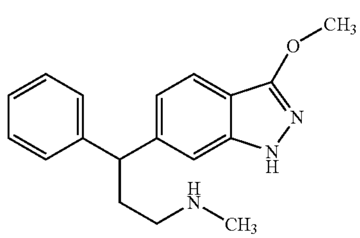 | [3-(3-Methoxy-1H-indazol-6-yl)-3-phenyl-propyl]-methyl-amine | 296 |
| 44 | 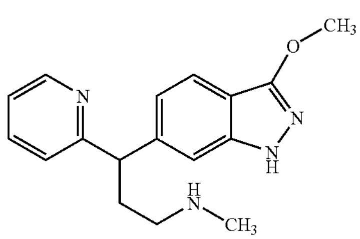 | [3-(3-Methoxy-1H-indazol-6-yl)-3-pyridin-2-yl-propyl]-methyl-amine | 297 |
| 45 | 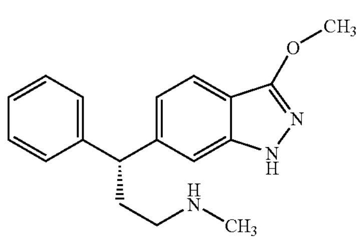 | [(R)-3-(3-Methoxy-1H-indazol-6-yl)-3-phenyl-propyl]-methyl-amine | 296 |

TABLE 1-continued

| # | Structure | Name (Sysname) | MP (°C.) or M + H |
|---|---|---|---|
| 46 | 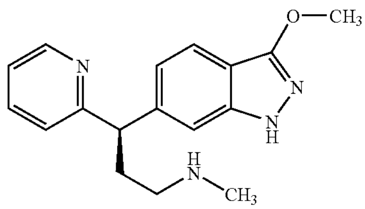 | [(R)-3-(3-Methoxy-1H-indazol-6-yl)-3-pyridin-2-yl-propyl]-methyl-amine | 297 |
| 47 | 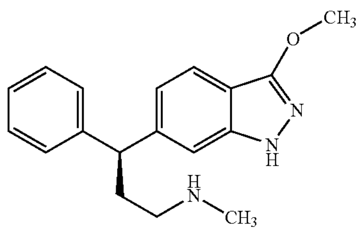 | [(S)-3-(3-Methoxy-1H-indazol-6-yl)-3-phenyl-propyl]-methyl-amine | 296 |
| 48 | 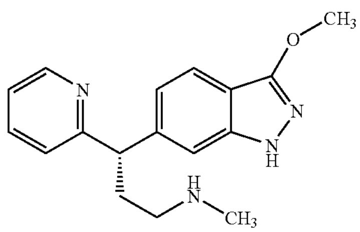 | [(S)-3-(3-Methoxy-1H-indazol-6-yl)-3-pyridin-2-yl-propyl]-methyl-amine | 297 |
| 49 | 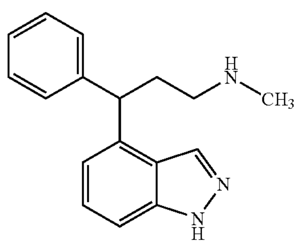 | [3-(1H-Indazol-4-yl)-3-phenyl-propyl]-methyl-amine | 130.6-133.1 (HCl salt) |
| 50 | 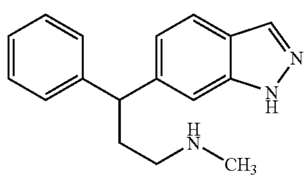 | [3-(1H-Indazol-6-yl)-3-phenyl-propyl]-methyl-amine | 83.7-85.2 (HCl salt) |
| 51 | 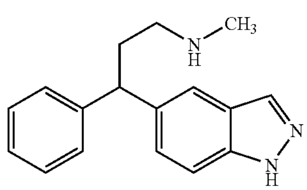 | [3-(1H-Indazol-5-yl)-3-phenyl-propyl]-methyl-amine hydrochloride | 84.2-85.3 (HCl salt) |
| 52 | 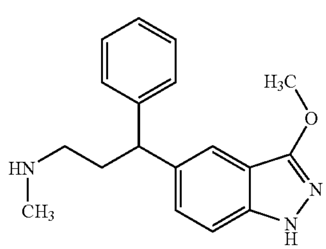 | [3-(3-Methoxy-1H-indazol-5-yl)-3-phenyl-propyl]-methyl-amine | 75.3-76.9 (TFA salt) |

TABLE 1-continued

| # | Structure | Name (Sysname) | MP (°C.) or M + H |
|---|---|---|---|
| 53 | 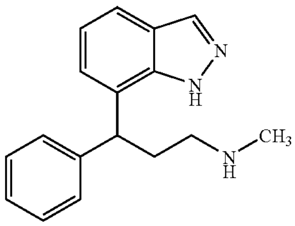 | [3-(1H-Indazol-7-yl)-3-phenyl-propyl]-methyl-amine | 76.0-85.9 (TFA salt) |
| 54 | 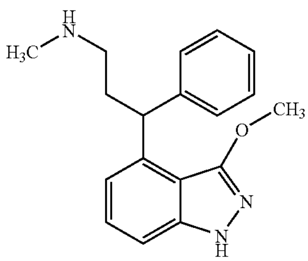 | [3-(3-Methoxy-1H-indazol-4-yl)-3-phenyl-propyl]-methyl-amine | 97.3-99.0 (TFA salt) |
| 55 | 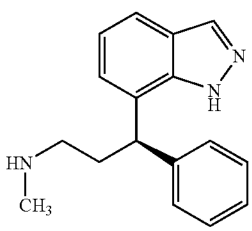 | [(R)-3-(1H-Indazol-7-yl)-3-phenyl-propyl]-methyl-amine | 61.9-65.7 (TFA salt) |
| 56 | 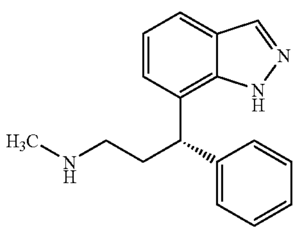 | [(S)-3-(1H-Indazol-7-yl)-3-phenyl-propyl]-methyl-amine | 62.0-68.1 (TFA salt) |
| 57 | 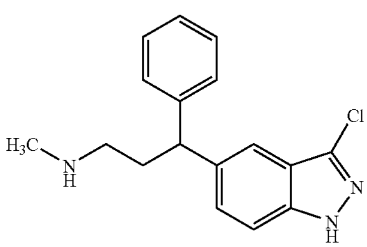 | [3-(3-Chloro-1H-indazol-5-yl)-3-phenyl-propyl]-methyl-amine | 104.5-105.6 (TFA salt) |
| 58 | 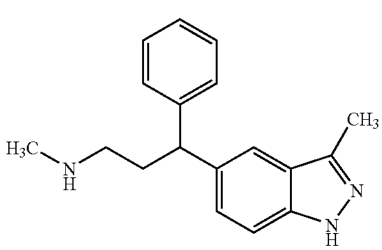 | Methyl-[3-(3-methyl-1H-indazol-5-yl)-3-phenyl-propyl]-amine | 64.5-66.0 (TFA salt) |

TABLE 1-continued

| # | Structure | Name (Sysname) | MP (°C.) or M + H |
|---|---|---|---|
| 59 | 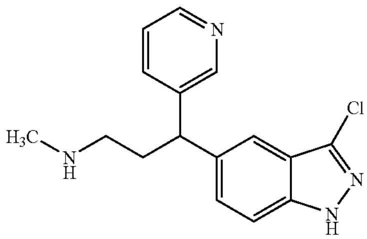 | [3-(3-Chloro-1H-indazol-5-yl)-3-pyridin-3-yl-propyl]-methyl-amine | 301 |
| 60 | 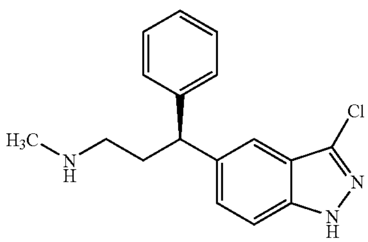 | [(S)-3-(3-Chloro-1H-indazol-5-yl)-3-phenyl-propyl]-methyl-amine | 84.7-86.1 (TFA salt) |
| 61 | 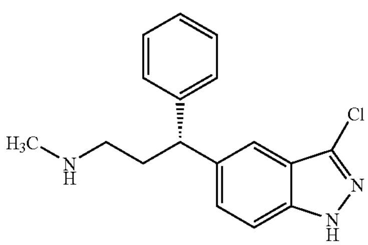 | [(R)-3-(3-Chloro-1H-indazol-5-yl)-3-phenyl-propyl]-methyl-amine trifluoracetate | 93.4-95.0 (TFA salt) |
| 62 | 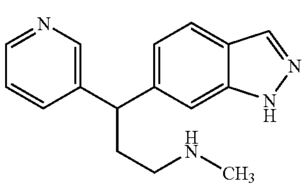 | [3-(1H-Indazol-6-yl)-3-pyridin-3-yl-propyl]-methyl-amine | 267 |
| 63 | 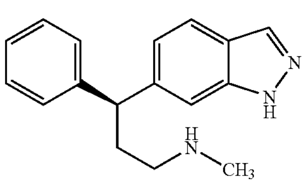 | [(S)-3-(1H-Indazol-6-yl)-3-phenyl-propyl]-methyl-amine | 85.9-87.0 (TFA salt) |
| 64 | 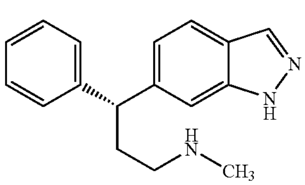 | [(R)-3-(1H-lndazol-6-yl)-3-phenyl-propyl]-methyl-amine | 83.5-85.0 (TFA salt) |

TABLE 1-continued

| # | Structure | Name (Sysname) | MP (°C.) or M + H |
|---|---|---|---|
| 65 | 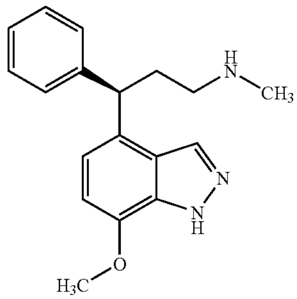 | [(R)-3-(7-Methoxy-1H-indazol-4-yl)-3-phenyl-propyl]-methyl-amine | 74.0-75.9 |
| 66 | 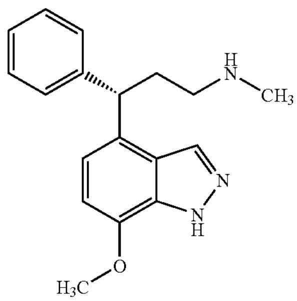 | [(S)-3-(7-Methoxy-1H-indazol-4-yl)-3-phenyl-propyl]-methyl-amine | 73.9-75.1 |
| 67 | 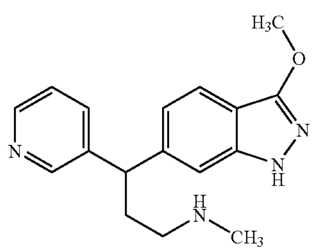 | [3-(3-Methoxy-1H-indazol-6-yl)-3-pyridin-3-yl-propyl]-methyl-amine | 297 |
| 68 | 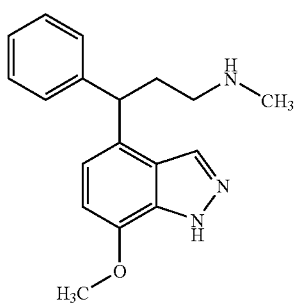 | [3-(7-Methoxy-1H-indazol-4-yl)-3-phenyl-propyl]-methyl-amine | 97.0-98.0 |
| 69 | 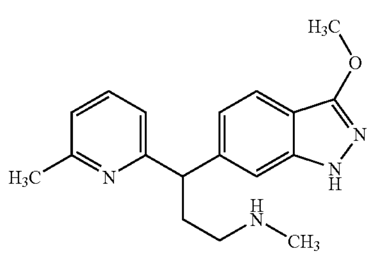 | [3-(3-Methoxy-1H-indazol-6-yl)-3-(6-methyl-pyridin-2-yl)-propyl]-methyl-amine | 311 |

TABLE 1-continued

| # | Structure | Name (Sysname) | MP (°C.) or M + H |
|---|---|---|---|
| 70 | 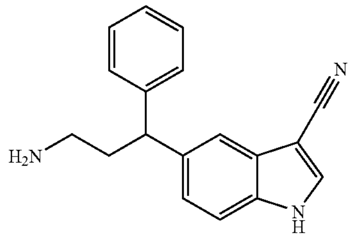 | 5-(3-Amino-1-phenyl-propyl)-1H-indole-3-carbonitrile | 277 |
| 71 | 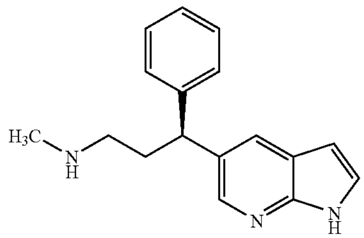 | Methyl-[(S)-3-phenyl-3-(1H-pyrrolo[2,3-b]pyridin-5-yl)-propyl]-amine | 140.7-141.3 |
| 72 | 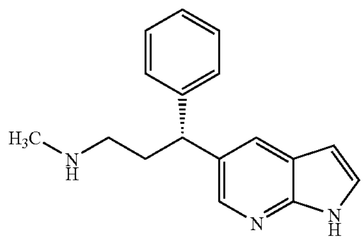 | Methyl-[(R)-3-phenyl-3-(1H-pyrrolo[2,3-b]pyridin-5-yl)-propyl]-amine | 141.5-142.2 |
| 73 | 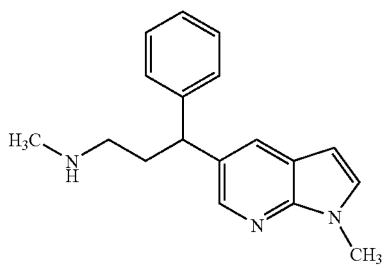 | Methyl-[3-(1-methyl-1H-pyrrolo[2,3-b]pyridin-5-yl)-3-phenyl-propyl]-amine hydrochloride | 184.9-186.2 (HCl Salt) |
| 74 | 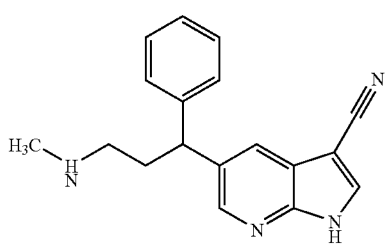 | 5-(3-Methylamino-1-phenyl-propyl)-1H-pyrrolo[2,3-b]pyridine-3-carbonitrile | 291 |
| 75 | 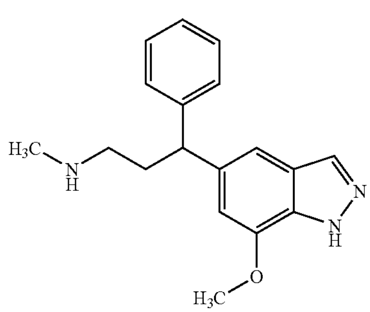 | [3-(7-Methoxy-1H-indazol-5-yl)-3-phenyl-propyl]-methyl-amine | 296 |

TABLE 1-continued

| # | Structure | Name (Sysname) | MP (°C.) or M + H |
|---|---|---|---|
| 76 | 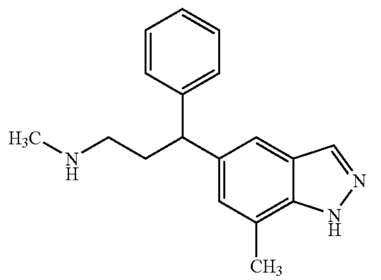 | Methyl-[3-(7-methyl-1H-indazol-5-yl)-3-phenyl-propyl]-amine | 280 |
| 77 | 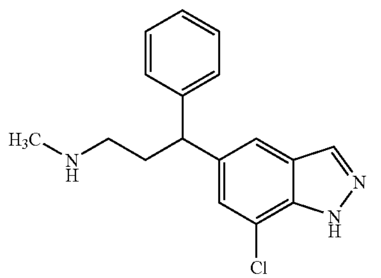 | [3-(7-Chloro-1H-indazol-5-yl)-3-phenyl-propyl]-methyl-amine | 300 |
| 78 | 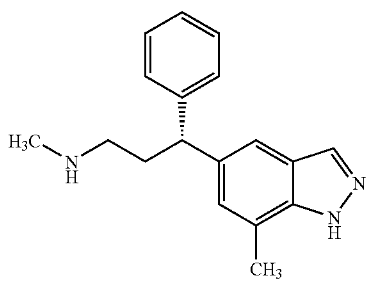 | Methyl-[3-(7-methyl-1H-indazol-5-yl)-3-(R)-phenyl-propyl]-amine | 280 |
| 79 | 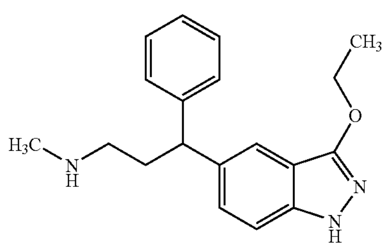 | [3-(3-Ethoxy-1H-indazol-5-yl)-3-phenyl-propyl]-methyl-amine | 310 |
| 80 | 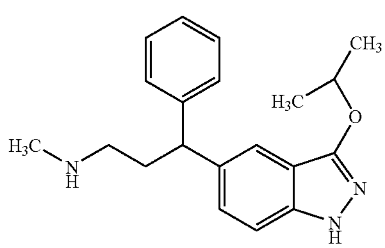 | [3-(3-Isopropoxy-1H-indazol-5-yl)-3-phenyl-propyl]-methyl-amine | 324 |

TABLE 1-continued

| # | Structure | Name (Sysname) | MP (°C.) or M + H |
|---|---|---|---|
| 81 | 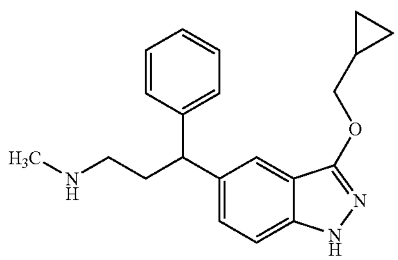 | [3-(3-Cyclopropylmethoxy-1H-indazol-5-yl)-3-phenyl-propyl]-methyl-amine | 336 |
| 82 | 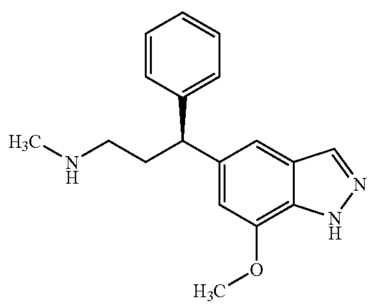 | [3-(7-Methoxy-1H-indazol-5-yl)-3-(S)-phenyl-propyl]-methyl-amine | 296 |
| 83 | 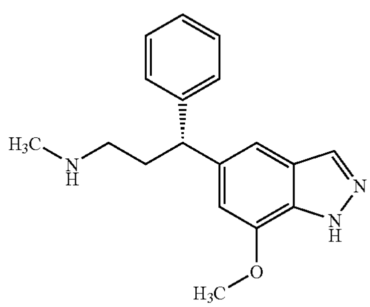 | [3-(7-Methoxy-1H-indazol-5-yl)-3-(R)-phenyl-propyl]-methyl-amine | 296 |
| 84 | 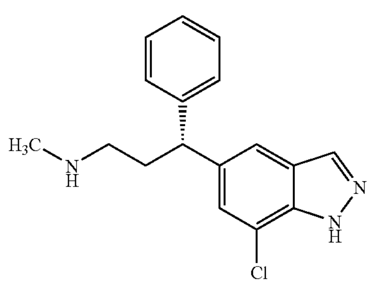 | [3-(7-Chloro-1H-indazol-5-yl)-3-(R)-phenyl-propyl]-methyl-amine | 300 |
| 85 | 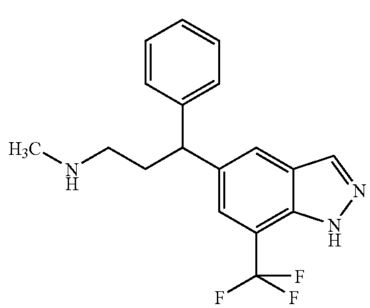 | Methyl-[3-phenyl-3-(7-trifluoromethyl-1H-indazol-5-yl)-propyl]-amine | 334 |

TABLE 1-continued

| # | Structure | Name (Sysname) | MP (°C.) or M + H |
|---|---|---|---|
| 86 | 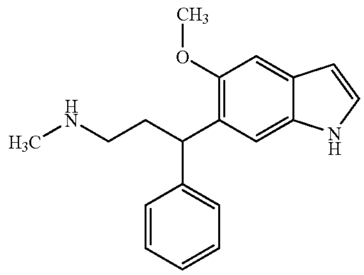 | [3-(5-Methoxy-1H-indol-6-yl)-3-phenyl-propyl]-methyl-amine | 296 |
| 87 | 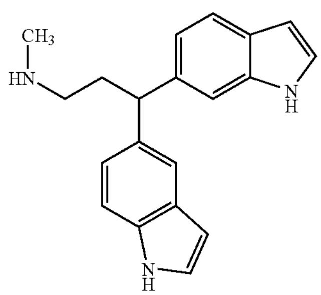 | [3-(1H-Indol-5-yl)-3-(1H-indol-6-yl)-propyl]-methyl-amine | 304 |
| 88 | 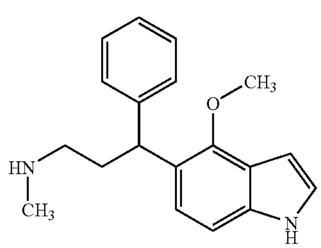 | [3-(4-Methoxy-1H-indol-5-yl)-3-phenyl-propyl]-methyl-amine | 296 |
| 89 | 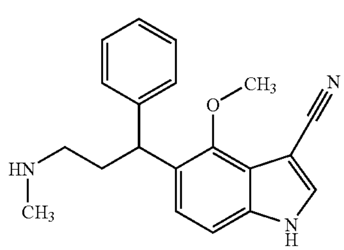 | 4-Methoxy-5-(3-methylamino-1-phenyl-propyl)-1H-indole-3-carbonitrile | 142.5-142.9 |
| 90 | 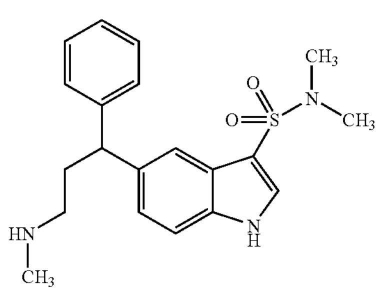 | 5-(3-Methylamino-1-phenyl-propyl)-1H-indole-3-sulfonic acid dimethylamide | 372 |

TABLE 1-continued

| # | Structure | Name (Sysname) | MP (°C.) or M + H |
|---|---|---|---|
| 91 | 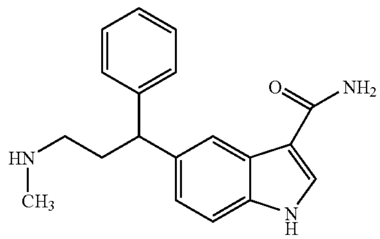 | 5-(3-Methylamino-1-phenyl-propyl)-1H-indole-3-carboxylic acid amide | 308 |
| 92 | 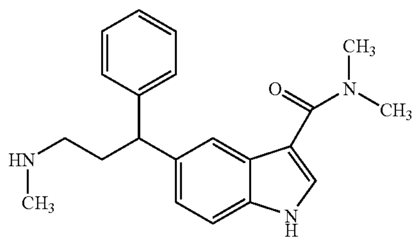 | 5-(3-Methylamino-1-phenyl-propyl)-1H-indole-3-carboxylic acid dimethylamide | 336 |
| 93 | 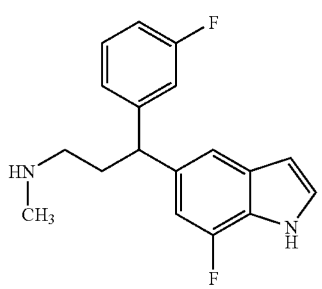 | [3-(7-Fluoro-1H-indol-5-yl)-3-(3-fluoro-phenyl)-propyl]-methyl-amine | 141.7-145.0 (HCl Salt) |
| 94 | 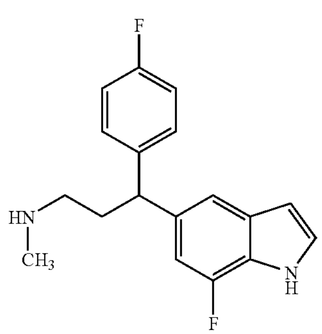 | [3-(7-Fluoro-1H-indol-5-yl)-3-(4-fluoro-phenyl)-propyl]-methyl-amine | 154.6-156.7 (HCl Salt) |
| 95 | 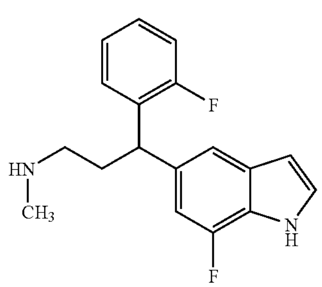 | [3-(7-Fluoro-1H-indol-5-yl)-3-(2-fluoro-phenyl)-propyl]-methyl-amine | 143.0-146.3 (HCl Salt) |

TABLE 1-continued

| # | Structure | Name (Sysname) | MP (°C.) or M + H |
|---|---|---|---|
| 96 | 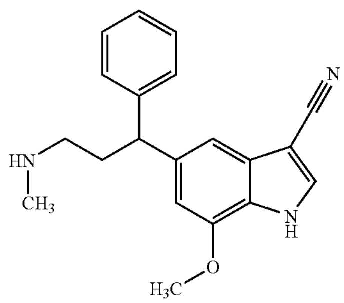 | 7-Methoxy-5-(3-methylamino-1-phenyl-propyl)-1H-indole-3-carbonitrile | 320 |
| 97 | 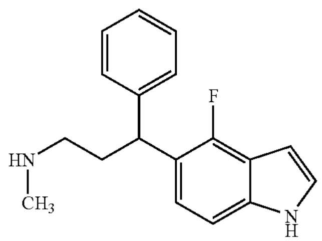 | [3-(4-Fluoro-1H-indol-5-yl)-3-phenyl-propyl]-methyl-amine | 283 |
| 98 | 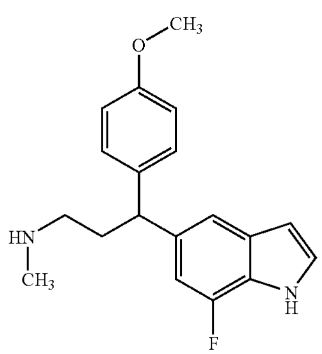 | [3-(7-Fluoro-1H-indol-5-yl)-3-(4-methoxy-phenyl)-propyl]-methyl-amine | 124.5-125.8 (HCl Salt) |
| 99 | 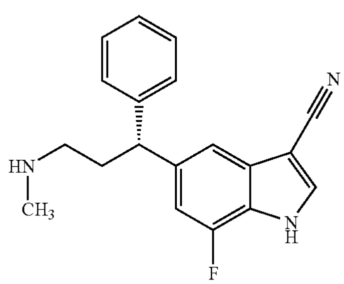 | 7-Fluoro-5-(3-methylamino-1-(R)-phenyl-propyl)-1H-indole-3-carbonitrile | 86.5-89.0 |
| 100 | 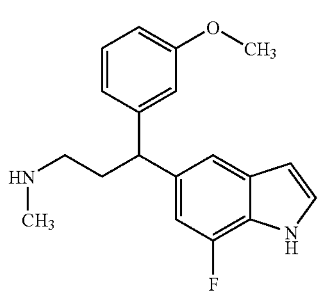 | [3-(7-Fluoro-1H-indol-5-yl)-3-(3-methoxy-phenyl)-propyl]-methyl-amine | 112.0-118.1 (HCl Salt) |

TABLE 1-continued

| # | Structure | Name (Sysname) | MP (°C.) or M + H |
|---|---|---|---|
| 101 | 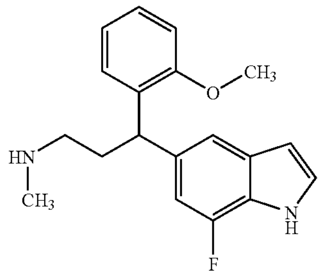 | [3-(7-Fluoro-1H-indol-5-yl)-3-(2-methoxy-phenyl)-propyl]-methyl-amine | 112.5-118.5 (HCl Salt) |
| 102 | 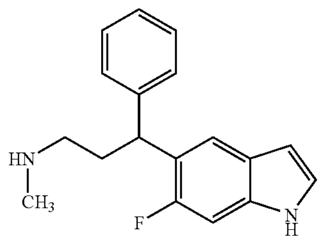 | [3-(6-Fluoro-1H-indol-5-yl)-3-phenyl-propyl]-methyl-amine | 283 |
| 103 | 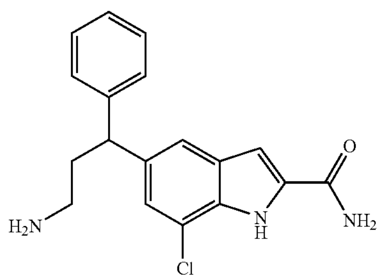 | 5-(3-Amino-1-phenyl-propyl)-7-chloro-1H-indole-2-carboxylic acid amide | 328 |
| 104 | 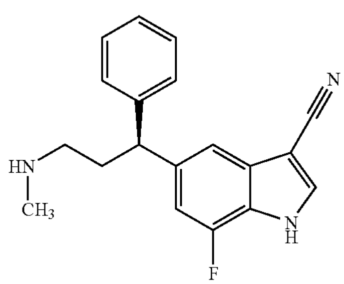 | 7-Fluoro-5-(3-methylamino-1-(S)-phenyl-propyl)-1H-indole-3-carbonitrile | 171.1-172.9 |
| 105 | 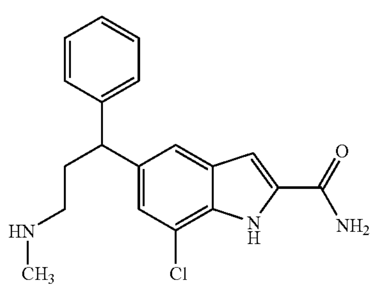 | 7-Chloro-5-(3-methylamino-1-phenyl-propyl)-1H-indole-2-carboxylic acid amide | 109.9-110.8 |

TABLE 1-continued

| # | Structure | Name (Sysname) | MP (°C.) or M + H |
|---|---|---|---|
| 106 | 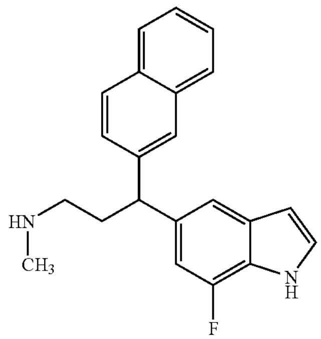 | [3-(7-Fluoro-1H-indol-5-yl)-3-naphthalen-2-yl-propyl]-methyl-amine | 149.5-152.0 (HCl Salt) |
| 107 | 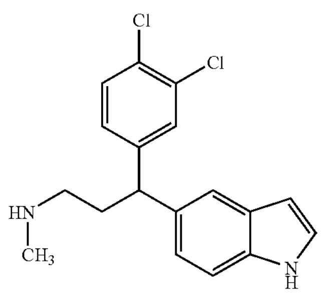 | [3-(3,4-Dichloro-phenyl)-3-(1H-indol-5-yl)-propyl]-methyl-amine | 140.0-146.0 (HCl Salt) |
| 108 | 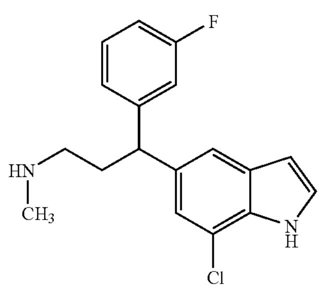 | 3-(7-Chloro-1H-indol-5-yl)-3-(3-fluoro-phenyl)-propyl]-methyl-amine | 317 |
| 109 | 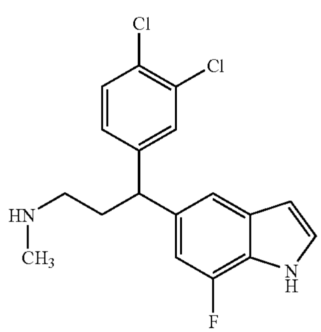 | [3-(3,4-Dichloro-phenyl)-3-(7-fluoro-1H-indol-5-yl)-propyl]-methyl-amine | 135.5-144.0 (HCl Salt) |
| 110 | 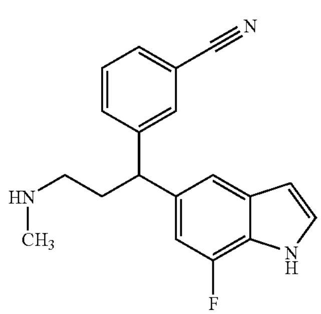 | 3-[1-(7-Fluoro-1H-indol-5-yl)-3-methylamino-propyl]-benzonitrile | 110.0-117.5 (HCl Salt) |

TABLE 1-continued

| # | Structure | Name (Sysname) | MP (°C.) or M + H |
|---|---|---|---|
| 111 | 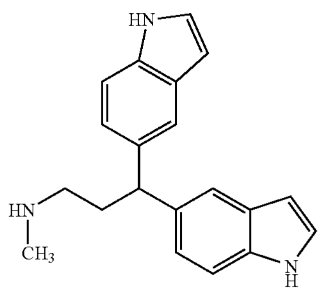 | [3,3-Bis-(1H-indol-5-yl)-propyl]-methyl-amine | 142.0-152.0 |
| 112 | 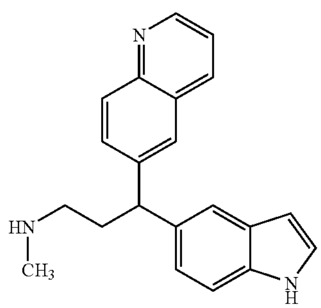 | [3-(1H-Indol-5-yl)-3-quinolin-6-yl-propyl]-methyl-amine | 102.0-104.0 |
| 113 | 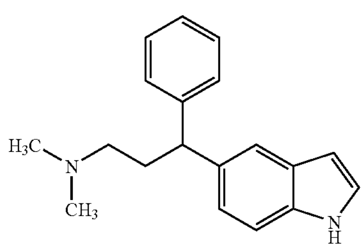 | [3-(1H-Indol-5-yl)-3-phenyl-propyl]-dimethyl-amine | 279 |
| 114 | 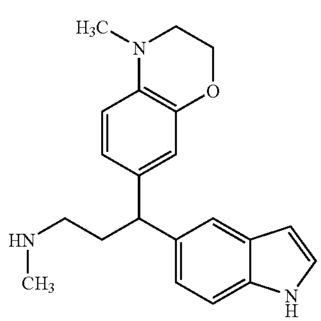 | [3-(1H-Indol-5-yl)-3-(4-methyl-3,4-dihydro-2H-benzo[1,4]oxazin-7-yl)-propyl]-methyl-amine | 62.5-70.5 |
| 115 | 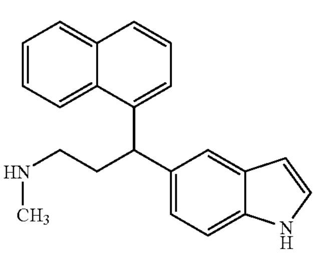 | [3-(1H-Indol-5-yl)-3-naphthalen-1-yl-propyl]-methyl-amine | 83.5-86.6 |

TABLE 1-continued

| # | Structure | Name (Sysname) | MP (°C.) or M + H |
|---|---|---|---|
| 116 | 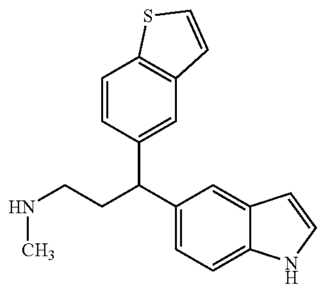 | [3-Benzo[b]thiophen-5-yl-3-(1H-indol-5-yl)-propyl]-methyl-amine | 70.9-75.9 |
| 117 | 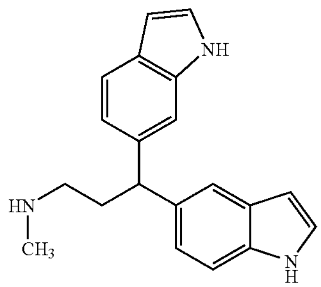 | [3-(1H-Indol-6-yl)-3-(1H-indol-5-yl)-propyl]-methyl-amine | 304 |
| 118 | 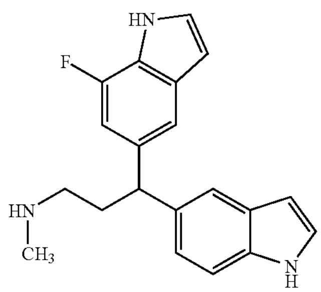 | [3-(7-Fluoro-1H-indol-5-yl)-3-(1H-indol-5-yl)-propyl]-methyl-amine | 150.3-154.9 |
| 119 | 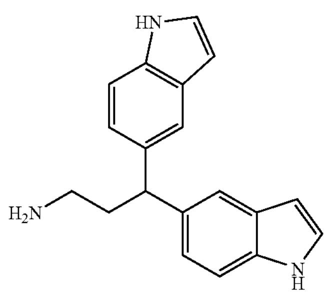 | 3,3-Bis-(1H-indol-5-yl)-propylamine | 72.0-77.6 |
| 120 | 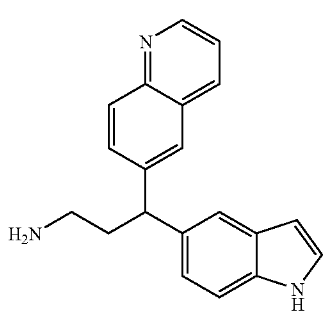 | 3-(1H-Indol-5-yl)-3-quinolin-6-yl-propylamine | 60.9-62.9 |

TABLE 1-continued

| # | Structure | Name (Sysname) | MP (°C.) or M + H |
|---|---|---|---|
| 121 | 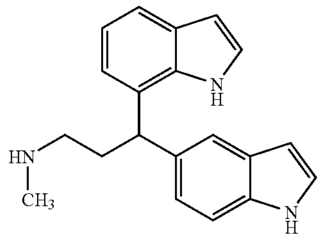 | [3-(1H-Indol-7-yl)-3-(1H-indol-5-yl)-propyl]-methyl-amine | 304 |
| 122 | 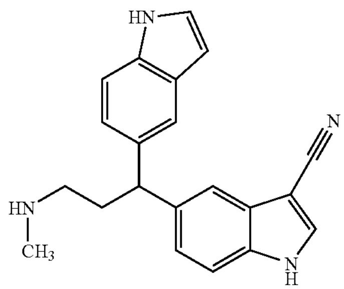 | 5-[1-(1H-Indol-5-yl)-3-methylamino-propyl]-1H-indole-3-carbonitrile | 120.9-127.7 |
| 123 | 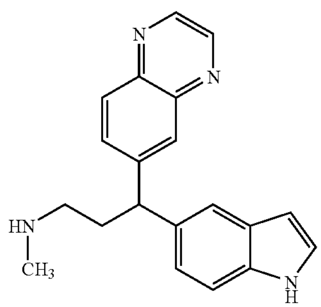 | [3-(1H-Indol-5-yl)-3-quinoxalin-6-yl-propyl]-methyl-amine | 60.3-62.0 |
| 124 | 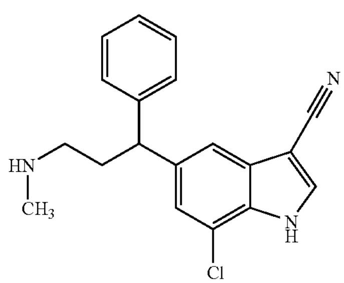 | 7-Chloro-5-(3-methylamino-1-phenyl-propyl)-1H-indole-3-carbonitrile | 193.9-198.0 |
| 125 | 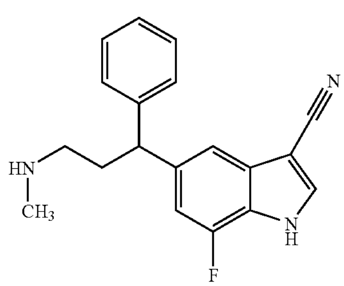 | 7-Fluoro-5-(3-methylamino-1-phenyl-propyl)-1H-indole-3-carbonitrile | 215.1-217.7 |

TABLE 1-continued

| # | Structure | Name (Sysname) | MP (°C.) or M + H |
|---|---|---|---|
| 126 | 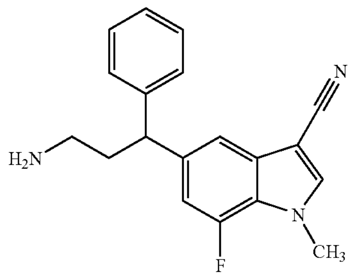 | 5-(3-Amino-1-phenyl-propyl)-7-fluoro-1-methyl-1H-indole-3-carbonitrile | 308 |
| 127 | 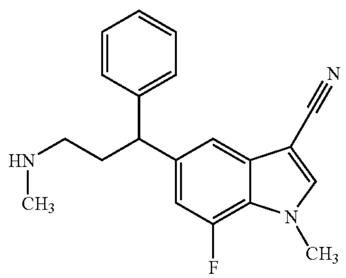 | 7-Fluoro-1-methyl-5-(3-methylamino-1-phenyl-propyl)-1H-indole-3-carbonitrile | 322 |
| 128 | 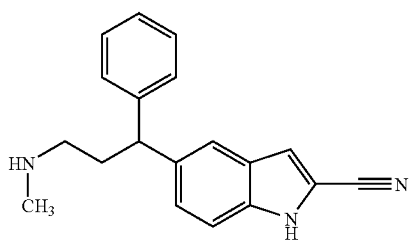 | 5-(3-Methylamino-1-phenyl-propyl)-1H-indole-2-carbonitrile | 290 |
| 129 | 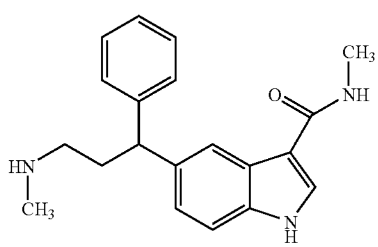 | 5-(3-Methylamino-1-phenyl-propyl)-1H-indole-3-carboxylic acid methylamide | 180.0-183.0 |
| 130 | 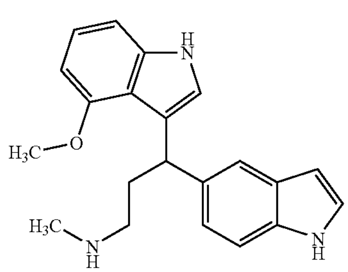 | [3-(1H-Indol-5-yl)-3-(4-methoxy-1H-indol-3-yl)-propyl]-methyl-amine | 121.5-124.0 |

TABLE 1-continued
| # | Structure | Name (Sysname) | MP (°C.) or M + H |
|---|---|---|---|
| 131 | 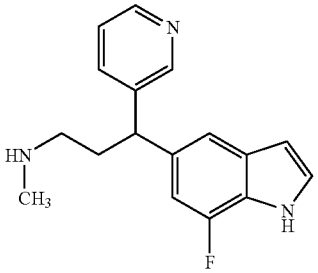 | [3-(7-Fluoro-1H-indol-5-yl)-3-pyridin-3-yl-propyl]-methyl-amine | 284 |
| 132 | 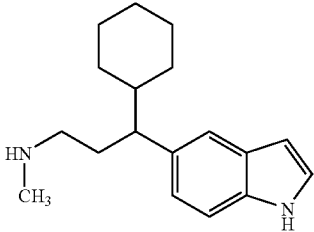 | [3-Cyclohexyl-3-(1H-indol-5-yl)-propyl]-methyl-amine | 120.3-124.9 (HCl Salt) |
| 133 | 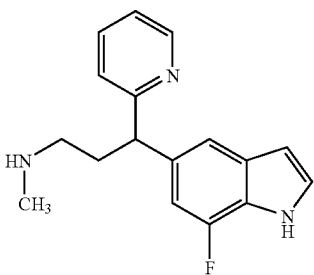 | [3-(7-Fluoro-1H-indol-5-yl)-3-pyridin-2-yl-propyl]-methyl-amine | 110.9-116.6 (HCl Salt) |
| 134 | 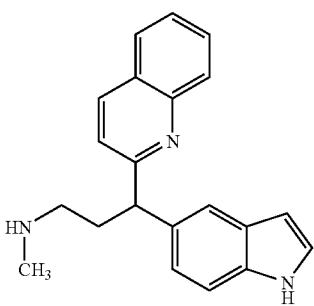 | [3-(1H-Indol-5-yl)-3-quinolin-2-yl-propyl]-methyl-amine | 73.0-76.0 |
| 145 | 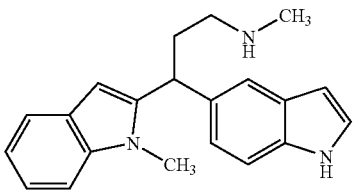 | [3-(1H-Indol-5-yl)-3-(1-methyl-1H-indol-2-yl)-propyl]-methyl-amine | 318 |
| 147 | 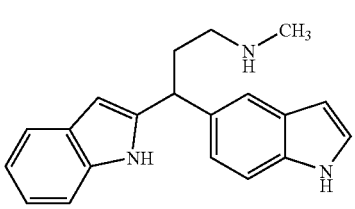 | [3-(1H-Indol-2-yl)-3-(1H-indol-5-yl)-propyl]-methyl-amine | 304 |

TABLE 1-continued

| # | Structure | Name (Sysname) | MP (°C.) or M + H |
|---|---|---|---|
| 137 | 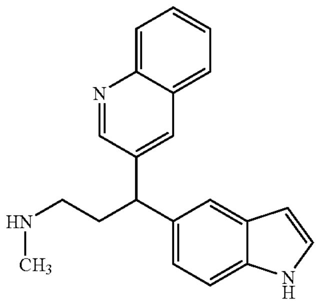 | [3-(1H-Indol-5-yl)-3-quinolin-3-yl-propyl]-methyl-amine | 56.0-58.0 |
| 138 | 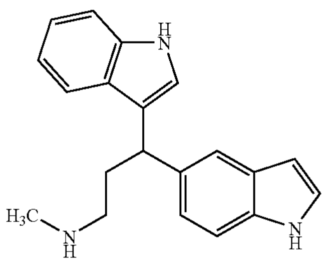 | [3-(1H-Indol-3-yl)-3-(1H-indol-5-yl)-propyl]-methyl-amine | 304 |
| 139 | 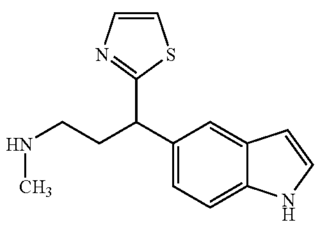 | [3-(1H-Indol-5-yl)-3-thiazol-2-yl-propyl]-methyl-amine | 74.5-75.7 (HCl Salt) |
| 140 | 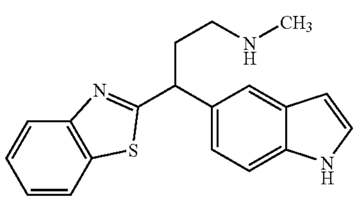 | [3-Benzothiazol-2-yl-3-(1H-indol-5-yl)-propyl]-methyl-amine | 76.0-81.0 (HCl Salt) |
| 141 | 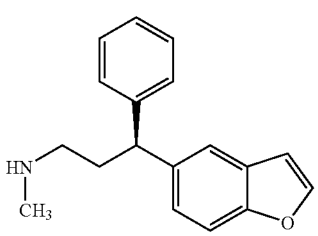 | (3-Benzofuran-5-yl-3-phenyl-propyl)-methyl-amine | 266 |
| 142 | 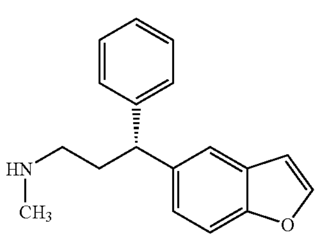 | (3-Benzofuran-5-yl-3-phenyl-propyl)-methyl-amine | 266 |

TABLE 1-continued

| # | Structure | Name (Sysname) | MP (°C.) or M + H |
|---|---|---|---|
| 143 | 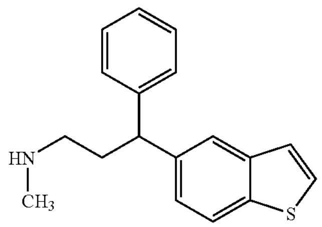 | (3-Benzo[b]thiophen-5-yl-3-phenyl-propyl)-methyl-amine | 282 |
| 144 | 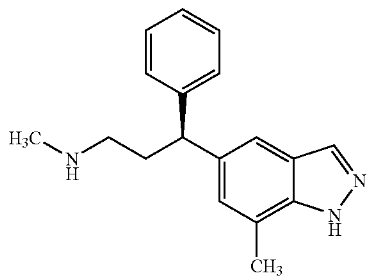 | Methyl-[3-(7-methyl-1H-indazol-5-yl)-3-(S)-phenyl-propyl]-amine | |

Synthesis

Compounds of the present invention can be made by a variety of methods depicted in the illustrative synthetic reaction schemes shown and described below.

The starting materials and reagents used in preparing these compounds generally are either available from commercial suppliers, such as aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein each of W is N or $CR^4$, X, Y, and Z each is independently CH or N, and m, $R^5$ and $R^6$ are as defined herein.

SCHEME A

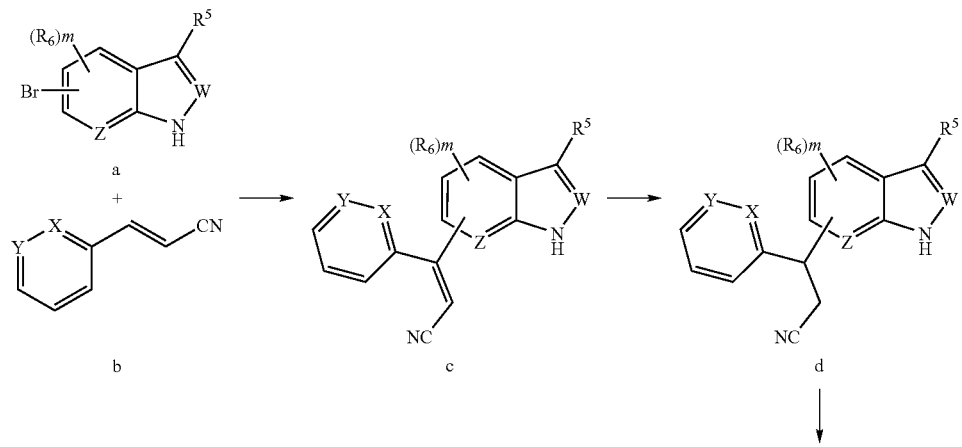

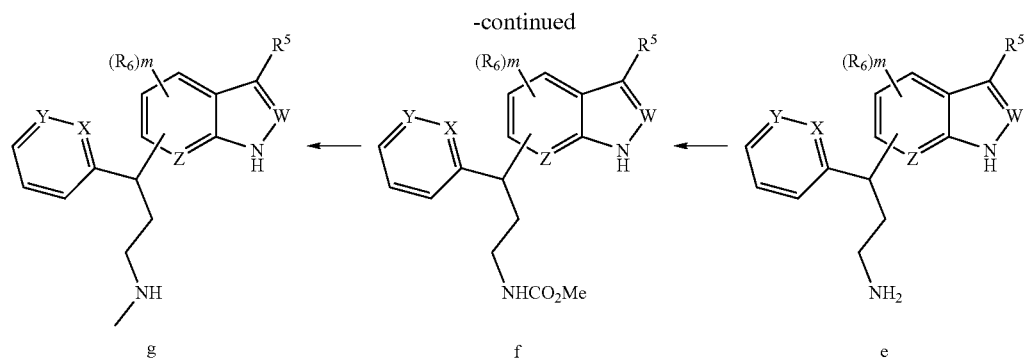

In Scheme A, heteroaryl compound a is coupled with a compound b using a palladium catalyst such as PdCl$_2$[(o-Tol)$_3$P]$_2$ or a mixture of Pd(OAc)$_2$ and (o-Tol)$_3$P to provide a coupled compound c. Compound b may comprise, for example, an aryl acrylonitrile or heteroaryl acrylonitrile, each of which may be optionally substituted as defined herein. Numerous substituted aryl and heteroaryl acrylonitrile compounds b are commercially available or are readily prepared by techniques well known to those skilled in the art.

Selective reduction of the benzylic double bond in compound c affords a cyano compound d. Various reducing agents are suitable for this selective reduction, including sodium borohydride.

Reduction of cyano compound e provides a 3-aminopropyl compound of formula e in accordance with the invention. This reduction may be achieved using lithium aluminum hydride, borane or borane complex, or other strong reducing agent. Alternatively, both the double bond and the cyano group maybe simultaneously reduced using a strong reducing agents or by hydrogenating compound b in the presence of a hydrogenation catalyst.

In some embodiments, compound e is reacted with methylchloroformate to afford a carbamate compound f.

Reduction of the carbamate functional group of compound f provides an N-methyl-3-aminopropyl compound of formula g in accordance with the invention.

Scheme B below illustrates another synthetic procedure that may be used in preparation of compounds of the invention, wherein each of W is N or CR$^4$, and X, Y, and Z each is independently CH or N, R$^a$ is alkyl, and m, R$^5$ and R$^6$ are as defined herein.

SCHEME B

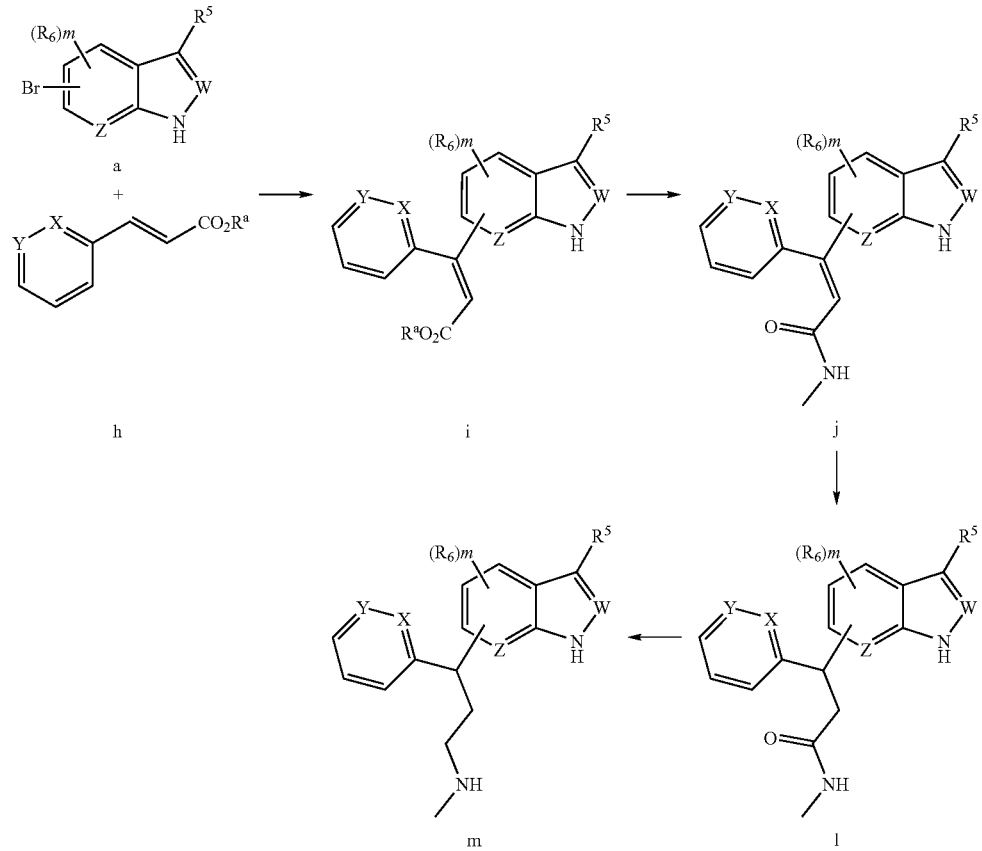

In Scheme B, the compound a is coupled with an acrylate compound h to afford a biaryl acrylate compound i. This coupling reaction can be carried out in a similar manner as discussed in Scheme A above. The biaryl acrylate compound i is then treated with an amine compound, such as ammonia, methyl amine or other alkyl amine compound, in the presence of a catalyst, such as hydrochloric acid or trialkylaluminum (e.g., Me₃Al), to afford a biaryl acrylamide compound j.

Hydrogenation of the benzylic double bond of compound i in the presence of a hydrogenation catalyst affords a biaryl amide compound l. Various palladium catalysts are known to selectively reduce the benzylic double bond. Exemplary hydrogenation catalysts that are suitable for selective reduction include Pd/C and Degoussa-type catalyst.

Reduction the amide group of compound l with a strong reducing reagent, such as lithium aluminum hydride, borane or borane complex, or other strong reducing agent, provides the amine compound m in accordance with the present invention.

Scheme C below illustrates yet another synthetic procedure that may be used in preparation of compounds of the invention, wherein each of W is N or CR⁴, X, Y, and Z each is independently CH or N, Rᵃ is alkyl, and m, R⁵ and R⁶ are as defined herein.

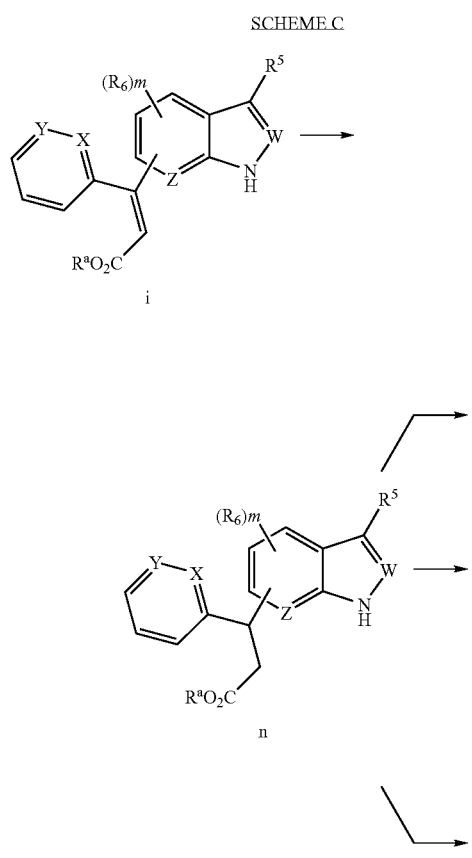

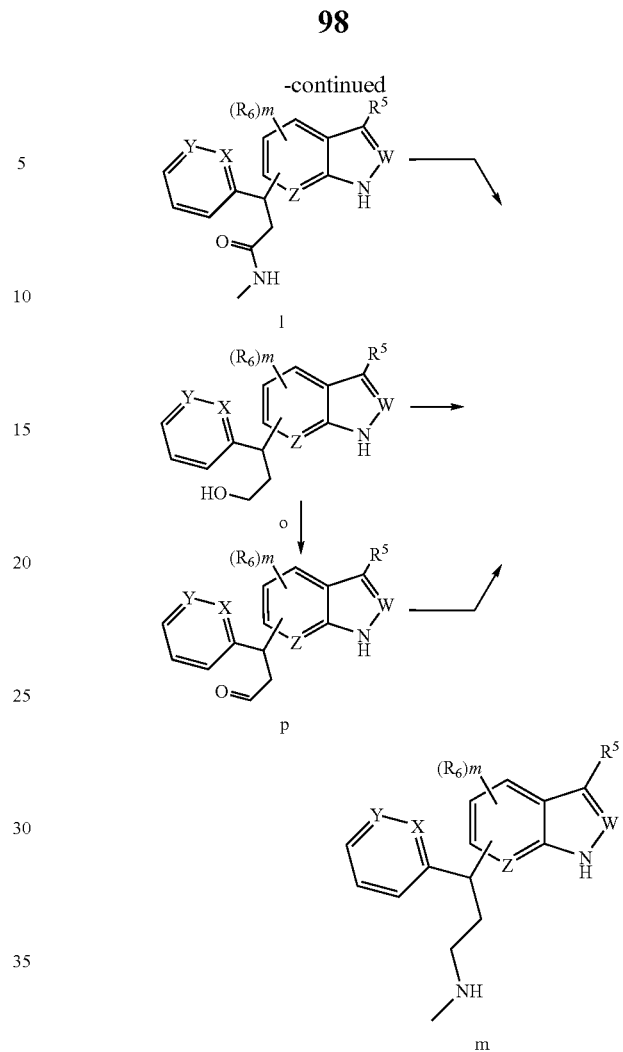

The biaryl acrylate compound i in Scheme C can be prepared as discussed in Scheme B above. In Scheme C, the benzylic double bond of compound i is selectively reduced first by hydrogenation in the presence of a hydrogenation catalyst to afford an ester compound n. Suitable hydrogenation catalysts include those discussed above for transforming the biaryl acrylamide compound j to the biaryl amide compound l.

The ester compound l maybe reacted with an amine compound to afford the biaryl amide compound n, which can then be reduced to the amine compound m in accordance with the present invention as discussed in Scheme B.

Alternatively, the ester compound n maybe reduced to an alcohol compound o using a reducing agent, such as Red-Al or other strong reducing agents known to one skilled in the art. The alcohol compound o maybe oxidized to an aldehyde compound p, which is then subjected to a reductive amination reaction conditions to afford the amine compound m. Suitable reductive amination reaction conditions are well known to one skilled in the art. For example, aldehyde compound p can be converted to the amine compound m by reacting the aldehyde compound p with methylamine in the presence of a reducing reagent, such as sodium cyanoborohydride.

The alcohol compound o maybe converted to the amine compound m by converting the alcohol group to a leaving group, e.g., mesylate or bromide group, and displacing the leaving group with an amine compound, such as methyl amine.

Still alternatively, partial reduction of the ester compound l affords the aldehyde compound p. Suitable reagents for effecting partial reduction an ester functional group to an aldehyde functional group are well known to one skilled in the art. For example, DIBAL-H is often used in transformation of an ester functional group to an aldehyde functional group.

Once the amine compound m is obtained, it may be converted to other compounds of the present invention. For example, when $R^5$ is a cyano group, it can be converted to a carboxamide group by hydrolysis under a basic condition.

Acidic salts of compound m may be prepared by treating compound m with an acid, such as HCl or trifluoroacetic acid.

Numerous variations on the procedures of Schemes A through C are possible and will be readily apparent to those skilled in the art. For example, while Schemes A-C illustrate preparation of N-methyl substituted amine compound m, it should be readily apparent, however, that ethyl, isopropyl or other N-alkyl amine compound m may be prepared accordingly.

Specific details for producing compounds of the invention are described in the Examples section below.

Utility

The compounds of the invention are usable for the treatment of diseases or conditions associated with serotonin neurotransmission, norepinephrine neuortransmission and/or dopamine neurotransmission. Such diseases and conditions include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, and haemorrhage.

The compounds of the invention are also usable for treatment of disorders and disease states of the urinary tract such as stress incontinence, urge incontinence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity.

The compounds of the invention also possess anti-inflammatory and/or analgesic properties in vivo, and accordingly, are expected to find utility in the treatment of disease states associated with pain conditions from a wide variety of causes, including, but not limited to, neuropathic pain, inflammatory pain, surgical pain, visceral pain, dental pain, premenstrual pain, central pain, pain due to burns, migrAlne or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

| ABBREVIATIONS | |
|---|---|
| AcOH | acetic acid |
| DCM | dichloromethane/methylene chloride |
| DMF | N,N-dimethylformamide |
| DMAP | 4-dimethylaminopyridine |
| EtOAc | ethyl acetate |
| EtOH | ethanol |
| $Et_2O$ | diethyl ether |
| gc | gas chromatography |
| HMPA | hexamethylphosphoramide |
| hplc | high performance liquid chromatography |
| mCPBA | m-chloroperbenzoic acid |
| MeCN | acetonitrile |
| MeOH | methanol |
| NMP | N-methyl pyrrolidinone |
| TEA | triethylamine |
| TFA | trifluoroacetic acid |
| THF | tetrahydrofuran |
| LDA | lithium diisopropylamine |
| TLC | thin layer chromatography |

Example 1

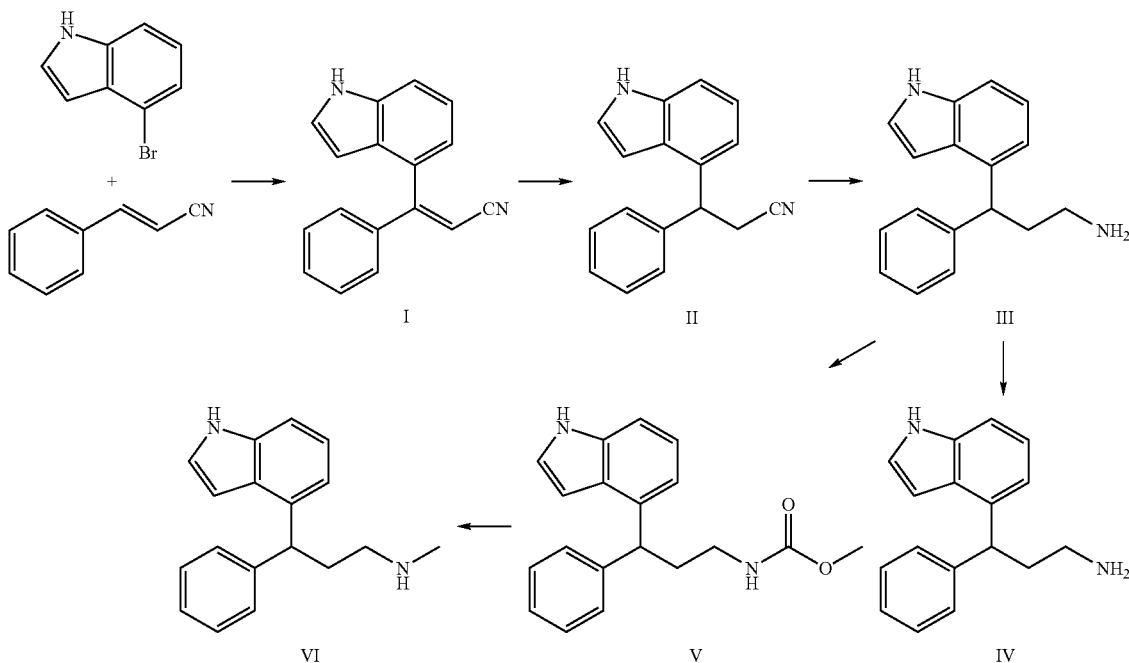

3-(1H-Indol-4-yl)-3-phenyl-acrylonitrile (I)

To a 50 mL tube was added 4-bromoindole (2.0 g, 10 mmol), cinammonitrile (1.3 ml, 10 mmol), $Pd(OAc)_2$ (0.11 g, 0.5 mmol), $(o-Tol)_3P$ (0.30 g, 1.0 mmol) and triethylamine (TEA) (1.4 ml, 10 mmol). The system was flushed with $N_2$, capped and stirred at 100° C. for 18 hours. The resulting solidified dark green mixture was diluted with 25 mL of dichloromethane (DCM) and filtered through a celite pad. The filtrate was concentrated onto silica gel and purified via flash chromatography (hexane/EtOAc) affording 3-(1H-indol-4-yl)-3-phenyl-acrylonitrile (I) as a yellow solid (1.44 g, 60% yield).

Synthesis of 3-(1H-Indol-4-yl)-3-phenyl-propionitrile (II)

To a stirring suspension of 3-(1H-indol-4-yl)-3-phenyl-acrylonitrile (I) (1.4 g, 5.7 mmol) in 2-propanol (30 ml) at room temperature, $NaBH_4$ (1.4 g, 37 mmol) was added portionwise in 30 minutes under $N_2$. The yellow-green mixture was refluxed for 45 hours, then cooled to room temperature, and the solvent was removed. Water was added to the residue and the mixture was extracted with $Et_2O$. The combined extracts were washed successively with water and brine, dried over $MgSO_4$, filtered, and concentrated to provide a quantitative yield of 3-(1H-indol-4-yl)-3-phenyl-propionitrile(II) as yellow solid (1.4 g, 95% pure).

Synthesis of 3-(1H-Indol-4-yl)-3-phenyl-propylamine (III)

To a 0° C. stirring suspension of $LiAlH_4$ (0.23 g, 6.0 mmol) in $Et_2O$ (15 ml) under $N_2$, was added a solution of 3-(1H-indol-4-yl)-3-phenyl-propionitrile (II) (1.34 g, 5.4 mmol) in $Et_2O$ (15 ml) and THF (5 ml). The reaction mixture was then refluxed under $N_2$. After 45 minutes, a suspension of $LiAlH_4$ (0.1 g, 2.6 mmol) in THF (8 ml) was added. After 3.5 hours, another suspension of $LiAlH_4$ (0.1 g, 2.6 mmol) in 8 ml of THF was added. After 4.5 hours at reflux, the reaction was cooled to 0° C. and quenched by addition of freshly crushed $Na_2SO_4 \cdot 10H_2O$ (24 g). After stirring for 30 minutes, the mixture was filtered, and the filter cake was washed with EtOAc. The filtrate was concentrated in vacuo and purified via flash chromatography ($DCM/MeOH/NH_4OH$) affording 3-(1H-indol-4-yl)-3-phenyl-propylamine(III) as a pale yellow oil (1.01 g, 78% yield).

Synthesis of 3-(1H-Indol-4-yl)-3-phenyl-propylamine hydrochloride (IV)

To a stirring solution of the amine (III) (0.14 g, 0.56 mmol) in EtOAc (5 ml) was added a solution of HCl (2 M in Et$_2$O, 0.28 ml). The mixture was concentrated in vacuo affording the hydrochloride salt (IV) as a brown solid (0.16 g, quantitative yield).

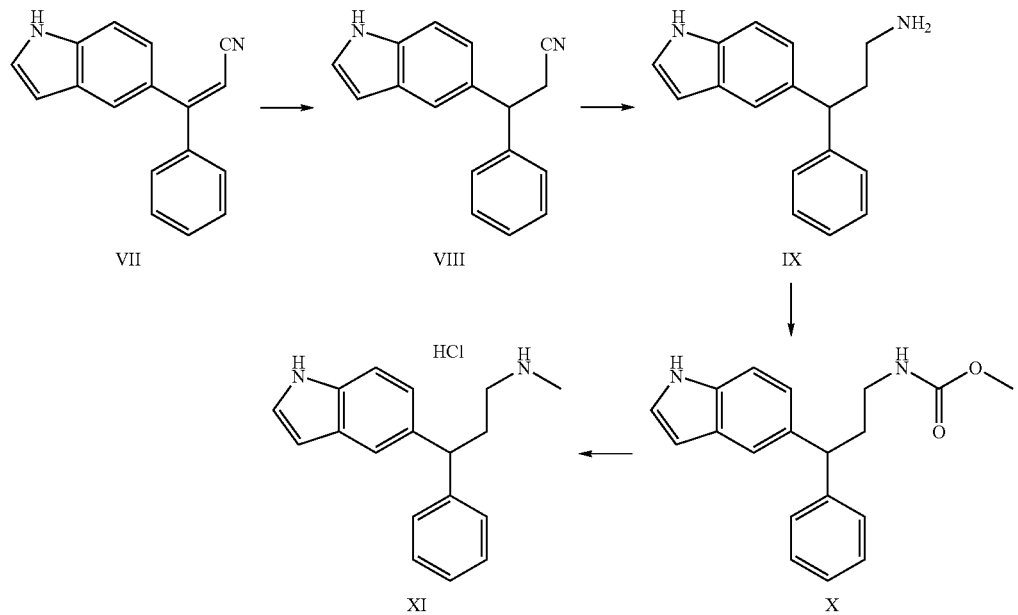

Synthesis of [3-(1H-Indol-4-yl)-3-phenyl-propyl]-carbamic acid methylester (V)

To a stirring solution of 3-(1H-indol-4-yl)-3-phenyl-propylamine (III) (0.40 g, 1.6 mmol) in DCM (15 ml), under N$_2$, was added TEA (0.23 ml, 1.7 mmol). The mixture was cooled to about 0° C. and methyl chloroformate (0.13 ml, 1.7 mmol) in DCM (10 ml) was added dropwise over 15 minutes. The mixture was stirred at room temperature for 30 minutes, quenched by addition of H$_2$O, and stirred for 10 min. The mixture was washed successively with H$_2$O and brine, dried over Na$_2$SO$_4$, filtered, and concentrated in vacuo to provide [3-(1H-indol-4-yl)-3-phenyl-propyl]-carbamic acid methylester (V) as a white solid (0.48 g, 98% yield).

Synthesis of [3-(1H-Indol-4-yl)-3-phenyl-propyl]-methyl-amine (VI)

To a 0° C. stirring suspension of LiAlH$_4$ (0.062 g, 1.69 mmol) in THF (12 ml) under N$_2$ was added a solution [3-(1H-indol-4-yl)-3-phenyl-propyl]-carbamic acid methylester (V) (0.46 g, 1.5 mmol) in THF (7 ml). The resulting mixture was stirred for 15 minutes at room temperature, after which a suspension of LiAlH$_4$ (0.11 g, 3 mmol) in THF (5 ml) was added. The reaction mixture was then refluxed for about 2.5 hours, cooled to about 0° C., and quenched by addition of freshly ground Na$_2$SO$_4$.10H$_2$O (8 g). The resulting mixture was stirred vigorously for about 30 minutes and filtered with the aid of EtOAc. The filtrate was concentrate and purified via flash chromatography (DCM/MeOH/NH$_4$OH) affording [3-(1H-Indol-4-yl)-3-phenyl-propyl]-methyl-amine (0.30 g, 75% yield). To a 0° C. stirring solution of the above amine (0.24 g, 0.90 mmol) in Et$_2$O (10 ml) was added HCl (2 M in Et$_2$O, 0.5 ml, 1.0 mmol). The resulting precipitate was filtered and washed with water and Et$_2$O. The white solid was dried in vacuo affording [3-(1H-indol-4-yl)-3-phenyl-propyl]-methyl-amine (VI) as a hydrochloride salt, (0.21 g, 78% yield). MS (M+H)=265.

Example 2

Synthesis of 3-(1H-Indol-5-yl)-3-phenyl-acrylonitrile (VII)

3-(1H-Indol-5-yl)-3-phenyl-acrylonitrile VII was prepared using the procedure described for 3-(1H-indol-4-yl)-3-phenyl-acrylonitrile I (see Example 1 above) as a white solid in 60% yield.

Synthesis of 3-(1H-Indol-4-yl)-3-phenyl-propionitrile (VIII)

To a stirring suspension of 3-(1H-indol-5-yl)-3-phenyl-acrylonitrile VII (2.8 g, 11.5 mmol) in 2-propanol (60 ml) at room temperature, under N$_2$ was added NaBH$_4$ (2.8 g, 74 mmol) portionwise over 90 min period. The mixture was refluxed for 20 hours and additional 2-propanol (25 ml) was added to facilitate the stirring. After 40 hours at reflux, additional NaBH$_4$ (0.5 g, 13.2 mmol) was added. After 60 hours at reflux, additional NaBH$_4$ (1 g, 26.4 mmol) and 2-propanol (20 ml) were added. After 110 hours at reflux, the mixture was cooled to room temperature, concentrated and the residue was partitioned between H$_2$O and Et$_2$O. The organic layer was separated, washed with brine, dried over MgSO$_4$, filtered and concentrated. The waxy dark yellow solid was re-subjected to the NaBH$_4$ reduction conditions at reflux for 40 hours. The reaction was cooled to room temperature and worked up as above affording 3-(1H-indol-4-yl)-3-phenyl-propionitrile VIII as a yellow-brown solid which was used as crude mixture for the next reaction.

Synthesis of 3-(1H-Indol-5-yl)-3-phenyl-propylamine (IX)

To a 0° C. solution of 3-(1H-indol-4-yl)-3-phenyl-propionitrile VIII (crude 2.8 g, 11.5 mmol) in THF (100 ml) was added LiAlH$_4$ (1.3 g, 35 mmol) over 2 min. The mixture was stirred 15 minutes at 0° C., 15 minutes at room temperature, and at reflux for 1.5 hours. The mixture was then cooled to 0° C. and freshly ground Na$_2$SO$_4$.10H$_2$O (60 g) was added slowly. The resulting mixture was vigorously stirred for 45 minutes, filtered, and the solid was washed with EtOAc. The filtrate was concentrated and the residue was purified via flash chromatography (DCM/MeOH/NH$_4$OH) affording 3-(1H-indol-5-yl)-3-phenyl-propylamineas a yellow syrup (0.96 g, 46% yield).

Synthesis of [3-(1H-Indol-5-yl)-3-phenyl-propyl]-carbamic acid methylester (X)

[3-(1H-Indol-5-yl)-3-phenyl-propyl]-carbamic acid methylester X (0.52 g, 91% yield) was prepared using the procedure for [3-(1H-indol-4-yl)-3-phenyl-propyl]-carbamic acid methylester V (see Example 1).

Synthesis of [3-(1H-Indol-5-yl)-3-phenyl-propyl]-methyl-amine (XI)

To a solution of [3-(1H-indol-5-yl)-3-phenyl-propyl]-carbamic acid methylester X (0.52 g, 1.7 mmol) in THF (35 ml), LiAlH$_4$ (321 mg, 8.4 mmol) was slowly added. The mixture was refluxed for 1.5 hours, cooled to room temperature, and quenched by slow addition of freshly ground Na$_2$SO$_4$.10H$_2$O. The mixture was stirred at room temperature for 1 hour, filtered through celite with EtOAc. The filtrate was evaporated and purified via flash chromatography (DCM/MeOH/NH$_4$OH) affording [3-(1H-indol-5-yl)-3-phenyl-propyl]-methyl-amine (XI) as an off-white foam (408 mg, 91% yield). The amine compound was dissolved in a Et$_2$O/THF mixture and HCl (2 M in Et$_2$O, 0.772 ml) was added. The precipitate was filtered, washed with Et$_2$O, and dried affording [3-(1H-indol-5-yl)-3-phenyl-propyl]-methyl-amine hydrochloride salt (371 mg, 80% yield). MS (M+H)=265.

Example 3

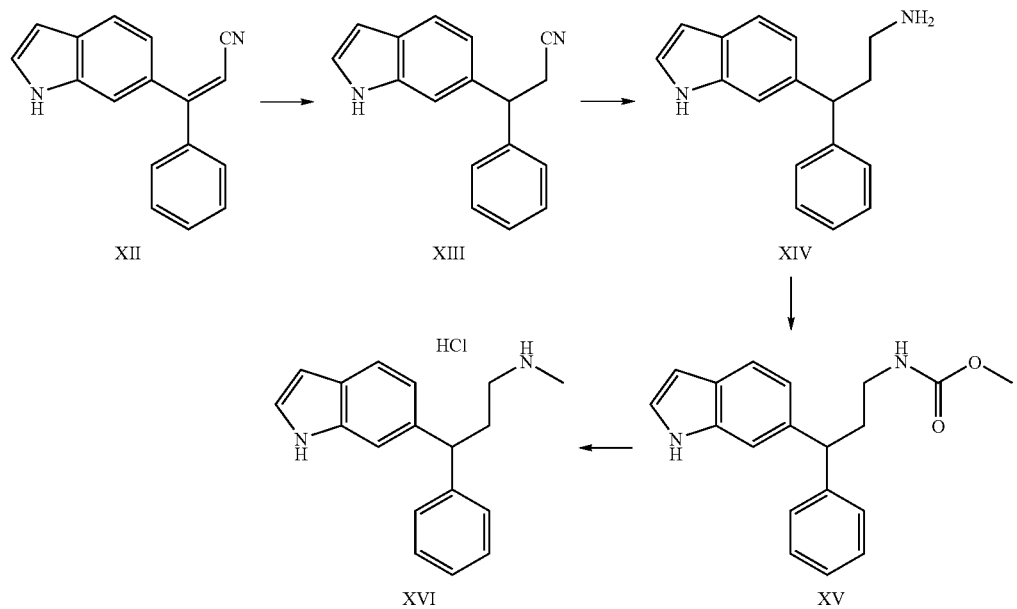

Synthesis of 3-(1H-Indol-6-yl)-3-phenyl-acrylonitrile (XII)

3-(1H-Indol-6-yl)-3-phenyl-acrylonitrile XII (1.46 g, 61% yield) was prepared from 6-bromo-indole using the procedure described for 3-(1H-indol-4-yl)-3-phenyl-acrylonitrile I.

Synthesis of 3-(1H-Indol-6-yl)-3-phenyl-propionitrile (XIII)

To a stirring suspension of 3-(1H-indol-6-yl)-3-phenyl-acrylonitrile XII (1.3 g, 5.3 mmol) in 2-propanol (30 ml), NaBH$_4$ (1.3 g, 34 mmol) was added portionwise over 30 min. The mixture was heated at reflux for 110 hours while occasionally adding 2-propanol to maintain the original volume. The mixture was cooled to room temperature and concentrated. The residue was partitioned between Et$_2$O and H$_2$O. The organic layer was separated, washed with brine, dried over MgSO$_4$, filtered and evaporated. The crude 3-(1H-indol-6-yl)-3-phenyl-propionitrile (1.2 g, 90% pure) was used without further purification for the next reaction.

Synthesis of 3-(1H-Indol-6-yl)-3-phenyl-propylamine (XIV)

To a 0° C. solution of 3-(1H-indol-6-yl)-3-phenyl-propionitrile XIII (1.1 g, 4.5 mmol) in THF (35 ml) was slowly added a suspension of LiAlH$_4$ (0.51 g, 13 mmol) in THF (10 ml). The mixture was stirred 10 min at 0° C. and 10 minutes at room temperature, then it was refluxed for 1.5 hours. The reaction mixture was cooled to 0° C., quenched by the careful addition of freshly ground Na$_2$SO$_4$.10H$_2$O (25 g), filtered, and the solid was washed with EtOAc. The filtrate was concentrated and purified via flash chromatography (DCM/MeOH/NH₄OH) affording 3-(1H-indol-6-yl)-3-phenyl-propylamine XIV as a colorless oil (0.68 g, 62% yield).

Synthesis of [3-(1H-Indol-6-yl)-3-phenyl-propyl]-carbamic acid methylester (XV)

[3-(1H-Indol-6-yl)-3-phenyl-propyl]-carbamic acid methylester XV (0.554 g, 89% yield) was prepared from 3-(1H-indol-6-yl)-3-phenyl-propylamine using the procedure described for [3-(1H-indol-4-yl)-3-phenyl-propyl]-carbamic acid methylester V (see Example 1).

Synthesis of [3-(1H-Indol-6-yl)-3-phenyl-propyl]-methyl-amine (XVI)

[3-(1H-Indol-6-yl)-3-phenyl-propyl]-methyl-amine (110 mg, 24% yield) XVI was prepared as a hydrochloride salt from [3-(1H-indol-6-yl)-3-phenyl-propyl]-carbamic acid methylester (XV), using the procedure described for preparation of [3-(1H-indol-5-yl)-3-phenyl-propyl]-methyl-amine XI (see Example 2). MS (M+H)=265.

Example 4

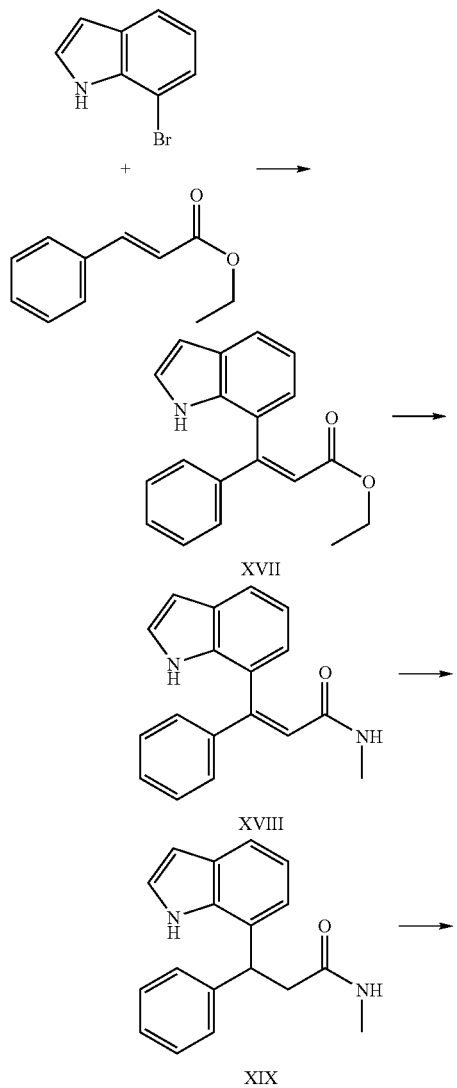

-continued

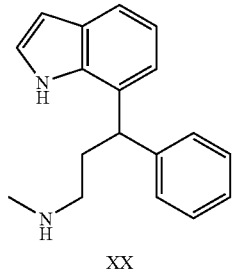

XX

Synthesis of 3-(1H-Indol-7-yl)-N-methyl-3-phenyl-acryl acid ethyl ester (XVII)

A mixture of 7-bromoindole (1 g, 5.1 mmol), ethyl cinammate (1.8 g, 10.2 mmol), tetra-butylammonium bromide (0.326 g, 1.02 mmol), TEA (1.42 ml, 10.2 mmol) and palladium dichloro-[bis(tri-ortho-tolyl)phophine] (200 mg, 0.255 mmol) in DMF (10 ml) was heated in a sealed vial at 110° C. for 21 hours. The reaction mixture was cooled to room temperature and diluted with H₂O and EtOAc. The aqueous layer was extracted with EtOAc. The organic layers were combined, dried over Na₂SO₄, filtered, and concentrated. The crude mixture was purified via flash chromatography (hexane/EtOAc) affording 3-(1H-indol-7-yl)-N-methyl-3-phenyl-acryl acid ethyl ester XVII as a yellow foamy oil (1.1 g, 74% yield).

Synthesis of 3-(1H-Indol-7-yl)-N-methyl-3-phenyl-acrylamide (XVIII)

To a 0° C. suspension of MeNH₂.HCl (302 mg, 4.48 mmol) in benzene (15 ml) was added Me₃Al (2 M in toluene, 2.24 ml, 4.48 mmol). The mixture was stirred at 0° C. for 10 minutes and at room temperature for 1-⅓ hours. A solution of 3-(1H-indol-7-yl)-N-methyl-3-phenyl-acryl acid ethyl ester XVII in benzene (12 ml) was added to the reaction mixture at room temperature. The reaction mixture was stirred for 10 minutes at room temperature, at reflux for 18 hours, and then cooled to room temperature. The reaction was quenched by adding HCl (0.5 M, 15 ml) and EtOAc. The aqueous layer was excractated with EtOAc. The organic layers were combined, dried over Na₂SO₄, and concentrated. The crude product was purified via flash chromatography (DCM/MeOH) affording 3-(1H-indol-7-yl)-N-methyl-3-phenyl-acrylamide XVIII as an off-white solid (443 mg, 72% yield).

Synthesis of 3-(1H-Indol-7-yl)-N-methyl-3-phenyl-propionamide (XIX)

To a solution of 3-(1H-indol-7-yl)-N-methyl-3-phenyl-acrylamide XVIII in EtOH (8 ml) was added Degussa's catalyst (10% Pd/C wet, 55 mg). The reaction mixture was subjected to a hydrogenation reaction in a Parr apparatus at 50 psi of H₂ for 20 hours. The reaction mixture was filtered through a celite pad, and the filter cake was washed with MeOH. The filtrate was concentrated affording 3-(1H-indol-7-yl)-N-methyl-3-phenyl-propionamide XIX as a white solid in quantitative yield (296 mg).

Synthesis of [3-(1H-Indol-7-yl)-3-phenyl-propyl]-methyl-amine (XX)

To a stirring solution of 3-(1H-indol-7-yl)-N-methyl-3-phenyl-propionamide XIX (296 mg, 1.06 mmol) in THF (8 ml) was added a suspension of LiAlH₄ (165 mg, 4.24 mmol)

in THF (6 ml) at room temperature. The mixture was refluxed for 5 hours, cooled to room temperature, and quenched by slow addition of freshly ground Na$_2$SO$_4$.10H$_2$O (4 g). The resulting mixture was stirred at room temperature for 45 minutes, and the solid was filtered and washed with EtOAc. The filtrate was concentrated and purified via flash chromatography (DCM/MeOH) affording [3-(1H-Indol-7-yl)-3-phenyl-propyl]-methyl-amine XX (182 mg, 65% yield). The free amine (100 mg) was dissolved in Et$_2$O (15 ml) and cooled to 0° C. To the resulting solution was was added HCl (1 M in Et$_2$O, 568 μl ), and the precipitate was filtered and dried in vacuo to afford the hydrochloride salt. (62 mg, 36% yield). MS (M+H)=265.

Example 5

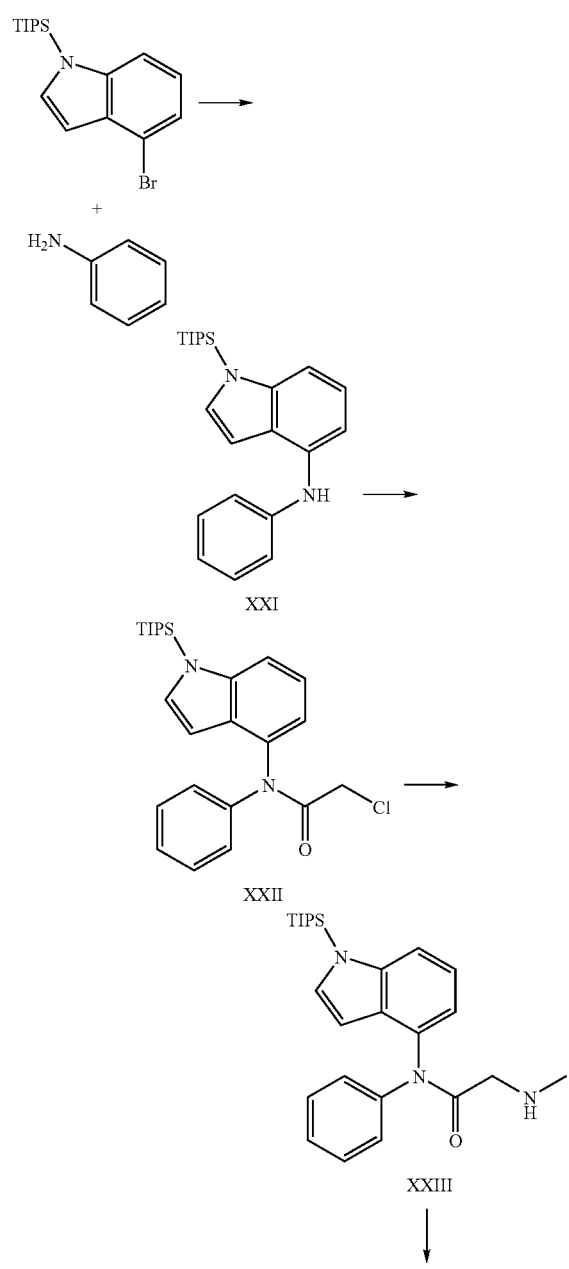

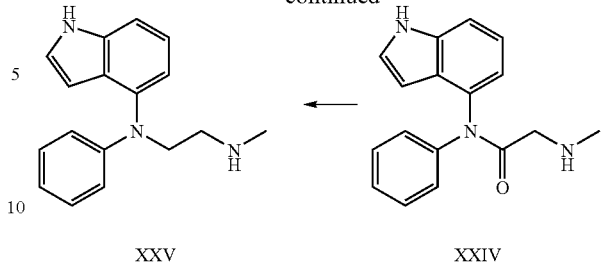

Synthesis of Phenyl-(1-triisopropylsilanyl-1H-indol-4-yl)-amine (XXI)

Aniline (328 μl, 3.6 mmol) was added to a room temperature mixture of 4-bromo-1-triisopropylsilanyl-1H-indole (1.06 g, 3 mmol), tris(dibenzylideneacetone)dipalladium 2-(dicyclohexylphosphino)-2,4,6-triisopropyl-1,1'-biphenylphosphine (Pd$_2$(dba)$_3$, 27.5 mg, 0.03 mmol), (72 mg, 0.05 mmol) and K$_2$CO$_3$ (1.04 g, 7.5 mmol) in t-BuOH (14 ml). The reaction mixture was stirred at 110° C. for 4 hours. The reaction was cooled, and the solid was filtered off. The filtrate was concentrated and the residue was partitioned between EtOAc and a saturated solution of NaHCO$_3$. The aqueous layer was extracted twice with EtOAc. The combined organic layers were dried over Na$_2$SO$_4$, filtered, concentrated, and purified via flash chromatography (hexane/EtOAc) affording the compound XXI as a yellow oil in quantitative yield (1.09 g).

Synthesis of 2-Chloro-N-phenyl-N-(1-triisopropylsilanyl-1H-indol-4-yl)-acetamide (XXII)

To a 0° C. solution of phenyl-(1-triisopropylsilanyl-1H-indol-4-yl)-amine XXI (1.09 g, 3 mmol) and TEA (1.35 ml, 9.7 mmol) in DCM (20 ml) was added 2-chloroacetyl chloride (773 μl, 9.7 mmol). The mixture was stirred for 5 minutes and then refluxed for 3 hours. The reaction was cooled to room temperature and partitioned between H$_2$O and DCM. The aqueous layer was extracted with DCM. The combined organic layers were dried over Na$_2$SO$_4$, filtered, concentrated, and purified via flash chromatography (hexane/EtOAc) affording 2-chloro-N-phenyl-N-(1-triisopropylsilanyl-1H-indol-4-yl)-acetamide XXII as an off-white solid (775 mg, 59% yield).

Synthesis of 2-Methylamino-N-phenyl-N-(1-triisopropylsilanyl-1H-indol-4-yl)-acetamide (XXIII)

A solution of 2-chloro-N-phenyl-N-(1-triisopropylsilanyl-1H-indol-4-yl)-acetamide XXII (192 mg, 0.435 mmol) and MeNH$_2$ (33% w in EtOH, 2 ml) was stirred for 2.5 h. The solvent was evaporated and the residue was partitioned between EtOAc and a saturated solution of NaHCO$_3$. The aqueous layer was extracted twice with EtOAc. The combined organic layers were dried over Na$_2$SO$_4$, filtered, concentrated, and the resulting crude 2-methylamino-N-phenyl-N-(1-triisopropylsilanyl-1H-indol-4-yl)-acetamide XXIII (180 mg) was used without further purification for the next reaction.

Synthesis of N-(1H-Indol-4-yl)-2-methylamino-N-phenyl-acetamide (XXIV)

To a room temperature solution of 2-methylamino-N-phenyl-N-(1-triisopropylsilanyl-1H-indol-4-yl)-acetamide XXIII in THF (5 ml) was added tetrabutylammonium fluoride (TBAF) (149 mg, 0.566 mmol). The mixture was stirred for 18 hours and then partitioned between EtOAc and a saturated solution of NaHCO$_3$. The aqueous layer was extracted twice with EtOAc. The combined organic layers were dried over Na$_2$SO$_4$, filtered and concentrated. The crude N-(1H-indol-4-yl)-2-methylamino-N-phenyl-acetamide XXIV (122 mg, pale yellow solid) was used without further purification for the next reaction.

Synthesis of N-(1H-Indol-4yl)-N'-methyl-N-phenyl-ethane-1,2-diamine (XXV)

To a room temperature solution of N-(1H-indol-4-yl)-2-methylamino-N-phenyl-acetamide XXIV (122 mg, crude 0.435 mmol) in THF (6 ml) was added BH$_3$.SMe$_2$ (2 M in THF, 653 μl, 1.31 mmol). The mixture was stirred at room temperature for 2 hours, at 50° C. for 2 hours, and at reflux for 2 hours. The resulting mixture was then kept at −18° C. for 5 days. It was then warmed at room temperature and BH$_3$.SMe$_2$ (2M in THF, 653 μl, 1.31 mmol) was added. The mixture was refluxed for 45 minutes, cooled to 0° C., and MeOH (1.5 ml) and HCl (conc., 9 drops) were added. The mixture was stirred at 0° C. for 5 minutes, at room temperature for 1 hour and at 50° C. for 2 hours. The reaction mixture was cooled to room temperature and diluted a saturated solution of NaHCO$_3$ and EtOAc. The aqueous layer was extracted with EtOAc. The combined organic layers were dried over Na$_2$SO$_4$, filtered, concentrated, and purified via flash chromatography (DCM/MeOH/NH$_4$OH). The chromatographed material was dissolved in p-xylene (9 ml) and Pd/C (5%, 14 mg) was added. The reaction mixture was refluxed for 3 hours, cooled to room temperature, and filtered through a celite pad with the aid of hot methanol. The filtrate was concentrated and purified via flash chromatography (DCM/MeOH/NH$_4$OH) affording N-(1H-indol-4yl)-N'-methyl-N-phenyl-ethane-1,2-diamine XXV (8 mg, light brown oil). MS (M+H)=266.

Example 6

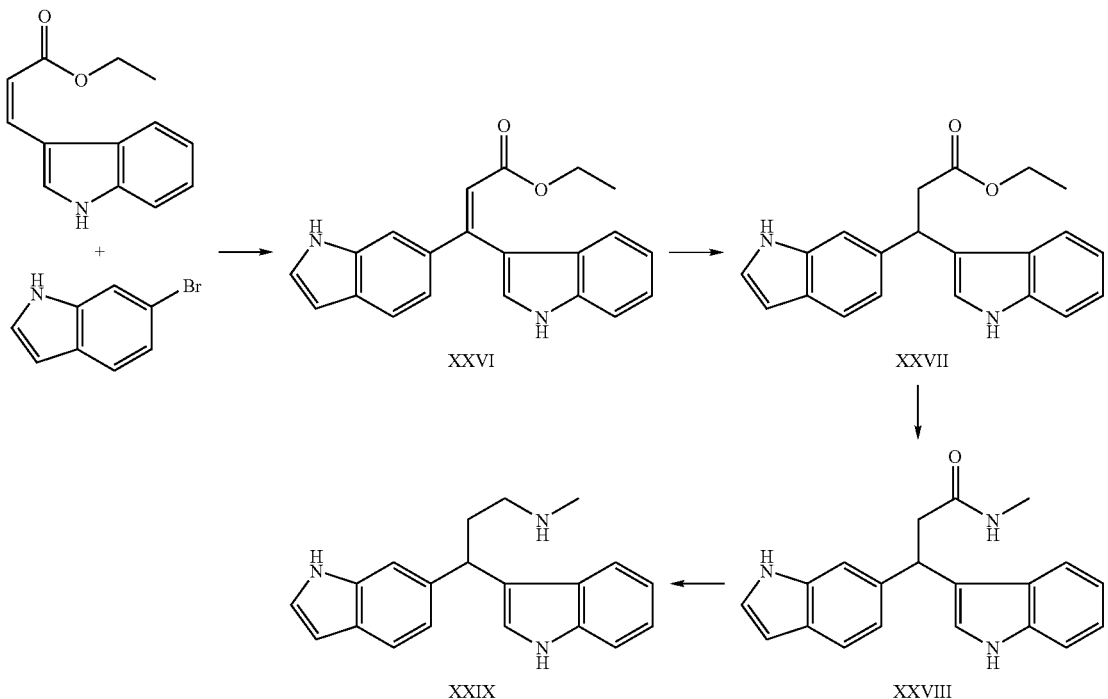

Synthesis of 3-(1H-Indol-6-yl)-3-(1H-indol-3-yl)-acrylic acid ethyl ester (XXVI)

A sealed tube flushed with N$_2$ was charged with 3-(1H-indol-3-yl)-acrylic acid ethyl ester (323 mg, 1.5 mmol), 6-bromoindole (196 mg, 1 mmol), tetra-butylammonium bromide (64.4 mg, 0.2 mmol), TEA (209 μl, 1.5 mmol) and palladium-dichloro-[bis(tri-ortho-tolyl)phophine] (39.3 mg, 0.05 mmol). The mixture was stirred at 114° C. for 1 hour, cooled to room temperature, dissolved in DCM, and purified via flash chromatography (hexane/EtOAc) to afford 3-(1H-indol-6-yl)-3-(1H-indol-3-yl)-acrylic acid ethyl ester XXVI (250 mg, yellow oil) as a mixture of geometric isomers.

Synthesis of 3-(1H-Indol-6-yl)-3-(1H-indol-3-yl)-propionic acid ethyl ester (XXVII)

To a solution of 3-(1H-indol-6-yl)-3-(1H-indol-3-yl)-acrylic acid ethyl ester XXVI in ethanol (15 ml) was added catalytic quantity of Pd(OH)$_2$/C (20%). The reaction mixture was hydrogenated in a Parr apparatus under 55 psi of H$_2$ for 24 hours. The catalyst was removed by filtration through a pad of celite with MeOH. The filtrate was concentrated to afford 3-(1H-indol-6-yl)-3-(1H-indol-3-yl)-propionic acid ethyl ester XXVII (241 mg) as a light brown solid, which was used in the next reaction without purification.

Synthesis of 3-(1H-Indol-6-yl)-3-(1H-indol-3-yl)-N-methyl-propionamide (XXVIII)

To a 0° C. suspension of MeNH$_2$.HCl (97.9 mg, 1.45 mmol) in benzene (4 ml) was added Me$_3$Al (2 M in toluene, 746 µl, 1.45 mmol). The mixture was stirred for 5 minutes and at room temperature for about 1.25 hours. A suspension of 3-(1H-indol-6-yl)-3-(1H-indol-3-yl)-propionic acid ethyl ester XXVII in benzene (15 ml) was added, and the resulting reaction mixture was stirred at reflux for 8 hours, and at room temperature for 16 hours. The reaction mixture was diluted with a saturated solution of NH$_4$Cl (20 ml) and extracted with EtOAc. The organic layers were combined, dried over Na$_2$SO$_4$, filtered, concentrated, and purified via flash chromatography (DCM/MeOH) affording 3-(1H-Indol-6-yl)-3-(1H-indol-3-yl)-N-methyl-propionamide XXVIII as a yellow oil (86 mg).

Synthesis of [3-(1H-Indol-6-yl)-3-(1H-indol-3-yl)-propyl]-methyl-amine (XXIX)

The [3-(1H-Indol-6-yl)-3-(1H-indol-3-yl)-propyl]-methyl-amine XXIX (52 mg, 62%) was prepared from 3-(1H-indol-6-yl)-3-(1H-indol-3-yl)-N-methyl-propionamide using the procedure described for [3-(1H-Indol-7-yl)-3-phenyl-propyl]-methyl-amine XX (see Example 4). MS (M+H)= 304.

Example 7

Synthesis of 3-(1H-Indol-6-yl)-3-(3-methoxy-phenyl)-propionic acid methyl ester (XXXI)

To a mixture of 3-methoxyphenylboronic acid (0.23 g, 1.5 mmol) and [RhCl(cod)]$_2$ (49 mg, 0.1 mmol) in degassed water (3 ml) was added 3-(1H-indol-6-yl)-acrylic acid methyl ester XXX (200 mg, 1.0 mmol). The mixture was stirred at 90° C. for 6 hours, cooled to room temperature, and extracted with EtOAc. The combined organic layers were washed with brine, dried over MgSO$_4$, filtered, concentrated, and purified via flash chromatography (hexane/EtOAc) to provide 3-(1H-indol-6-yl)-3-(3-methoxy-phenyl)-propionic acid methyl ester XXXI (190 mg, 61% yield) as a yellow film.

Synthesis of 3-(1H-Indol-6-yl)-3-(3-methoxy-phenyl)-N-methyl-propionamide (XXXII)

To a 5° C. stirring suspension of MeNH$_2$.HCl (70 mg, 1.04 mmol) in benzene (1 ml) was added Me$_3$Al (2M in toluene, 0.52 ml, 1.04 mmol) dropwise. The reaction mixture was stirred at RT for 1 h and a solution of 3-(1H-indol-6-yl)-3-(3-methoxy-phenyl)-propionic acid methyl ester XXXI (160 mg, 0.52 mmol) in benzene (5 ml) was added. The mixture was stirred at 90° C. for 4 h, cooled to RT, and diluted with HCl (5% in water, 6 ml). The resulting mixture was extracted 3 times with EtOAc. The organic layers were combined,

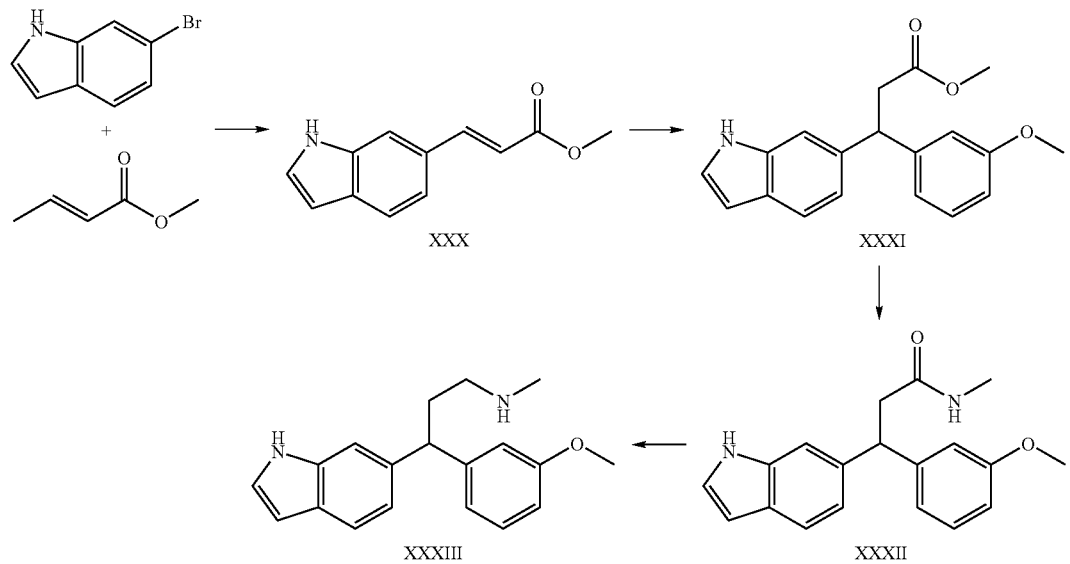

Synthesis of 3-(1H-Indol-6-yl)-acrylic acid methyl ester (XXX)

To a resealable reaction tube was added 6-bromoindole (5 g, 26 mmol), methyl acrylate (2.9 ml, 32 mmol), TEA (4.4 ml, 32 mmol), (o-Tol)$_3$P (0.78 g, 2.6 mmol) and Pd(OAc)$_2$ (0.29 g, 1.3 mmol). The reaction tube was sealed and the resulting mixture was stirred at 100° C. for 20 hours, then cooled to room temperature, diluted with DCM, and filtered through celite. The filter cake was washed with DCM. The filtrate was concentrated and purified via flash chromatography (hexane/EtOAc) to provide 3-(1H-indol-6-yl)-acrylic acid methyl ester XXX (3.8 g, 73% yield) as a bright yellow solid.

washed with H$_2$O (20 ml) and brine (10 ml), dried over MgSO$_4$, filtered, and concentrated to provide 3-(1H-indol-6-yl)-3-(3-methoxy-phenyl)-N-methyl-propionamide XXXII (160 mg, quantitative yield) as a yellow film.

Synthesis of [3-(1H-Indol-6-yl)-3-(3-methoxy-phenyl)-propyl]-methyl-amine (XXXIII)

[3-(1H-Indol-6-yl)-3-(3-methoxy-phenyl)-propyl]-methyl-amine XXXIII (100 mg, 94% yield) was prepared as a hydrochloride salt from 3-(1H-indol-6-yl)-3-(3-methoxy-phenyl)-N-methyl-propionamide using the procedure described for [3-(1H-Indol-7-yl)-3-phenyl-propyl]-methyl-amine XX (see Example 4). MS (M+H)=295.

Example 8

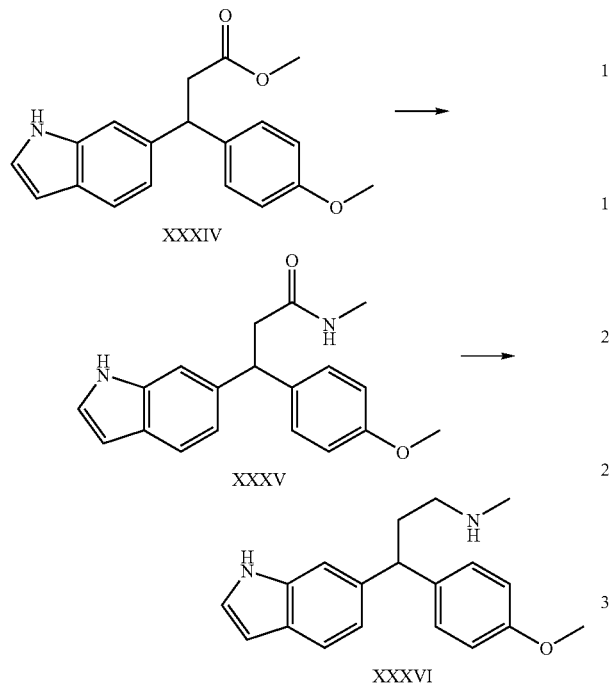

Synthesis of 3-(1H-Indol-6-yl)-3-(4-methoxy-phenyl)-propionic acid methyl ester (XXXIV)

3-(1H-Indol-6-yl)-3-(4-methoxy-phenyl)-propionic acid methyl ester XXXIV (0.51 g, 66% yield) was prepared from 4-methoxy boronic acid using the procedure described for preparation of 3-(1H-indol-6-yl)-3-(3-methoxy-phenyl)-propionic acid methyl ester XXXI (see Example 7).

Synthesis of 3-(1H-Indol-6-yl)-3-(4-methoxy-phenyl)-N-methyl-propionamide (XXXV)

To a 5° C. stirring suspension of MeNH$_2$.HCl (220 mg, 3.2 mmol) in benzene (3 ml) was added dropwise Me$_3$Al (2 M in toluene, 1.6 ml, 3.2 mmol). The mixture was stirred at room temperature for 45 minutes. A solution of 3-(1H-indol-6-yl)-3-(4-methoxy-phenyl)-propionic acid methyl ester XXXIV (480 mg, 1.6 mmol) in benzene (15 ml) was added and the resulting mixture was stirred at reflux for 3 hours. The reaction mixture was cooled to room temperature and additional mixture of MeNH$_2$.HCl (110 mg, 1.6 mmol) in benzene (1.5 ml) and Me$_3$Al (2M in toluene, 0.8 ml, 1.6 mmol) was added. The resulting mixture was stirred at reflux for 1.5 hours, cooled to room temperature, and the reaction was quenched by slow addition of HCl (1M, 35 ml). The mixture was stirred vigorously for 5 minutes and extracted with EtOAc (50 ml). The combined organic layers were washed with water and brine, dried over MgSO$_4$, filtered, concentrated and purified via flash chromatography (hexane/EtOAc) to provide 3-(1H-indol-6-yl)-3-(4-methoxy-phenyl)-N-methyl-propionamide XXXV (390 mg, 81% yield) as a white solid.

Synthesis of [3-(1H-Indol-6-yl)-3-(4-methoxy-phenyl)-propyl]-methyl-amine (XXXVI)

[3-(1H-Indol-6-yl)-3-(4-methoxy-phenyl)-propyl]-methyl-amine XXXVI was prepared as a hydrochloride salt (220 mg, 61%) from 3-(1H-indol-6-yl)-3-(4-methoxy-phenyl)-N-methyl-propionamide using the procedure described above for preparation of [3-(1H-indol-7-yl)-3-phenyl-propyl]-methyl-amine XX. MS (M+H)=295.

Example 9

Synthesis of 3-(1H-Indol-6-yl)-3-(2-methoxy-phenyl)-propionic acid methyl ester (XXXVII)

A mixture of 3-(1H-indol-6-yl)-acrylic acid methyl ester XXX (1.0 g, 5.0 mmol), 2-methoxyphenyl boronic acid (1.1 g, 7.2 mmol), [RhCl(cod)]$_2$ (110 mg, 0.25 mmol) and TEA (5 mmol) in H$_2$O (14 ml) and 1,4-dioxane (1 ml) was stirred at 90° C. in a sealed vial for 6 hours. The reaction mixture was cooled to room temperature and extracted with EtOAc. The combined organic layers were dried over MgSO$_4$, filtered, concentrated, and purified via flash chromatography (hexane/acetone) to provide 3-(1H-indol-6-yl)-3-(2-methoxy-phenyl)-propionic acid methyl ester XXXVII (300 mg, 20% yield) as a yellow film.

Synthesis of 3-(1H-Indol-6-yl)-3-(2-methoxy-phenyl)-N-methyl-propionamide (XXXVIII)

To a 5° C. stirring suspension of MeNH$_2$.HCl (160 mg, 2.4 mmol) in benzene (2 ml) under N$_2$, in a sealed tube was added dropwise Me₃Al (2M in toluene, 1.2 ml, 2.4 mmol). The mixture was stirred at room temperature for 1 hour and a solution of 3-(1H-Indol-6-yl)-3-(2-methoxy-phenyl)-propionic acid methyl ester XXXVII (340 mg, 1.1 mmol) in benzene (10 ml) was added. The resulting mixture was stirred at 90° C. for about 4.5 hours, cooled to room temperature, and the reaction was quenched by slowly adding HCl (1M, 25 ml). The resulting mixture was stirred for 10 minutes, diluted with H₂O, and extracted with EtOAc. The organic layer was washed with H₂O and brine, dried over MgSO₄, filtered and evaporated to provide 3-(1H-indol-6-yl)-3-(2-methoxy-phenyl)-N-methyl-propionamide XXXVIII (320 mg, 94% yield).

Synthesis of [3-(1H-Indol-6-yl)-3-(2-methoxy-phenyl)-propyl]-methyl-amine (XXXIX)

[3-(1H-Indol-6-yl)-3-(2-methoxy-phenyl)-propyl]-methyl-amine XXXIX was prepared from 3-(1H-indol-6-yl)-3-(2-methoxy-phenyl)-N-methyl-propionamide as a white solid in 76% yield using the procedure described above for [3-(1H-indol-7-yl)-3-phenyl-propyl]-methyl-amine XX (see Example 4). MS (M+H)=295

Example 10

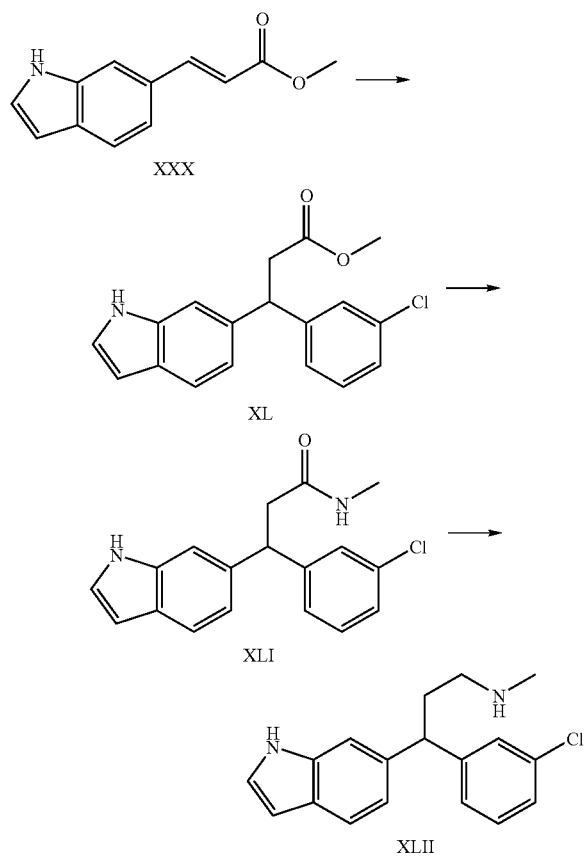

to room temperature, and partitioned between H₂O and EtOAc. The aqueous layer was extracted with EtOAc. The organic layers were combined, dried over MgSO₄, filtered, concentrated, and purified via flash chromatography (hexane/EtOAc) to provide 3-(1H-indol-6-yl)-3-(3-chloro-phenyl)-propionic acid methyl ester XL (90 mg, 62% yield) as a white foam.

Synthesis of 3-(1H-Indol-6-yl)-3-(3-chloro-phenyl)-N-methyl-propionamide (XLI)

3-(1H-Indol-6-yl)-3-(3-chloro-phenyl)-N-methyl-propionamide XLI (340 mg, 89% yield) was prepared from 3-(1H-indol-6-yl)-3-(3-chloro-phenyl)-propionic acid methyl ester using the procedure described above for 3-(1H-Indol-6-yl)-3-(2-methoxy-phenyl)-N-methyl-propionamide XXXVIII (see Example 9).

Synthesis of [3-(1H-Indol-6-yl)-3-(3-chloro-phenyl)-propyl]-methyl-amine (XLII)

[3-(1H-Indol-6-yl)-3-(3-chloro-phenyl)-propyl]-methyl-amine XLII was prepared as a hydrochloride salt (190 mg, 83% yield) from 3-(1H-indol-6-yl)-3-(3-chloro-phenyl)-N-methyl-propionamide, using the procedure described above for [3-(1H-indol-7-yl)-3-phenyl-propyl]-methyl-amine XX (see Example 4). MS (M+H)=299.

Example 11

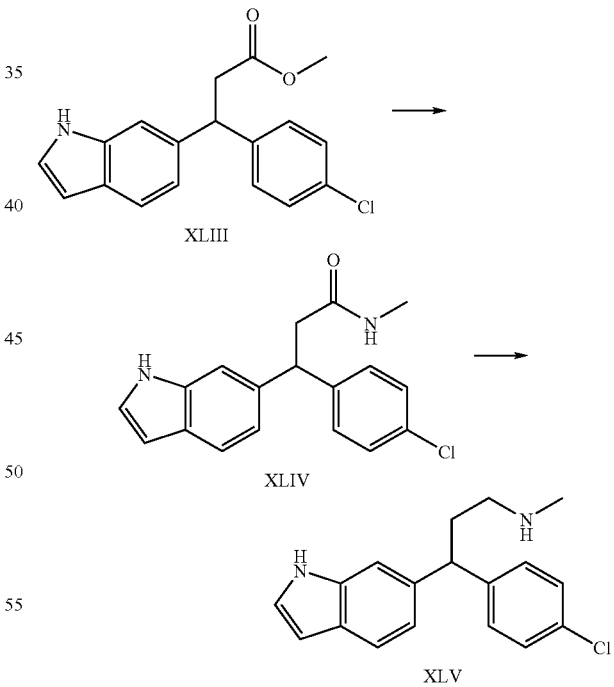

Synthesis of 3-(1H-Indol-6-yl)-3-(3-chloro-phenyl)-propionic acid methyl ester (XL)

A mixture of 3-(1H-indol-6-yl)-acrylic acid methyl ester XXX (0.4 g, 2.0 mmol), 3-chlorophenyl boronic acid (0.62 g, 4.0 mmol), [RhCl(cod)]₂ (49 mg, 0.10 mmol) and TEA (0.42 ml, 3.0 mmol) in water (6 ml) and 1,4-dioxane (1 ml) was stirred at 95° C. for 18 hours. The reaction mixture was cooled Synthesis of 3-(1H-Indol-6-yl)-3-(4-chloro-phenyl)-propionic acid methyl ester (XLIII)

3-(4-Chloro-phenyl)-3-(1H-indol-6-yl)-propionic acid methyl ester XLIII (0.40 g, 63%) was prepared using the procedure described above for 3-(1H-indol-6-yl)-3-(3-chloro-phenyl)-propionic acid methyl ester XL.

Synthesis of 3-(1H-Indol-6-yl)-3-(4-chloro-phenyl)-N-methyl-propionamide (XLIV)

3-(1H-Indol-6-yl)-3-(4-chloro-phenyl)-N-methyl-propionamide XLIV (370 mg, 97%) was prepared from 3-(1H-indol-6-yl)-3-(4-chloro-phenyl)-propionic acid methyl ester following the procedure for 3-(1H-indol-6-yl)-3-(2-methoxy-phenyl)-N-methyl-propionamide XXXVIII (see Example 9).

Synthesis of [3-(1H-Indol-6-yl)-3-(4-chloro-phenyl)-propyl]-methyl-amine (XLV)

[3-(1H-Indol-6-yl)-3-(4-chloro-phenyl)-propyl]-methyl-amine XLV was prepared as a hydrochloride (240 mg, 92% yield) from 3-(1H-indol-6-yl)-3-(4-chloro-phenyl)-N-methyl-propionamide, using the procedure described for [3-(1H-indol-7-yl)-3-phenyl-propyl]-methyl-amine XX (see Example 4). MS (M+H)=299.

Example 12

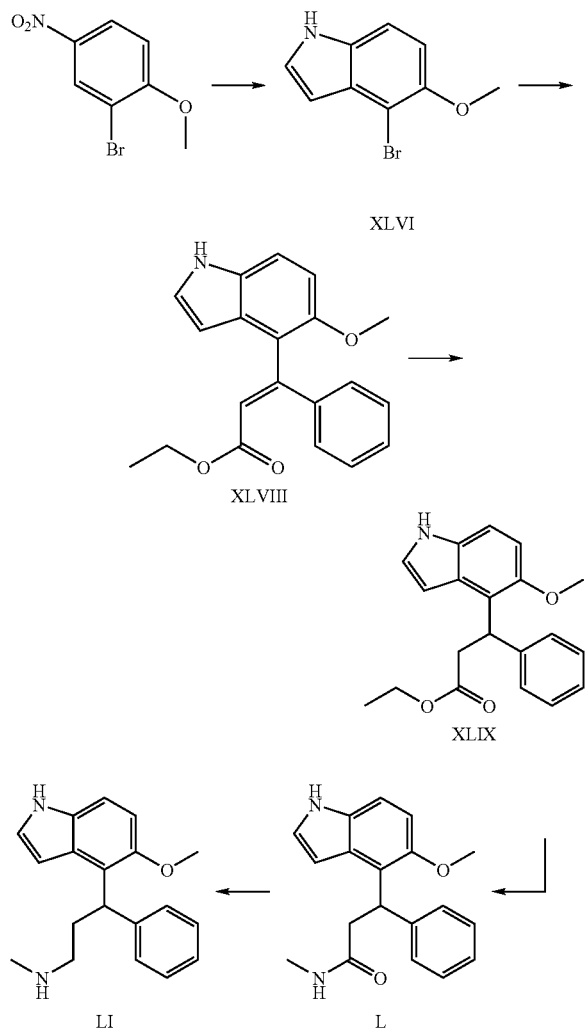

Synthesis of 4-bromo-5-methoxyindole (XLVI)

To a −40° C. solution of 2-bromo-4-nitro-anisole (1.16 g, 5 mmol) in THF (10 ml) was added vinylmagnesium bromide (1M in THF, 15 ml). The reaction mixture was stirred for 30 min while allowing the temperature to rise to −20° C. The reaction was quenched by addition of a saturated solution of NH$_4$Cl, diluted with Et$_2$O, and the aqueous layer was extracted twice with Et$_2$O. The combined organic layers were dried over Na$_2$SO$_4$, filtered, concentrated, and purified via flash chromatography (hexane/EtOAc) to provide 4-bromo-5-methoxyindole XLVI (38 mg, 3% yield) as an oil.

Synthesis of 3-(5-Methoxy-1H-Indol-4-yl)-3-phenyl-acrylic acid ethyl ester (XLVIII)

A mixture of 4-bromo-5-methoxyindole XLVI (104 mg, 0.46 mmol), ethyl cinammate (162 mg, 0.92 mmol), tetra-butylammonium bromide (29.6 mg, 0.092 mmol), TEA (128 μl, 0.092 mmol) and palladium-dichloro-[bis(tri-ortho-tolyl)phophine] (18 mg, 0.023 mmol) in DMF (2 ml) was stirred at 110° C. for 3 hours. The reaction mixture was cooled to room temperature and partitioned between brine and EtOAc. The organic layers were combined, dried over Na$_2$SO$_4$, filtered, concentrated, and purified via flash chromatography (hexane/EtOAc) affording 3-(5-Methoxy-1H-Indol-4-yl)-3-phenyl-acrylic acid ethyl ester XLVIII (37 mg, impure).

Synthesis of 3-(5-Methoxy-1H-Indol-4-yl)-3-phenyl-propionic acid ethyl ester (XLIX)

A mixture of 3-(5-Methoxy-1H-Indol-4-yl)-3-phenyl-acrylic acid ethyl ester XLVIII (37 mg, 0.115 mmol) in EtOH (4 ml) and a catalytic amount of Degoussa-type catalyst Pd/C wet (10%) was subjected to hydrogenation conditions in a Parr apparatus at 60 psi of H$_2$ for 20 hours. The reaction mixture was filtered through celite with MeOH. The filtrate was concentrated and subjected to the same hydrogenation conditions for 24 hours to provide 3-(5-Methoxy-1H-Indol-4-yl)-3-phenyl-propionic acid ethyl ester XLIX (37 mg) as a yellow oil.

Synthesis of 3-(5-Methoxy-1H-Indol-4-yl)-N-methyl-3-phenyl-propionamide (L)

To a 0° C. suspension of MeNH$_2$.HCl (15.6 mg, 0.231 mmol) in benzene (2 ml) was added Me$_3$Al (2M in toluene, 115 μl, 2.31 mmol). The mixture was stirred at 0° C. for 5 min and at RT for 2 hours after which a solution of 3-(5-methoxy-1H-Indol-4-yl)-3-phenyl-propionic acid ethyl ester XLIX in benzene (4 ml) was added. The reaction mixture was stirred at reflux for 5 hours and at room temperature for 16 hours, and quenched by addition of HCl (0.5 M). The aqueous layer was extracted with EtOAc. The organic layers were combined, dried over Na$_2$SO$_4$, filtered, and concentrated to yield crude 3-(5-Methoxy-1H-Indol-4-yl)-N-methyl-3-phenyl-propionamide L (37 mg, yellow oil), which was used without purification in the next step.

Synthesis of [3-(5-Methoxy-1H-Indol-4-yl)-3-phenyl-propyl]-methyl-amine (LI)

[3-(5-Methoxy-1H-Indol-4-yl)-3-phenyl-propyl]-methyl-amine LI (8 mg) was prepared using the procedure described above for [3-(1H-indol-7-yl)-3-phenyl-propyl]-methyl-amine XX (see Example 4). MS (M+H)=295.

Example 13

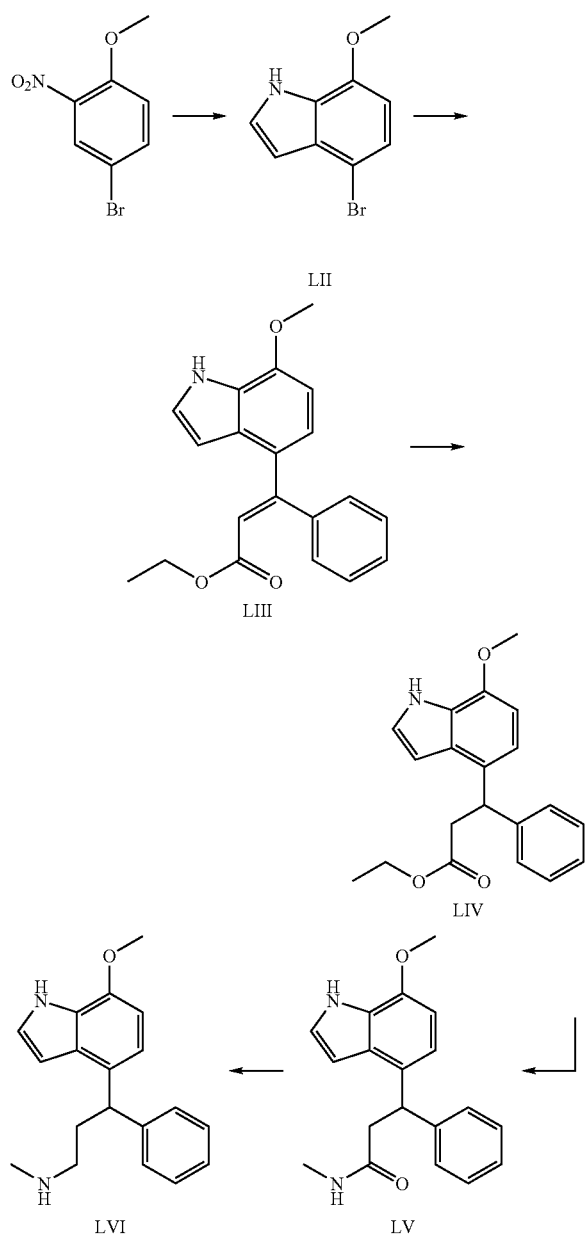

Synthesis of 4-bromo-7-methoxyindole (LII)

To a −60° C. solution of 4-bromo-2-nitroanisole (7.89 g, 33.3 mmol) in THF (300 was added vinylmagnesium bromide (1 M in THF, 100 ml, 0.1 mol) while maintaining the reaction temperature below −40° C. The resulting mixture was stirred allowing the temperature to rise to −40° C. in 2 hours. The reaction mixture was then quenched with a saturated solution of $NH_4Cl$ (700 ml) and extracted with $Et_2O$ (200 ml). The combined organic layers were washed with brine, dried over $MgSO_4$, filtered, concentrated, and purified through flash chromatography affording 4-bromo-7-methoxyindole LII (594 mg, 8% yield).

Synthesis of 3-(7-Methoxy-1H-Indol-4-yl)-3-phenyl-acrylic acid ethyl ester (LIII)

A stirring mixture of 4-bromo-7-methoxyindole LII (162 mg, 0.717 mmol), ethyl cinammate (254 mg, 1.43 mmol), tetra-butylammonium bromide (46 mg, 0.143 mmol), TEA (199 μl, 1.43 mmol) and palladium-dichloro-[bis-(tri-ortho-tolyl)phophine] (28 mg, 0.036 mmol) in DMF (2 ml) was heated in a sealed vial flushed with $N_2$, at 110° C. for 20 hours. The reaction was cooled to room temperature and partitioned between $H_2O$ and EtOAc. The organic layer was separated and the aqueous layer was extracted twice with EtOAc. The organics were combined dried over $Na_2SO_4$, filtered and evaporated. The crude mixture was purified via flash chromatography (hexane/EtOAc) affording 3-(7-methoxy-1H-Indol-4-yl)-3-phenyl-acrylic acid ethyl ester LIII (108 mg, 34% yield).

Synthesis of 3-(7-Methoxy-1H-Indol-4-yl)-3-phenyl-propionic acid ethyl ester (LIV)

3-(7-Methoxy-1H-Indol-4-yl)-3-phenyl-propionic acid ethyl ester LWV (102 g) was obtained from 3-(7-methoxy-1H-Indol-4-yl)-3-phenyl-acrylic acid ethyl ester LIII using the procedure described for 3-(1H-indol-7-yl)-N-methyl-3-phenyl-propionamide XIX (see Example 4).

Synthesis of 3-(7-Methoxy-1H-Indol-4-yl)-N-methyl-3-phenyl-propionamide (LV)

3-(7-Methoxy-1H-Indol-4-yl)-N-methyl-3-phenyl-propionamide LV was prepared from 3-(7-Methoxy-1H-Indol-4-yl)-3-phenyl-propionic acid ethyl ester using the procedure described for 3-(1H-indol-7-yl)-N-methyl-3-phenyl-acrylamide XVIII (see Example 4).

Synthesis of [3-(7-Methoxy-1H-Indol-4-yl)-3-phenyl-propyl]-methyl-amine (LVI)

To a 0° C. solution of 3-(7-methoxy-1H-Indol-4-yl)-N-methyl-3-phenyl-propionamide LV (0.315 mmol) in THF (3 ml) was added a suspension of $LiAlH_4$ (46.6 mg, 1.26 mmol) in THF (4 ml). The resulting mixture was stirred at 0° C. for 5 minutes, at reflux for 5 hours, then cooled to room temperature, and additional suspension of $LiAlH_4$ (46.6 mg, 1.26 mmol) in THF (4 ml) was added. The reaction was refluxed for additional 45 minutes, cooled to 0° C. and freshly ground $Na_2SO_4 \cdot 10H_2O$ (1 g) was added. The mixture was stirred at room temperature over the weekend. The solid was filtered and washed with EtOAc. The filtrate was concentrated and purified via flash chromatography (DCM/MeOH/$NH_4OH$) to provide the amine compound LVI as a yellow film (37 mg). The free amine was dissolved in $Et_2O$ (3 ml), cooled to 0° C., and HCl (1 M in $Et_2O$, 126 μl) was added. The precipitate was filtered affording the hydrochloride salt of [3-(7-Methoxy-1H-Indol-4-yl)-3-phenyl-propyl]-methyl-amine LVI as an off-white hygroscopic powder. MS (M+H)=295.

Example 14

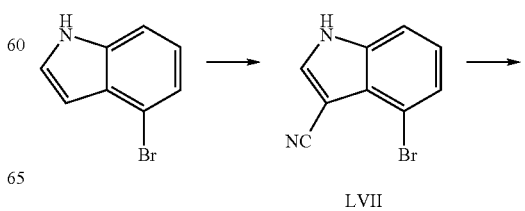

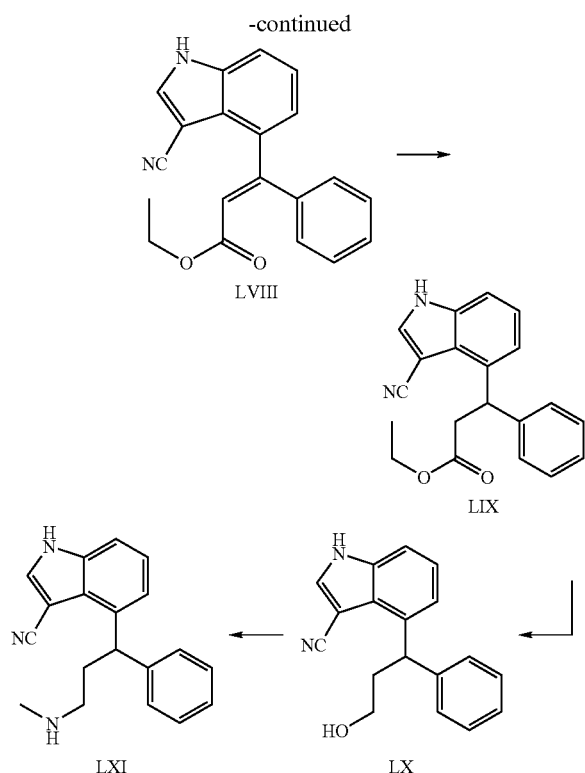

Synthesis of 4-bromo-1H-indole-3-carbonitrile (LVII)

To a 0° C. solution of 4-bromoindole (5 g, 25.5 mmol) in acetonitrile (50 ml) was added dropwise chlorsulfonylisocyanate (2.37 ml, 27.3 mmol) over a 5 minute period. The reaction mixture was stirred at 0° C. for 2 hours, and TEA (3.77 ml, 27.0) was added dropwise over a 10 minute period. The reaction mixture was allowed reach room temperature overnight, poured into ice/water mixture (200 ml), and the aqueous layer was extracted with EtOAc. The combined organic extracts were dried over $Na_2SO_4$, filtered, concentrated, and purified by flash chromatography to afford 4-bromo-1H-indole-3-carbonitrile LVII as an off-white solid (4.9 g, 87% yield).

Synthesis of 3-(3-Cyano-1H-Indol-4-yl)-3-phenyl-acrylic acid ethyl ester (LVIII)

A mixture of 4-bromo-1H-indole-3-carbonitrile LVII (2 g, 9.05 mmol), ethyl cinammate (3.19 g, 18.1 mmol), tetrabutylammonium bromide (582 mg, 1.81 mmol), TEA (2.52 ml, 18.1 mmol) and palladium-dichloro-[bis-(tri-ortho-tolyl)phophine] (357 mg, 0.453 mmol) in a sealed vial was stirred at 110° C. for 20 hours. The reaction mixture was cooled to room temperature, partitioned between $H_2O$ and DCM, and the aqueous layer was extracted with DCM. The organic extracts were combined, dried over $Na_2SO_4$, filtered, concentrated, and purified via flash chromatography (hexane/EtOAc) affording 3-(3-cyano-1H-Indol-4-yl)-3-phenyl-acrylic acid ethyl ester LVIII as a yellow solid (1.57 g, 55% yield).

Synthesis of 3-(3-Cyano-1H-Indol-4-yl)-3-phenyl-propionic acid ethyl ester (LIX)

To a solution of 3-(3-cyano-1H-Indol-4-yl)-3-phenyl-acrylic acid ethyl ester LVIII (620 mg, 1.96 mmol) in EtOH (30 ml) and EtOAc (15 ml) was added Degoussa-type catalyst (10% Pd/C wet, 70 mg). The reaction mixture was hydrogenated in a Parr apparatus at 55 psi of $H_2$ for 19 hours. The reaction mixture was filtered through celite with EtOH, MeOH and EtOAc. The filtrate was concentrated to afford 3-(3-cyano-1H-Indol-4-yl)-3-phenyl-propionic acid ethyl ester LIX as a white solid in quantitative yield (648 mg).

Synthesis of 4-(3-Hydroxy-1-pheny-propyl)-1H-indole-3-carbonitrile (LX)

To a 0° C. solution of 3-(3-cyano-1H-Indol-4-yl)-3-phenyl-propionic acid ethyl ester LIX (648 mg, 2.04 mmol) in THF (20 ml) was added Red-Al (65% w, 1.96 ml, 6.87 mmol) dropwise. The mixture was stirred at 0° C. for 3 hours, at room temperature for 30 minutes, and the reaction was quenched by addition of $H_2O$ (7 ml). The resulting mixture was stirred for 10 minutes and $H_2O$ (5 ml) and EtOAc (8 ml) were added. The mixture was then stirred overnight at room temperature. The solid was filtered off and washed with EtOAc. The organic layer was separated, dried over $Na_2SO_4$, filtered, concentrated, and purified via flash chromatography (hexane/EtOAc) affording 4-(3-hydroxy-1-pheny-propyl)-1H-indole-3-carbonitrile LX as a white solid (377 mg, 67% yield).

Synthesis of 4-(3-Methylamino-1-pheny-propyl)-1H-indole-3-carbonitrile (LXI)

To a 0° C. solution of 4-(3-hydroxy-1-pheny-propyl)-1H-indole-3-carbonitrile LX (377 mg, 1.36 mmol) in THF/DCM (1/1, 22 ml) was added MsCl (105 µl, 1.36 mmol) dropwise. The mixture was stirred at 0° C. for 10 minutes, and TEA (226 µl, 1.62 mmol) was added dropwise. The resulting mixture was stirred at 0° C. for 2.5 hours, poured into ice/water, and extracted with EtOAc. The combined organic layers were dried over $Na_2SO_4$, filtered, and concentrated affording methanesulfonic acid 3-(3-cyano-1H-indol-4-yl)-3-phenyl-propyl ester(not shown in above scheme) as a yellow oil. A solution of this crude mesylate in $MeNH_2$ (33% in EtOH, 8.5 ml) was placed in a sealed tube and stirred at 100° C. for 45 minutes. The reaction mixture was concentrated, and the residue was partitioned between a saturated solution of $NaHCO_3$ and EtOAc. The aqueous layer was extracted twice with EtOAc. The combined organic layers were dried over $Na_2SO_4$, filtered, concentrated, and purified via flash chromatography (DCM/MeOH/$NH_4OH$) affording 4-(3-methylamino-1-pheny-propyl)-1H-indole-3-carbonitrile LXI as a white foamy solid (346 mg). MS (M+H)=290.

Example 15

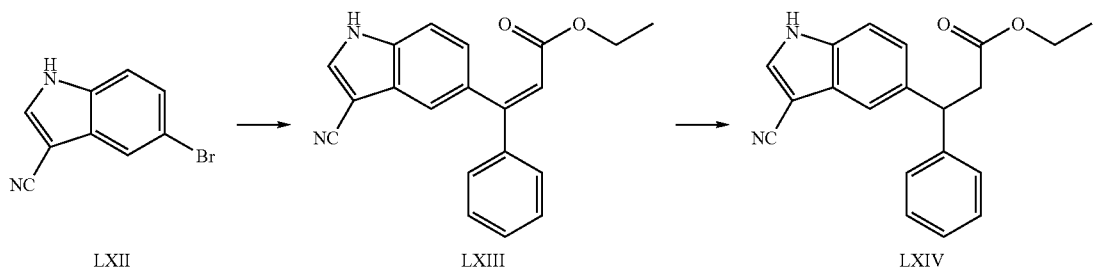

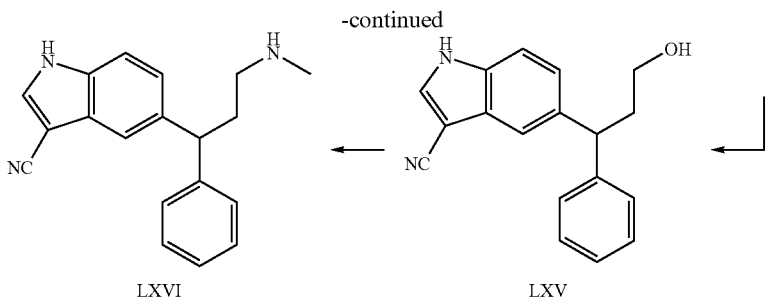

LXVI ← LXV

Synthesis of 5-bromo-1H-indole-3-carbonitrile (LXII)

5-Bromo-1H-indole-3-carbonitrile LXII (3.72 g, 66% yield) was prepared from 5-bromo-indole using the procedure described for 4-bromo-1H-indole-3-carbonitrile LVII (see Example 14).

Synthesis of 3-(3-Cyano-1H-Indol-5-yl)-3-phenyl-acrylic acid ethyl ester (LXIII)

3-(3-Cyano-1H-Indol-5-yl)-3-phenyl-acrylic acid ethyl ester LXIII (1.82 g, 85% yield) was prepared from 5-bromo-1H-indole-3-carbonitrile using the procedure described for 3-(3-cyano-1H-Indol-4-yl)-3-phenyl-acrylic acid ethyl ester LVIII.

Synthesis of 3-(3-Cyano-1H-Indol-5-yl)-3-phenyl-propionic acid ethyl ester (LXIV)

To a solution of 3-(3-cyano-1H-Indol-5-yl)-3-phenyl-acrylic acid ethyl ester LXIII (1.81 g, 5.71 mmol) in EtOH/EtOAc/MeOH (1/1/1, 60 ml) was added a catalytic amount of Pd/C (5%). The mixture was hydrogenated in a Parr apparatus at 60 psi of $H_2$ for 19 hours, filtered through celite, and the filter cake was washed with MeOH and EtOAc. The filtrate was concentrated to afford 3-(3-Cyano-1H-Indol-5-yl)-3-phenyl-propionic acid ethyl ester LXIV as a white foamy solid in quantitative yield (1.86 g).

Synthesis of 5-(3-Hydroxy-1-pheny-propyl)-1H-indole-3-carbonitrile (LXV)

5-(3-Hydroxy-1-pheny-propyl)-1H-indole-3-carbonitrile LXV (1.24 g, 79%) was prepared from 3-(3-cyano-1H-Indol-5-yl)-3-phenyl-propionic acid ethyl ester using the procedure described for 4-(3-hydroxy-1-pheny-propyl)-1H-indole-3-carbonitrile LX (see Example 14).

Synthesis of 5-(3-Methylamino-1-pheny-propyl)-1H-indole-3-carbonitrile (LXVI)

To a 0° C. solution of 5-(3-hydroxy-1-pheny-propyl)-1H-indole-3-carbonitrile LXV (600 mg, 2.17 mmol) in THF/DCM (1/1, 12 ml) was added dropwise MsCl (168 μl, 2.17 mmol). The mixture was stirred at 0° C. for 10 min and TEA (360 μl, 2.58 mmol) was added dropwise. The resulting mixture was stirred at 0° C. for 2 hours, diluted with THF (6 ml), stirred at 0° C. for additional 2 hours, poured into an ice/water mixture, and extracted with EtOAc. The combined organic layers were dried over $Na_2SO_4$, filtered and concentrated affording the metanesulfonic acid 3-(3-cyano-1H-indol-5-yl)-3-phenyl-propyl ester as a yellow oil. A solution of this mesylate in $MeNH_2$ (33% in EtOH, 10 ml) was heated in a sealed tube at 100° C. for 1 hour. The mixture was concentrated, and the residue was partitioned between a saturated solution of $NaHCO_3$ and DCM. The aqueous layer was extracted twice with DCM. The combined organic layers were dried over $Na_2SO_4$, filtered, concentrated and purified via flash chromatography (DCM/MeOH/$NH_4OH$) affording 5-(3-methylamino-1-pheny-propyl)-1H-indole-3-carbonitrile LXVI as a white solid (156 mg). MS (M+H)=290.

Example 16

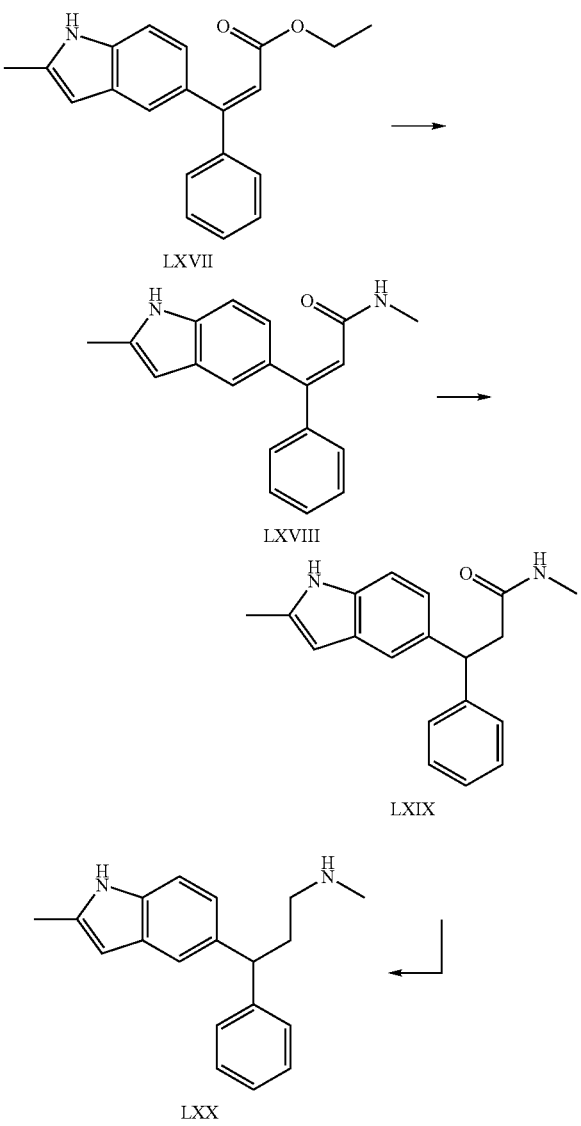

LXVII

LXVIII

LXIX

LXX

Synthesis of 3-(2-Methyl-1H-indol-5-yl)-3-phenyl-acrylic acid ethyl ester (LXVII)

3-(2-Methyl-1H-indol-5-yl)-3-phenyl-acrylic acid ethyl ester LXVII (1.25 g, 57%) was prepared from 2-methyl-5-bromoindole using the procedure described above for 3-(3-cyano-1H-Indol-4-yl)-3-phenyl-acrylic acid ethyl ester LVIII (see Example 14).

Synthesis of N-Methyl-3-(2-methyl-1H-indol-5-yl)-3-phenyl-acrylamide (LXVIII)

N-Methyl-3-(2-methyl-1H-indol-5-yl)-3-phenyl-acrylamide LXVIII (990 mg, 83%) was prepared from 3-(2-methyl-1H-indol-5-yl)-3-phenyl-acrylic acid ethyl ester using the procedure described for 3-(1H-indol-7-yl)-N-methyl-3-phenyl-acrylamide XVIII (see Example 4).

Synthesis of N-Methyl-3-(2-methyl-1H-indol-5-yl)-3-phenyl-propionamide (LXIX)

To a solution of N-methyl-3-(2-methyl-1H-indol-5-yl)-3-phenyl-acrylamide LXVIII (990 mg, 3.41 mmol) in EtOH/EtOAc/MeOH (5/2/1, 40 ml) was added Pd/C (5%, 90 mg). The mixture was hydrogenated in a Parr apparatus at 60 psi of $H_2$ for 48 hours. Degoussa-type catalyst (10% Pd/C, catalytic amount) was added to the mixture. The mixture was hydrogenated in a Parr apparatus at 60 psi of $H_2$ for additional 6 hours. The reaction mixture was filtered through celite, and the filter cake was washed with MeOH, hot EtOH and DCM. The filtrate was concentrated affording N-methyl-3-(2-methyl-1H-indol-5-yl)-3-phenyl-propionamide LXIX as a light orange foamy solid in quantitative yield (1.05 g).

Synthesis of Methyl-[3-(2-methyl-1H-indol-5-yl)-3-phenyl-propyl]-amine (LXX)

Methyl-[3-(2-methyl-1H-indol-5-yl)-3-phenyl-propyl]-amine LXX was prepared as a hydrochloride (220 mg, 78% yield) from N-methyl-3-(2-methyl-1H-indol-5-yl)-3-phenyl-propionamide using the procedure described above for [3-(1H-indol-7-yl)-3-phenyl-propyl]-methyl-amine XX (see Example 4). MS (M+H)=279.

Example 17

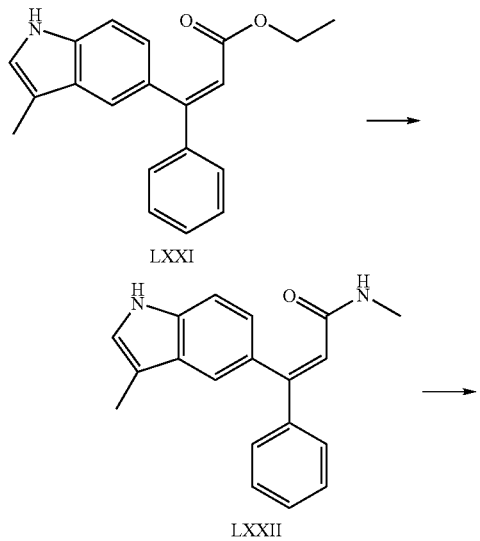

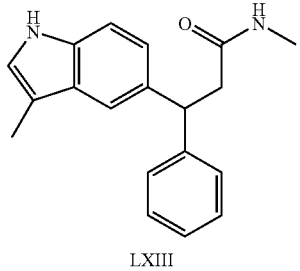

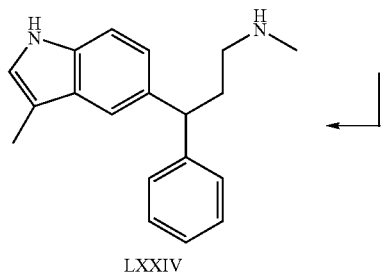

Synthesis of 3-(3-Methyl-1H-indol-5-yl)-3-phenyl-acrylic acid ethyl ester (LXXI)

3-(3-Methyl-1H-indol-5-yl)-3-phenyl-acrylic acid ethyl ester LXXI (656 mg, 90% yield) was prepared from 3-methyl-5-bromoindole using the procedure described above for 3-(3-cyano-1H-Indol-4-yl)-3-phenyl-acrylic acid ethyl ester LVIII (see Example 14).

Synthesis of N-Methyl-3-(3-methyl-1H-indol-5-yl)-3-phenyl-acrylamide (LXXII)

N-Methyl-3-(3-methyl-1H-indol-5-yl)-3-phenyl-acrylamide LXXII (386 mg, 62% yield) was prepared from 3-(3-methyl-1H-indol-5-yl)-3-phenyl-acrylic acid ethyl ester using the procedure described above for preparation of 3-(3-cyano-1H-Indol-4-yl)-3-phenyl-acrylic acid ethyl ester XVIII (see Example 4).

Synthesis of N-Methyl-3-(3-methyl-1H-indol-5-yl)-3-phenyl-propionamide (LXXIII)

To a solution of N-methyl-3-(3-methyl-1H-indol-5-yl)-3-phenyl-acrylamide LXXII (386 mg, 1.33 mmol) in EtOH/EtOAc/DCM (2/1.5/1, 55 ml) was added Degoussa-type catalyst (Pd/C 10%, 40 mg), and the mixture was hydrogenated in a Parr apparatus at 50 psi of $H_2$ for 20 hours. The reaction mixture was filtered through celite, and the filter cake was washed with MeOH, EtOAc and DCM. The filtrate was concentrated to afford N-Methyl-3-(3-methyl-1H-indol-5-yl)-3-phenyl-propionamide LXXIII as a white foamy solid (341 mg, 89% yield).

Synthesis of Methyl-[3-(3-methyl-1H-indol-5-yl)-3-phenyl-propyl]-amine (LXXIV)

Methyl-[3-(3-methyl-1H-indol-5-yl)-3-phenyl-propyl]-amine LXXIV (221 mg, 68% yield) was prepared from N-methyl-3-(2-methyl-1H-indol-5-yl)-3-phenyl-propionamide using the procedure described above for [3-(1H-indol-7-yl)-3-phenyl-propyl]-methyl-amine XX (see Example 4). MS (M+H)=279.

Example 18

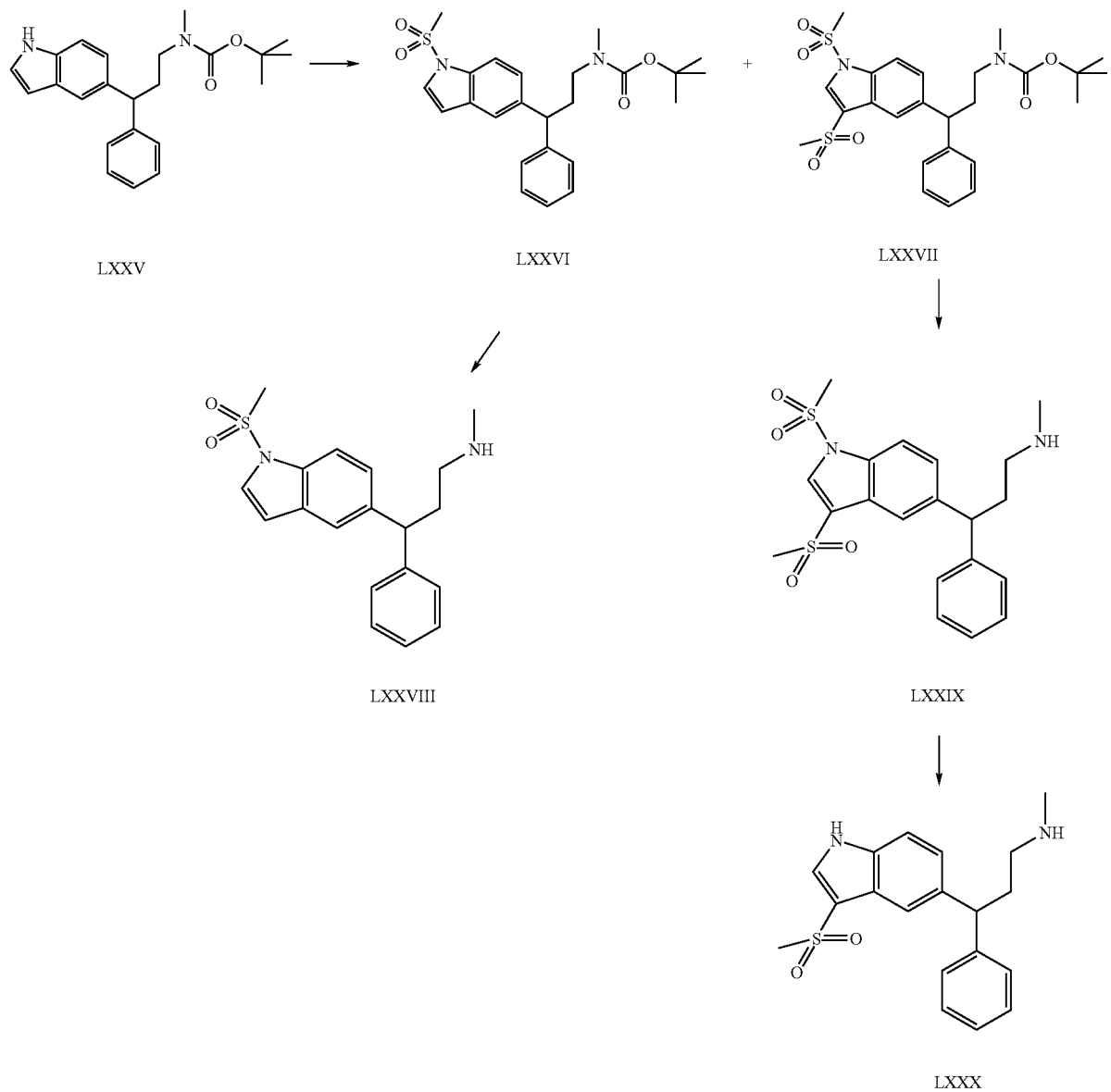

Synthesis of [3-(1H-indol-5-yl)-3-phenyl-propyl]-methyl-carbamic acid tert-butyl ester (LXXV)

To a solution of [3-(1H-indol-5-yl)-3-phenyl-propyl]-methyl-amine XI (see Example 2) (515 mg, 1.95 mmol) in 1,4-dioxane (15 ml) was added (BOC)$_2$O (510 mg, 2.34 mmol) and a solution of NaOH (156 mg, 3.9 mmol) in H$_2$O (4 ml). The reaction mixture was stirred at room temperature for 40 minutes. The reaction mixture was concentrated, and the residue was partitioned between a saturated solution of NaHCO$_3$ and Et$_2$O. The aqueous layer was extracted with Et$_2$O, and the combined organic layers were dried over Na$_2$SO$_4$, filtered, concentrated and purified via flash chromatography (hexane/EtOAc) affording [3-(1H-indol-5-yl)-3-phenyl-propyl]-methyl-carbamic acid tert-butyl ester LXXV as a foamy white solid (486 mg, 69% yield).

Synthesis of [3-(1-Methanesulfonyl-1H-indol-5-yl)-3-phenyl-propyl]-methyl-carbamic acid tert-butyl ester (LXXVI) and [3-(1,3-Bis-methanesulfonyl-1H-indol-5-yl)-3-phenyl-propyl]-methyl-carbamic acid tert-butyl ester (LXXVII)

A suspension of NaH (23.4 mg, 0.928 mmol) in DMSO (1.2 ml, 16.9 mmol) was stirred at RT for 20 min. To this mixture was added a solution of [3-(1H-indol-5-yl)-3-phenyl-propyl]-methyl-carbamic acid tert-butyl ester LXXV (307 mg, 0.843 mmol) in Et$_2$O (9 ml). The reaction mixture was stirred at room temperature for 40 minutes, after which MsCl (78.2 µl, 1.01 mmol) was added. The reaction mixture was stirred at room temperature for 2.5 hours followed by reflux for 2 hours. The mixture was partitioned between a saturated solution of NaHCO$_3$ and Et$_2$O. The aqueous layer was extracted with Et$_2$O, and the combined organic layers were dried over Na$_2$SO$_4$, filtered, concentrated, and purified via flash chromatography (hexane/EtOAc) affording [3-(1-Methanesulfonyl-1H-indol-5-yl)-3-phenyl-propyl]-methyl-carbamic acid tert-butyl ester LXXVI (56 mg, 15% yield) in a first fraction, and [3-(1,3-Bis-methanesulfonyl-1H-indol-5-yl)-3-phenyl-propyl]-methyl-carbamic acid tert-butyl ester LXXVII (45 mg, 10% yield) in a second fraction.

Synthesis of [3-(1-Methanesulfonyl-1H-indol-5-yl)-3-phenyl-propyl]-methyl-amine (LXXVIII)

To a 0° C. solution of [3-(1-Methanesulfonyl-1H-indol-5-yl)-3-phenyl-propyl]-methyl-carbamic acid tert-butyl ester LXXVI (56 mg, 0.127 mmol) in DCM (3 ml) was added triethylsilane (300 µl) and TFA (1.5 ml). The resulting mixture was stirred at 0° C. for 5 minutes and at room temperature for 40 minutes. The mixture was concentrated, and the residue was partitioned between a saturated solution of NaHCO$_3$ and EtOAc. The combined organic layers were dried over Na$_2$SO$_4$, filtered, concentrated, and purified via flash chromatography (DCM/MeOH/NH$_4$OH) affording [3-(1-Methanesulfonyl-1H-indol-5-yl)-3-phenyl-propyl]-methyl-amine LXXVIII as a white solid (31 mg, 71% yield). The amine LXXVIII (31 mg, 71% yield) was dissolved in Et$_2$O (3 ml) and HCl (1M in Et$_2$O, 95 µl) was added. The precipitate was filtered, washed with Et$_2$O and dried in vacuo to afford the hydrochloride as a white powder (33 mg, 96% yield). MS (M+H)=343

Synthesis of [3-(1,3-Bis-methanesulfonyl-1H-indol-5-yl)-3-phenyl-propyl]-methyl-amine (LXXIX)

[3-(1,3-Bis-methanesulfonyl-1H-indol-5-yl)-3-phenyl-propyl]-methyl-carbamic acid tert-butyl ester LXXVII was deprotected following the same procedure described above for [3-(1-Methanesulfonyl-1H-indol-5-yl)-3-phenyl-propyl]-methyl-carbamic acid tert-butyl ester LXXVI to afford [3-(1,3-Bis-methanesulfonyl-1H-indol-5-yl)-3-phenyl-propyl]-methyl-amine LXXIX as a colorless oil in quantitative yield.

Synthesis of [3-(3-Methanesulfonyl-1H-indol-5-yl)-3-phenyl-propyl]-methyl-amine (LXXX)

To a solution of [3-(1,3-bis-methanesulfonyl-1H-indol-5-yl)-3-phenyl-propyl]-methyl-amine LXXIX (36 mg, 0.0865 mmol) in MeOH (3 ml) was added a solution of KOH (7.29 mg, 0.13 mmol) in MeOH. After stirring for 50 minutes at room temperature, the mixture was concentrated, and the residue was partitioned between EtOAc and H$_2$O. The combined organic layers were dried over Na$_2$SO$_4$, filtered, concentrated, and purified via flash chromatography (DCM/MeOH/NH$_4$OH) to provide [3-(3-methanesulfonyl-1H-indol-5-yl)-3-phenyl-propyl]-methyl-amine LXXX as a white powder (13 mg, 36% yield). MS (M+H)=343.

Example 19

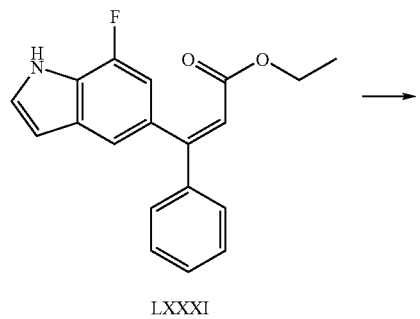

LXXXI

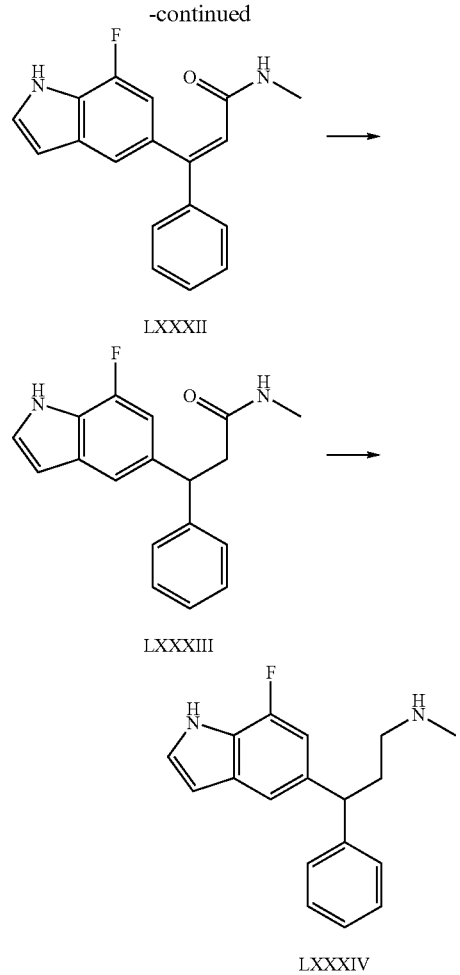

Synthesis of 3-(7-Fluoro-1H-indol-5-yl)-3-phenyl-acrylic acid ethyl ester (LXXXI)

3-(7-Fluoro-1H-indol-5-yl)-3-phenyl-acrylic acid ethyl ester LXXXI (215 mg, 74% yield) was prepared from 5-bromo-7-fluoroindole using the procedure described for 3-(7-Methoxy-1H-Indol-4-yl)-3-phenyl-acrylic acid ethyl ester LIII (Example 13).

Synthesis of 3-(7-Fluoro-1H-indol-5-yl)-N-Methyl-3-phenyl-acrylamide (LXXXII)

3-(7-Fluoro-1H-indol-5-yl)-N-Methyl-3-phenyl-acrylamide LXXXII (120 mg, 59% yield) was prepared from 3-(7-fluoro-1H-indol-5-yl)-3-phenyl-acrylic acid ethyl ester using the procedure described above for 3-(1H-Indol-7-yl)-N-methyl-3-phenyl-acrylamide XVIII (see Example 4).

Synthesis of 3-(7-Fluoro-1H-indol-5-yl)-N-Methyl-3-phenyl-propionamide (LXXXIII)

3-(7-Fluoro-1H-indol-5-yl)-N-Methyl-3-phenyl-propionamide LXXXIII (127 mg, quantitative yield) was obtained from 3-(7-fluoro-1H-indol-5-yl)-N-methyl-3-phenyl-acrylamide using the procedure described above for preparation of 3-(1H-Indol-7-yl)-N-methyl-3-phenyl-propionamide XIX.

Preparation of [3-(7-Fluoro-1H-indol-5-yl)-3-phenyl-propyl]-amine (LXXXIV)

[3-(7-Fluoro-1H-indol-5-yl)-3-phenyl-propyl]-amine LXXXIV was obtained from 3-(7-fluoro-1H-indol-5-yl)-N-methyl-3-phenyl-propionamide as a hydrochloride (41 mg, 87% yield) using the procedure described above for preparation of [3-(1H-Indol-7-yl)-3-phenyl-propyl]-methyl-amine (Example 4). MS (M+H)=283.

Example 20

Synthesis of 3-(3-Cyano-7-fluoro-1H-indol-5-yl)-3-phenyl-propionic acid ethyl ester (LXXXVII)

3-(3-Cyano-7-fluoro-1H-indol-5-yl)-3-phenyl-propionic acid ethyl ester LXXXVII was prepared from 3-(3-cyano-7-fluoro-1H-indol-5-yl)-3-phenyl-propionic acid ethyl ester using the procedure described above for preparation of 3-(1H-Indol-7-yl)-N-methyl-3-phenyl-propionamide (Example 4).

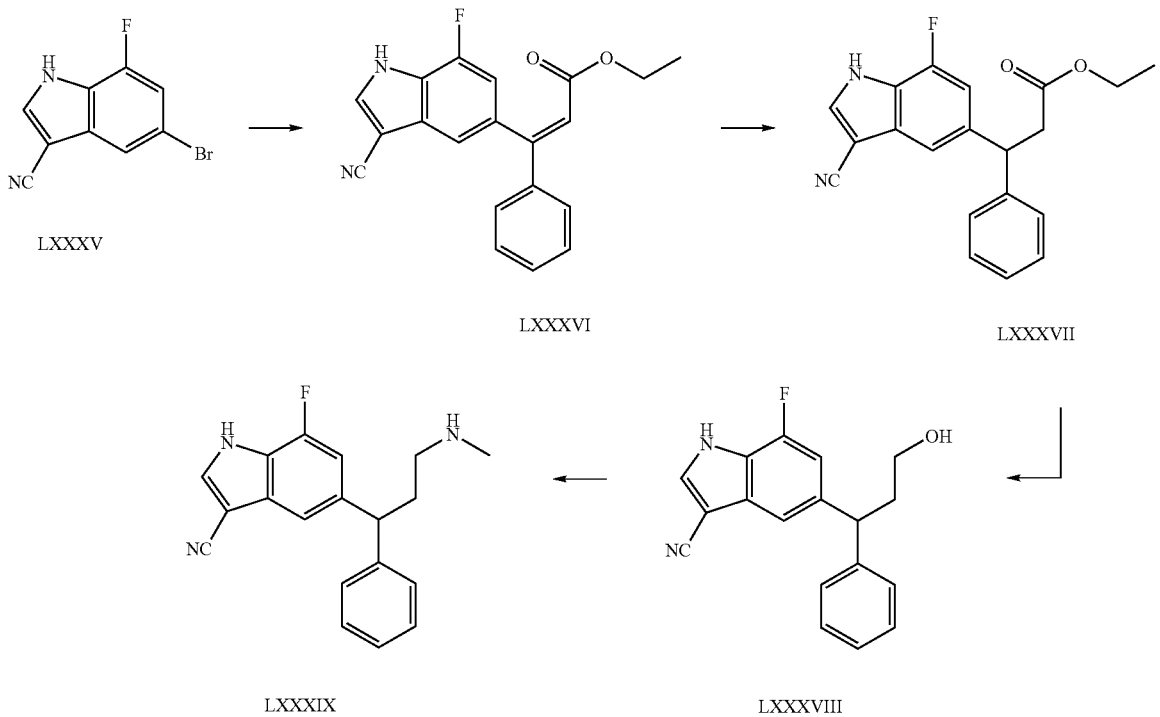

LXXXV

LXXXVI

LXXXVII

LXXXIX

LXXXVIII

Synthesis of 5-Bromo-7-fluoro-1H-indole-3-carbonitrile (LXXXV)

5-Bromo-7-fluoro-1H-indole-3-carbonitrile LXXXV, 72% yield (800 mg), was prepared from 5-bromo-7-fluoro-indole using the procedure described above for preparation of 4-bromo-1H-indole-3-carbonitrile (Example 14).

Synthesis of 3-(3-Cyano-7-fluoro-1H-indol-5-yl)-3-phenyl-acrylic acid ethyl ester (LXXXVI)

3-(3-Cyano-7-fluoro-1H-indol-5-yl)-3-phenyl-acrylic acid ethyl ester (LXXXVI (841 mg, 82% yield) was prepared from 5-bromo-7-fluoro-1H-indole-3-carbonitrileusing the procedure described above for preparation of 3-(7-Methoxy-1H-Indol-4-yl)-3-phenyl-acrylic acid ethyl ester (Example 13).

Synthesis of 7-Fluoro-5-(3-hydroxy-1-phenyl-propyl)-1H-indole-3-carbonitrile (LXXXVIII)

7-Fluoro-5-(3-hydroxy-1-phenyl-propyl)-1H-indole-3-carbonitrile LXXXVIII (328 mg) was prepared from 3-(3-cyano-7-fluoro-1H-indol-5-yl)-3-phenyl-propionic acid ethyl ester using the procedure described above for preparation of -(3-Hydroxy-1-pheny-propyl)-1H-indole-3-carbonitrile LX (Example 14).

Synthesis of 7-Fluoro-5-(3-Methylamino-1-phenyl-propyl)-1H-indole-3-carbonitrile (LXXXIX)

7-Fluoro-5-(3-Methylamino-1-phenyl-propyl)-1H-indole-3-carbonitrile LXXXIX (197 mg) was prepared from 7-fluoro-5-(3-hydroxy-1-phenyl-propyl)-1H-indole-3-carbonitrile using the procedure described above for preparation of 5-(3-Methylamino-1-pheny-propyl)-1H-indole-3-carbonitrile LXVI (Example 16). MS (M+H)=308.

Example 21

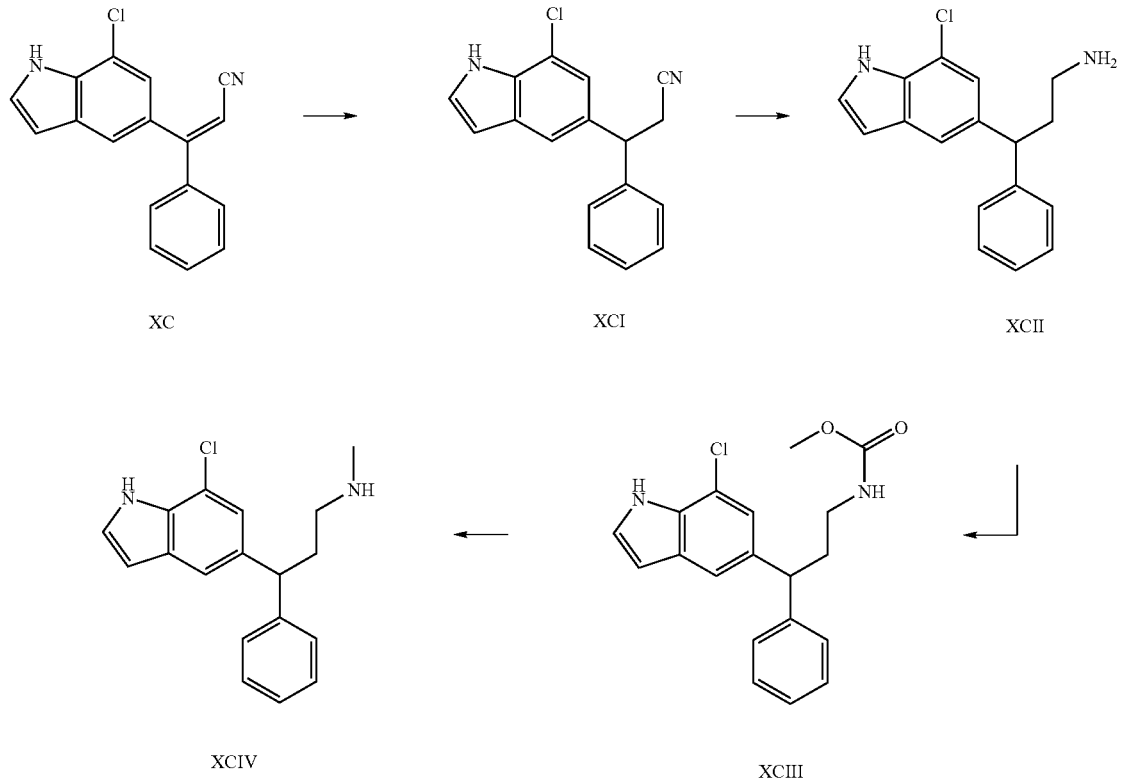

Synthesis of 3-(7-Chloro-1H-indol-5-yl)-3-phenyl-acrylonitrile (XC)

A 50 ml tube was charged with 5-bromo-7-chloro-indole (840 mg, 3.6 mmol, see *J. Med. Chem.*, 2002, 45, 1697), cinammonitrile (0.69 ml, 5.5 mmol), palladium acetate (41 mg, 0.18 mmol), tri-ortho-tolyl-phosphine (0.11 g, 0.36 mmol), and TEA (0.76 ml, 5.5 mmol). The mixture was stirred at 100° C. for 18 h. To the resulting solidified dark green mixture was added DCM (25 ml), and the mixture was filtered through celite. The filtrate was concentrated onto silica gel and purified via flash chromatography (hexane/ EtOAc) affording 3-(7-Chloro-1H-indol-5-yl)-3-phenyl-acrylonitrile XC as a yellow solid (0.81 g, 81% yield).

Synthesis of 3-(7-Chloro-1H-indol-5-yl)-3-phenyl-propionitrile (XCI)

Crude 3-(7-Chloro-1H-indol-5-yl)-3-phenyl-propionitrile XCI was obtained from 3-(7-chloro-1H-indol-5-yl)-3-phenyl-acrylonitrile using the procedure described above for preparation of 3-(1H-Indol-4-yl)-3-phenyl-propionitrile II (Example 1).

Synthesis of 3-(7-Chloro-1H-indol-5-yl)-3-phenyl-propylamine (XCII)

3-(7-Chloro-1H-indol-5-yl)-3-phenyl-propylamine XCII (0.60 g) was prepared from 3-(7-chloro-1H-indol-5-yl)-3-phenyl-propionitrile using the procedure described above for preparation of 3-(1H-Indol-4-yl)-3-phenyl-propylamine III (Example 1).

Synthesis of [3-(7-Chloro-1H-indol-5-yl)-3-phenyl-propyl]-carbamic acid methylester (XCIII)

[3-(7-Chloro-1H-indol-5-yl)-3-phenyl-propyl]-carbamic acid methylester XCIII (0.31 g, 48% yield) was prepared from 3-(7-Chloro-1H-indol-5-yl)-3-phenyl-propylamine using the procedure described above for preparation of [3-(1H-Indol-4-yl)-3-phenyl-propyl]-carbamic acid methylester V (Example 1).

Synthesis of [3-(7Chloro-1H-indol-5-yl)-3-phenyl-propyl]-methyl-amine (XCIV)

[3-(7Chloro-1H-indol-5-yl)-3-phenyl-propyl]-methyl-amine XCIV was obtained as a white solid (130 mg, 48% yield) from [3-(7-Chloro-1H-indol-5-yl)-3-phenyl-propyl]-carbamic acid methylester using the procedure described above for preparation of [3-(1H-Indol-5-yl)-3-phenyl-propyl]-methyl-amine XI (Example 2). MS (M+H)=299.

Example 22

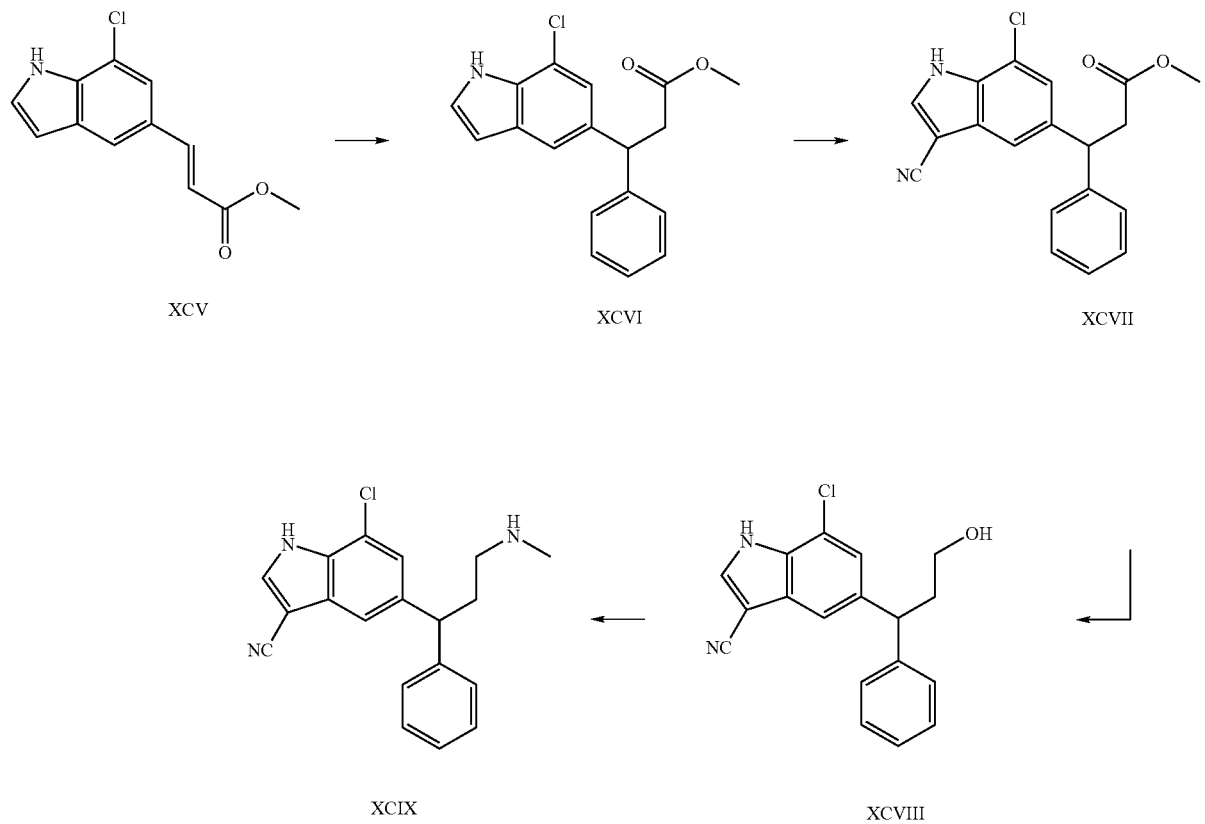

Synthesis of 3-(7-Chloro-1H-indol-5-yl)-acrylic acid methyl ester (XCV)

3-(7-Chloro-1H-indol-5-yl)-acrylic acid methyl ester XCV (51% yield, 510 mg) wqas obtained from 5-bromo-7-chloroindole using the procedure described above for preparation of 3-(1H-Indol-6-yl)-acrylic acid methyl ester XXX (Example 7).

Synthesis of 3-(7-Chloro-1H-indol-5-yl)-3-phenyl-propionic acid methyl ester (XCVI)

3-(7-Chloro-1H-indol-5-yl)-3-phenyl-propionic acid methyl ester XCVI (209 mg, 50% yield) was obtained from 3-(7-Chloro-1H-indol-5-yl)-acrylic acid methyl ester using the procedure described above for preparation of 3-(1H-Indol-6-yl)-3-(2-methoxy-phenyl)-propionic acid methyl ester XXXVII (Example 9).

Synthesis of 3-(7-Chloro-3-cyano-1H-indol-5-yl)-3-phenyl-propionic acid methyl ester (XCVII)

3-(7-Chloro-3-cyano-1H-indol-5-yl)-3-phenyl-propionic acid methyl ester XCVII (110 mg, 64% yield) was obtained from 3-(7-chloro-1H-indol-5-yl)-3-phenyl-propionic acid methyl ester using the procedure described above for preparation of 4-bromo-1H-indole-3-carbonitrile LVII (Example 14).

Synthesis of 7-Chloro-5-(3-hydroxy-1-phenyl-propyl)-1H-indole-3-carbonitrile (XCVIII)

Crude 7-Chloro-5-(3-hydroxy-1-phenyl-propyl)-1H-indole-3-carbonitrile XCVIII was obtained from 3-(7-chloro-3-cyano-1H-indol-5-yl)-3-phenyl-propionic acid methyl ester using the procedure described above for preparation of 4-(3-Hydroxy-1-pheny-propyl)-1H-indole-3-carbonitrile LX (Example 14).

Synthesis of 7-Chloro-5-(3-Methylamino-1-phenyl-propyl)-1H-indole-3-carbonitrile (XCIX)

7-Chloro-5-(3-Methylamino-1-phenyl-propyl)-1H-indole-3-carbonitrile XCIX was obtained from 7-chloro-5-(3-hydroxy-1-phenyl-propyl)-1H-indole-3-carbonitrile using the procedure described above for preparation of 4-(3-Methylamino-1-pheny-propyl)-1H-indole-3-carbonitrile LXVI (Example 14). MS (M+H)=324.

Example 23

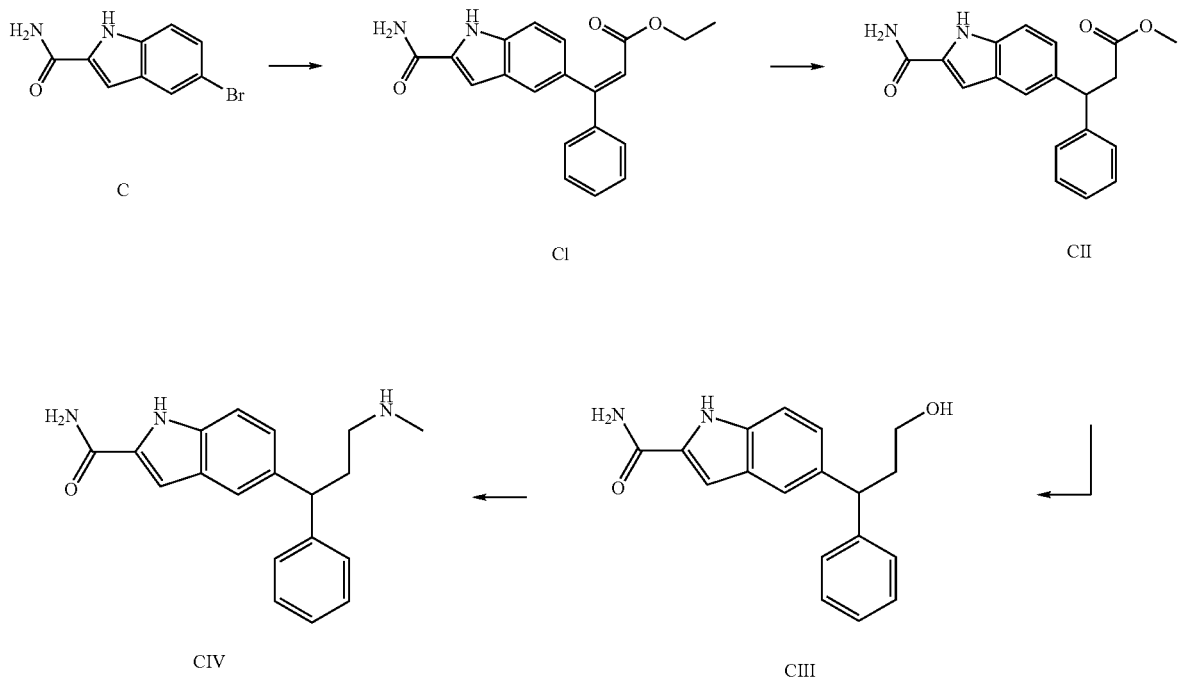

Synthesis of 5-Bromo-1H-indole-2-carboxylic acid amide (C)

To a solution of 5-bromo-1H-indole-2-carboxylic acid (4 g, 16.7 mmol) in DMF (50 ml) at room temperature was added diisopropylethylamine (DIPEA) (5.71 ml, 32.8 mmol), PyBOP (13 g, 25.0 mmol) and HOBT (3.39 g, 25.0 mmol). After stirring the mixture for 30 minutes, $NH_4Cl$ (1.75 g, 32.8 mmol) was added and the resulting yellow suspension was stirred at room temperature for 6 hours. The reaction was quenched by addition of $H_2O$. The yellow foamy precipitate was discarded and the mother liquor was extracted with EtOAc. The organic layers were combined, washed with NaOH (1M) and brine, dried over $Na_2SO_4$, filtered and concentrated. The residue was then dissolved in EtOAc and washed with HCl (1 M) and brine, dried over $Na_2SO_4$, filtered and concentrated. The oily residue was triturated with DCM affording, after filtration, 5-Bromo-1H-indole-2-carboxylic acid amide C as a light yellow solid (2.12 g, 53% yield).

Synthesis of 3-(2-Carbamoyl-1H-indol-5-yl)-3-phenyl-acrylic acid ethyl ester (CI)

3-(2-Carbamoyl-1H-indol-5-yl)-3-phenyl-acrylic acid ethyl ester CI (745 mg, 74% yield) was prepared from 5-bromo-1H-indole-2-carboxylic acid amide using the procedure described above for preparation of 3-(3-Cyano-1H-Indol-4-yl)-3-phenyl-acrylic acid ethyl ester LVIII (Example 14).

Synthesis of 3-(2-Carbamoyl-1H-indol-5-yl)-3-phenyl-propionic acid ethyl ester (CII)

3-(2-Carbamoyl-1H-indol-5-yl)-3-phenyl-propionic acid ethyl ester CII (628 mg) was prepared from 3-(2-carbamoyl-1H-indol-5-yl)-3-phenyl-acrylic acid ethyl ester using the procedure described above for preparation of 3-(1H-Indol-7-yl)-N-methyl-3-phenyl-propionamide XIX (Example 4).

Synthesis of 5-(3-Hydroxy-1-phenyl-propyl)-1H-indole-5-yl)-2-carboxylic acid amide (CIII)

5-(3-Hydroxy-1-phenyl-propyl)-1H-indole-5-yl)-2-carboxylic acid amide CIII (182 mg) was prepared from 3-(2-carbamoyl-1H-indol-5-yl)-3-phenyl-propionic acid ethyl ester using the procedure described above for preparation of 4-(3-Hydroxy-1-pheny-propyl)-1H-indole-3-carbonitrile LX (Example 14).

Synthesis of 5-(3-Methylamino-1-phenyl-propyl)-1H-indole-2-carboxylic acid amide (CIV)

5-(3-Methylamino-1-phenyl-propyl)-1H-indole-2-carboxylic acid amide CIV (10 mg) was prepared from 5-(3-hydroxy-1-phenyl-propyl)-1H-indole-5-yl)-2-carboxylic acid amide using the procedure described above for preparation of 5-(3-Methylamino-1-pheny-propyl)-1H-indole-3-carbonitrile LXVI (Example 15). MS (M+H)=308.

Example 24

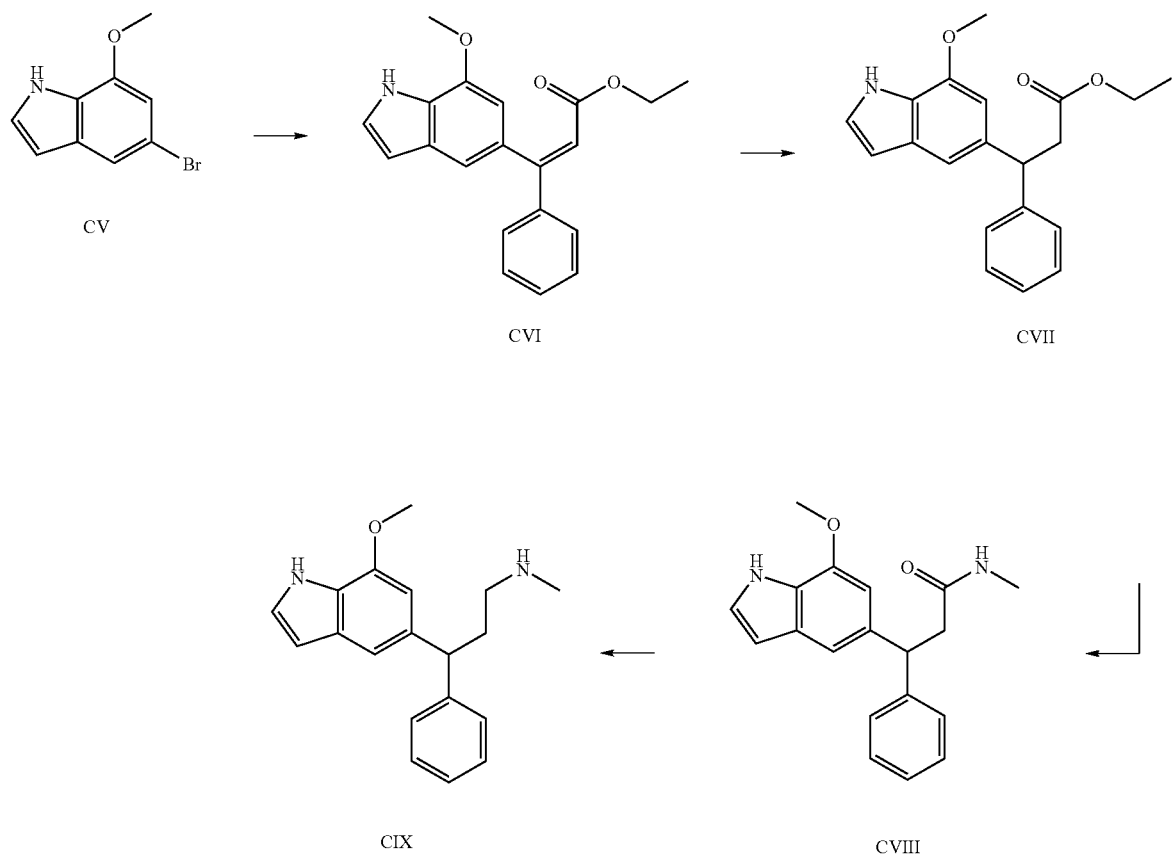

Synthesis of 5-Bromo-7-methoxyindole (CV)

5-Bromo-7-methoxyindole CV was prepared from 5-bromo-2-nitroanisole using the procedure described above for preparation of 4-bromo-7-methoxyindole LII (Example 13).

Synthesis of 3-(7-Methoxy-1H-indol-5-yl)-3-phenyl-acrylic acid ethyl ester (CVI)

3-(7-Methoxy-1H-indol-5-yl)-3-phenyl-acrylic acid ethyl ester CVI (120 mg, 50% yield) was prepared from 5-bromo-7-methoxyindole using the procedure described above for preparation of 3-(7-Methoxy-1H-Indol-4-yl)-3-phenyl-acrylic acid ethyl ester LIII (Example 13).

Synthesis of 3-(7-Methoxy-1H-indol-5-yl)-3-phenyl-propionic acid ethyl ester (CVII)

3-(7-Methoxy-1H-indol-5-yl)-3-phenyl-propionic acid ethyl ester CVII was obtained in quantitative yield from 3-(7-methoxy-1H-indol-5-yl)-3-phenyl-acrylic acid ethyl ester using the procedure described above for preparation of 3-(3-Cyano-1H-Indol-4-yl)-3-phenyl-propionic acid ethyl ester LIX (Example 14).

Synthesis of 3-(7-Methoxy-1H-indol-5-yl)-N-Methyl-3-phenyl-propionamide (CVIII)

3-(7-Methoxy-1H-indol-5-yl)-N-Methyl-3-phenyl-propionamide CVIII was obtained from 3-(7-methoxy-1H-indol-5-yl)-3-phenyl-propionic acid ethyl este using the procedure described above for preparation of 3-(1H-Indol-7-yl)-N-methyl-3-phenyl-acrylamide XVIII (see Example 4).

Synthesis of [3-(7-Methoxy-1H-indol-5-yl)-3-phenyl-propyl]-amine (CIX)

[3-(7-Methoxy-1H-indol-5-yl)-3-phenyl-propyl]-amine CIX was obtained as a hydrochloride salt (41 mg) from 3-(7-methoxy-1H-indol-5-yl)-N-Methyl-3-phenyl-propionamide following the procedure described above for preparation of [3-(1H-Indol-7-yl)-3-phenyl-propyl]-methyl-amine XX (Example 4). MS (M+H)=295.

Example 25

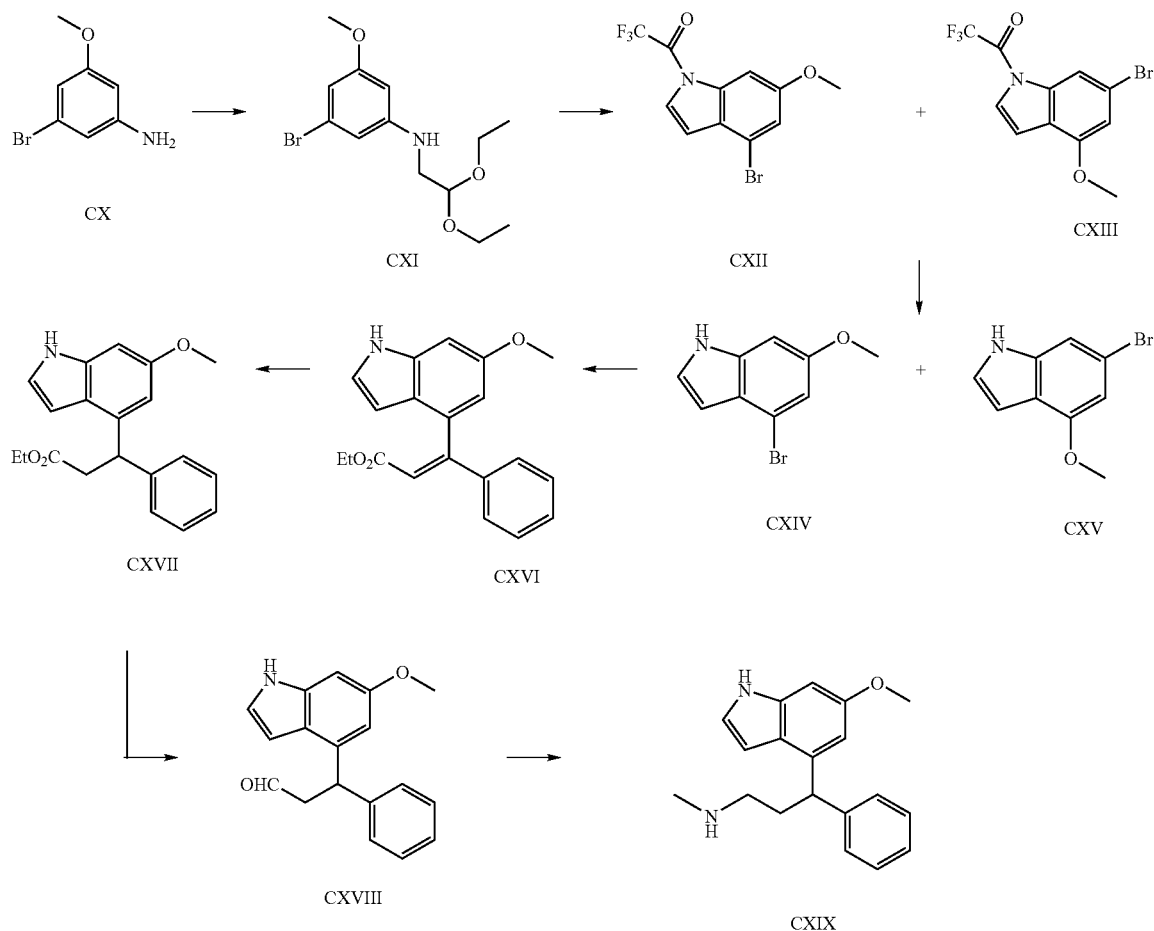

Synthesis of 3-Bromo-5-methoxy-phenylamine (CX)

A slurry of 1-bromo-3-methoxy-5-nitrobenzene (9.9 g, 43 mmol) in EtOH (140 ml) was slowly added at RT to $SnCl_2.2H_2O$ (48 g, 213 mmol). The mixture was refluxed for 2 h, cooled to RT, and poured into ice/water mixture (150 ml). A solution of NaOH (12 M, 250 ml) was added until the pH>12. The resulting mixture was extracted with EtOAc. The combined organic layers were washed with brine, dried over $Na_2SO_4$, filtered, and concentrated. The residue was dissolved in $CHCl_3$ (30 ml) and filtered. The filtrate was concentrated to afford 3-Bromo-5-methoxy-phenylamine CX as an off-white solid (8.2 g, 95% yield).

Synthesis of (3-Bromo-5-methoxy-phenyl)-(2,2-diethoxy-ethyl)-amine (CXI)

A solution of 3-Bromo-5-methoxy-phenylamine CX (4.0 g, 20 mmol), bromoacetaldehyde diethyl acetal (3.1 ml, 20 mmol) and $NaHCO_3$ (1.8 g, 21 mmol) in DMF (25 ml) was stirred at reflux for 72 hours. The mixture was cooled to room temperature and the solvent was partially evaporated. The residue was dissolved in $Et_2O$ (100 ml), washed with $H_2O$ (50 ml) and brine (25 ml), dried over $Na_2SO_4$, filtered, concentrated, and purified via flash chromatography (hexane/EtOAc) affording the compound CXI as a yellow oil (4.8 g, 75% yield).

Synthesis of 1-(4-Bromo-6-methoxy-indol-1-yl)-2,2,2-trifluoro-ethanone (CXII) and 1-(6-Bromo-4-methoxy-indol-1-yl)-2,2,2-trifluoro-ethanone (CXIII)

A 0° C. mixture of TFA/TFAA (1/1, 25 ml) was added to (3-Bromo-5-methoxy-phenyl)-(2,2-diethoxy-ethyl)-amine CXI (4.0 g, 12.6 mmol) at 0° C. The mixture was stirred at 0° C. for 30 minutes and TFA (20 ml) was added. The reaction was allowed to warm to room temperature and then was refluxed for 65 hours. The mixture was cooled to room temperature, and the solvent was removed by distillation in vacuo. The residue was dissolved in DCM and purified via flash chromatography (DCM/hexane). 1-(4-Bromo-6-methoxy-indol-1-yl)-2,2,2-trifluoro-ethanone CXII and 1-(6-Bromo-4-methoxy-indol-1-yl)-2,2,2-trifluoro-ethanone CXIII were obtained as a mixture (5/1, light yellow solid, 3.5 g, 85% yield).

Synthesis of 4-Bromo-6-methoxy-indole (CXIV) and 6-Bromo-4-methoxy-indole (CXV)

A 5/1 mixture of 1-(4-Bromo-6-methoxy-indol-1-yl)-2,2,2-trifluoro-ethanone CXII and 1-(6-Bromo-4-methoxy-indol-1-yl)-2,2,2-trifluoro-ethanone CXIII (3.18 g, 9.9 mmol) was dissolved in a 5% KOH solution in MeOH (30 ml). The reaction mixture was stirred at room temperature for 15 minutes, concentrated, and the residue was partitioned between Et$_2$O (100 ml) and aqueous NaHCO$_3$ (1M). The aqueous layer was extracted with Et$_2$O, and the combined organic layers were dried over Na$_2$SO$_4$, filtered, concentrated, and purified via flash chromatography (hexane/DCM) affording 4-Bromo-6-methoxy-indole CXIV (1.4 g, 64% yield) as a first fraction, and 6-Bromo-4-methoxy-indole CXV (0.33 g, 15% yield) as a second fraction, both as a white crystalline solid.

Synthesis of 3-(6-Methoxy-1H-Indol-4-yl)-3-phenyl-acrylic acid ethyl ester (CXVI)

A mixture of 4-bromo-6-methoxy-indole CXIV (920 mg, 4.1 mmol), ethyl cinammate (1.03 ml, 6.1 mmol), TEA (850 μl, 6.1 mmol), Pd(OAc)$_2$ (46 mg, 0.20 mmol) and (o-Tol)$_3$P (120 mg, 0.41 mmol) was heated in a sealed vial to 100° C. for 27 hours. The reaction mixture was cooled to room temperature, diluted with DCM, and the mixture was filtered through celite. The filtrate was concentrated and purified via flash cromatography (hexane/EtOAc) to afford 3-(6-methoxy-1H-Indol-4-yl)-3-phenyl-acrylic acid ethyl ester CXVI as a yellow-brown waxy solid (440 mg, 34% yield).

Synthesis of 3-(6-Methoxy-1H-Indol-4-yl)-3-phenyl-propionic acid ethyl ester (CXVII)

Degoussa-type catalyst (50% Pd/C, 45 mg) was added to a solution of 3-(6-Methoxy-1H-Indol-4-yl)-3-phenyl-acrylic acid ethyl ester CXVI (0.40 g, 1.2 mmol) in EtOH/DCM (6/1, 40 ml). The resulting mixture was hydrogenated in a Parr apparatus at 50 psi of H$_2$ for 16 hours, filtered through celite, and the filter cake was washed with EtOH and DCM. The filtrate was concentrated, affording 3-(6-Methoxy-1H-Indol-4-yl)-3-phenyl-propionic acid ethyl ester CXVII.

Synthesis of 3-(6-Methoxy-1H-Indol-4-yl)-3-phenyl-propionaldeyde (CXVIII)

To a −78° C. solution of 3-(6-Methoxy-1H-Indol-4-yl)-3-phenyl-propionic acid ethyl ester CXVII (0.39 g, 1.2 mmol) in DCM (10 ml) was added DIBALH (1M in hexane, 4.0 ml, 4.0 mmol). After stirring for 90 minutes at −78° C., more DIBALH (1M in hexane, 1.2 ml, 1.2 mmol) was added. The resulting mixture was stirred for 2.25 hours, after which EtOH (2 ml) and a saturated solution of NaHCO$_3$ (2 ml) were added. The mixture was then stirred at room temperature for 30 min, filtered, and the filter cake was washed with EtOAc. The filtrate was concentrated and washed with a saturated solution of NaHCO$_3$, dried over Na$_2$SO$_4$, filtered, concentrated, and purified via flash chromatography (hexane/EtOAc) affording 3-(6-Methoxy-1H-Indol-4-yl)-3-phenyl-propionaldeyde CXVIII as a colorless syrup (0.27 g, 82% yield).

Synthesis of [3-(6-Methoxy-1H-indol-4-yl)-3-phenyl-propyl]-methyl-amine (CXIX)

To a mixture of MeNH$_2$.HCl (0.60 g, 9 mmol) and KOH (0.1 g, 1.8 mmol) in MeOH (5 ml) was added a solution of 3-(6-Methoxy-1H-Indol-4-yl)-3-phenyl-propionaldeyde CXVIII (0.25 g, 0.89 mmol) in MeOH (6 ml) at RT. The resulting mixture was stirred at room temperature for 5 minutes and NaCNBH$_4$ (21 mg, 0.33 mmol) was added. The reaction mixture was stirred for 45 minutes at room temperature and then quenched with HCl (1M, 50 ml). The resulting mixture was extracted with Et$_2$O (25 ml), and the aqueous layer was basified until pH>12 by addition of a saturated solution of NaOH (50 ml). The aqueous layer was extracted with Et$_2$O (35 ml). The combined organic layers were dried over Na$_2$SO$_4$, filtered, concentrated, and purified via flash chromatography (DCM/MeOH/NH$_4$OH) to afford [3-(6-Methoxy-1H-indol-4-yl)-3-phenyl-propyl]-methyl-amine compound CXIX (33 mg, 13% yield). MS (M+H)=295.

Example 26

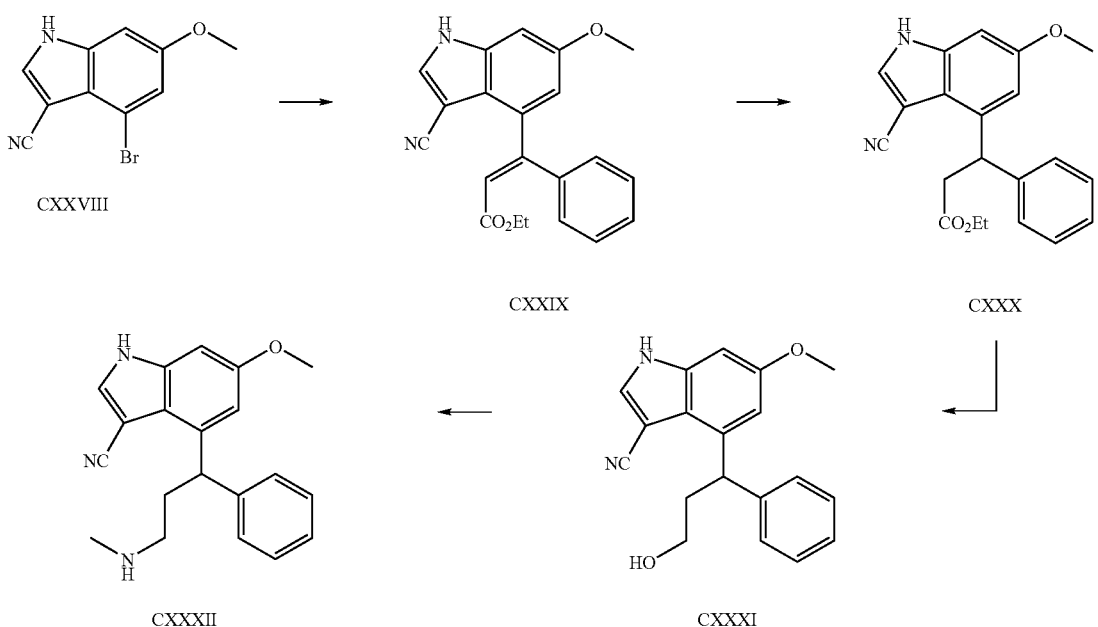

Synthesis of 4-Bromo-6-methoxy-1H-indole-3-carbonitrile (CXXVIII)

4-Bromo-6-methoxy-1H-indole-3-carbonitrile CXXVIII (1.2 g, 57% yield) was obtained from 4-bromo-6-methoxy-indole using the procedure described above for preparation of 4-bromo-1H-indole-3-carbonitrile LVII (Example 14).

Synthesis of 3-(3-Cyano-6-methoxy-1H-indol-4-yl)-3-phenyl-acrylic acid ethyl ester (CXXIX)

3-(3-Cyano-6-methoxy-1H-indol-4-yl)-3-phenyl-acrylic acid ethyl ester CXXIX (0.81 g, 54% yield) was prepared from 4-bromo-6-methoxy-1H-indole-3-carbonitrile using the procedure described above for preparation of 3-(3-Cyano-1H-Indol-4-yl)-3-phenyl-acrylic acid ethyl ester LVIII (Example 14).

Synthesis of 3-(3-Cyano-6-methoxy-1H-indol-4-yl)-3-phenyl-propionic acid ethyl ester (CXXX)

3-(3-Cyano-6-methoxy-1H-indol-4-yl)-3-phenyl-propionic acid ethyl ester CXXX was prepared from 3-(3-cyano-6-methoxy-1H-indol-4-yl)-3-phenyl-acrylic acid ethyl ester using the procedure described above for preparation of 3-(1H-Indol-7-yl)-N-methyl-3-phenyl-propionamide XIX (Example 4).

Synthesis of 4-(3-Hydroxy-1-phenyl-propyl)-6-methoxy-1H-indole-3-carbonitrile (CXXXI)

4-(3-Hydroxy-1-phenyl-propyl)-6-methoxy-1H-indole-3-carbonitrile CXXXI (0.48 g) was prepared from 3-(3-cyano-6-methoxy-1H-indol-4-yl)-3-phenyl-propionic acid ethyl ester using the procedure described above for preparation of 4-(3-Hydroxy-1-pheny-propyl)-1H-indole-3-carbonitrile LX (Example 14).

Synthesis of 6-Methoxy-4-(3-methylamino-1-phenyl-propyl)-1H-indole-3-carbonitrile (CXXXII)

6-Methoxy-4-(3-methylamino-1-phenyl-propyl)-1H-indole-3-carbonitrile CXXXII (90 mg) was prepared from 4-(3-hydroxy-1-phenyl-propyl)-6-methoxy-1H-indole-3-carbonitrile using the procedure described above for preparation of 5-(3-Methylamino-1-pheny-propyl)-1H-indole-3-carbonitrile LXVI. MS (M+H)=320.

Example 27

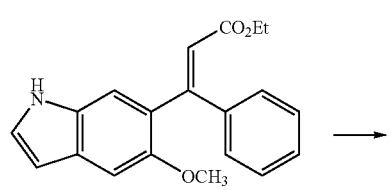

CXXXIII

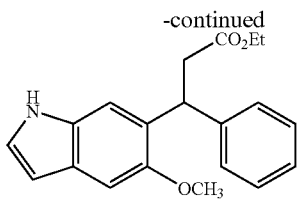

CXXXIV

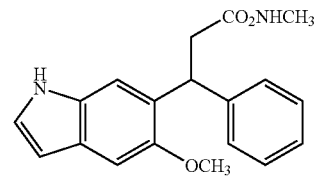

CXXXV

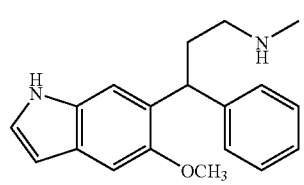

CXXXVI

Synthesis of 3-(5-Methoxy-1H-indol-6-yl)-3-phenyl-acrylic acid ethyl ester (CXXXIII)

3-(5-Methoxy-1H-indol-6-yl)-3-phenyl-acrylic acid ethyl ester CXXXIII was prepared from 6-bromo-5-methoxyindole XLVII uisng the procedure described above for preparation of 3-(5-Methoxy-1H-Indol-4-yl)-3-phenyl-acrylic acid ethyl ester XLVIII (Example 12).

Synthesis of 3-(5-Methoxy-1H-indol-6-yl)-3-phenyl-propionic acid ethyl ester (CXXXIV)

3-(5-Methoxy-1H-indol-6-yl)-3-phenyl-propionic acid ethyl ester CXXXIV was prepared from 3-(5-methoxy-1H-indol-6-yl)-3-phenyl-acrylic acid ethyl ester using the procedure described above for preparation of 3-(3-Cyano-1H-Indol-4-yl)-3-phenyl-propionic acid ethyl ester LIX (Example 14)

Synthesis of 3-(5-Methoxy-1H-indol-6-yl)-N-methyl-3-phenyl-propionamide (CXXXV)

3-(5-Methoxy-1H-indol-6-yl)-N-methyl-3-phenyl-propionamide CXXXV was obtained from 3-(5-methoxy-1H-indol-6-yl)-3-phenyl-propionic acid ethyl ester using the procedure described above for preparation of 3-(1H-Indol-7-yl)-N-methyl-3-phenyl-acrylamide XVIII (see Example 4).

Synthesis of [3-(5-Methoxy-1H-indol-6-yl)-3-phenyl-propyl]-methyl-amine (CXXXVI)

[3-(5-Methoxy-1H-indol-6-yl)-3-phenyl-propyl]-methyl-amine CXXXVI was prepared from 3-(5-Methoxy-1H-indol-6-yl)-N-methyl-3-phenyl-propionamide using the procedure described above for [3-(1H-Indol-7-yl)-3-phenyl-propyl]-methyl-amine XX (Example 4). MS (M+H)=295.

Example 28

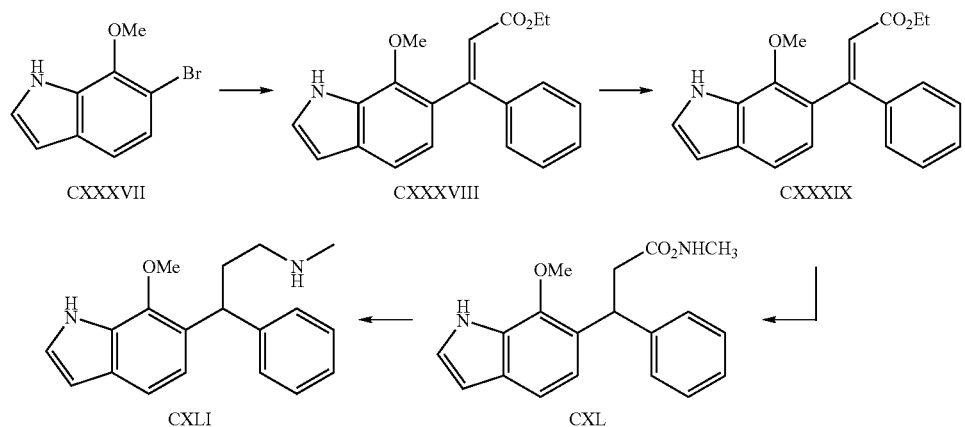

Synthesis of 6-Bromo-7-methoxy-1H-indole (CXXXVII)

6-Bromo-7-methoxy-1H-indole CXXXVII (14% yield) was prepared from 2-bromo-6-nitro-anisole using the procedure described above for preparation of 4-bromo-5-methoxy-indole XLVI (Example 12).

Synthesis of 3-(7-Methoxy-1H-indol-6-yl)-3-phenyl-acrylic acid ethyl ester (CXXXVIII)

3-(7-Methoxy-1H-indol-6-yl)-3-phenyl-acrylic acid ethyl ester CXXXVIII was prepared from 6-bromo-7-methoxy-1H-indole using the procedure described above for preparation of 3-(5-Methoxy-1H-Indol-4-yl)-3-phenyl-acrylic acid ethyl ester XLVIII (Example 12).

Synthesis of 3-(7-Methoxy-1H-indol-6-yl)-N-methyl-3-phenyl-acrylamide (CXXXIX)

3-(7-Methoxy-1H-indol-6-yl)-N-methyl-3-phenyl-acrylamide CXXXIX was obtained from 3-(7-Methoxy-1H-indol-6-yl)-3-phenyl-acrylic acid ethyl ester using the procedure described above for preparation of 3-(1H-Indol-7-yl)-N-methyl-3-phenyl-acrylamide XVIII (see Example 4).

Synthesis of 3-(7-Methoxy-1H-indol-6-yl)-N-methyl-3-phenyl-propionamide (CXL)

3-(7-Methoxy-1H-indol-6-yl)-N-methyl-3-phenyl-propionamide CXL was prepared from 3-(7-methoxy-1H-indol-6-yl)-N-methyl-3-phenyl-acrylamide using the procedure described above for preparation of 3-(1H-Indol-7-yl)-N-methyl-3-phenyl-propionamide XIX (Example 4).

Synthesis of [3-(7-Methoxy-1H-indol-6-yl)-3-phenyl-propyl]-methyl-amine (CXLI)

[3-(7-Methoxy-1H-indol-6-yl)-3-phenyl-propyl]-methyl-amine CXLI was prepared from 3-(1H-Indol-7-yl)-N-methyl-3-phenyl-propionamide using the procedure described above for preparation of [3-(1H-Indol-7-yl)-3-phenyl-propyl]-methyl-amine XX (Example 4). MS (M+H)=295.

Example 29

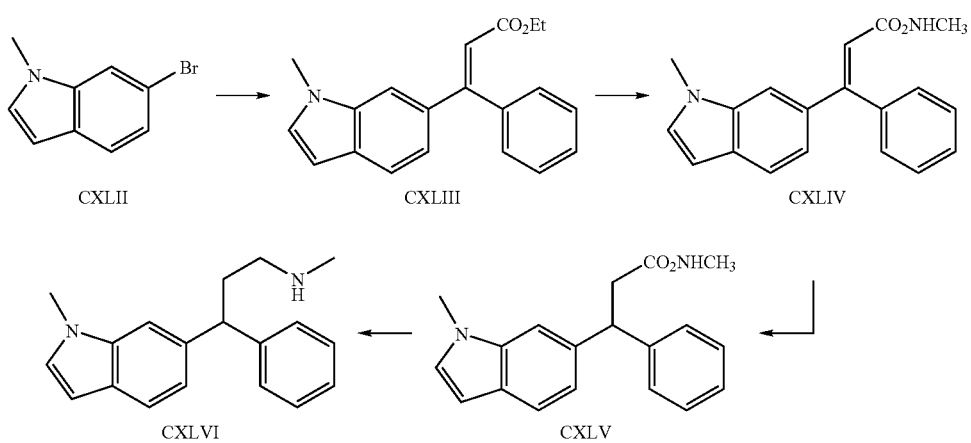

Synthesis of 6-Bromo-1-methyl-1H-indole (CXLII)

To a solution of 6-bromo-1H-indole (2.5 g, 12.8 mmol) in DMF (10 ml) was slowly added NaH (354 mg, 14.0 mmol) at room temperature. The resulting mixture was stirred for 20 min at RT after which MeI (956 µl, 15.4 mmol) was added. The mixture was stirred for 1 hour at room temperature and then partitioned between DCM and brine. The combined organic layers were washed with brine, dried over $Na_2SO_4$, filtered, and concentrated to provide 6-Bromo-1-methyl-1H-indole CXLII in quantitative yield (2.7 g).

Synthesis of 3-(1-Methyl-1H-indol-6-yl)-3-phenyl-acralic acid ethyl ester (CXLIII)

3-(1-Methyl-1H-indol-6-yl)-3-phenyl-acrylic acid ethyl ester CXLIII (78% yield) was prepared from 6-bromo-1-methyl-1H-indole using the procedure described above for preparation of 3-(3-cyano-1H-Indol-4-yl)-3-phenyl-acrylic acid ethyl ester LVIII (Example 14).

Synthesis of N-Methyl-3-(1-methyl-1H-indol-6-yl)-3-phenyl-acrylamide (CXLIV)

N-Methyl-3-(1-methyl-1H-indol-6-yl)-3-phenyl-acrylamide CXLIV was prepared from 3-(1-methyl-1H-indol-6-yl)-3-phenyl-acrylic acid ethyl ester using the procedure described above for preparation of 3-(1H-Indol-7-yl)-N-methyl-3-phenyl-acrylamide XVIII (see Example 4).

Synthesis of N-Methyl-3-(1-methyl-1H-indol-6-yl)-3-phenyl-propionamide (CXLV)

N-Methyl-3-(1-methyl-1H-indol-6-yl)-3-phenyl-propionamide CXLV was prepared from N-Methyl-3-(1-methyl-1H-indol-6-yl)-3-phenyl-acrylamide using the procedure described above for preparation of 3-(1H-Indol-7-yl)-N-methyl-3-phenyl-propionamide XIX (Example 4).

Synthesis of Methyl-[3-(1-methyl-1H-indol-6-yl)-3-phenyl-propyl]-amine (CXLVI)

Methyl-[3-(1-methyl-1H-indol-6-yl)-3-phenyl-propyl]-amine CXLVI was prepared as a hydrochloride salt from N-methyl-3-(1-methyl-1H-indol-6-yl)-3-phenyl-propionamide using the procedure described above for preparation of [3-(1H-Indol-7-yl)-3-phenyl-propyl]-methyl-amine XX (Example 4). MS (M+H)=279.

Example 30

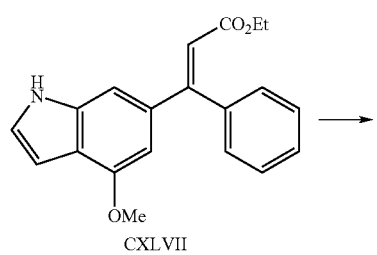

CXLVII

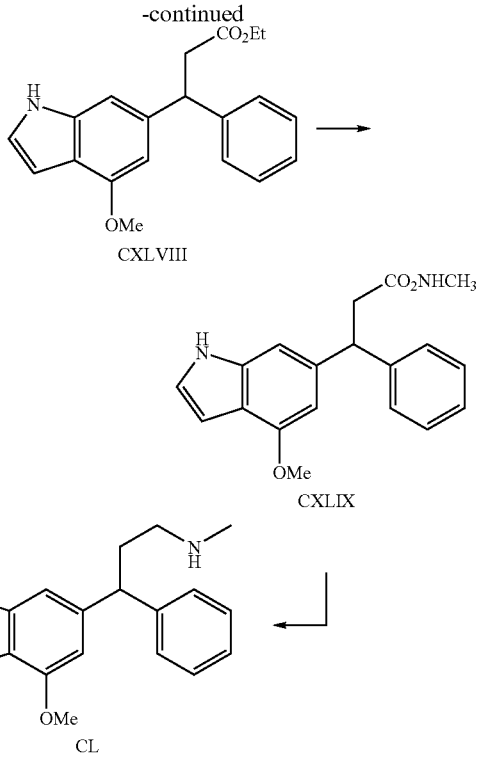

Synthesis of 3-(4-Methoxy-1H-indol-6-yl)-3-phenyl-acrylic acid ethyl ester (CXLVII)

3-(4-Methoxy-1H-indol-6-yl)-3-phenyl-acrylic acid ethyl ester CXLVII was prepared from 6-bromo-4-methoxy-indole using the procedure described above for preparation of 4-Bromo-6-methoxy-indole CXVI (Example 25).

Synthesis of 3-(4-Methoxy-1H-indol-6-yl)-3-phenyl-propionic acid ethyl ester (CXLVIII)

3-(4-Methoxy-1H-indol-6-yl)-3-phenyl-propionic acid ethyl ester CXXXV was prepared from 3-(4-methoxy-1H-indol-6-yl)-3-phenyl-acrylic acid ethyl ester using the procedure described above for preparation of 3-(1H-Indol-7-yl)-N-methyl-3-phenyl-propionamide XIX (Example 4).

Synthesis of 3-(4-Methoxy-1H-indol-6-yl)-N-methyl-3-phenyl-propionamide (CXLIX)

3-(4-Methoxy-1H-indol-6-yl)-N-methyl-3-phenyl-propionamide CXLIX was obtained from 3-(4-methoxy-1H-indol-6-yl)-3-phenyl-propionic acid ethyl ester using the procedure described above for preparation of 3-(1H-Indol-7-yl)-N-methyl-3-phenyl-acrylamide XVIII (see Example 4).

Synthesis of [3-(4-Methoxy-1H-indol-6-yl)-3-phenyl-propyl]-methyl-amine (CL)

[3-(4-Methoxy-1H-indol-6-yl)-3-phenyl-propyl]-methyl-amine CL was prepared from 3-(4-methoxy-1H-indol-6-yl)-N-methyl-3-phenyl-propionamide using the procedure described above for preparation of [3-(1H-Indol-7-yl)-3-phenyl-propyl]-methyl-amine XX (Example 4). MS (M+H)=295.

Example 31

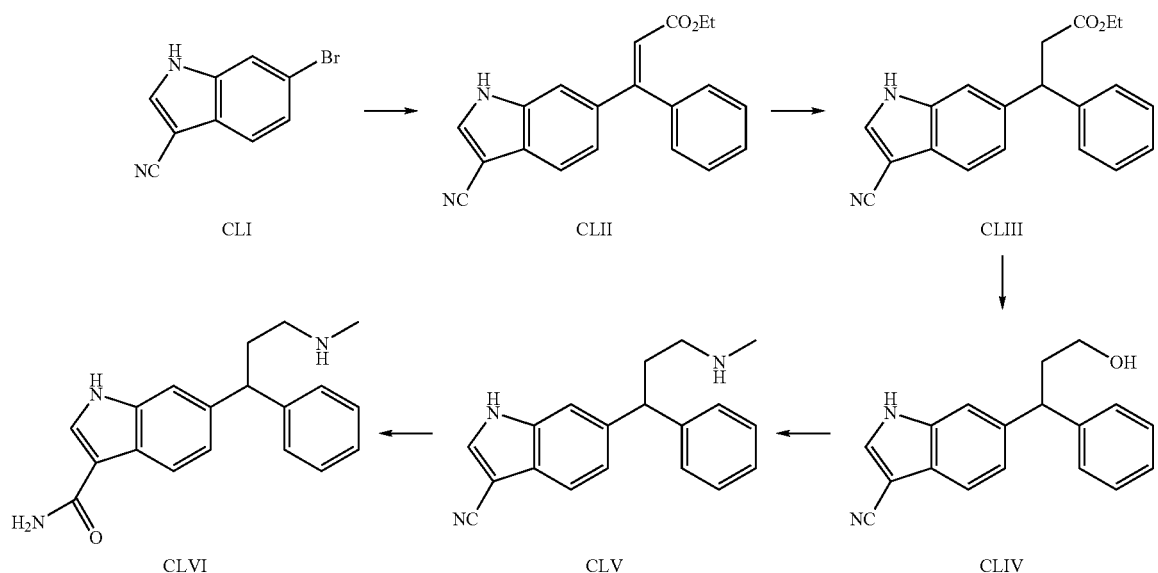

Synthesis of 6-Bromo-1H-indole-3-carbonitrile (CLI)

6-Bromo-1H-indole-3-carbonitrile CLI was obtained from 6-bromo-1H-indole using the procedure described above for preparation of 4-bromo-1H-indole-3-carbonitrile LVII (Example 14).

Synthesis of 3-(3-Cyano-1H-indol-6-yl)-3-phenyl-acrylic acid ethyl ester (CLII)

3-(3-Cyano-1H-indol-6-yl)-3-phenyl-acrylic acid ethyl ester CLII was prepared from 6-bromo-1H-indole-3-carbonitrile using the procedure described above for preparation of 3-(6-Methoxy-1H-Indol-4-yl)-3-phenyl-acrylic acid ethyl ester CXVI (Example 25).

Synthesis of 3-(3-Cyano-1H-indol-6-yl)-3-phenyl-propionic acid ethyl ester (CLIII)

3-(3-Cyano-1H-indol-6-yl)-3-phenyl-propionic acid ethyl ester CLIII was prepared from 3-(3-cyano-1H-indol-6-yl)-3-phenyl-acrylic acid ethyl ester using the procedure described above for preparation of 3-(1H-Indol-7-yl)-N-methyl-3-phenyl-propionamide XIX (Example 4).

Synthesis of 6-(3-Hydroxy-1-phenyl-propyl)-1H-indole-3-carbonitrile (CLIV)

The alcohol compound CLIV was prepared using the procedure described above for preparation of compound LX using 3-(3-cyano-1H-indol-6-yl)-3-phenyl-propionic acid ethyl ester. Compound CLIV was obtained as an off-white solid (71% yield).

Synthesis of 6-(3-Methylamino-1-phenyl-propyl)-1H-indole-3-carbonitrile (CLV)

6-(3-Hydroxy-1-phenyl-propyl)-1H-indole-3-carbonitrile CLV was prepared from 6-(3-hydroxy-1-phenyl-propyl)-1H-indole-3-carbonitrile using the procedure described above for preparation of 4-(3-Methylamino-1-pheny-propyl)-1H-indole-3-carbonitrile LXI (Example 14).

Synthesis of 6-(3-Methylamino-1-phenyl-propyl)-1H-indole-3-carboxylic acid amide (CLVI)

To a solution of 6-(3-Methylamino-1-phenyl-propyl)-1H-indole-3-carbonitrile CLV (170 mg, 0.59 mmol) in EtOH (5 ml) was added 50% aqueous solution of NaOH (5 ml). The mixture was refluxed for 90 minutes and excess KOH was added. The resulting mixture was refluxed for additional 48 hours, cooled to room temperature, and concentrated. The residue was partitioned between $H_2O$ and $CHCl_3$, and the aqueous layer was extracted with $CHCl_3$. The combined organic layers were washed with brine, dried over $Na_2SO_4$, filtered, concentrated and purified via flash chromatography ($DCM/MeOH/NH_4OH$) affording 6-(3-Methylamino-1-phenyl-propyl)-1H-indole-3-carboxylic acid amide CLVI as a white powder (59 mg, 33% yield). MS (M+H)=308.

Example 32

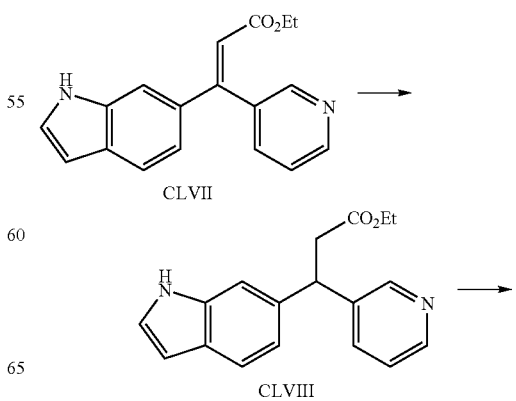

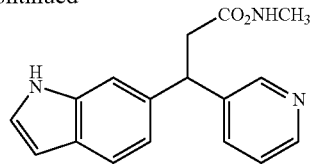

CLIX

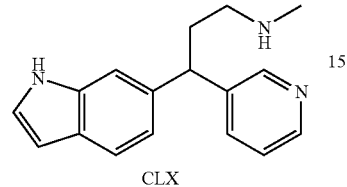

CLX

Synthesis of 3-(1H-Indol-6-yl)-3-pyridin-3-yl-acrylic acid ethyl ester (CLVII)

3-(1H-Indol-6-yl)-3-pyridin-3-yl-acrylic acid ethyl ester CLVII was prepared from 6-bromo-1H-indole and 3-pyridin-3-yl-acrylic acid ethyl ester using the procedure described above for preparation of 3-(3-Cyano-1H-Indol-4-yl)-3-phenyl-acrylic acid ethyl ester LVIII (Example 14).

Synthesis of 3-(1H-Indol-6-yl)-3-pyridin-3-yl-propionic acid ethyl ester (CLVIII)

3-(1H-Indol-6-yl)-3-pyridin-3-yl-propionic acid ethyl ester CLVIII was prepared from 3-(1H-indol-6-yl)-3-pyridin-3-yl-acrylic acid ethyl ester using the procedure described above for preparation of 3-(3-Cyano-1H-Indol-4-yl)-3-phenyl-propionic acid ethyl ester LIX (Example 14).

Synthesis of 3-(1H-Indol-6-yl)-N-methyl-3-pyridin-3-yl-propionamide (CLIX)

3-(1H-Indol-6-yl)-N-methyl-3-pyridin-3-yl-propionamide CLIX was obtained from 3-(1H-indol-6-yl)-3-pyridin-3-yl-propionic acid ethyl ester following the procedure described above for preparation of 3-(1H-Indol-7-yl)-N-methyl-3-phenyl-acrylamide XVIII (see Example 4).

Synthesis of [3-(1H-Indol-6-yl)-3-pyridin-3-yl-propyl]-methyl-amine (CLX)

[3-(1H-Indol-6-yl)-3-pyridin-3-yl-propyl]-methyl-amine CLX was prepared from 3-(1H-indol-6-yl)-N-methyl-3-pyridin-3-yl-propionamide using the procedure described above for preparation of [3-(1H-Indol-7-yl)-3-phenyl-propyl]-methyl-amine XX (Example 4). MS (M+H)=266.

Example 33

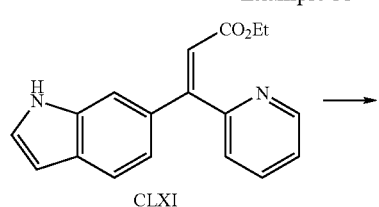

CLXI

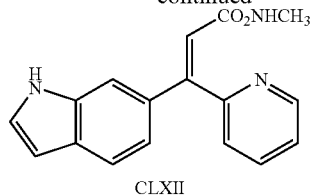

CLXII

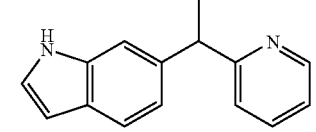

CLXIII

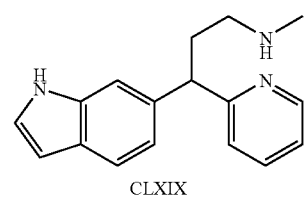

CLXIX

Synthesis of 3-(1H-Indol-6-yl)-3-pyridin-2-yl-acrylic acid ethyl ester (CLXI)

3-(1H-Indol-6-yl)-3-pyridin-2-yl-acrylic acid ethyl ester CLVII was prepared from 6-bromo-1H-indole and 3-pyridin-2-yl-acrylic acid ethyl ester using the procedure described for preparation of 3-(3-Cyano-1H-Indol-4-yl)-3-phenyl-acrylic acid ethyl ester LVIII (Example 14).

Synthesis of 3-(1H-Indol-6-yl)-N-methyl-3-pyridin-2-yl-acralamide (CLXII)

3-(1H-Indol-6-yl)-N-methyl-3-pyridin-2-yl-acrylamide CLXII was obtained from 3-(1H-indol-6-yl)-3-pyridin-2-yl-acrylic acid ethyl ester following the procedure described for preparation of 3-(1H-Indol-7-yl)-N-methyl-3-phenyl-acrylamide XVIII (see Example 4).

Synthesis of 3-(1H-Indol-6-yl)-N-methyl-3-pyridin-2-yl-propionamide (CLXIII)

3-(1H-Indol-6-yl)-N-methyl-3-pyridin-2-yl-propionamide CLXIII was prepared from 3-(1H-indol-6-yl)-N-methyl-3-pyridin-2-yl-acrylamide using the procedure described for preparation of 3-(1H-Indol-7-yl)-N-methyl-3-phenyl-propionamide XIX using.

Synthesis of [3-(1H-Indol-6-yl)-3-pyridin-2-yl-propyl]-methyl-amine (CLXIX)

[3-(1H-Indol-6-yl)-3-pyridin-2-yl-propyl]-methyl-amine CLXIX was prepared as a hydrochloride salt from 3-(1H-indol-6-yl)-N-methyl-3-pyridin-2-yl-propionamide using the procedure described for preparation of [3-(1H-Indol-7-yl)-3-phenyl-propyl]-methyl-amine XX (Example 4). MS (M+H)=266.

Example 34

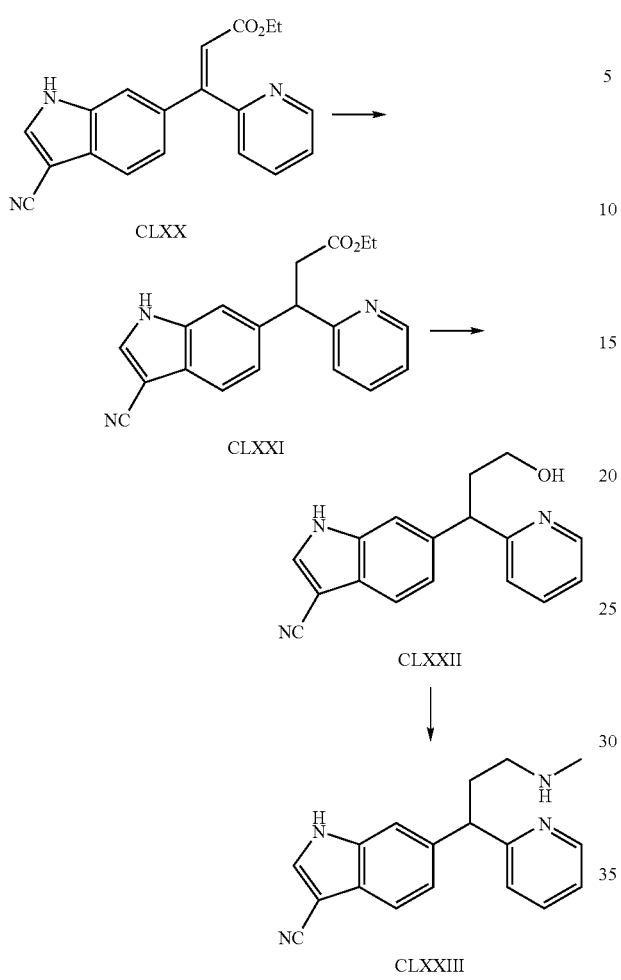

Synthesis of 3-(3-Cyano-1H-ndol-6-yl)-3-pyridin-2-yl-acrylic acid ethyl ester (CLXX)

3-(3-Cyano-1H-ndol-6-yl)-3-pyridin-2-yl-acrylic acid ethyl ester CLXX was prepared from 6-bromo-1H-indole-3-carbonitrile (CLI) and 3-pyridin-2-yl-acrylic acid ethyl ester using the procedure described for preparation of 3-(3-Cyano-1H-Indol-4-yl)-3-phenyl-acrylic acid ethyl ester LVIII (Example 14).

Synthesis of 3-(3-Cyano-1H-indol-6-yl)-3-pyridin-2-yl-propionic acid ethyl ester (CLXXI)

3-(3-Cyano-1H-indol-6-yl)-3-pyridin-2-yl-propionic acid ethyl ester CLXXI was prepared from 3-(1H-indol-6-yl)-N-methyl-3-pyridin-2-yl-acrylamide using the procedure described for preparation of 3-(1H-Indol-7-yl)-N-methyl-3-phenyl-propionamide XIX (Example 4).

Synthesis of 6-(3-Hydroxy-1-pyridin-2-yl-propyl)-1H-indole-3-carbonitrile (CLXXII)

6-(3-Hydroxy-1-pyridin-2-yl-propyl)-1H-indole-3-carbonitrile CLXXII was prepared from 3-(3-cyano-1H-indol-6-yl)-3-pyridin-2-yl-propionic acid ethyl ester using the procedure described for preparation of 4-(3-Hydroxy-1-phenypropyl)-1H-indole-3-carbonitrile LX (Example 14).

Synthesis of 6-(3-Methylamino-1-pyridin-2-yl-propyl)-1H-indole-3-carbonitrile (CLXXIII)

To a stirring solution of 6-(3-methylamino-1-pyridin-2-yl-propyl)-1H-indole-3-carbonitrile CLXXII (50 mg, 0.181 mmol) in DCM (5 ml) at room temperature was added Dess-Martin periodane (153 mg, 0.361 mmol). The reaction mixture was stirred at room temperature for 1 hour and NaHCO$_3$ was added. The mixture was extracted with DCM, and the combined organic layers were dried over Na$_2$SO$_4$, filtered and concentrated under reduced pressure. The resulting residue was dissolved in MeOH (4 ml) and added to a mixture of MeNH$_2$.HCl (193 mg, 2.86 mmol) and NaOH (29 mg, 0.71 mmol) in MeOH (4 ml). The reaction mixture was stirred at room temperature for 5 minutes and NaCNBH$_3$ was added (11 mg, 0.18 mmol). The mixture was then stirred at room temperature for 2.5 hours, concentrated, and the residue was partitioned between NaHCO$_3$ and EtOAc. The combined organic layers were dried over Na$_2$SO$_4$, filtered, concentrated and purified via flash chromatography (DCM/MeOH/NH$_4$Cl) affording 6-(3-Methylamino-1-pyridin-2-yl-propyl)-1H-indole-3-carbonitrile as an off-white oil. MS (M+H)=291.

Example 35

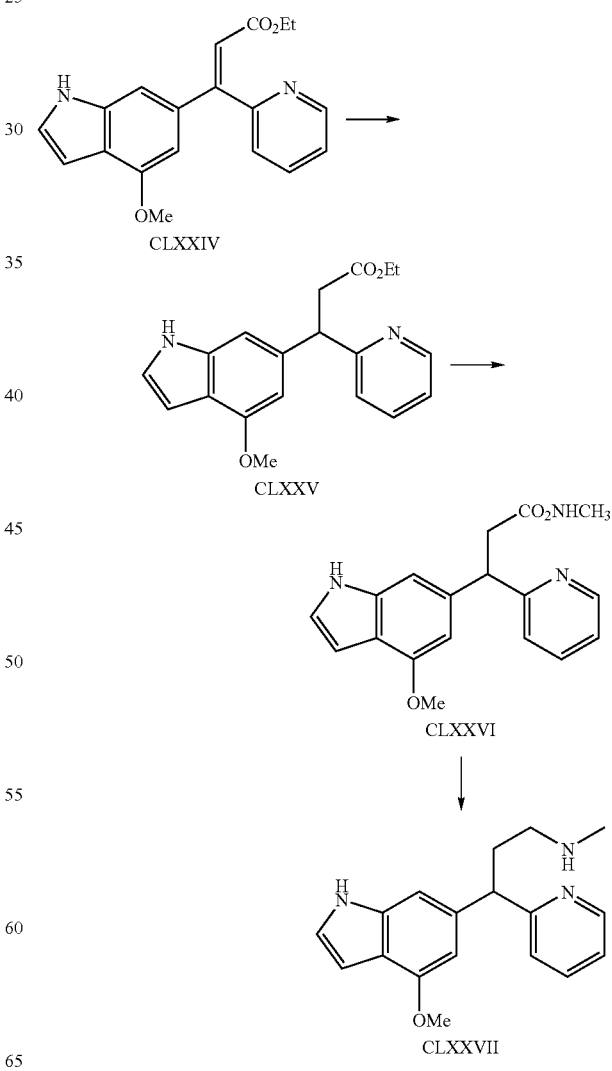

Synthesis of 3-(4-Methoxy-1H-indol-6-yl)-3-pyridin-2-yl-acrylic acid ethyl ester (CLXXIV)

3-(4-Methoxy-1H-indol-6-yl)-3-pyridin-2-yl-acrylic acid ethyl ester CLXXIV was prepared from 4-methoxy-6-bromo-1H-indole and 3-pyridin-2-yl-acrylic acid ethyl este using the procedure described for preparation of 3-(3-Cyano-1H-Indol-4-yl)-3-phenyl-acrylic acid ethyl ester LVIII (Example 14).

Synthesis of 3-(4-Methoxy-1H-indol-6-yl)-3-pyridin-2-yl-propionic acid ethyl ester (CLXXV)

3-(4-Methoxy-1H-indol-6-yl)-3-pyridin-2-yl-propionic acid ethyl ester CLXXV was prepared from 3-(4-methoxy-1H-indol-6-yl)-3-pyridin-2-yl-acrylic acid ethyl ester using the procedure described for preparation of 3-(1H-Indol-7-yl)-N-methyl-3-phenyl-propionamide XIX (Example 4).

Synthesis of 3-(4-Methoxy-1H-indol-6-yl)-N-methyl-3-pyridin-2-yl-propionamide (CLXXVI)

3-(4-Methoxy-1H-indol-6-yl)-N-methyl-3-pyridin-2-yl-propionamide CLXXVI was obtained from following the procedure described for preparation of 3-(1H-Indol-7-yl)-N-methyl-3-phenyl-acrylamide XVIII (see Example 4).

Synthesis of [3-(4-Methoxy-1H-indol-6-yl)-3-pyridin-2-yl-propyl]-methyl-amine (CLXXVII)

[3-(4-Methoxy-1H-indol-6-yl)-3-pyridin-2-yl-propyl]-methyl-amine CLXXVII was prepared from 3-(4-methoxy-1H-indol-6-yl)-N-methyl-3-pyridin-2-yl-propionamide using the procedure described for preparation of [3-(1H-Indol-7-yl)-3-phenyl-propyl]-methyl-amine XX (Example 4). MS (M+H)=297.

Example 36

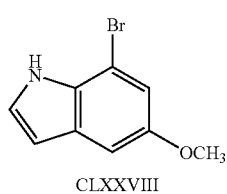
CLXXVIII

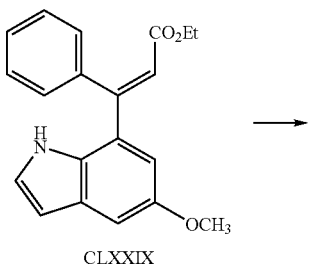
CLXXIX

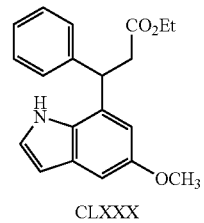
CLXXX

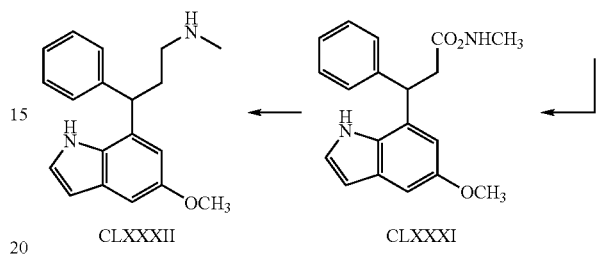
CLXXXII      CLXXXI

Synthesis of 7-Bromo-5-methoxy-1H-indole (CLXXVIII)

7-Bromo-5-methoxy-1H-indole CLXXVIII was prepared from 3-bromo-4-nitro-anisole using the procedure described for preparation of 4-bromo-5-methoxyindole XLVI (Example 12).

Synthesis of 3-(5-Methoxy-1H-indol-7-yl)-3-phenyl-acaylic acid ethyl ester (CLXXIX)

3-(5-Methoxy-1H-indol-7-yl)-3-phenyl-acrylic acid ethyl ester CLXXIX was prepared from 5-methoxy-7-bromo-1H-indole and 3-pyridin-2-yl-acrylic acid ethyl ester using the procedure described for preparation of 3-(3-Cyano-1H-Indol-4-yl)-3-phenyl-acrylic acid ethyl ester LVIII (Example 14).

Synthesis of 3-(5-Methoxy-1H-indol-7-yl)-3-phenyl-propionic acid ethyl ester (CLXXX)

3-(5-Methoxy-1H-indol-7-yl)-3-phenyl-propionic acid ethyl ester CLXXX was prepared from 3-(5-methoxy-1H-indol-7-yl)-3-phenyl-acrylic acid ethyl ester using the procedure described for preparation of 3-(1H-Indol-7-yl)-N-methyl-3-phenyl-propionamide XIX (Example 4).

Synthesis of 3-(5-Methoxy-1H-indol-7-yl)-N-methyl-3-phenyl-propionamide (CLXXXI)

3-(5-Methoxy-1H-indol-7-yl)-N-methyl-3-phenyl-propionamide CLXXXI was obtained from 3-(5-methoxy-1H-indol-7-yl)-3-phenyl-propionic acid ethyl ester following the procedure described for preparation of 3-(1H-Indol-7-yl)-N-methyl-3-phenyl-acrylamide XVIII (see Example 4).

Synthesis of [3-(5-Methoxy-1H-indol-7-yl)-3-phenyl-propyl]-methyl-amine (CLXXXII)

[3-(5-Methoxy-1H-indol-7-yl)-3-phenyl-propyl]-methyl-amine CLXXXII was prepared from 3-(5-methoxy-1H-indol-7-yl)-N-methyl-3-phenyl-propionamide using the procedure described for preparation of [3-(1H-Indol-7-yl)-3-phenyl-propyl]-methyl-amine XX (Example 4). MS (M+H)= 296.

Example 37

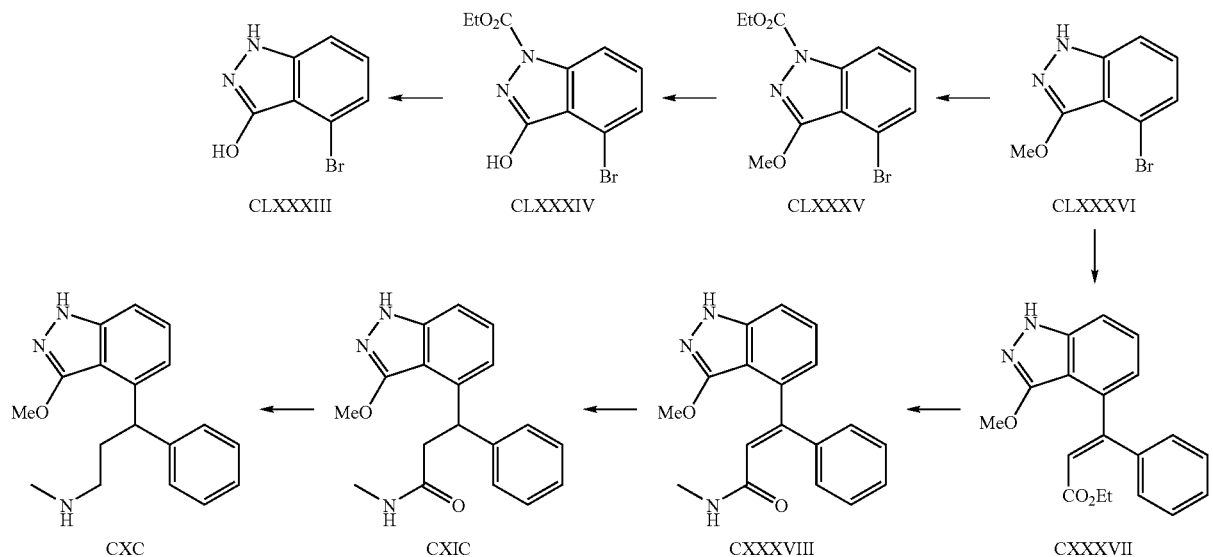

Synthesis of 4-Bromo-1H-indazol-3-ol (CLXXXIII)

To a mixture of 3-bromo-2-carboxyaniline (6.6 g, 30.6 mmol, see *Aust. J. Chem.*, 1999, 52, 1061) in H$_2$O (28 ml) and HCl (conc., 6 ml) was added a solution of NaNO$_2$ (2.11 g, 30 mmol) in H$_2$O (5 ml) at 0° C. The mixture was stirred at 0° C. for 30 minutes then a solution of Na$_2$SO$_3$ (10.4 g, 82.5 mmol) in H$_2$O (28 ml) was added slowly. The mixture was stirred at room temperature for 2 hours and HCl (conc., 9 ml) was slowly added. The resulting mixture was stirred at room temperature for additional 18 hours, then at 80° C. for 4 hours, and finally cooled to room temperature. The reaction mixture was basified to dissolve the precipitate and then reacidified. The precipitated 4-Bromo-1H-indazol-3-ol CLXXXIII was filtered and dried in vacuo (yellow powder, 3.19 g, 49% yield).

Synthesis of 4-Bromo-3-hydroxy-indazole-1-carboxylic acid ethyl ester (CLXXXIV)

To a room temperature suspension of 4-Bromo-1H-indazol-3-ol CLXXXIII (3.19 g, 15.0 mmol) in pyridine (13 ml) and H$_2$O (20 ml) was dropwise added ethyl chloroformate (1.43 ml, 15.0 mmol). After stirring 18 hours at room temperature, the mixture was cooled to 0° C., and the precipitate was filtered and washed with cold AcOH (10 ml in 5 ml of H$_2$O). The solid was dried in vacuo affording 4-Bromo-3-hydroxy-idazole-1-carboxylic acid ethyl ester CLXXXIV as a yellow powder (2.97 g, 69% yield).

Synthesis of 4-Bromo-3-methoxy-indazole-1-carboxylic acid ethyl ester (CLXXXV)

To a 0° C. mixture of KOH (50% in H$_2$O, 50 ml) and Et$_2$O (150 ml), N-nitrosomethylurea (10.7 g, 103 mmol) was added portionwise over 40 minute period. After stirring for additional 20 minutes, the mixture was cooled to −78° C. and the upper bright yellow layer was poured into a 0° C. suspension of 4-Bromo-3-hydroxy-indazole-1-carboxylic acid ethyl ester CLXXXIV (2.96 g, 10.4 mmol) in a mixture of Et$_2$O (100 ml) and THF (30 ml). After 2 hours, the yellow solution was warmed to room temperature and was left to stand at room temperature for 24 hours. The mixture was then washed with H$_2$O and brine. The organic layer was dried over MgSO$_4$, filtered, concentrated, and purified via flash chromatography (hexane/EtOAc) affording 4-Bromo-3-methoxy-idazole-1-carboxylic acid ethyl ester CLXXXV as an off-white solid (40% yield).

Synthesis of 4-Bromo-3-methoxy-1H-indazole (CLXXXVI)

To a stirring solution of 4-Bromo-3-methoxy-indazole-1-carboxylic acid ethyl ester CLXXXV (1.27 g, 4.14 mmol) in THF (28 ml) and H$_2$O (9 ml) was added LiOH (397 mg, 16.6 mmol). The reaction mixture was stirred at reflux for 2 hours then at room temperature for 15 hours. The mixture was concentrated. The residue was diluted with EtOAc (50 ml), washed with HCl (1M) and brine, dried over MgSO$_4$, filtered and concentrated affording 4-Bromo-3-methoxy-1H-indazole CLXXXVI as an off-white solid (98% yield), which was used without further purification in the next step.

Synthesis of 3-(3-Methoxy-1H-indazol-4-yl)-3-phenyl-acrylic acid ethyl ester (CLXXXVII)

3-(3-Methoxy-1H-indazol-4-yl)-3-phenyl-acrylic acid ethyl ester CLXXXVII was prepared from 4-bromo-3-methoxy-1H-indazole using the procedure described for preparation of 3-(7-Methoxy-1H-Indol-4-yl)-3-phenyl-acrylic acid ethyl ester LIII (Example 13).

Synthesis of 3-(3-Methoxy-1H-indazol-4-yl)-N-methyl-3-phenyl-acrylamide (CLXXXVIII)

3-(3-Methoxy-1H-indazol-4-yl)-N-methyl-3-phenyl-acrylamide CLXXXVIII was prepared from 3-(3-methoxy-1H-indazol-4-yl)-3-phenyl-acrylic acid ethyl ester using the procedure described for preparation of 3-(1H-Indol-7-yl)-N-methyl-3-phenyl-acrylamide XVIII (see Example 4).

Synthesis of 3-(3-Methoxy-1H-indazol-4-yl)-N-methyl-3-phenyl-propionamide (CLXXXIX)

3-(3-Methoxy-1H-indazol-4-yl)-N-methyl-3-phenyl-propionamide CLXXXIX was obtained from 3-(3-methoxy-1H-indazol-4-yl)-N-methyl-3-phenyl-acrylamide following the procedure described for preparation of 3-(1H-Indol-7-yl)-N-methyl-3-phenyl-propionamide XIX (Example 4).

Synthesis of [3-(3-Methoxy-1H-indazol-4-yl)-3-phenyl-propyl]-methyl-amine (CXC)

[3-(3-Methoxy-1H-indazol-4-yl)-3-phenyl-propyl]-methyl-amine CXC was prepared as a trifluoroacetate from 3-(3-methoxy-1H-indazol-4-yl)-N-methyl-3-phenyl-propionamide and trifluoroacetic acid, using the procedure described for prepration of [3-(1H-Indol-7-yl)-3-phenyl-propyl]-methyl-amine XX (Example 4). MS (M+H)=297.

Example 38

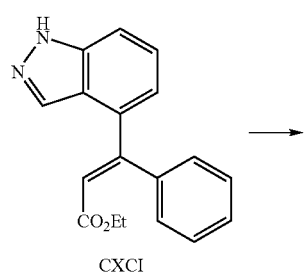
CXCI

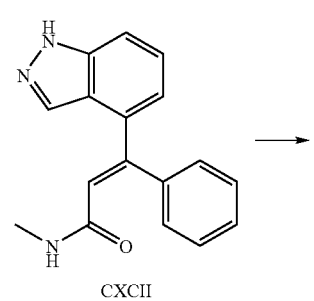
CXCII

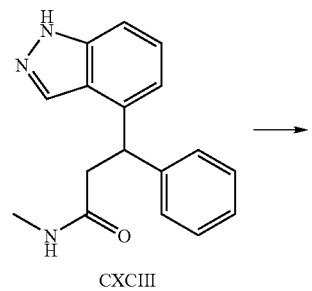
CXCIII

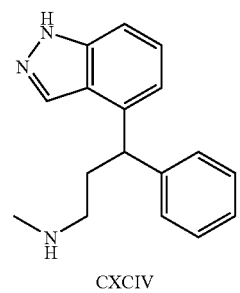
CXCIV

Synthesis of 3-(1H-Indazol-4-yl)-3-phenyl-acrylic acid ethyl ester (CXCI)

3-(1H-Indazol-4-yl)-3-phenyl-acrylic acid ethyl ester CXCI was prepared from using 4-bromo-1H-idazole using the procedure described for preparation of 3-(7-Methoxy-1H-Indol-4-yl)-3-phenyl-acrylic acid ethyl ester LIII (Example 13).

Synthesis of 3-(1H-Indazol-4-yl)-N-methyl-3-phenyl-acrylamide (CXCII)

3-(1H-Indazol-4-yl)-N-methyl-3-phenyl-acrylamide CXCII was prepared from 3-(1H-indazol-4-yl)-3-phenyl-acrylic acid ethyl ester using the procedure described for preparation of 3-(1H-Indol-7-yl)-N-methyl-3-phenyl-acrylamide XVIII (see Example 4).

Synthesis of 3-(1H-Indazol-4-yl)-N-methyl-3-phenyl-propionamide (CXCIII)

3-(1H-Indazol-4-yl)-N-methyl-3-phenyl-propionamide CXCIII was obtained from 3-(1H-indazol-4-yl)-N-methyl-3-phenyl-acrylamide following the procedure described for preparation of 3-(1H-Indol-7-yl)-N-methyl-3-phenyl-propionamide XIX (Example 4).

Synthesis of [3-(1H-Indazol-4-yl)-3-phenyl-propyl]-methyl-amine (CXCIV)

[3-(1H-Indazol-4-yl)-3-phenyl-propyl]-methyl-amine was prepared as a hydrochloride salt from 3-(1H-indazol-4-yl)-N-methyl-3-phenyl-propionamide using the procedure described for preparation of [3-(1H-Indol-7-yl)-3-phenyl-propyl]-methyl-amine XX (Example 4). MS (M+H)=266.

Example 39

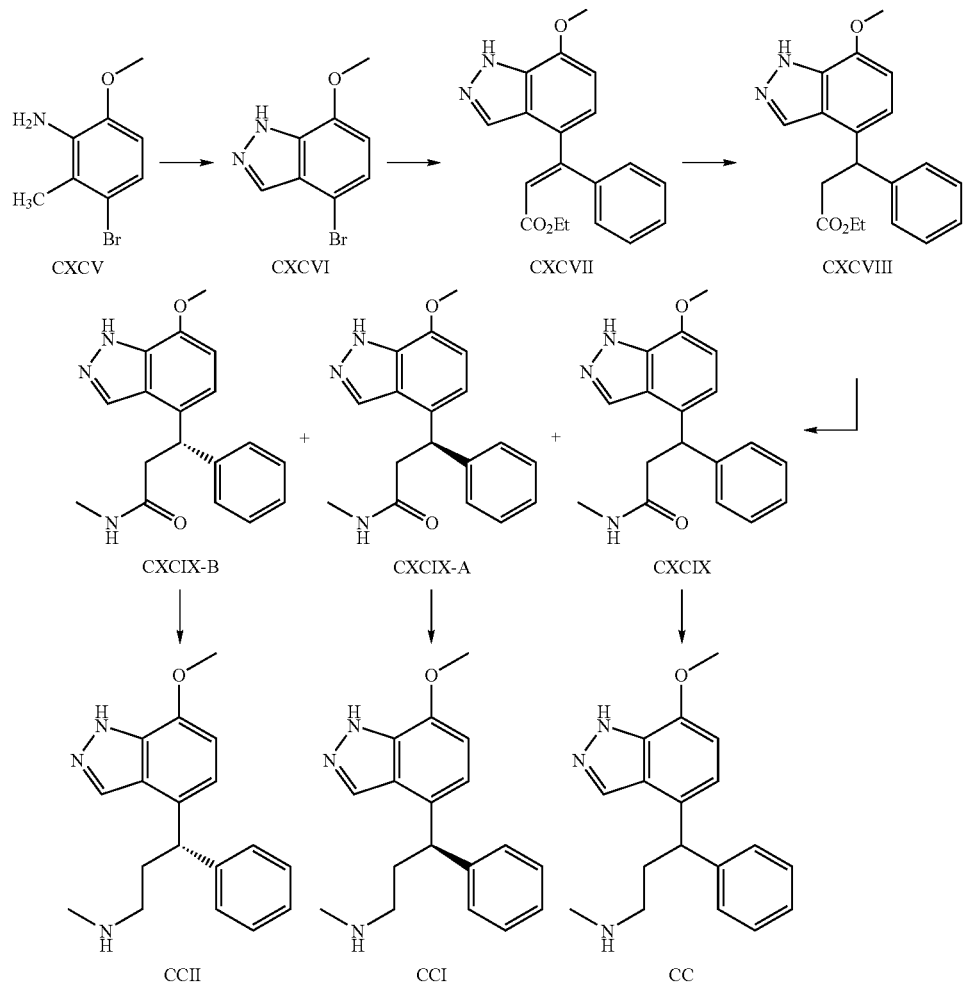

Synthesis of 3-Bromo-6-methoxy-2-methyl-phenylamine (CXCV)

To a stirring mixture of 1-bromo-4-methoxy-2-methyl-3-nitrobenzene (2.0 g, 8.13 mmol, see Tet. Lett., 2002, 43, 1063) in NH$_4$OH (40 ml) was added a solution of (NH$_4$)$_2$Fe(SO$_4$)$_2$ (19.1 g, 48.8 mmol) in H$_2$O (40 ml). The reaction mixture was stirred at reflux for 4 hours, cooled to room temperature, diluted with Et$_2$O (120 ml), and filtered through celite. The filter cake was washed with Et$_2$O. The aqueous layer was extracted with Et$_2$O (50 ml). The combined organic layers were concentrated, and the residue was dissolved in Et$_2$O and extracted with HCl (1M, 30 ml). The aqueous layer was basified until about pH 4 by addition of (NaOH 50%, 10 ml) and extracted with Et$_2$O. The combined organic layers were dried over MgSO$_4$, filtered, and concentrated affording 3-Bromo-6-methoxy-2-methyl-phenylamine CXCV as an off-white solid (0.98 g, 56% yield).

Synthesis of 4-Bromo-7-methoxy-1H-indazole (CXCVI)

To a 0° C. solution of 3-Bromo-6-methoxy-2-methyl-phenylamine CXCV (1.04 g, 4.82 mmol) in CHCl$_3$ (10 ml) was added Ac$_2$O (1.05 ml, 11.1 mmol) dropwise. The mixture was warmed to room temperature and stirred for 1 hour. To the resulting reaction mixture was added KOAc (142 mg, 1.45 mmol) and isoamyl nitrile (1.39 ml, 10.4 mmol). The reaction mixture was stirred at reflux for 20 hours, cooled to room temperature, concentrated, and the residue was diluted with H$_2$O. Concentration of the aqueous solution provided a yellow solid which was treated with HCl (conc, 5 ml). The mixture was stirred at 50° C. for 2 hours, cooled to room temperature, and quenched by addition of KOH (50%) until about pH 14. The resulting mixture was extracted with EtOAc (30 ml). The combined organic layers were washed with brine (30 ml), dried over MgSO$_4$, filtered through silica plug and concentrated to afford 4-Bromo-7-methoxy-1H-indazole CXCVI as an orange solid (1.06 g, 97% yield), which was used without further purifications for the next step.

Synthesis of 3-(7-Methoxy-1H-indazol-4-yl)-3-phenyl-acrylic acid ethyl ester (CXCVII)

Compound CXCVII was prepared from 4-Bromo-7-methoxy-1H-indazole using the procedure described for preparation of 3-(3-Cyano-1H-Indol-4-yl)-3-phenyl-acrylic acid ethyl ester LVIII (Example 14).

Synthesis of 3-(7-Methoxy-1H-indazol-4-yl)-3-phenyl-propionic acid ethyl ester (CXCVIII)

3-(7-Methoxy-1H-indazol-4-yl)-3-phenyl-propionic acid ethyl ester CXCVIII was obtained from 3-(7-methoxy-1H-indazol-4-yl)-3-phenyl-acrylic acid ethyl ester following the procedure described for preparation of 3-(1H-Indol-7-yl)-N-methyl-3-phenyl-propionamide XIX (Example 4).

Synthesis of 3-(7-Methoxy-1H-indazol-4-yl)-N-methyl-3-phenyl-propionamide (CXCIX)

3-(7-Methoxy-1H-indazol-4-yl)-N-methyl-3-phenyl-propionamide CXCIX was prepared from 3-(7-methoxy-1H-indazol-4-yl)-3-phenyl-propionic acid ethyl ester using the procedure described for preparation of 3-(1H-Indol-7-yl)-N-methyl-3-phenyl-acrylamide XVIII (see Example 4). Part of the crude 3-(7-Methoxy-1H-indazol-4-yl)-N-methyl-3-phenyl-propionamide CXCIX was used without further purification for the next step. A second portion of 3-(7-Methoxy-1H-indazol-4-yl)-N-methyl-3-phenyl-propionamide was purified on chiral HPLC by multiple injections onto 20×250 mm Chiralpak AD preparative column using a mixture of 70/30 hexane/EtOH at 7 ml/min in order to separate the enantiomers CXCIX-A and CXCIX-B.

Synthesis of racemic and non-racemic [3-(7-Methoxy-1H-indazol-4-yl)-3-phenyl-propyl]-methyl-amine CC, CCI and CCII

[3-(7-Methoxy-1H-indazol-4-yl)-3-phenyl-propyl]-methyl-amines CC, CCI and CCII were prepared from racemic (CXCIX) and non-racemic (CXCIX-A and CXCIX-B) 3-(7-methoxy-1H-indazol-4-yl)-N-methyl-3-phenyl-propionamide using the procedure described for preparation of [3-(1H-Indol-7-yl)-3-phenyl-propyl]-methyl-amine XX (Example 4). MS (M+H)=296.

Example 40

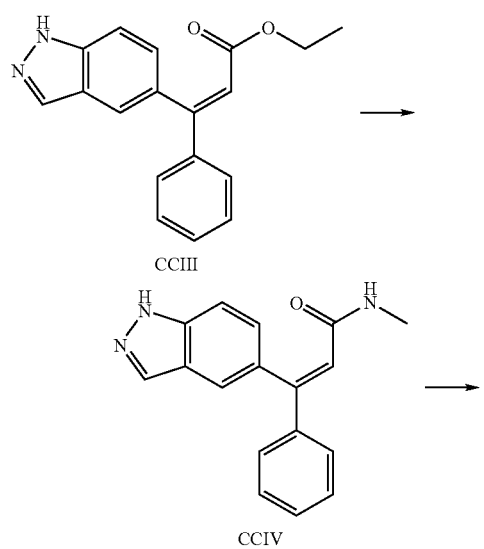

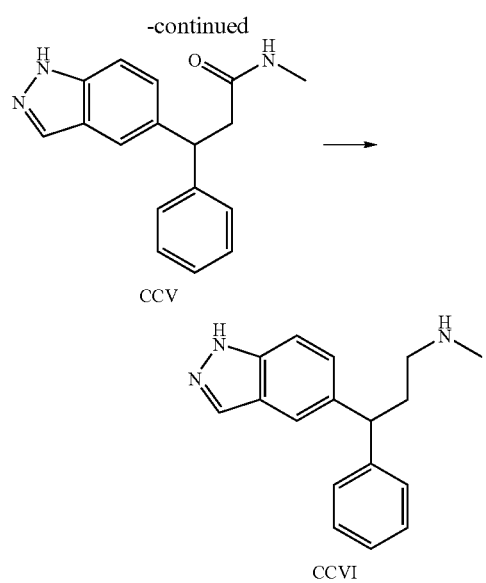

Synthesis of 3-(1H-Indazol-5-yl)-3-phenyl-acrylic acid ethyl ester (CCIII)

3-(1H-Indazol-5-yl)-3-phenyl-acrylic acid ethyl ester CCIII was prepared from 5-bromo-1H-indazole using the procedure described for preparation of 3-(7-Methoxy-1H-Indol-4-yl)-3-phenyl-acrylic acid ethyl ester LIII (Example 13).

Synthesis of 3-(1H-Indazol-5-yl)-N-methyl 3-phenyl-acrylamide (CCIV)

3-(1H-Indazol-5-yl)-N-methyl 3-phenyl-acrylamide CCIV was prepared from 3-(1H-indazol-5-yl)-3-phenyl-acrylic acid ethyl ester using the procedure described for preparation of 3-(1H-Indol-7-yl)-N-methyl-3-phenyl-acrylamide XVIII (see Example 4).

Synthesis of 3-(1H-Indazol-5-yl)-N-methyl-3-phenyl-propionamide (CCV)

3-(1H-Indazol-5-yl)-N-methyl-3-phenyl-propionamide CCV was obtained from 3-(1H-indazol-5-yl)-N-methyl 3-phenyl-acrylamide following the procedure described for preparation of 3-(1H-Indol-7-yl)-N-methyl-3-phenyl-propionamide XIX (Example 4).

Synthesis of [3-(1H-Indazol-5-yl)-3-phenyl-propyl]-methyl-amine (CCVI)

[3-(1H-Indazol-5-yl)-3-phenyl-propyl]-methyl-amine CCVI was prepared as a hydrochloride salt from 3-(1H-indazol-5-yl)-N-methyl-3-phenyl-propionamide using the procedure described for preparation of [3-(1H-Indol-7-yl)-3-phenyl-propyl]-methyl-amine XX (Example 4). MS (M+H)=266.

Example 41

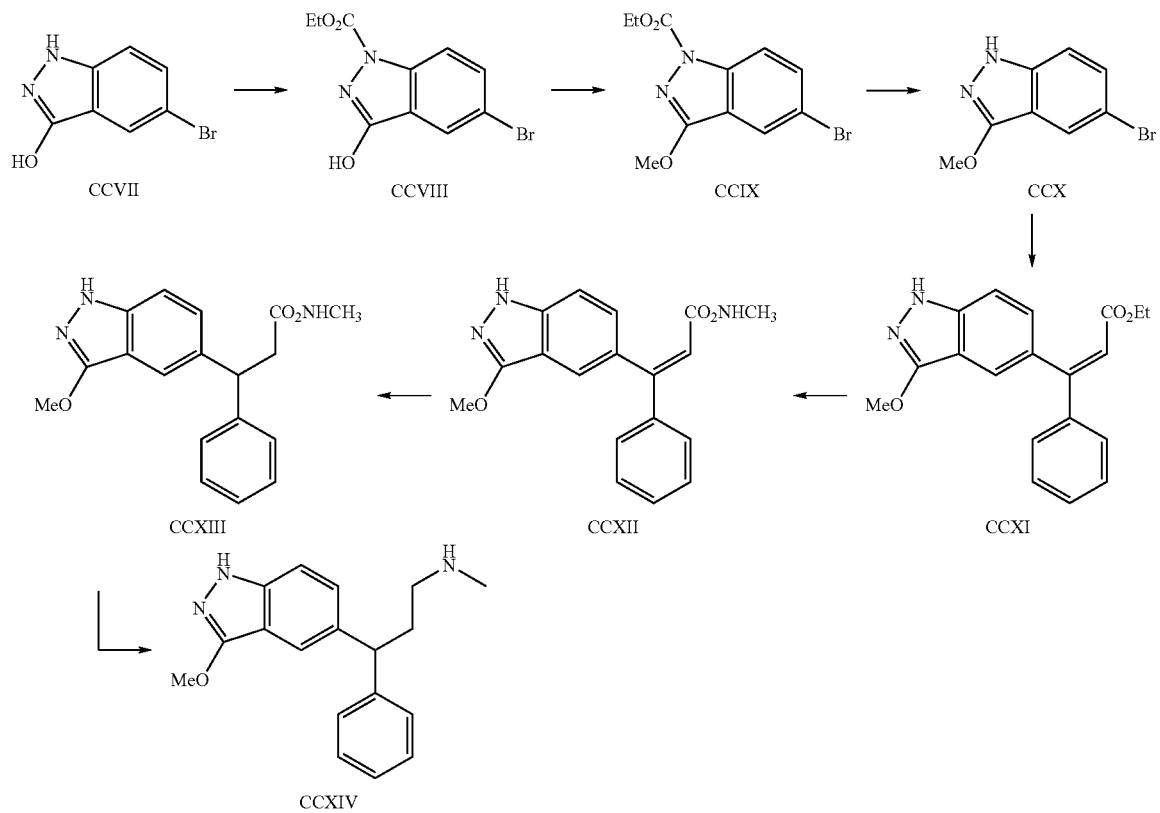

Synthesis of 5-Bromo-1H-indazol-3-ol (CCVII)

5-Bromo-1H-indazol-3-ol CCVII was prepared from 4-bromo-2-carboxyaniline using the procedure described for preparation of 4-Bromo-1H-indazol-3-ol CLXXXIII (Example 37).

Synthesis of 5-Bromo-3-hydroxy-indazole-1-carboxylic acid ethyl ester (CCVIII)

5-Bromo-3-hydroxy-indazole-1-carboxylic acid ethyl ester CCVIII was prepared from 5-bromo-1H-indazol-3-ol using the procedure described for preparation of 4-Bromo-3-hydroxy-indazole-1-carboxylic acid ethyl ester CLXXXIV (Example 37).

Synthesis of 5-Bromo-3-methoxy-indazole-1-carboxylic acid ethyl ester (CCIX)

5-Bromo-3-methoxy-indazole-1-carboxylic acid ethyl ester CCIX was prepared from 5-bromo-3-hydroxy-idazole-1-carboxylic acid ethyl ester using the procedure described for preparation of 4-Bromo-3-methoxy-indazole-1-carboxylic acid ethyl ester CLXXXV (Example 37).

Synthesis of 5-Bromo-3-methoxy-1H-indazole (CCX)

5-Bromo-3-methoxy-1H-indazole CCX was prepared from 5-Bromo-3-methoxy-indazole-1-carboxylic acid ethyl ester using the procedure described for preparation of 4-Bromo-3-methoxy-1H-indazole CLXXXVI (Example 37).

Synthesis of 3-(3-Methoxy-1H-indazol-5-yl)-3-phenyl-acrylic acid ethyl ester (CCXI)

3-(3-Methoxy-1H-indazol-5-yl)-3-phenyl-acrylic acid ethyl ester CCXI was prepared from 5-bromo-3-methoxy-1H-indazole,using the procedure described for preparation of 3-(7-Methoxy-1H-Indol-4-yl)-3-phenyl-acrylic acid ethyl ester LIII (Example 13).

Synthesis of 3-(3-Methoxy-1H-indazol-5-yl)-N-methyl 3-phenyl-acrylamide (CCXII)

The amide compound CCXII was prepared from 3-(3-methoxy-1H-indazol-5-yl)-3-phenyl-acrylic acid ethyl ester using the procedure described for preparation of 3-(1H-Indol-7-yl)-N-methyl-3-phenyl-acrylamide XVIII (see Example 4).

Synthesis of 3-(3-Methoxy-1H-indazol-5-yl)-N-methyl-3-phenyl-propionamide (CCXIII)

3-(3-Methoxy-1H-indazol-5-yl)-N-methyl-3-phenyl-propionamide CCXIII was obtained from 3-(3-methoxy-1H-indazol-5-yl)-N-methyl 3-phenyl-acrylamide following the procedure described for preparation of 3-(1H-Indol-7-yl)-N-methyl-3-phenyl-propionamide XIX (Example 4).

Synthesis of [3-(3-Methoxy-1H-indazol-5-yl)-3-phenyl-propyl]-methyl-amine (CCXIII)

[3-(3-Methoxy-1H-indazol-5-yl)-3-phenyl-propyl]-methyl-amine CCXIII was prepared as a trifluoroacetate from 3-(3-methoxy-1H-indazol-5-yl)-N-methyl-3-phenyl-propionamide and trifluoroacetic acid using the procedure described for preparation of [3-(1H-Indol-7-yl)-3-phenyl-propyl]-methyl-amine XX (Example 4). MS (M+H)=297.

Example 42

Synthesis of 3-(3-Chloro-1H-indazol-5-yl)-3-phenyl-acrylic acid ethyl ester (CCXV)

3-(3-Chloro-1H-indazol-5-yl)-3-phenyl-acrylic acid ethyl ester CCXV was prepared from 5-bromo-3-chloro-1H-indazole using the procedure described for preparation of 3-(7-Methoxy-1H-Indol-4-yl)-3-phenyl-acrylic acid ethyl ester LIII (Example 13).

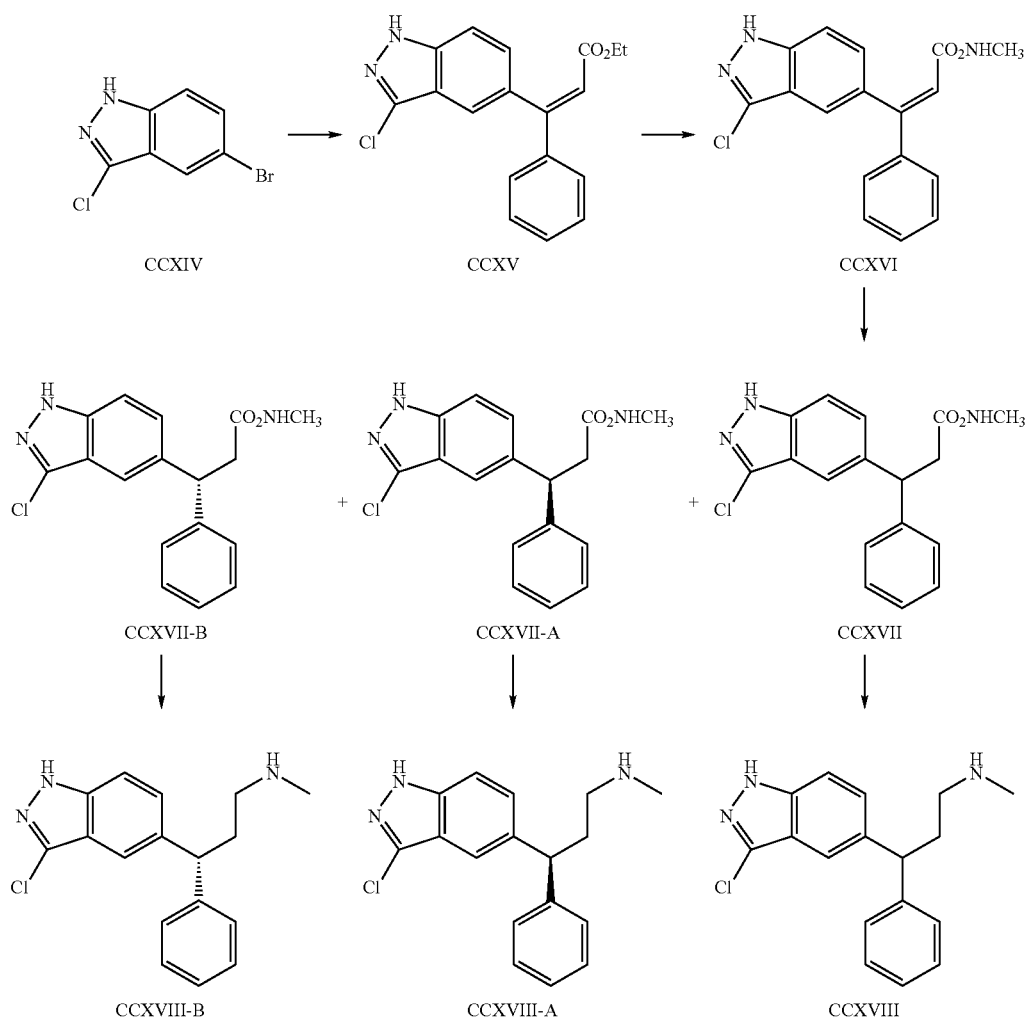

Synthesis of 5-Bromo-3-chloro-1H-indazole (CCXIV)

To a room temperature solution of 3-chloro-1H-indazole (10.0 g, 65.5 mmol) in AcOH (250 ml) was added $Br_2$ (3.54 ml, 68.8 mmol) dropwise. The reaction mixture was stirred at room temperature for 18 hours, then diluted with EtOAc (500 ml), washed with aqueous NaOH solution (10%), saturated aqueous $NaHCO_3$ and brine. The organic layer was dried over $MgSO_4$, filtered, concentrated, and the residue was recrystallized from toluene. The solid was washed with hexanes and dried in vacuo affording 5-Bromo-3-chloro-1H-indazole CCXIV as a white solid (54% yield).

Synthesis of 3-(3-Chloro-1H-indazol-5-yl)-N-methyl 3-phenyl-acrylamide (CCXVI)

3-(3-Chloro-1H-indazol-5-yl)-N-methyl 3-phenyl-acrylamide CCXVI was prepared from 3-(3-chloro-1H-indazol-5-yl)-3-phenyl-acrylic acid ethyl ester using the procedure described for preparation of 3-(1H-Indol-7-yl)-N-methyl-3-phenyl-acrylamide XVIII (see Example 4).

Synthesis of 3-(3-Chloro-1H-indazol-5-yl)-N-methyl-3-phenyl-propionamide (CCXVII)

3-(3-Chloro-1H-indazol-5-yl)-N-methyl-3-phenyl-propionamide CCXVII (quantitative yield, yellow foam) was obtained from 3-(3-chloro-1H-indazol-5-yl)-N-methyl 3-phenyl-acrylamide using the procedure described for preparation of 3-(1H-Indol-7-yl)-N-methyl-3-phenyl-propionamide XIX (Example 4). A portion of the crude 3-(3-Chloro-1H-indazol-5-yl)-N-methyl-3-phenyl-propionamide CCXVII was used without further purification in the next step. Another portion of 3-(3-Chloro-1H-indazol-5-yl)-N-methyl-3-phenyl-propionamide was purified via chiral HPLC by multiple injections onto 30×250 mm ID Chiralpak IA preparative column using a mixture of 85/15 hexanes/isopropanol at 16 ml/min in order to separate the enantiomers CCXVII-A and CCXVII-B. MS (M+H)=300.

Synthesis of racemic and non-racemic [3-(3-Chloro-1H-indazol-5-yl)-3-phenyl-propyl)-methyl-amine trifluoroacetate (CCXVIII, CCXVIII-A CCXVIII-B)

[3-(3-Chloro-1H-indazol-5-yl)-3-phenyl-propyl]-methyl-amines CCXVIII, CCXVIII-A and CCXVIII-B were prepared from 3-(3-chloro-1H-indazol-5-yl)-N-methyl-3-phenyl-propionamides CCXVII, CCXVII-A and CCXVII-B respectively, using the procedure described for preparation of [3-(1H-Indol-7-yl)-3-phenyl-propyl]-methyl-amine XX (Example 4).

Synthesis of 3-(3-Methyl-1H-indazol-5-yl)-3-phenyl-acrylic acid ethyl ester (CCXIX)

3-(3-Methyl-1H-indazol-5-yl)-3-phenyl-acrylic acid ethyl ester CCXIX) was prepared from 3-methyl-5-bromo-1H-indazole using the procedure described for preparation of 3-(3-Cyano-1H-Indol-4-yl)-3-phenyl-acrylic acid ethyl ester LVIII (Example 14).

Synthesis of 3-(3-Methyl-1H-indazol-5-yl)-N-methyl 3-phenyl-acrylamide (CCXX)

3-(3-Methyl-1H-indazol-5-yl)-N-methyl 3-phenyl-acrylamide CCXX was prepared from 3-(3-methyl-1H-indazol-5-yl)-3-phenyl-acrylic acid ethyl ester using the procedure described for preparation of 3-(1H-Indol-7-yl)-N-methyl-3-phenyl-acrylamide XVIII (see Example 4).

Synthesis of 3-(3-Methyl-1H-indazol-5-yl)-N-methyl-3-phenyl-propionamide (CCXXI)

3-(3-Methyl-1H-indazol-5-yl)-N-methyl-3-phenyl-propionamide CCXXI was obtained from 3-(3-methyl-1H-indazol-5-yl)-N-methyl 3-phenyl-acrylamide following the procedure described for preparation of 3-(1H-Indol-7-yl)-N-methyl-3-phenyl-propionamide XIX (Example 4).

Synthesis of [3-(3-Methyl-1H-indazol-5-yl)-3-phenyl-propyl]-methyl-amine (CCXXII)

[3-(3-Methyl-1H-indazol-5-yl)-3-phenyl-propyl]-methyl-amine CCXXII was prepared as a trifluoroacetate from 3-(3-methyl-1H-indazol-5-yl)-N-methyl-3-phenyl-propionamide using the procedure described for preparation of [3-(1H-Indol-7-yl)-3-phenyl-propyl]-methyl-amine XX (Example 4). MS (M+H)=280.

Example 43

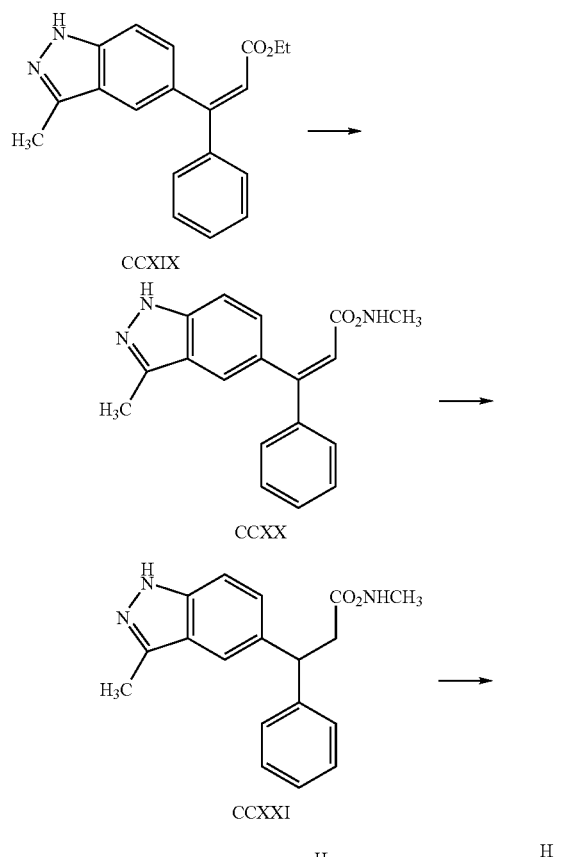

Example 44

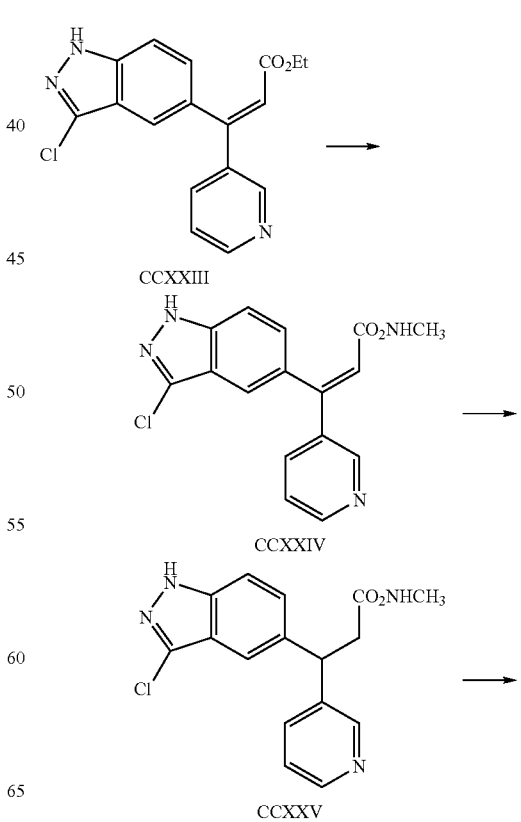

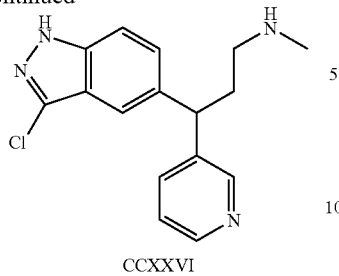

CCXXVI

Synthesis of 3-(3-Chloro-1H-indazol-5-yl)-3-pyridin-3-yl-acrylic acid ethyl ester (CCXXIII)

3-(3-Chloro-1H-indazol-5-yl)-3-pyridin-3-yl-acrylic acid ethyl ester CCXXIII was prepared from 5-bromo-3-chloro-1H-indazole and 3-pyridin-3-yl-acrylic acid ethyl ester using the procedure described for preparation of 3-(3-Cyano-1H-Indol-4-yl)-3-phenyl-acrylic acid ethyl ester LVIII (Example 14).

Synthesis of 3-(3-Chloro-1H-indazol-5-yl)-N-methyl 3-pyridin-3-yl-acrylamide (CCXXIV)

3-(3-Chloro-1H-indazol-5-yl)-N-methyl 3-pyridin-3-yl-acrylamide CCXXIV was prepared from 3-(3-chloro-1H-indazol-5-yl)-3-pyridin-3-yl-acrylic acid ethyl ester using the procedure described for preparation of 3-(1H-Indol-7-yl)-N-methyl-3-phenyl-acrylamide XVIII (see Example 4).

Synthesis of 3-(3-Chloro-1H-indazol-5-yl)-N-methyl-3-pyridin-3-yl-propionamide (CCXXV)

3-(3-Chloro-1H-indazol-5-yl)-N-methyl-3-pyridin-3-yl-propionamide CCXXV was obtained from 3-(3-chloro-1H-indazol-5-yl)-N-methyl 3-phenyl-acrylamide following the procedure described for preparation of 3-(1H-Indol-7-yl)-N-methyl-3-phenyl-propionamide XIX (Example 4).

Synthesis of [3-(3-Chloro-1H-indazol-5-yl)-3-pyridin-3-yl-propyl]-methyl-amine (CCXXVI)

[3-(3-Chloro-1H-indazol-5-yl)-3-pyridin-3-yl-propyl]-methyl-amine CCXXVI was prepared as a trifluoracetate from 3-(3-chloro-1H-indazol-5-yl)-N-methyl-3-phenyl-propionamide using the procedure described for preparation of [3-(1H-Indol-7-yl)-3-phenyl-propyl]-methyl-amine XX (Example 4). MS (M+H)=301.

Example 45

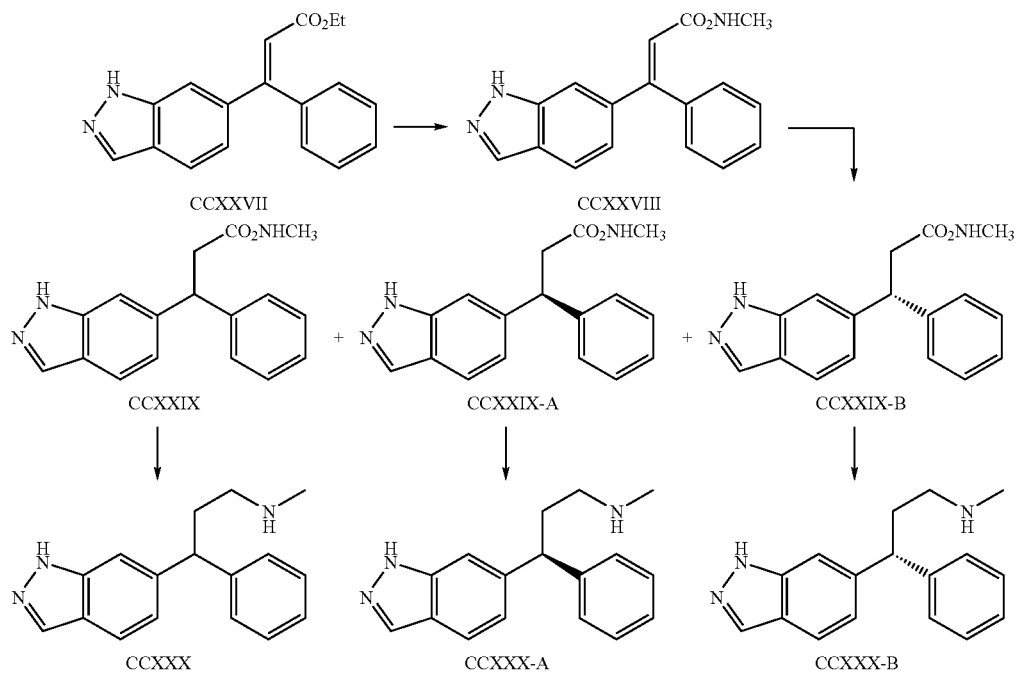

Synthesis of 3-(1H-Indazol-6-yl)-3-phenyl-acrylic acid ethyl ester (CCXXVII)

3-(1H-Indazol-6-yl)-3-phenyl-acrylic acid ethyl ester CCXXVII was prepared from 6-bromo-1H-indazole using the procedure described for preparation of 3-(7-Methoxy-1H-Indol-4-yl)-3-phenyl-acrylic acid ethyl ester LIII (Example 13).

Synthesis of 3-(1H-Indazol-6-yl)-N-methyl-3-phenyl-acrylamide (CCXXVIII)

3-(1H-Indazol-6-yl)-N-methyl-3-phenyl-acrylamide CCXXVIII was obtained from 3-(1H-indazol-6-yl)-3-phenyl-acrylic acid ethyl ester following the procedure described for preparation of 3-(1H-Indol-7-yl)-N-methyl-3-phenyl-acrylamide XVIII (see Example 4).

Synthesis of 3-(1H-Indazol-6-yl)-N-methyl-3-phenyl-propionamide (CCXXIX)

3-(1H-Indazol-6-yl)-N-methyl-3-phenyl-propionamide CCXXIX was prepared from 3-(1H-indazol-6-yl)-N-methyl-3-phenyl-acrylamide using the procedure described for preparation of 3-(1H-Indol-7-yl)-N-methyl-3-phenyl-propionamide XIX (Example 4). A portion of the 3-(1H-Indazol-6-yl)-N-methyl-3-phenyl-propionamide CCXXIX was used without further purification in the next step, while a portion was purified via chiral preparative HPLC. The two enantiomers CCXXIX-A and CCXXIX-B were separated by multiple injections onto 50×500 mm Chiralpak AD preparative column using a mixture of 85/15 hexane/isopropanol at 50 ml/minute.

Synthesis of Racemic and Non-racemic [3-(1H-Indazol-6-yl)-3-phenyl-propyl]-methyl-amine (CCXXX, CCXXIX-A and CCXXIX-B)

[3-(1H-Indazol-6-yl)-3-phenyl-propyl]-methyl-amines CCXXX, CCXXIX-A and CCXXIX-B were prepared as hydrochloride salts from -(1H-Indazol-6-yl)-N-methyl-3-phenyl-propionamide using the procedure described for preparation of [3-(1H-Indol-7-yl)-3-phenyl-propyl]-methyl-amine XX (Example 4). MS (M+H)=266.

Example 46

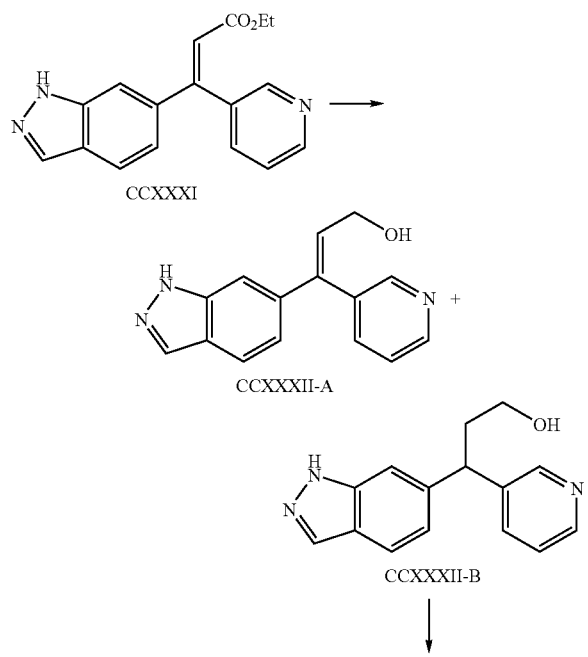

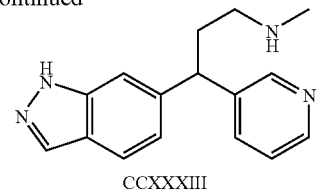

Synthesis of 3-(1H-Indazol-6-yl)-3-pyridin-3-yl-acrylic acid ethyl ester (CCXXXI)

3-(1H-Indazol-6-yl)-3-pyridin-3-yl-acrylic acid ethyl ester CCXXXI was prepared from 6-bromo-1H-indazole and 3-pyridin-3-yl-acrylic acid ethyl ester using the procedure described for preparation of 3-(3-Cyano-1H-Indol-4-yl)-3-phenyl-acrylic acid ethyl ester LVIII (Example 14).

Synthesis of 3-(1H-Indazol-6-yl)-3-pyridin-3-yl-prop-2-en-1-ol (CCXXXII-A) and 3-(1H-Indazol-6-yl)-3-pyridin-3-yl-propan-1-ol (CCXXXII-B)

To a −78° C. solution of 3-(1H-Indazol-6-yl)-3-pyridin-3-yl-acrylic acid ethyl ester CCXXXI (415 mg, 1.42 mmol) in THF (30 ml) was added 1 M solution of $LiAlH_4$ (in THF, 2.81 ml) dropwise. The reaction mixture was stirred at room temperature for 1 hour and was quenched by addition of freshly ground $Na_2SO_4 \cdot 10H_2O$ (2 g). After stirring for 30 minutes, the solid residue was filtered off and washed with EtOAc. The filtrate was dried over $MgSO_4$, filtered, concentrated, and purified via flash chromatography (DCM/MeOH) affording 3-(1H-Indazol-6-yl)-3-pyridin-3-yl-prop-2-en-1-ol CCXXXII-A as a yellow oil (62 mg, 17% yield) in a first fraction, and 3-(1H-Indazol-6-yl)-3-pyridin-3-yl-propan-1-ol CCXXXII-B as a yellow foam (64 mg, 18% yield) in a second fraction.

Synthesis of [3-(1H-Indazol-6-yl)-3-pyridin-3-yl-propyl]-methyl-amine (CCXXXIII)

To a −78° C. solution of 3-(1H-Indazol-6-yl)-3-pyridin-3-yl-propan-1-ol CCXXXII-B (62 mg, 0.245 mmol) in THF (5 ml) was added MsCl (25 μl, 0.319 mmol), followed by TEA (55 μl, 0.392 mmol). The reaction was allowed to reach room temperature, and after 5 minutes was cooled again to −78° C., and the same amounts of TEA and MsCl were added. The reaction was then allowed to reach room temperature and the solvent was removed in vacuo. To the residue was added $MeNH_2$ (2.0 M in THF, 10 ml), and the mixture was transferred to a sealed vial and stirred at 80° C. for 48 hours. The reaction mixture was concentrated and the residue was purified via flash chromatography (DCM/MeOH) and preparative HPLC to provide [3-(1H-Indazol-6-yl)-3-pyridin-3-yl-propyl]-methyl-amine CCXXXIII as a white foam (10 mg, 11% yield). MS (M+H)=267.

Example 47

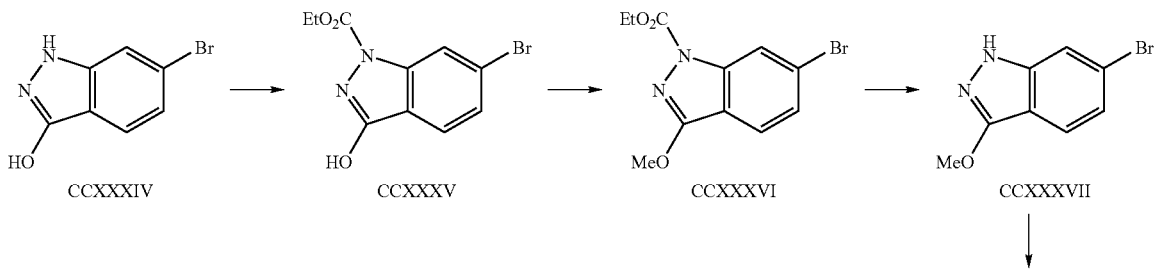

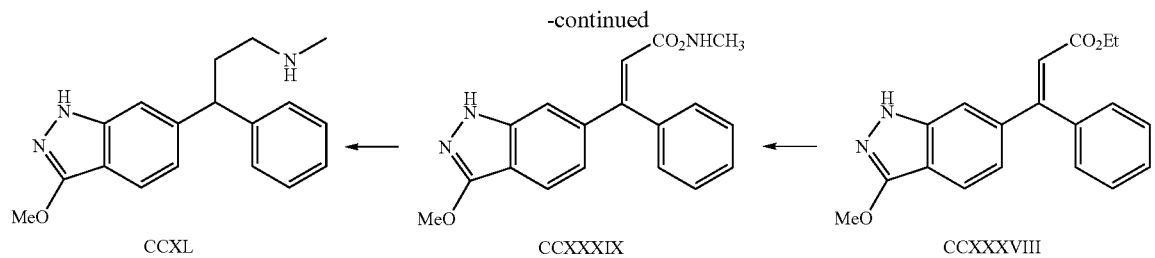

Synthesis of 6-Bromo-1H-indazol-3-ol (CCXXXIV)

6-Bromo-1H-indazol-3-ol CCVII was prepared from 5-bromo-2-carboxyaniline (JOC, 1997, 62, 1240) using the procedure described for preparation of 4-Bromo-1H-indazol-3-ol CLXXXIII (Example 37).

Synthesis of 6-Bromo-3-hydroxy-indazole-1-carboxylic acid ethyl ester (CCXXXV)

6-Bromo-3-hydroxy-indazole-1-carboxylic acid ethyl ester CCXXXV was prepared from 6-bromo-1H-indazol-3-ol using the procedure described for preparation of 4-Bromo-3-hydroxy-indazole-1-carboxylic acid ethyl ester CLXXXIV (Example 37).

Synthesis of 5-Bromo-3-methoxy-indazole-1-carboxylic acid ethyl ester (CCXXXVI)

5-Bromo-3-methoxy-indazole-1-carboxylic acid ethyl ester CCXXXVI was prepared from 6-bromo-3-hydroxy-idazole-1-carboxylic acid ethyl ester using the procedure described for preparation of 4-Bromo-3-methoxy-indazole-1-carboxylic acid ethyl ester CLXXXV (Example 37).

Synthesis of 6-Bromo-3-methoxy-1H-indazole (CCXXXVII)

6-Bromo-3-methoxy-1H-indazole CCXXXVII was prepared from 6-bromo-3-methoxy-idazole-1-carboxylic acid ethyl ester using the procedure described for preparation of 4-Bromo-3-methoxy-1H-indazole CLXXXVI (Example 37).

Synthesis of 3-(3-Methoxy-1H-indazol-6-yl)-3-phenyl-acrylic acid ethyl ester (CCXXXVIII)

3-(3-Methoxy-1H-indazol-6-yl)-3-phenyl-acrylic acid ethyl ester CCXXXVIII was prepared using the procedure described for preparation of 3-(3-Cyano-1H-Indol-4-yl)-3-phenyl-acrylic acid ethyl ester LVIII (Example 14).

Synthesis of 3-(3-Methoxy-1H-indazol-6-yl)-N-methyl-3-phenyl-acrylamide (CCXXXIX)

3-(3-Methoxy-1H-indazol-6-yl)-N-methyl-3-phenyl-acrylamide CCXXXIX was obtained from 3-(3-methoxy-1H-indazol-6-yl)-3-phenyl-acrylic acid ethyl ester following the procedure described for preparation of 3-(1H-Indol-7-yl)-N-methyl-3-phenyl-acrylamide XVIII (see Example 4).

Synthesis of [3-(3-Methoxy-1H-indazol-6-yl)-3-phenyl-propyl]-methyl-amine (CCXL)

[3-(3-Methoxy-1H-indazol-6-yl)-3-phenyl-propyl]-methyl-amine CCXL was prepared from 3-(3-methoxy-1H-indazol-6-yl)-N-methyl-3-phenyl-acrylamide using the procedure described for preparation of [3-(1H-Indol-7-yl)-3-phenyl-propyl]-methyl-amine XX (Example 4). MS (M+H)= 297.

Example 48

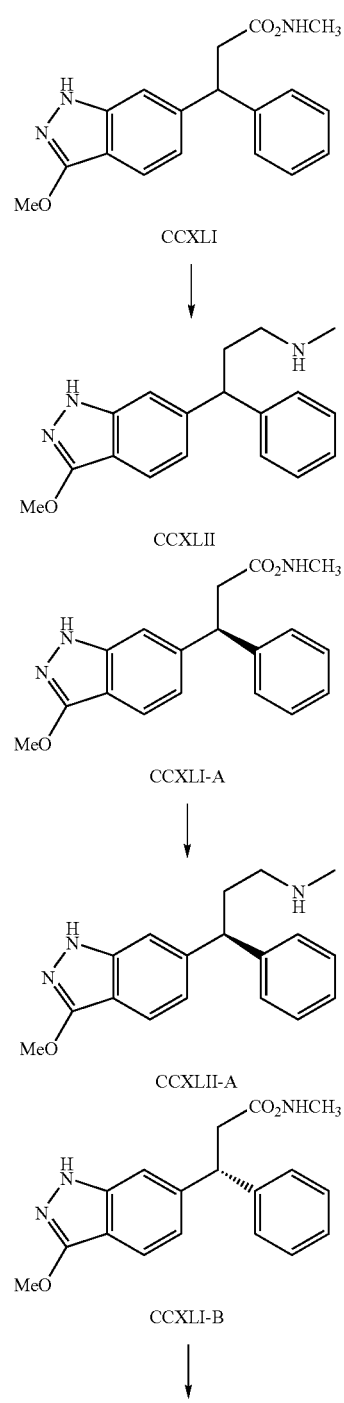

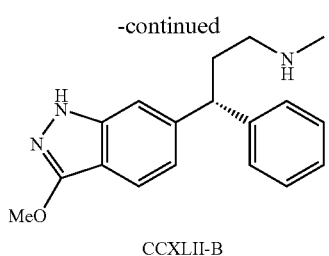

CCXLII-B

Synthesis of 3-(3-Methoxy-1H-indazol-6-yl)-N-methyl-3-phenyl-propionamide (CCXLI)

3-(3-Methoxy-1H-indazol-6-yl)-N-methyl-3-phenyl-propionamide CCXLI was prepared from using the procedure described for preparation of 3-(1H-Indol-7-yl)-N-methyl-3-phenyl-propionamide XIX (Example 4). The enantiomers CCXLII-A and CCXLII-B were then separated via chiral preparative HPLC by multiple injections onto 50×500 mm Chiralpak AD preparative column using a mixture of 60/40 hexanes/isopropanol at 50 ml/min affording compound CCXLI-A ($\alpha_D$=−8.7°) and compound CCXLI-B ($\alpha_D$=+4.7°).

Synthesis of [3-(3-Methoxy-1H-indazol-6-yl)-3-phenyl-propyl]-methyl-amines (CCXLII CCXLII-A and CCXLII-B)

[3-(3-Methoxy-1H-indazol-6-yl)-3-phenyl-propyl]-methyl-amines CCXLII, CCXLII-A and CCXLII-B were prepared from 3-(3-methoxy-1H-indazol-6-yl)-N-methyl-3-phenyl-acrylamides CCXLI, CCXLI-A and CCXLI-B respectively using the procedure described for preparation of [3-(1H-Indol-7-yl)-3-phenyl-propyl]-methyl-amine XX (Example 4). MS (M+H)=297.

Example 49

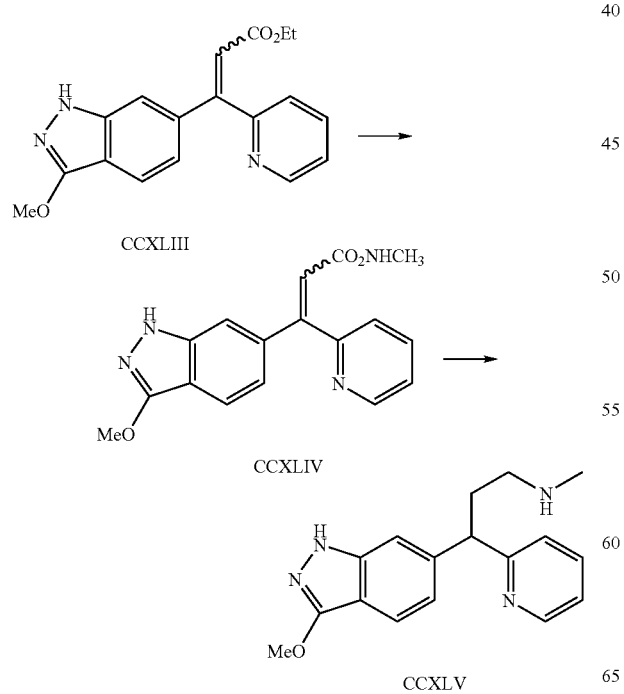

Synthesis of 3-(3-Methoxy-1H-indazol-6-yl)-3-pyridin-2yl-acrylic acid ethyl ester (CCXLIII)

3-(3-Methoxy-1H-indazol-6-yl)-3-pyridin-2yl-acrylic acid ethyl ester CCXLIII was prepared from 6-bromo-3-methoxy-1H-indazole and 3-pyridin-2-yl-acrylic acid ethyl ester using the procedure described for preparation of 3-(3-Cyano-1H-Indol-4-yl)-3-phenyl-acrylic acid ethyl ester LVIII (Example 14).

Synthesis of 3-(3-Methoxy-1H-indazol-6-yl)-N-methyl-3-pyridin-2yl-acrylamide (CCXLIV)

3-(3-Methoxy-1H-indazol-6-yl)-N-methyl-3-pyridin-2yl-acrylamide CCXLIV was obtained from 3-(3-methoxy-1H-indazol-6-yl)-3-pyridin-2yl-acrylic acid ethyl ester following the procedure described for preparation of 3-(1H-Indol-7-yl)-N-methyl-3-phenyl-acrylamide XVIII (see Example 4).

Synthesis of [3-(3-Methoxy-1H-indazol-6-yl)-3-pyridin-2yl-propyl]-methyl-amine (CCXLV)

[3-(3-Methoxy-1H-indazol-6-yl)-3-pyridin-2yl-propyl]-methyl-amine CCXLV was prepared from 3-(3-methoxy-1H-indazol-6-yl)-N-methyl-3-pyridin-2yl-acrylamide using the procedure described for preparation of [3-(1H-Indol-7-yl)-3-phenyl-propyl]-methyl-amine XX (Example 4). MS (M+H)=298.

Example 50

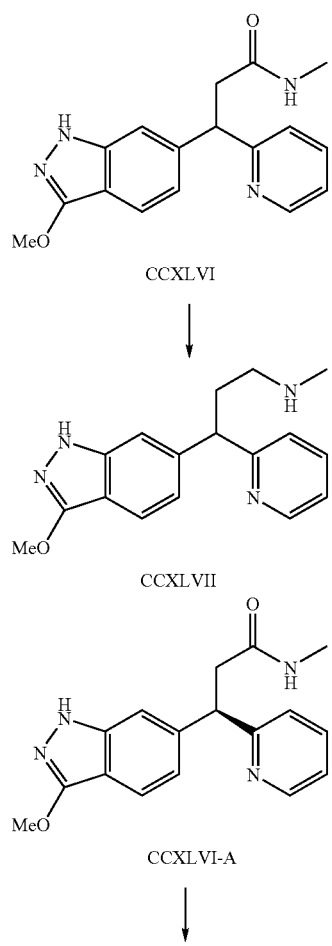

-continued

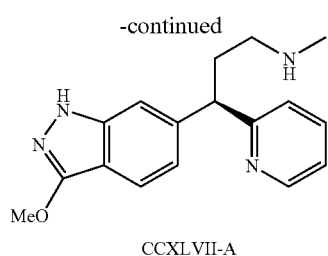

CCXLVII-A

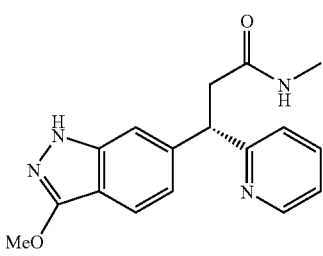

CCXLVI-B

↓

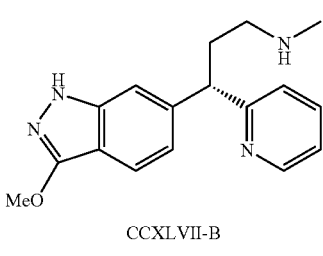

CCXLVII-B

Synthesis of 3-(3-Methoxy-1H-indazol-6-yl)-N-methyl-3-pyridin-2yl-propionamide (CCXLVI)

3-(3-Methoxy-1H-indazol-6-yl)-N-methyl-3-pyridin-2yl-propionamide CCXLVI was prepared from 3-(3-methoxy-1H-indazol-6-yl)-N-methyl-3-pyridin-2yl-acrylamide using the procedure described for preparation of 3-(1H-Indol-7-yl)-N-methyl-3-phenyl-propionamide XIX (Example 4). The crude product (90% yield) was purified via chiral preparative HPLC by multiple injections onto 20×250 mm Chiralpak AD preparative column using a mixture of 60/40 hexane/isopropanol at 7 ml/min affording the enatiomer CCXLVI-A ($\alpha_D$=−0.269°) and the enantiomer CCXLVI-B ($\alpha_D$=+0.209°).

Synthesis of [3-(3-Methoxy-1H-indazol-6-yl)-3-pyridin-2yl-propyl]-methyl-amines (CCXLVII, CCXLVII-A and CCXLVII-B)

[3-(3-Methoxy-1H-indazol-6-yl)-3-pyridin-2yl-propyl]-methyl-amines CCXLVII, CCXLVII-A and CCXLVII-B were prepared as bis-trifluoroacetates from 3-(3-methoxy-1H-indazol-6-yl)-N-methyl-3-pyridin-2yl-propionamides CCXLVI, CCXLVI-A and CCXLVI-B respectively and trifluoroacetic acid, using the procedure described for preparation of [3-(1H-Indol-7-yl)-3-phenyl-propyl]-methyl-amine XX (Example 4). MS (M+H)=298.

Example 51

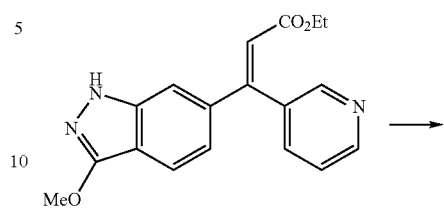

CCXLVIII

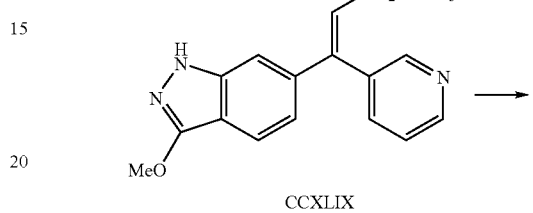

CCXLIX

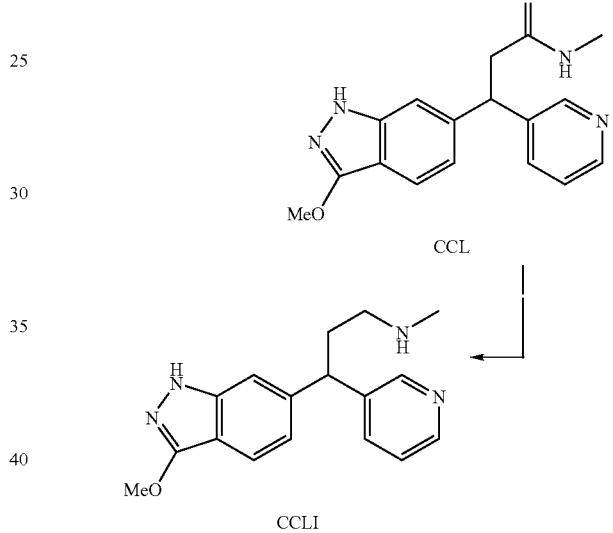

CCL

↓

CCLI

Synthesis of 3-(3-Methoxy-1H-indazol-6-yl)-3-pyridin-3yl-acrylic acid ethyl ester (CCXLVIII)

3-(3-Methoxy-1H-indazol-6-yl)-3-pyridin-3yl-acrylic acid ethyl ester was prepared from 6-bromo-3-methoxy-1H-indazole and 3-pyridin-3-yl-acrylic acid ethyl ester using the procedure described for preparation of 3-(3-Cyano-1H-Indol-4-yl)-3-phenyl-acrylic acid ethyl ester LVIII (Example 14).

Synthesis of 3-(3-Methoxy-1H-indazol-6-yl)-N-methyl-3-pyridin-3-yl-acrylamide (CCXLIX)

3-(3-Methoxy-1H-indazol-6-yl)-N-methyl-3-pyridin-3-yl-acrylamide CCXLIX was obtained from 3-(3-methoxy-1H-indazol-6-yl)-3-pyridin-3yl-acrylic acid ethyl ester following the procedure described for preparation of 3-(1H-Indol-7-yl)-N-methyl-3-phenyl-acrylamide XVIII (see Example 4).

Synthesis of 3-(3-Methoxy-1H-indazol-6-yl)-N-methyl-3-pyridin-3-yl-propionamide (CCL)

3-(3-Methoxy-1H-indazol-6-yl)-N-methyl-3-pyridin-3-yl-propionamide CCL was prepared from 3-(3-methoxy-1H- indazol-6-yl)-N-methyl-3-pyridin-3-yl-acrylamide using the procedure described for preparation of 3-(1H-Indol-7-yl)-N-methyl-3-phenyl-propionamide XIX (Example 4).

Synthesis of [3-(3-Methoxy-1H-indazol-6-yl)-3-pyridin-3-yl-propyl]-methyl-amine (CCLI)

[3-(3-Methoxy-1H-indazol-6-yl)-3-pyridin-3-yl-propyl]-methyl-amine CCLI was prepared from 3-(3-methoxy-1H-indazol-6-yl)-N-methyl-3-pyridin-3yl-propionamide and TFA using the procedure described for preparation of [3-(1H-Indol-7-yl)-3-phenyl-propyl]-methyl-amine XX (Example 4). MS (M+H)=298.

Example 52 for preparation of 3-(3-Cyano-1H-Indol-4-yl)-3-phenyl-acrylic acid ethyl ester LVIII (Example 14).

Synthesis of 3-(3-Methoxy-1H-indazol-6-yl)-N-methyl-3-(6-methyl-pyridin-2yl)-acryl amide (CCLIV)

3-(3-Methoxy-1H-indazol-6-yl)-N-methyl-3-(6-methyl-pyridin-2yl)-acryl amide CCLIV was obtained from 3-(3-methoxy-1H-indazol-6-yl)-3-(6-methyl-pyridin-2-yl)-acrylic acid ethyl ester following the procedure described for preparation of 3-(1H-Indol-7-yl)-N-methyl-3-phenyl-acrylamide XVIII (see Example 4).

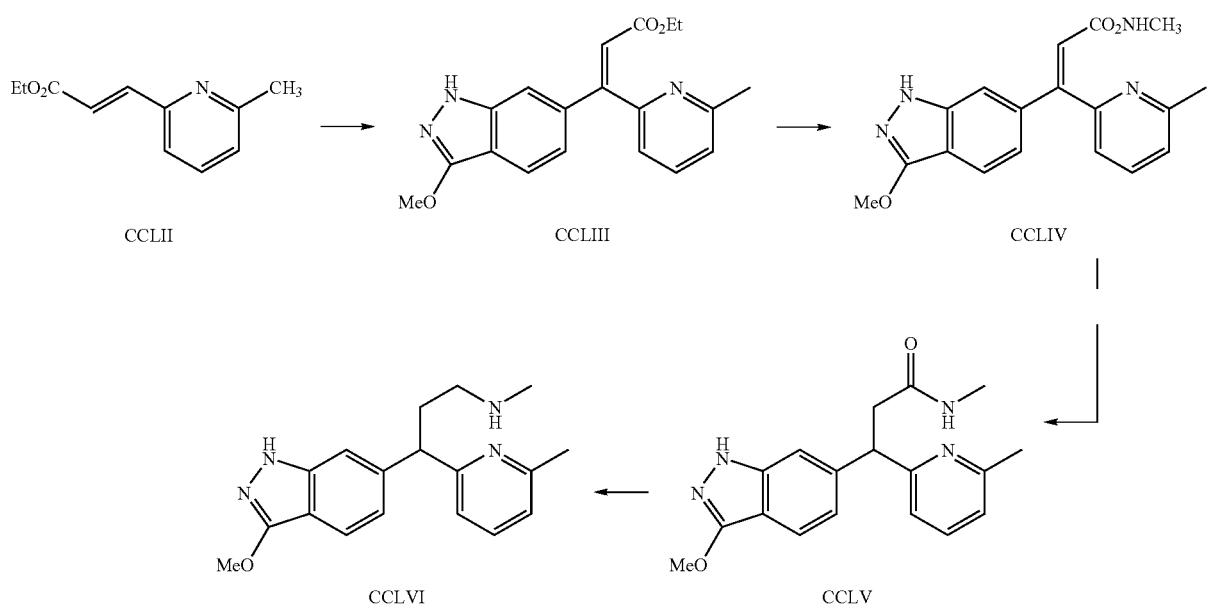

Synthesis of 3-(6-Methyl-pyridin-2-yl)-acrylic acid ethyl ester (CCLII)

A mixture of 6-methyl-pyridine-2-carbaldeyde (3.0 g, 24.8 mmol) and carbethoxymethylene triphenylphosphorane (9.5 g, 27.2 mmol) in toluene (20 ml) was stirred at room temperature overnight. The precipitate was filtered and washed with toluene. The filtrate was concentrated, and the residue was purified via flash chromatography (DCM/MeOH) affording 3-(6-Methyl-pyridin-2-yl)-acrylic acid ethyl ester CCLII in 63% yield (2.95 g).

Synthesis of 3-(3-Methoxy-1H-indazol-6-yl)-3-(6-methyl-pyridin-2yl)-acrylic acid ethyl ester (CCLIII)

3-(3-Methoxy-1H-indazol-6-yl)-3-(6-methyl-pyridin-2-yl)-acrylic acid ethyl ester CCLIII was prepared from 6-bromo-3-methoxy-1H-indazole and 3-(6-methyl-pyridin-2-yl)-acrylic acid ethyl ester using the procedure described Synthesis of 3-(3-Methoxy-1H-indazol-6-yl)-N-methyl-3-(6-methyl-pyridin-2yl)-propionamide (CCXLV)

3-(3-Methoxy-1H-indazol-6-yl)-N-methyl-3-(6-methyl-pyridin-2yl)-propionamide CCXLV was prepared from 3-(3-methoxy-1H-indazol-6-yl)-N-methyl-3-(6-methyl-pyridin-2yl)-acrylamide using the procedure described for preparation of 3-(1H-Indol-7-yl)-N-methyl-3-phenyl-propionamide XIX (Example 4).

Synthesis of [3-(3-Methoxy-1H-indazol-6-yl)-3-(6-methyl-pyridin-2yl)-propyl]-methyl-amine (CCXLVI)

[3-(3-Methoxy-1H-indazol-6-yl)-3-(6-methyl-pyridin-2yl)-propyl]-methyl-amine CCXLVI was prepared from 3-(3-methoxy-1H-indazol-6-yl)-N-methyl-3-(6-methyl-pyridin-2yl)-propionamide and TFA as a bis-trifluoroacetate using the procedure described for preparation of [3-(1H-Indol-7-yl)-3-phenyl-propyl]-methyl-amine XX (Example 4). MS (M+H)=MS 311.

Example 53

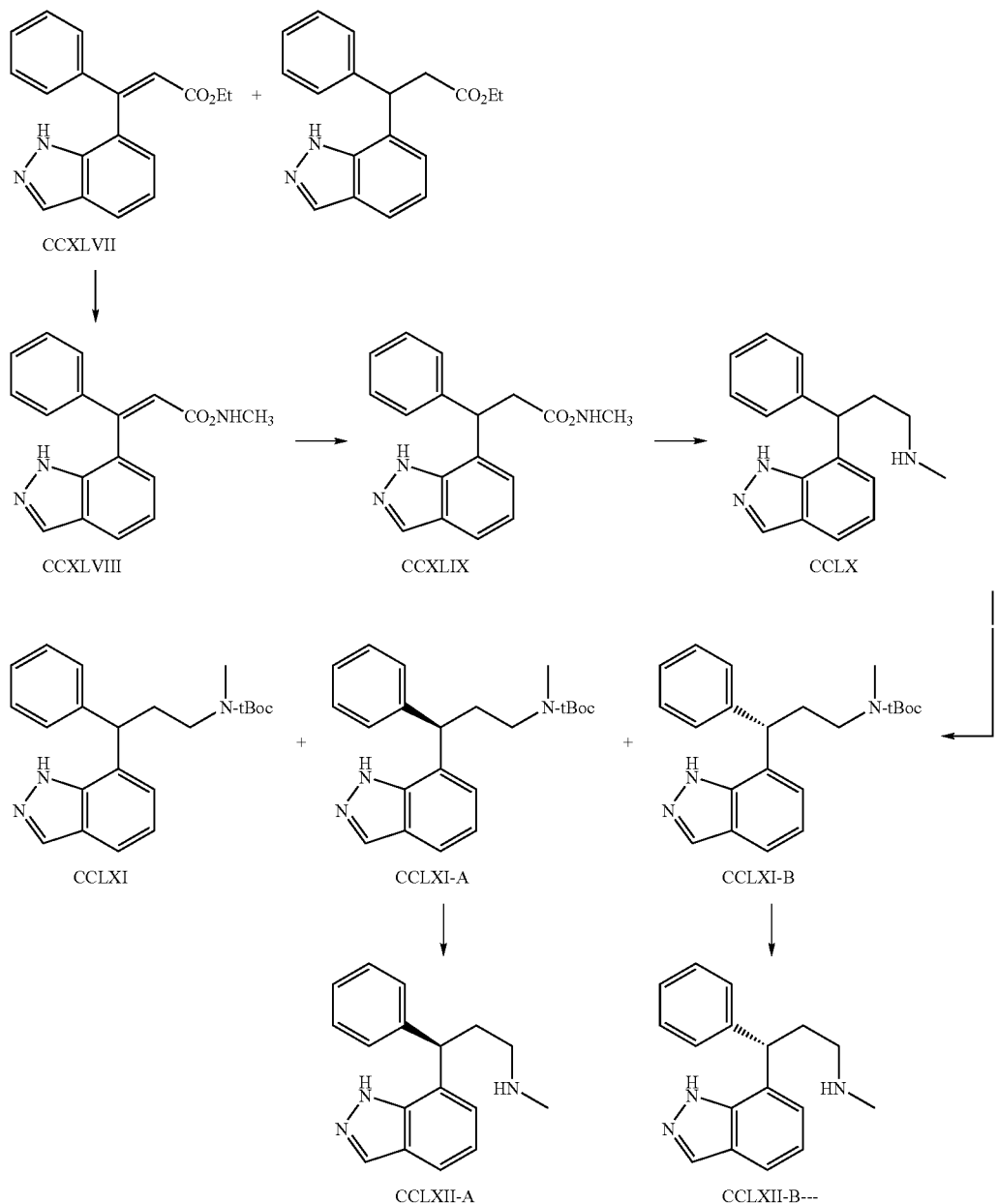

Synthesis of 3-(1H-Indazol-7-yl)-3-phenyl-acrylic acid ethyl ester (CCXLVII)

3-(1H-Indazol-7-yl)-3-phenyl-acrylic acid ethyl ester CCXLVII was prepared from 7-bromo-1H-indazole using the procedure described for preparation of 3-(7-Methoxy-1H-Indol-4-yl)-3-phenyl-acrylic acid ethyl ester LIII (Example 13).

Synthesis of 3-(1H-Indazol-7-yl)-N-methyl-3-phenyl-acrylamide (CCXLVIII)

3-(1H-Indazol-7-yl)-N-methyl-3-phenyl-acrylamide CCXLVIII was obtained from 3-(1H-indazol-7-yl)-3-phenyl-acrylic acid ethyl ester following the procedure described for preparation of 3-(1H-Indol-7-yl)-N-methyl-3-phenyl-acrylamide XVIII (see Example 4).

Synthesis of 3-(1H-Indazol-7-yl)-N-methyl-3-phenyl-propionamide (CCXLIX)

3-(1H-Indazol-7-yl)-N-methyl-3-phenyl-propionamide CCXLIX was prepared from 3-(1H-indazol-7-yl)-N-methyl-3-phenyl-acrylamide using the procedure described for preparation of 3-(1H-Indol-7-yl)-N-methyl-3-phenyl-propionamide XIX (Example 4).

Synthesis of [3-(1H-Indazol-7-yl)-3-phenyl-propyl]-methyl-amine (CCLX)

[3-(1H-Indazol-7-yl)-3-phenyl-propyl]-methyl-amine CCLX was prepared from 3-(1H-indazol-7-yl)-N-methyl-3-phenyl-propionamide and TFA using the procedure described for preparation of [3-(1H-Indol-7-yl)-3-phenyl-propyl]-methyl-amine XX (Example 4).

Synthesis of [3-(1H-Indazol-7-yl)-3-phenyl-propyl]-methyl-carbamic acid ter-butyl esters (CCLXI, CCLXI-A and CCLXI-B)

To a room temperature solution of [3-(1H-Indazol-7-yl)-3-phenyl-propyl]-methyl-amine trifluoroacetate CCLX (243 mg, 0.64 mmol) in DCM (20 ml) was added (BOC)$_2$O (140 mg, 0.641 mmol) and TEA (0.48 ml, 1.28 mmol). The resulting mixture was stirred for 24 hours at room temperature, then diluted with DCM (30 ml) and washed successively with H$_2$O, a saturated aqueous NaHCO$_3$ and brine. The organic layer was dried over MgSO$_4$, filtered, and concentrated affording racemic [3-(1H-Indazol-7-yl)-3-phenyl-propyl]-methyl-carbamic acid ter-butyl ester CCLXI as a yellow oil in quantitative yield. The enantiomers CCLXI-A and CCLXI-B were separated via chiral preparative HPLC by multiple injections onto 30×250 mm ID Chiralpak IA preparative column using a mixture of 80/20 hexane/isopropanol at 16 ml/min, affording compound CCLXI-A (37% yield) and compound CCLXI-B (40%). MS (M+H)=266.

Preparation of [3-(1H-Indazol-7-yl)-3-phenyl-propyl]-methyl-amine (CCLXII-A)

To a room temperature solution of [3-(1H-Indazol-7-yl)-3-phenyl-propyl]-methyl-carbamic acid ter-butyl ester CCLXI-A (87 mg, 0.238 mmol) in DCM (5 ml) under N$_2$ was added TFA (0.18 ml, 2.38 mmol). The mixture was stirred for 20 hours, concentrated, and the residue was purified via flash chromatography (DCM/MeOH) affording the trifluoroacetate salt of [3-(1H-Indazol-7-yl)-3-phenyl-propyl]-methyl-amine CCLXII-A as a white foam (69% yield).

Synthesis of [3-(1H-Indazol-7-yl)-3-phenyl-propyl]-methyl-amine (CCLXII-B)

To a room temperature solution of [3-(1H-Indazol-7-yl)-3-phenyl-propyl]-methyl-carbamic acid ter-butyl ester CCLXI-B (93 mg, 0.255 mmol) in DCM (5 ml) was added TFA (0.20 ml, 2.55 mmol). The mixture was stirred for 20 hours, concentrated, and the residue was purified via flash chromatography (DCM/MeOH) affording the trifluoroacetate salt of [3-(1H-Indazol-7-yl)-3-phenyl-propyl]-methyl-amine CCLXII-B as a white foam (85% yield).

Example 54

CCLXIII

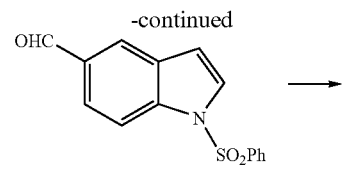
CCLXIV

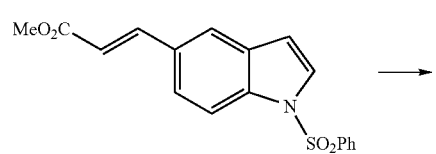
CCLXV

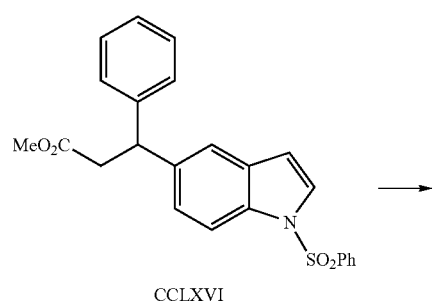
CCLXVI

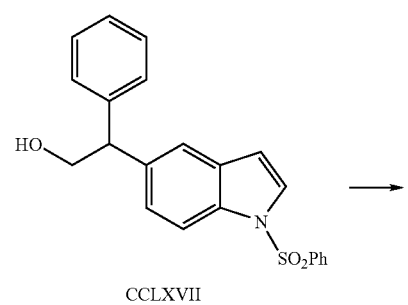
CCLXVII

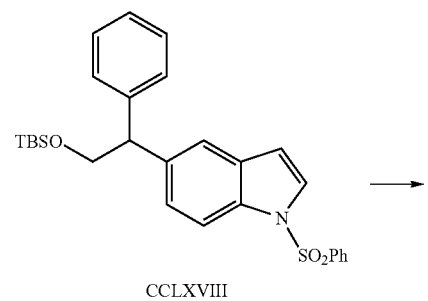
CCLXVIII

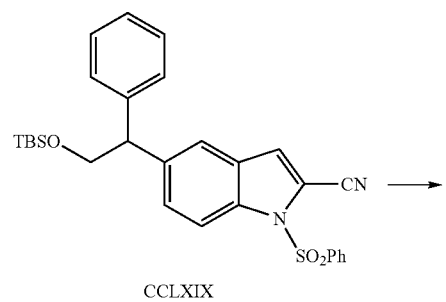
CCLXIX

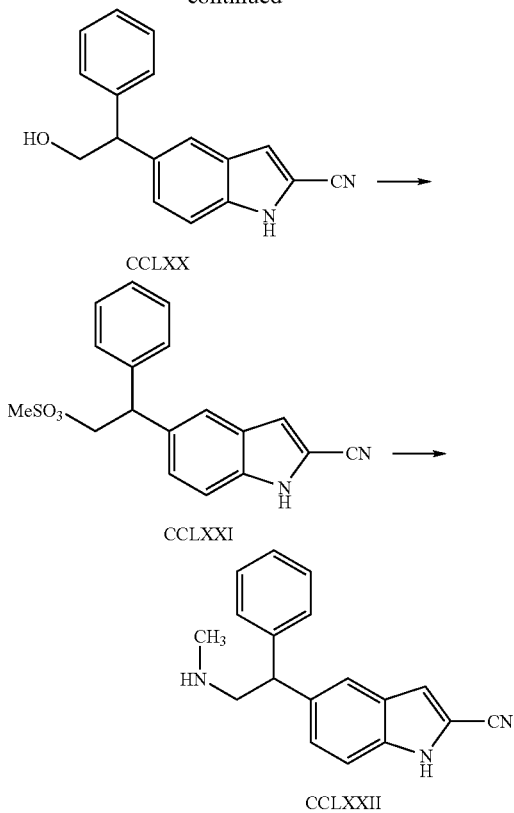

CCLXX

CCLXXI

CCLXXII

Synthesis of 1-benzenesulfonyl-1H-indole-5-carbaldehyde (CCLXIV)

To a solution of 1H-indole-5-carbaldehyde CCLXIII (2.00 g, 13.778 mmol, 1 eq.) in dichloromethane (40 mL) was added, at room temperature, tetrabutylammonium hydrogen sulfate (0.1 eq.) followed by a solution of sodium hydroxide (10.0 eq.) in water (20 mL). Phenylsulfonyl chloride (1.2 eq.) was then slowly added and the resulting mixture was stirred at room temperature for 4 hours. The reaction mixture was then diluted with water and extracted with dichloromethane. The combined organic extracts were dried over anhydrous sodium sulfate, filtered and evaporated under reduced pressure. The crude residue was purified by flash chromatography (EtOAc/hexane, 20/80 to 35/65) to give 3.671 g (93% yield) of 1-benzenesulfonyl-1H-indole-5-carbaldehyde CCLXIV as a white solid.

Synthesis of 3-(1-benzenesulfonyl-1H-indol-5-yl)-acrylic acid methyl ester (CCLXV)

A mixture of 1-benzenesulfonyl-1H-indole-5-carbaldehyde CCKXIV (3.671 g, 12.866 mmol) and methyl(triphenylphosphoranylidene)acetate (5.38 g, 16.082 mmol) in toluene (80 mL) was heated to 110° C. for 68 hours. The resulting mixture was concentrated under reduced pressure and the crude residue was purified by flash chromatography (EtOAc/hexane, 20/80 to 35/65) to afford 4.479 g of 3-(1-benzenesulfonyl-1H-indol-5-yl)-acrylic acid methyl ester CCLXV as a white solid in a mixture 10/1 of (E) and (Z) diastereomers.

Synthesis of 3-(1-benzenesulfonyl-1H-indol-5-yl)-3-phenyl-propionic acid methyl ester (CCLXVI)

A mixture of 3-(1-benzenesulfonyl-1H-indol-5-yl)-acrylic acid methyl ester CCLXV (4.479 g, 13.120 mmol), phenyl boronic acid (2.40 g, 19.68 mmol), hydroxy(1,5-cyclooctadiene)rhodium(I)dimer (320 mg, 0.656 mmol) and triethylamine (2.8 mL, 19.68 mmol) in a mixture of 1,4-dioxane and water (6/1, 42 mL) was heated at 105° C. for 1.5 hours. More hydroxy(1,5-cyclooctadiene)rhodium(I)dimer (320 mg, 0.656 mmol) was added and the resulting mixture was heated at 90° C. for an additional hour. The resulting mixture was diluted with water and extracted with dichloromethane. The combined organic extracts were dried over anhydrous magnesium sulfate, filtered and evaporated under reduced pressure to give a 1/1 mixture of product: 3-(1-benzenesulfonyl-1H-indol-5-yl)-3-phenyl-propionic acid methyl ester and starting material: 3-(1-benzenesulfonyl-1H-indol-5-yl)-acrylic acid methyl ester. This crude residue was resubjected twice to the same reaction conditions to obtain after purification by flash chromatography (EtOAc/hexane, 10/90 to 20/80) 4.816 g of 3-(1-benzenesulfonyl-1H-indol-5-yl)-3-phenyl-propionic acid methyl ester CCLXVI.

Synthesis of 2-(1-benzenesulfonyl-1H-indol-5-yl)-2-phenyl-ethanol (CCLXVII)

A solution of lithium aluminum hydride (1.0 M in THF, 5.9 mL) was added dropwise to a solution of the above obtained mixture 10/1: 3-(1-benzenesulfonyl-1H-indol-5-yl)-3-phenyl-propionic acid methyl ester and 3-(1-benzenesulfonyl-1H-indol-5-yl)-acrylic acid methyl ester CCLXVI (1.654 g, 3.935 mmol) in tetrahydrofuran (30 mL) at 0° C. After stirring for 1 hour the reaction was quenched by slow addition, at 0° C., of Rochelle salt and water. The resulting mixture was diluted with ethyl acetate and stirred at room temperature overnight. The organic layer was separated, washed with brine, dried over anhydrous sodium sulfate, filtered and evaporated under reduced pressure. The residue was purified by flash chromatography to afford 1.06 g (69% yield) of 2-(1-benzenesulfonyl-1H-indol-5-yl)-2-phenyl-ethanol CCLXVII.

Synthesis of 1-benzenesulfonyl-5-[2-(tert-butyl-dimethyl-silanyloxy)-1-phenyl-ethyl]-1H-indole (CCLXVIII)

A mixture of 2-(1-benzenesulfonyl-1H-indol-5-yl)-2-phenyl-ethanol CCLXVII (1.06 g, 2.707 mmol), tert-butyldimethylchlorosilane (0.45 g, 2.978 mmol) and imidazole (200 mg, 2.978 mmol) in N,N-dimethylformamide (20 mL) was stirred at room temperature for 4 hours. The resulting mixture was diluted with water and extracted with diethyl ether. The organic layer was washed with water and brine, dried over anhydrous sodium sulfate, filtered and evaporated under reduced pressure. The crude residue was purified by flash chromatography (EtOAc/hexane, 10/90) to give 1-benzenesulfonyl-5-[2-(tert-butyl-dimethyl-silanyloxy)-1-phenyl-ethyl]-1H-indole CCLXVIII as a yellow oil.

Synthesis of 1-benzenesulfonyl-5-[2-(tert-butyl-dimethyl-silanyloxy)-1-phenyl-ethyl]-1H-indole-2-carbonitrile (CCLXIX)

A solution of tert-butyllithium (1.7 M in pentane, 3.42 mmol) was added at −78° C. to a mixture of 1-benzenesulfonyl-5-[2-(tert-butyl-dimethyl-silanyloxy)-1-phenyl-ethyl]-1H-indole CCLXVIII (865 mg, 1.71 mmol) and N,N,N',N'-tetramethylethylenediamine (0.51 mL, 3.42 mmol) in tetrahydrofuran (20 mL). The resulting mixture was stirred for 1 hour and then a solution of phenyl isocyanate (300 mg, 2.565 mmol) in tetrahydrofuran (2 mL) was added dropwise at −78° C. The resulting mixture was stirred at −78° C. for 1.5 hour and at 0° C. for 1.5 hours. The reaction was then quenched by addition of a saturated aqueous solution of ammonium chloride. The resulting mixture was diluted with water and diethyl ether. The organic layer was separated, washed with brine, dried over anhydrous sodium sulfate, filtered and evaporated under reduced pressure. The crude residue was purified by flash chromatography (EtOAc/hexane, 10/90 to 20/80) to give 0.56 g (62% yield) of 1-benzenesulfonyl-5-[2-(tert-butyl-dimethyl-silanyloxy)-1-phenyl-ethyl]-1H-indole-2-carbonitrile CCLXIX.

Synthesis of 5-(2-hydroxy-1-phenyl-ethyl)-1H-indole-2-carbonitrile (CCLXX)

A solution of tetrabutylammonium fluoride (1.0 M in THF, 1.6 mL) was added to a solution of -benzenesulfonyl-5-[2-(tert-butyl-dimethyl-silanyloxy)-1-phenyl-ethyl]-1H-indole-2-carbonitrile (0.56 g, 1.055 mmol) and the resulting mixture was refluxed for several hours. The solvent was evaporated under reduced pressure and the residue was diluted with water and ethyl acetate. The organic layer was separated, washed with brine, dried over anhydrous sodium sulfate filtered and evaporated under reduced pressure. The crude residue was purified by flash chromatography (EtOAc/hexane, 35/65 to 50/50) to afford 218 mg (75% yield) of 5-(2-hydroxy-1-phenyl-ethyl)-1H-indole-2-carbonitrile CCLXX as a light yellow foam.

Synthesis of methanesulfonic acid 2-(2-cyano-1H-indol-5-yl)-2-phenyl-ethyl ester (CCLXXI)

To a solution of 5-(2-hydroxy-1-phenyl-ethyl)-1H-indole-2-carbonitrile CCLXX (218 mg, 0.789 mmol) in tetrahydrofuran (10 mL) was added at 0° C. methanesulfonyl chloride (73 µL, 0.947 mmol) followed by triethylamine (0.16 mL, 1.183 mmol) and the resulting mixture was stirred at 0° C. for 3 hours. The precipitate which formed was filtered off and the filtrate was evaporated under reduced pressure. The crude residue was purified by flash chromatography to give 240 mg of methanesulfonic acid 2-(2-cyano-1H-indol-5-yl)-2-phenyl-ethyl ester CCLXXI.

Synthesis of 5-(2-methylamino-1-phenyl-ethyl)-1H-indole-2-carbonitrile (CCLXXII)

A mixture of methanesulfonic acid 2-(2-cyano-1H-indol-5-yl)-2-phenyl-ethyl ester CCLXXI (0.24 g) and a solution of methylamine (33% in EtOH, 15 mL) was heated at reflux for 2 hours. The resulting mixture was evaporated under reduced pressure and the residue was purified by flash chromatography (DCM/(DCM+MeOH+NH$_4$OH 60/10/1), 70/30 to 50/50) to give 80 mg of 5-(2-methylamino-1-phenyl-ethyl)-1H-indole-2-carbonitrile CCLXXII as a light yellow foam. MS=290 [M+H]$^+$.

Example 55

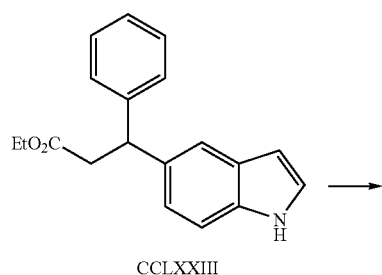

CCLXXIII

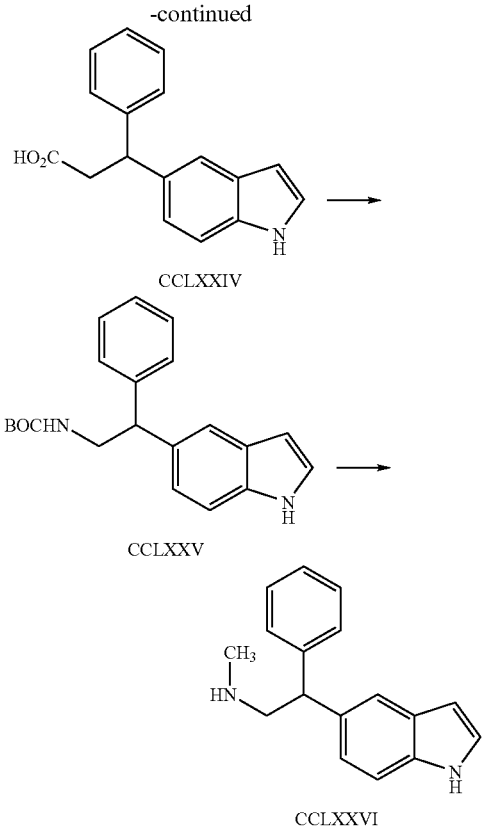

CCLXXIV

CCLXXV

CCLXXVI

Synthesis of 3-(1H-indol-5-yl)-3-phenyl-propionic acid (CCLXXIV)

To a solution of 3-(1H-indol-5-yl)-3-phenyl-propionic acid ethyl ester CCLXXIII (0.48 g, 1.6 mmol) in ethanol (30 mL) was added water (ca. 5 mL) followed by potassium hydroxide in pellets (ca. 0.6 g) and the resulting mixture was stirred at room temperature overnight. The reaction mixture was evaporated under reduced pressure to remove the organic solvent and the residue was diluted with water (50 mL) and diethyl ether (50 mL). The resulting mixture was acidified by addition of an aqueous solution of hydrochloric acid (1 M) and was extracted twice with diethyl ether (50 mL). The combined organic extracts were washed with brine, dried over anhydrous magnesium sulfate, filtered and evaporated under reduced pressure to afford 0.42 g (98% yield) of 3-(1H-indol-5-yl)-3-phenyl-propionic acid CCLXXIV as a yellow solid without further purifications.

Synthesis of [2-(1H-Indol-5-yl)-2-phenyl-ethyl]-carbamic acid tert-butyl ester (CCLXXV)

To a solution of 3-(1H-indol-5-yl)-3-phenyl-propionic acid CCLXXIV (0.43 g, 1.6 mmol) in tert-butanol (10 mL) was added, under nitrogen atmosphere, triethylamine (0.18 g, 1.8 mmol), followed by diphenylphosphoryl azide (0.49 g, 1.8 mmol) and the resulting mixture was heated at reflux for 3 hours. The reaction mixture was cooled to room temperature and evaporated under reduced pressure to a syrup. This residue was diluted with ethyl acetate (50 mL) and washed with an aqueous solution of citric acid (5%), water, a saturated aqueous solution of sodium bicarbonate and brine (ca. 10-20 mL of each solution). The organic layer was dried over anhydrous sodium sulfate, filtered and evaporated under reduced pressure to a light brown film. This crude residue was purified by flash chromatography (hexane/EtOAc, 100/0 to 75/25) to give 0.10 g (19% yield) of [2-(1H-indol-5-yl)-2-phenyl-ethyl]-carbamic acid tert-butyl ester CCLXXV as a colorless film.

Synthesis of [2-(1H-indol-5-yl)-2-phenyl-ethyl]-methyl-amine CCLXXVI

Lithium aluminum hydride (54 mg, 1.4 mmol) was added, under nitrogen atmosphere, to a solution of [2-(1H-indol-5-yl)-2-phenyl-ethyl]-carbamic acid tert-butyl ester CCLXXV (100 mg, 0.30 mmol) in tetrahydrofuran (3 mL) and the resulting mixture was heated at reflux for 95 minutes. The reaction mixture was cooled to room temperature and then at 0° C., freshly crushed sodium sulfate decahydrate (3 g) was then added portionwise and the resulting mixture was stirred for 1.5 hours. The reaction mixture was filtered and the filter cake was washed with ethyl acetate. The filtrate was evaporated under reduced pressure to a light yellow oil. This crude residue was purified by flash chromatography (DCM/(DCM/MeOH/NH$_4$OH) 100/0 to 25/75) to give [2-(1H-indol-5-yl)-2-phenyl-ethyl]-methyl-amine CCLXXVI. MS=251 [M+H]$^+$.

Example 56

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |

| Composition for Oral Administration -continued | |
|---|---|
| Ingredient | Amount |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 57

Screening for Human Serotonin Transporter (hSERT) Antagonists Using a Scilntillation Proximity Assay (SPA)

The screening assay of this example was used to determine the affinity of ligands at the hSERT transporter by competition with [$^3$H]-Citalopram.

Scintillation Proximity Assay (SPA) works by bringing radioligand within close proximity to the bead's scintillant to stimulate light emission. In this assay, the receptor-containing membranes were pre-coupled to the SPA beads and the binding of the appropriate radioligand to the transporter was measured. The light emission was proportional to the amount of bound radioligand. Unbound radioligand produced no signal as a result of distant proximity to scintillant (lack of energy transfer).

HEK-293 cells (Tatsumi et al., Eur. J. Pharmacol. 1997, 30, 249-258) stably expressing recombinant hSERT were maintained with media (DMEM high glucose with 10% FBS, 300 μg/ml G418 and 2 mM L-Glutamine) and incubated at 37° C. with 5% $CO_2$. Cells are released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube (7.5×10$^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3 mg/ml (w:v). and stored at −80° C.

For Scintillation Proximity Assay $IC_{50}/K_i$ determination, 50 mM Tris-HCl and 300 mM NaCl, (pH 7.4) buffers were utilized. Compounds of the invention were diluted from 10 mM to 0.1 nM FAC (10 point curves, whole log/half log dilutions) via a Beckman Biomek 2000 using a serial dilution protocol. The test compounds were then transferred (20 μl/well) and the [$^3$H]-Citalopram radioligand was added at 50 μl/well. Membrane and beads were prepared to a ratio of 10 μg: 0.7 mg, with 0.7 mg PVT-WGA Amersham beads (Cat# RPQ0282V) added per well. 130 μl of the membrane: bead mixture was added to the assay plate. The mixtures were allowed to stand at room temperature for one hour, and were then counted on a Packard TopCount LCS, a generic Scintillation Proximity Assay counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound counts per minute (CPM) at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for human serotonin transporter. For example, 6-(3-Methylamino-1-phenyl-propyl)-1H-indole-3-carbonitrile exhibited an $IC_{50}$ of approximately 9.4 using the above assay.

Example 58

Screening for Compounds Active at Human Norepinephrine Transporter (hNET) Using a Scintillation Proximity Assay (SPA)

This assay was used to determine the affinity of ligands for the hNET transporter by competition with [$^3$H]-Nisoxetine. As in the hSERT assay of the above example, receptor-containing membranes were pre-coupled to the SPA beads and the binding of the appropriate radioligand to the transporter was measured. The light emission was proportional to the amount of bound radioligand, with unbound radioligand producing no signal.

HEK-293 cells (Tatsumi et al., Eur. J. Pharmacol. 1997, 30, 249-258) stably expressing recombinant hNET (Clone: HEK-hNET #2) were maintained with media (DMEM hi glucose with 10% FBS, 300 μg/ml G418 and 2 mM L-Glutamine) and incubated at 37° C. with 5% $CO_2$. Cells were released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube (7.5×10$^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3-6 mg/ml (w:v). and stored at −80° C.

$^3$[H] Nisoxetine radioligand (Amersham Cat. # TRK942 or Perkin Elmer Cat. # NET1084, specific activity: 70-87 Ci/mmol, stock concentration: 1.22 e-5 M, final concentration: 8.25 e-9 M), and 50 mM Tris-HCl, 300 mM NaCl, (pH 7.4) buffers were used for Scintillation Proximity Assay $IC_{50}$/ $K_i$ determination. Compounds of the invention were diluted from 10 mM to 0.1 nM FAC (10 point curves, whole log/half log dilutions) via a Beckman Biomek 2000 using a serial dilution protocol. The test compounds were then transferred (20 μl/well) and the radioligand was added at 50 μl/well. Membrane and beads were prepared to a ratio of 10 μg: 0.7 mg, with 0.7 mg PVT-WGA Amersham beads (Cat# RPQ0282V) added per well. 130 μl of the membrane: bead mixture was added to the assay plate. The mixtures were allowed to stand at room temperature for one hour, and were then counted on a Packard TopCount LCS, a generic SPA counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound CPM at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for the human norepinephrine transporter. For example, 3-(7-Chloro-1H-indol-5-yl)-3-phenyl-propyl]-methyl-amine exhibited an $IC_{50}$ of approximately 9.0 using the above assay.

Example 59

Screening for Compounds Active at Human Dopamine Transporter Using a Scintillation Proximity Assay (SPA)

This assay was used to determine the affinity of ligands for the dopamine transporter by competition with [$^3$H]-Vanoxerine.

HEK-293 cells (Tatsumi et al., Eur. J. Pharmacol. 1997, 30, 249-258) stably expressing recombinant hDAT were maintained with media (DMEM hi glucose with 10% FBS, 300 μg/ml G418 and 2 mM L-Glutamine) and incubated at 37° C. with 5% $CO_2$. Cells were plated four hours prior to experiment by placing approximately 30,000 cells per well (in PBS) on white, opaque Cell-Tak coated 96 well plates. Extra buffer was apriated from the cell plates using an ELx405 plate washer.

$^3$[H] vanoxerine (GBR 12909) radioligand, specific activity approximately 59 Ci/mmol, stock concentration, 400 nM, and 50 mM Tris-HCl, 300 mM NaCl, (pH 7.4) buffers were used for Scintillation Proximity Assay $IC_{50}/K_i$ determination. Compounds of the invention were diluted from 10 mM to 0.1 nM FAC (10 point curves, whole log/half log dilutions) via a Beckman Biomek 2000 using a 10-point dilution protocol. The mixtures were allowed to stand at room temperature for 30 minutes, and were then counted on a Packard TopCount LCS, a generic SPA counting protocol settings, Count Time (min.): 0.40, Background Subtract: none, Half-Life Correction: none, Quench Indicator: tSIS, Platemap blank subtraction: none, Cross talk reduction: Off).

The % inhibition was calculated for each compound tested [(Compound CPM at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki. Using the above procedure, compounds of the invention were found to have affinity for the human dopamine transporter. For example, 3-(7-Chloro-1H-indol-5-yl)-3-phenyl-propyl]-methyl-amine exhibited an $IC_{50}$ of approximately 7.0 using the above assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of formula I:

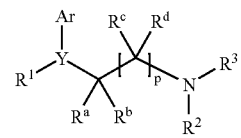

or a pharmaceutically acceptable salt thereof,
wherein:
  p is 1 or 2;
  Y is $CR^c$;
  Ar is:
    (a) indolyl selected from indol-4-yl, indol-5-yl, indol-6-yl, and indol-7-yl, each optionally substituted;
  $R^1$ is:
    (a) aryl selected from phenyl and naphthyl, each optionally substituted; or
    (b) heteroaryl selected from indolyl, indazolyl, pyridinyl, thienyl, furanyl, pyrimidinyl, pyridazinyl, pyrazinyl, oxazolyl, thiazolyl, isoxazolyl, isothiazolyl, imidazolyl, pyrazolyl, quinolinyl, isoquinolinyl, quinoxalinyl, benzothiazolyl, benzofuranyl, benzothiophenyl or benzoxazinyl, each optionally substituted;
    (c) optionally substituted arylalkyl;
    (d) optionally substituted heteroarylalkyl;
    (e) cycloalkyl; or
    (f) cycloalkylmethyl;
  $R^2$ and $R^3$ each independently is:
    (a) hydrogen;
    (b) alkyl;
    (c) hydroxyalkyl;
    (d) alkoxyalkyl;
    (e) benzyl; or
    (f) $R^2$ and $R^3$ together with the nitrogen to which they are attached may form an optionally substituted four to seven membered ring that optionally includes an additional heteroatom selected from N, O and S;

$R^a$ is:
  hydrogen;
  fluoro; or
  alkyl;

$R^b$ is:
  hydrogen;
  alkyl;
  hydroxy;
  alkoxy;
  fluoro; or
  hydroxyalkyl;

or one of $R^2$ and $R^3$ together with one of $R^a$ and $R^b$ and the atoms to which they are attached may form a five or six membered ring that optionally includes an additional heteroatom selected from O, N and S;

$R^c$ and $R^d$ each independently is:
  hydrogen; or
  alkyl;

or $R^c$ and $R^d$ together form =O, =S, or =$NR^f$, wherein $R^f$ is hydrogen, alkyl, or
  —$OR^g$, wherein $R^g$ is hydrogen or alkyl;

or one of $R^2$ and $R^3$ together with one of $R^c$ and $R^d$ together with the atoms to which they are attached may form a four to six membered ring that optionally includes an additional heteroatom selected from O, N and S; and $R^e$ is hydrogen or alkyl.

2. The compound according to claim 1, wherein p is 1.

3. The compound according to claim 1, wherein $R^1$ is phenyl, indolyl, or pyridinyl, each of which is optionally substituted.

4. The compound according to claim 1, wherein each of $R^2$ and $R^3$ is independently hydrogen or alkyl.

5. The compound according to claim 1, wherein $R^a$ and $R^b$ are hydrogen.

6. The compound according to claim 1, wherein $R^c$ and $R^d$ together form =O or $R^c$ and $R^d$ are hydrogen.

7. The compound according to claim 1, wherein Y is CH.

8. The compound according to claim 1 of the formula:

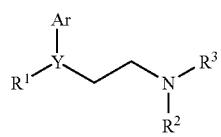

II or a pharmaceutically acceptable salt thereof,
wherein:
  $R^2$ and $R^3$ each independently is hydrogen or alkyl; and
  Ar, Y and $R^1$ are as recited in claim 1.

9. The compound according to claim 6, wherein $R^1$ is phenyl, indolyl, or pyridinyl, each of which is optionally substituted.

10. The compound according to claim 8, wherein Ar is: indol-5-yl or indol-6-yl each optionally substituted.

11. The compound according to claim 8, wherein Y is CH.

12. The compound according to claim 8, of the formula:

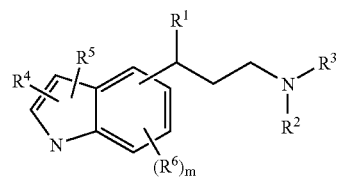

III wherein
  m is an integer from 0 to 3;
  $R^4$ and $R^5$ each independently is: hydrogen; alkoxy, cyano, alkyl, halo, —$S(O)_T R^f$; and
    C(=O)$NR^g R^h$; wherein r is an integer from 0 to 2, and each of $R^f$, $R^g$, and $R^h$ is independently hydrogen or alkyl;
  each $R^6$ is independently: alkoxy, cyano, alkyl, halo, $S(O)_T R^f$; and —C(=O)$NR^g R^h$; wherein r is an integer from 0 to 2, and each of $R^f$, $R^g$, and $R^h$ is independently hydrogen or alkyl; and
  $R^1$, $R^2$ and $R^3$ are as recited in claim 1.

13. The compound according to claim 12, wherein $R^1$ is optionally substituted phenyl or optionally substituted pyridinyl.

14. The compound according to claim 12, wherein one of $R^2$ and $R^3$ is hydrogen and the other is alkyl.

15. The compound according to claim 12, wherein in is 0, 1 or 2 and $R^6$ is halo, alkyl, alkoxy or cyano.

16. The compound according to claim 12, wherein $R^4$ and $R^5$ are hydrogen.

17. The compound according to claim 12 of the formula:

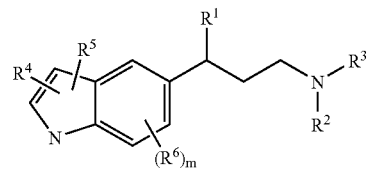

IV wherein m, $R^1$, $R^2$, $R^3$, $R^4$, $R^5$ and $R^6$ are as recited in claim 12.

18. The compound according to claim 12 of the formula:

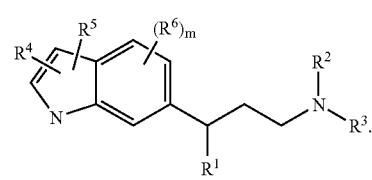

V

19. A pharmaceutical composition comprising a compound of claim 1 and a pharmaceutically acceptable carrier.

20. A method for treating depression, anxiety, or a combination thereof, said method comprising administering to a subject in need thereof an effective amount of a compound of claim 1.

* * * * *